US011466004B2

(12) United States Patent
Burn

(10) Patent No.: US 11,466,004 B2
(45) Date of Patent: Oct. 11, 2022

(54) SOLID FORMS OF AN FGFR INHIBITOR AND PROCESSES FOR PREPARING THE SAME

(71) Applicant: Incyte Corporation, Wilmington, DE (US)

(72) Inventor: Timothy C. Burn, Hockessin, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/402,955

(22) Filed: May 3, 2019

(65) Prior Publication Data

US 2019/0337948 A1 Nov. 7, 2019

Related U.S. Application Data

(60) Provisional application No. 62/815,539, filed on Mar. 8, 2019, provisional application No. 62/667,166, filed on May 4, 2018.

(51) Int. Cl.
*C07D 471/14* (2006.01)
*C07D 471/04* (2006.01)
*A61K 9/00* (2006.01)
*A61P 35/00* (2006.01)

(52) U.S. Cl.
CPC .......... *C07D 471/14* (2013.01); *A61K 9/0053* (2013.01); *A61P 35/00* (2018.01); *C07D 471/04* (2013.01); *C07B 2200/13* (2013.01)

(58) Field of Classification Search
None
See application file for complete search history.

(56) References Cited

U.S. PATENT DOCUMENTS

| | | |
|---|---|---|
| 850,370 A | 4/1907 | Hynes |
| 3,894,021 A | 7/1975 | Denzel et al. |
| 4,271,074 A | 6/1981 | Lohmann et al. |
| 4,339,267 A | 7/1982 | Levitt |
| 4,347,348 A | 8/1982 | Chernikhov et al. |
| 4,402,878 A | 9/1983 | D'Alelio et al. |
| 4,405,519 A | 9/1983 | D'Alelio et al. |
| 4,405,520 A | 9/1983 | D'Alelio et al. |
| 4,405,786 A | 9/1983 | D'Alelio et al. |
| 4,460,773 A | 7/1984 | Suzuki et al. |
| 4,874,803 A | 10/1989 | Baron et al. |
| 4,940,705 A | 7/1990 | Boshagen et al. |
| 5,159,054 A | 10/1992 | Keller |
| 5,240,941 A | 8/1993 | Bruneau |
| 5,480,887 A | 1/1996 | Hornback et al. |
| 5,521,184 A | 5/1996 | Zimmermann et al. |
| 5,536,725 A | 7/1996 | Cullen et al. |
| 5,541,324 A | 7/1996 | TenBrink et al. |
| 5,760,068 A | 6/1998 | Talley et al. |
| 5,783,577 A | 7/1998 | Houghten et al. |
| 5,845,025 A | 12/1998 | Garito et al. |
| 5,994,364 A | 11/1999 | Njoroge et al. |
| 6,465,484 B1 | 10/2002 | Bilodeau et al. |
| 6,998,408 B2 | 2/2006 | Pinto |
| 7,074,801 B1 | 7/2006 | Yoshida et al. |
| 7,125,880 B1 | 10/2006 | Chen |
| 7,488,802 B2 | 2/2009 | Collins et al. |
| 7,618,975 B2 | 11/2009 | Cai et al. |
| 7,642,255 B2 | 1/2010 | Sim |
| 7,648,973 B2 | 1/2010 | DeLuca et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,217,149 B2 | 7/2012 | Irving et al. |
| 8,759,398 B2 | 1/2014 | Nelson |
| 8,754,114 B2 | 6/2014 | Yao et al. |
| 8,889,711 B2 | 11/2014 | Bedjeguelal |
| 9,266,892 B2 | 2/2016 | Zhuo et al. |
| 9,388,185 B2 | 7/2016 | Lu et al. |
| 9,533,954 B2 | 1/2017 | Yao et al. |
| 9,533,984 B2 | 1/2017 | Sun et al. |
| 9,580,423 B2 | 2/2017 | Lu et al. |
| 9,611,267 B2 | 4/2017 | Wu et al. |
| 9,708,318 B2 | 7/2017 | Lu et al. |
| 9,745,311 B2 | 8/2017 | Lu et al. |
| 9,801,889 B2 | 10/2017 | Lu et al. |
| 9,890,156 B2 | 2/2018 | Lu et al. |
| 10,016,348 B2 | 7/2018 | Lu et al. |
| 10,040,790 B2 | 8/2018 | Sun et al. |
| 10,131,667 B2 | 11/2018 | Wu et al. |

(Continued)

FOREIGN PATENT DOCUMENTS

| | | |
|---|---|---|
| CL | 2014003355 | 6/2015 |
| CL | 2015002628 | 8/2016 |

(Continued)

OTHER PUBLICATIONS

Borad et al., Fibroblast growth factor receptor 2 fusions as a target for treating cholangiocarcinoma. Current opinion in Gastroenterology, 2015, 31, 264-268.*
Costa Rican Office Action in Costa Rican Application No. 2015-0578, dated Jun. 11, 2020, 15 pages.
Indonesian Office Action in Indonesian Application No. PID201705977, dated Jun. 5, 2020, 5 pages.
Bavin, "Polymorphism in Process Development," Chemistry & Industry, Society of Chemical Industry, Aug. 1989, 527-529.
Chilean Office Action in Chilean Application No. 2122-2017, dated Nov. 15, 2019, 15 pages.
Colombian Office Action in Colombian Application No. NC2019/0009690, dated Jan. 22, 2020, 20 pages.

(Continued)

*Primary Examiner* — Po-Chih Chen
(74) *Attorney, Agent, or Firm* — Fish & Richardson P.C.

(57) ABSTRACT

The present disclosure relates to 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one, solid forms and polymorphs thereof, methods of preparation thereof, and intermediates in the preparation thereof, which are useful in the treatment of the FGFR-associated or mediated diseases such as cancer.

60 Claims, 84 Drawing Sheets

Specification includes a Sequence Listing.

(56) References Cited

U.S. PATENT DOCUMENTS

| | | | |
|---|---|---|---|
| 10,208,024 B2 | 2/2019 | Andrews et al. |
| 10,213,427 B2 | 2/2019 | Yao et al. |
| 10,214,528 B2 | 2/2019 | Lu et al. |
| 10,251,892 B2 | 4/2019 | Sokolsky et al. |
| 10,308,644 B2 | 6/2019 | Wu et al. |
| 10,350,240 B2 | 6/2019 | Gore et al. |
| 10,357,431 B2 | 7/2019 | Staric et al. |
| 10,450,313 B2 | 10/2019 | Lu et al. |
| 10,611,762 B2 | 4/2020 | Jia et al. |
| 10,632,126 B2 | 4/2020 | Lu et al. |
| 10,738,048 B2 | 8/2020 | Lu et al. |
| 10,813,930 B2 | 10/2020 | Yao et al. |
| 10,851,105 B2 | 12/2020 | Wu et al. |
| 10,947,230 B2 | 3/2021 | Sun et al. |
| 11,014,923 B2 | 5/2021 | Lu et al. |
| 11,053,246 B2 | 7/2021 | Wu et al. |
| 11,173,162 B2 | 11/2021 | Sokolsky et al. |
| 11,174,257 B2 | 11/2021 | Jia et al. |
| 2003/0078255 A1 | 4/2003 | Pinto |
| 2003/0078277 A1 | 4/2003 | Hibi et al. |
| 2003/0181622 A1 | 9/2003 | Chiu et al. |
| 2004/0044012 A1 | 3/2004 | Dobrusin et al. |
| 2004/0067948 A1 | 4/2004 | Hallett |
| 2004/0097493 A1 | 5/2004 | Chen et al. |
| 2004/0122029 A1 | 6/2004 | Liu et al. |
| 2004/0127538 A1 | 7/2004 | Oinuma et al. |
| 2004/0204427 A1 | 10/2004 | Chen et al. |
| 2005/0009876 A1 | 1/2005 | Bhagwat et al. |
| 2005/0070542 A1 | 3/2005 | Hodgetts et al. |
| 2005/0148603 A1 | 7/2005 | Jimenez et al. |
| 2005/0197340 A1 | 9/2005 | Arora et al. |
| 2005/0222171 A1 | 10/2005 | Bold et al. |
| 2006/0222637 A1 | 10/2006 | Bamdad |
| 2006/0270849 A1 | 11/2006 | Nishino et al. |
| 2007/0116984 A1 | 5/2007 | Park et al. |
| 2007/0197510 A1 | 8/2007 | Ohmoto et al. |
| 2007/0225286 A1 | 9/2007 | Ren et al. |
| 2007/0280943 A1 | 12/2007 | Friedman et al. |
| 2008/0249301 A1 | 10/2008 | Hornberger et al. |
| 2009/0098086 A1 | 4/2009 | Zask et al. |
| 2009/0099165 A1 | 4/2009 | Hurley et al. |
| 2009/0099190 A1 | 4/2009 | Flynn et al. |
| 2009/0105233 A1 | 4/2009 | Chua et al. |
| 2009/0131467 A1 | 5/2009 | Kanazawa et al. |
| 2009/0163545 A1 | 6/2009 | Goldfarb |
| 2009/0246198 A1 | 10/2009 | Dong et al. |
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0204235 A1 | 8/2010 | Lizos |
| 2010/0210636 A1 | 8/2010 | Ishikawa et al. |
| 2010/0216798 A1 | 8/2010 | Nakai et al. |
| 2010/0239496 A1 | 9/2010 | Gangadharmath et al. |
| 2011/0045511 A1 | 2/2011 | Graus Porta et al. |
| 2011/0159604 A1 | 6/2011 | Fan et al. |
| 2011/0160203 A1 | 6/2011 | Liu et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0035153 A1 | 2/2012 | Saxty et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0210825 A1 | 8/2013 | Rehwinkel et al. |
| 2013/0338134 A1* | 12/2013 | Wu ..................... C07D 498/14 514/210.18 |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0171405 A1 | 6/2014 | Zhuo et al. |
| 2014/0187559 A1 | 7/2014 | Miduturu |
| 2014/0194430 A1 | 7/2014 | Eis et al. |
| 2014/0228370 A1 | 8/2014 | Eis et al. |
| 2014/0243308 A1 | 8/2014 | Yao et al. |
| 2014/0288069 A1 | 9/2014 | Eis et al. |
| 2014/0296233 A1 | 10/2014 | D'Agostino et al. |
| 2014/0315902 A1 | 10/2014 | Sun et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Litmanen et al. |
| 2015/0011560 A1 | 1/2015 | Legeai-Mallet |
| 2015/0011579 A1 | 1/2015 | Clary-Ceccato et al. |
| 2015/0038485 A1 | 2/2015 | Eis et al. |
| 2015/0197519 A1 | 7/2015 | Bifulco |
| 2016/0115164 A1 | 4/2016 | Wu et al. |
| 2016/0244448 A1 | 8/2016 | Lu et al. |
| 2016/0244449 A1 | 8/2016 | Lu et al. |
| 2016/0244450 A1 | 8/2016 | Lu et al. |
| 2016/0280713 A1 | 9/2016 | Lu et al. |
| 2017/0107216 A1 | 4/2017 | Wu |
| 2017/0119782 A1 | 5/2017 | Lu et al. |
| 2017/0137424 A1 | 5/2017 | Wu et al. |
| 2017/0145025 A1 | 5/2017 | Li et al. |
| 2017/0165263 A1 | 6/2017 | Yao et al. |
| 2017/0166564 A1 | 6/2017 | Sun et al. |
| 2017/0174671 A1 | 6/2017 | Wu et al. |
| 2017/0174679 A1 | 6/2017 | Lajkiewicz et al. |
| 2017/0260168 A1 | 9/2017 | Andrews et al. |
| 2017/0290839 A1 | 10/2017 | Lu et al. |
| 2017/0320875 A1 | 11/2017 | Li et al. |
| 2017/0320877 A1 | 11/2017 | Wu et al. |
| 2017/0342060 A1 | 11/2017 | Lu et al. |
| 2017/0362253 A1 | 12/2017 | Xiao et al. |
| 2018/0008610 A1 | 1/2018 | Lu et al. |
| 2018/0016260 A1 | 1/2018 | Yu et al. |
| 2018/0057486 A1 | 3/2018 | Wu et al. |
| 2018/0072718 A1 | 3/2018 | Liu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0244672 A1 | 8/2018 | Lu et al. |
| 2018/0273519 A1 | 9/2018 | Wu et al. |
| 2019/0040082 A1 | 2/2019 | Xiao et al. |
| 2019/0055237 A1 | 2/2019 | Pan et al. |
| 2019/0062327 A1 | 2/2019 | Sun et al. |
| 2019/0062345 A1 | 2/2019 | Xiao et al. |
| 2019/0071439 A1 | 3/2019 | Li et al. |
| 2019/0092767 A1 | 3/2019 | Li et al. |
| 2019/0127376 A1 | 5/2019 | Wu et al. |
| 2019/0127467 A1 | 5/2019 | Shah et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0240220 A1 | 8/2019 | Yao et al. |
| 2019/0241560 A1 | 8/2019 | Lu et al. |
| 2019/0269693 A1 | 9/2019 | Lu et al. |
| 2019/0284187 A1 | 9/2019 | Wu et al. |
| 2019/0300524 A1 | 10/2019 | Wu et al. |
| 2019/0345170 A1 | 11/2019 | Wu et al. |
| 2020/0002338 A1 | 1/2020 | Jia et al. |
| 2020/0055853 A1 | 2/2020 | Ellies et al. |
| 2020/0095244 A1 | 3/2020 | Sun et al. |
| 2020/0255424 A1 | 8/2020 | Wu et al. |
| 2020/0270245 A1 | 8/2020 | Pan et al. |
| 2020/0277309 A1 | 9/2020 | Wu et al. |
| 2020/0306256 A1 | 10/2020 | Lu et al. |
| 2020/0377504 A1 | 12/2020 | Wu et al. |
| 2020/0399267 A1 | 12/2020 | Lu et al. |
| 2021/0009582 A1 | 1/2021 | Vechorkin et al. |

(56) References Cited

U.S. PATENT DOCUMENTS

| | | | |
|---|---|---|---|
| 2021/0094935 | A1 | 4/2021 | Vechorkin |
| 2021/0106588 | A1 | 4/2021 | Vechorkin et al. |
| 2021/0115053 | A1 | 4/2021 | Shvartsbart et al. |
| 2021/0171522 | A1 | 6/2021 | Tao et al. |
| 2021/0171535 | A1 | 6/2021 | McCammant et al. |
| 2021/0214366 | A1 | 7/2021 | Roach et al. |
| 2021/0380587 | A1 | 12/2021 | Wu et al. |
| 2021/0395246 | A1 | 12/2021 | Sun et al. |
| 2022/0009921 | A1 | 1/2022 | Lu et al. |

FOREIGN PATENT DOCUMENTS

| | | |
|---|---|---|
| CL | 2017000654 | 12/2017 |
| CL | 2018000089 | 5/2018 |
| CL | 2018000124 | 5/2018 |
| CL | 201702117 | 6/2018 |
| CL | 2018000036 | 6/2018 |
| CL | 2018000128 | 6/2018 |
| CL | 2018003322 | 1/2019 |
| CN | 1863774 | 11/2006 |
| CN | 101007778 | 8/2007 |
| CN | 101679408 | 3/2010 |
| CN | 101715451 | 5/2010 |
| CN | 102399220 | 4/2012 |
| CN | 102399233 | 4/2012 |
| CN | 102666536 | 9/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| EP | 3184521 | 6/2017 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001/035664 | 2/2001 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 200628027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2008198769 | 8/2008 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 20119348 | 1/2011 |
| JP | 201144637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 201349251 | 3/2013 |
| JP | 2013179181 | 9/2013 |
| JP | 2015517376 | 6/2015 |
| JP | 2018507214 | 3/2018 |
| JP | 2018511573 | 4/2018 |
| JP | 6336665 | 6/2018 |
| KR | 20010043829 | 5/2001 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| WO | WO 1988/03025 | 5/1988 |
| WO | WO 1991/09835 | 7/1991 |
| WO | WO 1991/10172 | 7/1991 |
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/09495 | 2/2000 |
| WO | WO 2002/000196 | 2/2000 |
| WO | WO 2000/24744 | 5/2000 |
| WO | WO 2000/053595 | 9/2000 |
| WO | WO 2000/68186 | 11/2000 |
| WO | WO 2001/02369 | 1/2001 |
| WO | WO 2001/014402 | 3/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |

(56) References Cited

FOREIGN PATENT DOCUMENTS

| | | |
|---|---|---|
| WO | WO 2001/58899 | 8/2001 |
| WO | WO 2001/64655 | 9/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/074754 | 9/2002 |
| WO | WO 2002/076953 | 10/2002 |
| WO | WO 2002/083648 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/024967 | 3/2003 |
| WO | WO 2003/037347 | 5/2003 |
| WO | WO 2003/037891 | 5/2003 |
| WO | WO 2003/040131 | 5/2003 |
| WO | WO 2003/042402 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099771 | 12/2003 |
| WO | WO 2003/099818 | 12/2003 |
| WO | WO 2003/101985 | 12/2003 |
| WO | WO 2004/002986 | 1/2004 |
| WO | WO 2004/005281 | 1/2004 |
| WO | WO 2004/0143 82 | 2/2004 |
| WO | WO 2004/011465 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046120 | 6/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056786 | 7/2004 |
| WO | WO 2004/056822 | 7/2004 |
| WO | WO 2004/056830 | 7/2004 |
| WO | WO 2004/065378 | 8/2004 |
| WO | WO 2004/080980 | 9/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/028444 | 5/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/056399 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |

(56) References Cited

FOREIGN PATENT DOCUMENTS

| | | |
|---|---|---|
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/037459 | 4/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2008/156712 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/050183 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/085185 | 7/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/124755 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/148916 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/009735 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/036959 | 4/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/062571 | 6/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/075074 | 7/2010 |

(56) References Cited

FOREIGN PATENT DOCUMENTS

| | | |
|---|---|---|
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/089411 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/053518 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/066342 | 6/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082400 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101409 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2011/159877 | 12/2011 |
| WO | WO 2011/161699 | 12/2011 |
| WO | WO 2011/163330 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061156 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |

(56) References Cited

FOREIGN PATENT DOCUMENTS

| | | |
|---|---|---|
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/078777 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/084704 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/129344 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/041634 | 3/2013 |
| WO | WO 2013/049352 | 4/2013 |
| WO | WO 2013/053051 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/108992 | 7/2015 |
| WO | WO 2016/064960 | 4/2016 |
| WO | WO 2016/134314 | 8/2016 |
| WO | WO 2016/192680 | 12/2016 |
| WO | WO 2017/028314 | 2/2017 |
| WO | WO 2017/223414 | 12/2017 |
| WO | WO 2018/041091 | 3/2018 |
| WO | WO 2018/049214 | 3/2018 |
| WO | WO 2018/067512 | 4/2018 |
| WO | WO 2018/093029 | 5/2018 |
| WO | WO 2018/093215 | 5/2018 |
| WO | WO 2018/105972 | 6/2018 |
| WO | WO 2018/105973 | 6/2018 |
| WO | WO 2018/234354 | 12/2018 |
| WO | WO 2019/037640 | 2/2019 |
| WO | WO 2019/079369 | 4/2019 |
| WO | WO 2019/105886 | 6/2019 |
| WO | WO 2019/213506 | 11/2019 |
| WO | WO 2020/049017 | 3/2020 |
| WO | WO 2020/131627 | 6/2020 |
| WO | WO 2020/131674 | 6/2020 |

OTHER PUBLICATIONS

Costa Rican Office Action in Costa Rican Application No. 2014-0577, dated Apr. 15, 2020, 18 pages.
Edmondson et al., "Aminopiperidine-fused imidazoles as dipeptidyl peptidase-IV inhibitors," Bioorg & Med Chem Lett., 2009, 19(15):4097-4101.
Erian at al., "2-Aryl-1,1-dicyano-3-phenylsulfonylpropenes in heterocyclic synthesis. A synthetic strategy towards heterocyclic sulfones," Monatshefte fuer Chemie, 1998, 129(10): 1049-1056.
Furniss "Acidic/Basic characteristics for purification," Vogel's Textbook of Practican Organic Chemistry, 5th edition, 1989, 131-133, 135-143.
Gennaro et al., "Pharmaceutical Sciences," Remington's Pharmaceutical Sciences 17th Ed., Jan. 1985, 14-18 and 1409-1423.
International Search Report and Written Opinion in International Application No. PCT/US2019/030578, dated Jul. 11, 2019, 26 pages.
Neidle et al., "Failure Modes in the Discovery Process," Cancer Drug Design, 2008, pp. 427-431.
New Zealand Office Action in New Zealand Application No. 713074, dated Feb. 18, 2020, 3 pages.
New Zealand Office Action in New Zealand Application No. 752422, dated Feb. 18, 2020, 2 pages.
Philippine Office Action in Philippine Application No. 1/2017/501483, dated Dec. 12, 2019, 5 pages.
STN Search Report dated Jan. 6, 2020, 88 pages.
Taiwan Office Action in Taiwan Application No. 107146498, dated Dec. 19, 2019, 7 pages.
Taiwan Office Action in Taiwan Application No. 105104993, dated Feb. 11, 2020, 9 pages.
Ukraine Office Action in Ukraine Application No. a201709220, dated Dec. 9, 2019, 11 pages.
"Sabiosciences.com" [online]. "FGF Pathway," 2000-2012, [retrieved on Jun. 23, 2015], Retrieved from the Internet: URL <http://www.sabiosciences.com/pathway.php?sn=FGF_Signaling>, 3 pages.
"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.

(56) References Cited

OTHER PUBLICATIONS

Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.
Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.
Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.
Arai et al., "Characterization of the cell or origin and propagation potential of the fibroblast growth factor 9-induced mouse model of lung adenocarcinoma," J. Pathol., Mar. 2015, 235(4): 593-605.
Argentina Office Action in Argentina Application No. 20140101651, dated Nov. 21, 2019, 5 pages.
Ash and Ash, "Handbook of Pharmaceutical Additives," Gower Publishing Company, 2007, 3rd ed, Cover Page, 1 page.
Australian Office Action in Australian Application No. 2013287176, dated Sep. 12, 2017, 4 pages.
Australian Office Action in Australian Application No. 2014253798, dated Jul. 31, 2017, 4 pages.
Australian Office Action in Australian Application No. 2018208772, dated Jul. 1, 2018, 5 pages.
Australian Office Action in Australian Application No. 2016219822, dated Jul. 8, 2019, 4 pages.
Australian Office Action in Australian Application No. 2016219816, dated Aug. 26, 2019, 3 pages.
Australian Office Action in Australian Application No. 2019200066, dated Aug. 27, 2019, 6 pages.
Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Bazyl et al., "The selective ortho-methoxylation of pentafluorobenzoic acid—a new way to tetrafluorosalicylic acid and its derivatives," J Flour Chem., Feb. 11, 1999, 94(1): 11-13.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Berge et al., "Pharmaceutical Salts", Journal of Pharmaceutical Science, 1977, 66(2): 1-19.
Bergwitz and Juppner, "Regulation of Phosphate Homeostasis by PTH, Vitamin D, and FGF23," Annu. Rev. Med., 2010, 61:91-104.

Bhide et al., "Discovery and Preclinical Studies of (R)-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistiy, 2006, 49(7): 2143-2146.
Billerey et al., "Frequent FGFR3 Mutations in Papillary Non-Invasive Bladder (pTa) Tumors," American Journal of Pathology, Jun. 2001, 158(6): 1955-1959.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
BioCentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blom et al., "Optimizing Preparative LC-MS Configurations and Methods for Parallel Synthesis Purification", J. Combi Chem., 5, 670 (2003).
Blom et al., Preparative LC-MS Purification: Improved Compound Specific Method Optimization, J. Combi. Chem. 2004, 6(6), 874-883.
Blom, K., "Two-Pump at Column Dilution Configuration for Preparative LC-MS", J. Combi Chem., 4, 295 (2002).
Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.
Bono et al., "Inhibition of Tumor Angiogenesis and Growth by a Small-Molecule Multi-FGF Receptor Blocker with Allosteric Properties," Cancer Cell, Apr. 2013, 477-488.
Brooks et al., "Fibroblast growth factor signaling: a new therapeutic opportunity in cancer," Clinical Cancer Research, 2012, 1-23.
Caira, "Crystalline Polymorphism of Organic Compounds,"Topics in Current Chemistry, Jan. 1, 1998, 198:163-208.
Cancer [online], [retrieved on Jul. 6, 2007] Retrieved from the Internet, URL: http://www.nlm.nih.gov/medlineplus/cancer.html.
Cappellen et al., "Frequent activating mutations of FGFR3 in human bladder and cervix carcinomas," Nature Genetics, Sep. 1999, 23: 18-20.
Capelletti et al., "Identification of Recurrent FGFR3-TACC3 Fusion Oncogenes from Lung Adenocarcinoma," AACR Journals, 2014, 6551-6558.
Carmichael et al., "Familial Tumoral Calcinosis: A Forty-Year Follow-up on One Family," The Journal of Bone & Joint Surgery, 2009, 664-671.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistiy, Mar. 2009, 284(10): 6227-6240.
Chandrani et al., "Drug-sensitive FGFR3 mutations in lung adenocarcinoma," Annals of Oncology, 2017, 28:597-603.
Chase et al., "Activity of TKI258 against primary cells and cell lines with FGFR1 fusion genes associated with the 8p11 myeloproliferative syndryome," Blood, 2007, 110:3729-3734.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b>]pyrrole-Based Selective Fibroblast Growth Factor Receptors 1 (FRGR1) Inhibitors: Design, Synthesis, and Biological Activity," Jounal of Medicinal Chemistry, 2011, 54:3732-3745.

(56) References Cited

OTHER PUBLICATIONS

Chen et al., "FGFR3 as a therapeutic target of the small molecule inhibitor PKC412 in hematopoietic malignancies," Oncogene, 2005, 24: 8259-8267.
Chen et al., "Genome-Wide Loss of Heterozygosity and DNA Copy Number Aberration in HPV-Negative Oral Squamous Cell Carcinoma and Their Associations with Disease-Specific Survival," PLOS ONE, Aug. 2015, 23 pages.
Chesi et al., "Activated fibroblast growth factor receptor 3 is an oncogene that contributes to tumor progression in multiple myeloma," Blood, 2001, 97:729-736.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chilean Office Action in Chilean Application No. 2015-003089, dated Apr. 24, 2017, 13 pages (English Summary).
Chilean Office Action in Chilean Application No. 3355-2014, dated Jan. 18, 2017, 17 pages (with English translation).
Chilean Opposition in Chilean Application No. 3355-2014, received Feb. 3, 2017, 3 pages (English translation only).
Chilean Office Action in Chilean Application No. 2015-003089, dated Jan. 23, 2018, 8 pages.
Chilean Office Action in Chilean Application No. 2122-2017, dated Apr. 22, 2019, 25 pages.
Chilean Office Action in Chilean Application No. 1984-2017, dated Sep. 12, 2019, 9 pages.
Chinese Office Action in Chinese Application No. 2013 80041027.9, dated Feb. 13, 2017, 10 pages (with English translation).
Chinese Office Action in Chinese Application No. 2013 80041027.9, dated Jul. 12, 2016, 11 pages (with English translation).
Chinese Office Action in Chinese Application No. 201380041027.9, dated Oct. 28, 2015, 17 pages (with English translation).
Chinese Office Action in Chinese Application No. 201480028858.7, dated Aug. 19, 2016, 18 pages (English Translation).
Chinese Office Action in Chinese Application No. 201480028858.7, dated Jul. 12, 2017, 10 pages (English Translation).
Chinese Office Action in Chinese Application No. 201710874686.0, dated Feb. 25, 2019, 17 pages.
Chinese Office Action in Chinese Application No. 201710395346.X, dated Jan. 22, 2019, 17 pages.
Chinese Office Action in Chinese Application No. 201480028858.7, dated Apr. 4, 2018, 10 pages (English Translation).
Chinese Office Action in Chinese Application No. 201710395346.X, dated Sep. 9, 2019, 10 pages.
Chinese Office Action in Chinese Application No. 201680011348.8, dated Aug. 2, 2019, 14 pages.
Chinese Office Action in Chinese Application No. 201680011332.7, dated Aug. 5, 2019, 14 pages.
Chinese Office Action in Chinese Application No. 10874686.0, dated Oct. 8, 2019, 10 pages.
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Cole et al., "Inhibition of FGFR2 and FGFR1 increases cisplatin sensitivity in ovarian cancer," Cancer Biol. Therapy, Sep. 1, 2010, 10(5):495-504.
Coleman, "Positive and negative regulation of cellular sensitivity to anti-cancer drugs by FGF-2," Drug Resistance Updates, 2003, 85-94.
Colombian Office Action in Colombian Application No. 14-275934-6, dated May 31, 2016, 3 pages (English translation only).
Colombian Office Action in Colombian Application No. 14-275934-6, dated Nov. 17, 2015, 12 pages (English translation only).
Colombian Office Action in Colombian Application No. 16100866, dated Aug. 10, 2017, 9 pages.
Colombian Office Action in Colombian Application No. NC2017/0008795, dated Aug. 29, 2017, 2 pages.
Colombian Office Action in Colombian Application No. NC2017/0008795, dated Nov. 29, 2018, 8 pages.
Colombian Office Action in Colombian Application No. NC2017/0008824, dated Aug. 31, 2017, 3 pages.
Colombian Office Action in Colombian Application No. NC2017/0008824, dated Nov. 29, 2018, 8 pages.
Colombian Office Action in Colombian Application No. NC2017/0008795, dated Aug. 16, 2019, 6 pages.
Corre et al., "Synthesis and biological evaluation of a triazole-based library of pyrido[2,3-d]pyrimidines as FGFR3 tyrosine kinase inhibitors," Organic & Biomolecular Chemistry, 2010, 8:2164-2173.
Costa Rican Opposition in Costa Rican Application No. PCT/US2013/045309, dated Jun. 29, 2015, 14 pages (English Translation).
Costa Rican Office Action in Costa Rican Application No. 2014-0577, dated Jun. 13, 2019, 17 pages.
Covic et al., "Vascular calcification in chronic kidney disease," Clinical Science, 2010, 119: 111-121.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Desnoyers et al., "Targeting FGF19 inhibits tumor growth in colon cancer xenograft and FGF19 transgenic hepatocellular carcinoma models," Oncogene, 2008, 27:85-97.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Ding et al., "Somatic mutations affect key pathways in lung adenocarcinoma," Nature., Oct. 23, 2008, 455:1069-1075.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Eissa, "Synthesis and evaluation of some surface active agents from long chain fatty amine," Spanish National Research Council, Jan. 2007, 58(4):379-389.
Elsheikh et al., "FGFR1 amplification in breast carcinomas: a chromogenic in situ hybridisation analysis," Breast Cancer Research, Mar. 2007, 9(2): 1-12.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.
Eurasian Office Action in Eurasian Application No. 201590005, dated Oct. 21, 2015, 6 pages.

(56) References Cited

OTHER PUBLICATIONS

Eurasian Office Action in Eurasian Application No. 201791866, dated Feb. 19, 2018, 10 pages (English Translation).
Eurasian Office Action in Eurasian Application No. 201590005, Mar. 28, 2018, 6 pages.
Eurasian Office Action in Eurasian Application No. 201791867, dated Apr. 4, 2018, 4 pages (English Translation).
European Communication pursuant to Article 94(3) EPC in European Application No. 13783125.1, dated Jan. 26, 2016, 4 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Faul et al., "FGF23 induces left ventricular hypertrophy," The Journal of Clinical Investigation, 2010, 1-16.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cell lung cancer cells: therapeutic implications and synergism with epidermal growth factor receptor inhibition," Mol Cancer Therapy, 2008, 3408-3419.
French et al., Targeting FGFR4 inhibits hepatocellular carcinoma in preclinical mouse models, PLoS One 2012;7:e36713.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosishyperphosphatemia syndrome and familial tumoral calcinosis are allelic disorders," J Mol Med, 2005, 83:33-38.
Fukumoto and Yamashita, "FGF23 is a hormone-regulating phophate metabolism—Unique biological characteristics of FGF23," Bone, 2007, 1190-1195.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi—2a and NaPi—2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno[b] Thieno(Pyridines, Quinolines, Oxazines and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed, 559 pages.

Goetz et al., "Isolated C-terminal tail of FGF23 alleviates hypophosphatemia by inhibiting FGF23-FGFR-Klotho complex formation," PNAS, Jan. 2010, 107(1): 407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma: inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999), 799 pages.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54:7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 Is a Rational Therapeutic Target in Bladder Cancer," Molecular Cancer Therapeutics, Jul. 2013, 12(7): 1245-1254.
Hackam, et al. JAMA, 296(14), 2006, 1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinrich et al., "Fragment-based discovery of new highly substituted 1H-pyrrolo[2,3-b]- and 3H-imidazolo[4,5-b]-pyridines as focal adhesion kinase inhibitors," J of Med Chem., Jan. 8, 2013, 56(3):1160-1170.
Heinzle et al., "Is Fibroblast growth factor receptor 4 a suitable target of cancer therapy?" Cur. Pharm. Des., May 1, 2014, 20:2881-2898.
Heinzle C, et al., "Differential Effects of Polymorphic Alleles of FGF Receptor 4 on Colon Cancer Growth and Metastasis," Cancer Research, Nov. 2012, 72(22):5767-5777.
Heinzle et al., "Is fibroblast growth factor receptor 4 a suitable target of cancer therapy?," Cur. Pharm. Des., 2014, 20:2881-2898.
Heinzle et al., "Targeting fibroblast-growth-factor-receptor-dependent signaling for cancer therapy," Expert Opinion, 2011, 1-18.

(56) References Cited

OTHER PUBLICATIONS

Helsten et al., "The FGFR Landscape in Cancer: Analysis of 4,853 Tumors by Next-Generation Sequencing," Clin. Cancer Res., Jan. 2016, 22:259-267.
Hideshima and Anderson, "Preclinical Studies of Novel Targeted Therapies," Hematol Oncol Clin N Am, 2007, 1071-1091.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
ICH Harmonised Tripartite Guideline, "Specifications:Test Procedures and Acceptance Criteria for New Drug Substances and New Drug Products Chemical Substances," ICHTRRPHU, Oct. 6, 1999, 35 pages.
Indian Office Action in Indian Application No. 9781/DELNP/2015, dated Jan. 18, 2019, 6 pages.
Indian Office Action in Indian Application No. 10665/DELNP/2014, dated Jun. 25, 2018, 8 pages.
Indian Office Action in Indian Application No. 201717030267, dated Dec. 3, 2019, 7 pages.
Indian Office Action in Indian Application No. 201717030265, dated Dec. 12, 2019, 5 pages.
Indonesian Office Action in Indonesian Application No. P00201507153, dated Apr. 27, 2018, 5 pages (English Translation).
Inokuchi et al., "Therapeutic targeting of fibroblast growth factor receptors in gastric cancer," Gastroenterol Res Pract., Apr. 27, 2015, 2015:796380, 8 pages.
International Preliminary Report on Patentability and Written Opinion in International Application No. PCT/US2011/066473, dated Jun. 25, 2013, 10 pages.
International Preliminary Report on Patentability in International Application No. PCT/US2013/045309, dated Dec. 24, 2014, 11 pages.
International Preliminary Report on Patentability in International Application No. PCT/US2013/054361, dated Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Preliminary Report on Patentability in International Application No. PCT/US2018/034559, dated Nov. 26, 2019, 8 pages.
International Search Report and Written Opinion for International Application No. PCT/US2015/056583, dated Dec. 15, 2015, 10 pages.
International Search Report and Written Opinion in International Application No. PCT/US2013/045309, dated Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, dated Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report dated Jun. 19, 2012 for International Appln. No. PCT/US2011/066473 (15 pgs.).
International Search Report and Written Opinion in International Application No. PCT/US2018/034559, dated Mar. 8, 2019, 14 pages.
International Search Report and Written Opinion in International Application No. PCT/US2019/030633, dated Nov. 28, 2019, 21 pages.
International Invitation to Pay Fees in International Appln. No. PCT/US2019/030633, dated Aug. 12, 2019, 5 pages.
Invitation to Pay Additional Fees and, Where Applicable, Protest Fee in International Application No. PCT/US2013/045309, dated Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Jackson et al., "8p11 Myeloproliferative syndrome: a review," Human Pathology, Apr. 1, 2010, 41:461-476.
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2016-509131, dated Feb. 20, 2018, 5 pages (English Translation).
Japanese Office Action in Japanese Application No. 2018-228352, dated Aug. 20, 2019, 6 pages.

(56) References Cited

OTHER PUBLICATIONS

Japanese Office Action in Japanese Application No. 2015-517376, dated Feb. 21, 2017, 5 pages (with English translation).
Japanese Office Action in Japanese Application No. 2017-543981, dated Dec. 3, 2019, 4 pages (with English Translation).
Japanese Office Action in Japanese Application No. 2017-544021, dated Nov. 26, 2019, 6 pages.
Jebar et al., "FGFR3 and Ras gene mutations are mutually exclusive genetic events in urothelial cell carcinoma," Oncogene, 2005, 24: 5218-5225.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jiang et al., "miR-99a promotes proliferation targeting FGFR3 in human epithelial ovarian cancer cells," Biomedicine & Pharmacotherapy, 2014, 68: 163-169.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, V.C. Nature Reviews: Drug Discovery, 2, 2003, 205.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known P2X$_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS ONE, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Korean Office Action in Korean Application No. 10-2015-7000701, dated Aug. 26, 2019, 19 pages.

Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistiy, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Parameteres and Prognosis," Pathobiology, Mar. 2010, 77: 231-240.
Kurosu et al., "Regulation of Fibroblast Growth Factor-23 Signaling by Klotho," The Journal of Biological Chemistiy, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," BLOOD, Mar. 2005, 105(5): 2115-2123.

(56) References Cited

OTHER PUBLICATIONS

Malaysian Office Action in Malaysian Application No. 2014003396, dated Dec. 15, 2017, 4 pages.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "In vitro Anti-leukaemia Activity of Pyrrolo[1,2-b][1,2,5]benzothiadiaze-pines (PBTDs)," Recent Patents on Anti-Cancer Drug Discoveiy, 2010, 58-68.
Marks et al., "Mutational Analysis of EGFR and Related Signaling Pathway Genes in Lung Adenocarcinomas Identifies a Novel Somatic Kinase Domain Mutation in FGFR4," PLoS ONE, May 9, 2007, 2:e426.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martino et al., "Mutant fibroblast growth factor receptor 3 induces intracellular signaling and cellular transformation in a cell type- and mutation-specific manner," Oncogene, 2009, 28: 4306-4316.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Mexican Office Action in Mexican Application No. MX/a/2014/015192, dated Jan. 24, 2018, 6 pages.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.
Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)—mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
New Zealand Office Action in New Zealand Application No. 743274, dated Jul. 19, 2018, 5 pages.
New Zealand Examination Report in New Zealand Application No. 743274, dated Jul. 18, 2018, 4 pages.
New Zealand Office Action in New Zealand Application No. 702747, dated Sep. 16, 2016, 3 pages.
New Zealand Office Action in New Zealand Application No. 702747, dated Mar. 8, 2019, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Office Action from the Intellectual Property Office of the Philippines in Application No. 1-2014-502772, dated Mar. 17, 2016, 3 pages.
Philippine Office Action in Philippine Application No. 1/2015/502383, dated Jul. 8, 2019, 7 pages.
Philippine Office Action in Philippine Application No. 1-2017-501481, dated Oct. 29, 2019, 4 pages.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.
Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Peruvian Office Action in Peruvian Application No. 2433, dated Nov. 27, 2018, 13 pages.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.

(56) References Cited

OTHER PUBLICATIONS

Pollock et al., "Frequent activating FGFR2 mutations in endometrial carcinomas parallel germline mutations associated with craniosynostosis and skeletal dysplasia syndromes," Oncogene, 2007, 26:7158-7162.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.
Remington's Pharmaceutical Sciences, 17th ed., Mack Publishing Company, Easton, Pa., 1985, p. 1418*.
Remington, "The Science and Practice of Pharmacy," Lippincott Williams & Wilkins, 2005, 21st edition, Cover Page, 1 page.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Rowe et al., "Handbook of Pharmaceutical Excipients," The Pharmaceutical Press and the American Pharmaceutical Association, 2009, 6th Edition, 917 pages.
Ryan et al., "Toxicologic Pathology of Unique Biotechnology Agents and Biotherapies," Toxicologic Pathology, 1999, 27(1): 78-86.
Sakurai et al., "A novel angiogenesis inhibitor, Ki23057, is useful for preventing the progression of colon cancer and the spreading of cancer cells to the liver," European Journal of Cancer, 2007, 2612-2620.

Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistiy, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search, Science IP, Apr. 2012, 78 pages.
Science IP Order 3101926, Chemical Structure Search, Science IP, Jan. 2015, 50 pages.
Science IP Order 3101983, Chemical Structure Search, Science IP, Jan. 2015, 70 pages.
Science IP Order 3104564, Patent Chemical Structure Search, Science IP, Mar. 2015, 90 pages.
Science IP Order 3104565, Patent Chemical Structure Search, Science IP, Mar. 2015, 521 pages.
Segev et al., "Restrained chondrocyte proliferation and maturation with abnormal growth plate vascularization and ossification in human FRFR-3$^{G380R}$ transgenic mice," Human Molecular Genetics, 2000, 9(2): 249-258.
Seitzer et al., "A single nucleotide change in the mouse genome accelerates breast cancer progression," Cancer Res., Jan. 2010, 70(2):802-812.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.
Shinya et al., "Fgf signalling through MAPK cascade is required for development of the subpallial telencephalon in zebrafish embryos," Development, 2001, 4153-4164.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-IIIc mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.

(56) References Cited

OTHER PUBLICATIONS

Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (F1k-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Taiwanese Office Action in Taiwan Application No. 102120946, dated Nov. 9, 2016, 9 pages (English translation).
Taiwanese Office Action in Taiwanese Application No. 102120946, dated Jul. 13, 2017, 7 pages (English Translation).
Taiwan Office Action in Taiwan Application No. 105105018, dated Oct. 22, 2019, 7 pages (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Takii et al., "Serotonin Derivative, N-(p-Coumaroyl)serotonin, Isolated from Safflower (*Carthamus tinctorius* L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Tan et al., "Development of covalent inhibitors that can overcome resistance to first-generation FGFR kinase inhibitors," PNAS, Oct. 2014, E4869-E4877.
Taylor et al., "Identification of FGFR4-activating mutations in human rhabdomyasarcomas that promote metastasis in xenotransplanted models," J Clin Invest., Nov. 2009, 119(11):3395-3407.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Taiwan Office Action in Taiwan Application No. 103114284, dated Apr. 9, 2018, 4 pages (English Search Report).
Tang et al., "Role of fibroblast growth factor receptor 4 in cancer," Cancer Science, Oct. 2018, 109(10):3024-3031.
Thai Office Action in Thai Application No. 1401007417, dated Jun. 5, 2016, 7 pages (with English translation).
The Cancer Genome Atlas Research Network, "Comprehensive molecular characterization of urothelial bladder carcinoma," Nature, 2014, 507: 315-22.
Thome and Weil, "Post-translational modifications regulate distinct functions of CARMA1 and BCL10," TRENDS in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistry Letters 12:1219-1223, 2002.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Thussbas et al., "FGFR4 Arg388 Allele Is Associated With Resistance to Adjuvant Therapy in Primaiy Breast Cancer," J. Clin. Oncol., Aug. 10, 2006, 23:3747-3755.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis int(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine Kinaselnhibitor, for the Treatment of t(4;14) Multiple Myeloma," Presentation, Presented at International Myeloma Foundation, Apr. 2005, 18 pages.
Turkington et al., "Fibroblast growth factor receptor 4 (FGFR4): a targetable regulator of drug resistance in colorectal cancer," Cell Death Dis., Feb. 6, 2014, 5:e1046.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.
Ukraine Office Action in Ukraine Application No. a201500191, dated Dec. 13, 2016, 10 pages (with English translation).
Ukraine Office Action in Ukraine Application No. a201511370, dated Nov. 12, 2018, 6 pages (with English translation).
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
Van Oers et al., "FGFR3 Mutations Indicate Better Survival in Invasive Upper Urinary Tract and Bladder Tumours," European Urology, 2009, 650-658.
Vätsveen et al., "FGFR3 is expressed and is important for survival in INA-6, a human myeloma cell line without a t(4; 14)," Eur. J. Haematol., 83:5, Jul. 6, 2009, 471-476.
Vietnamese Office Action in Vietnamese Application No. 1-2015-00102, dated Mar. 18, 2015, 4 pages.
Von Massenhausen et al., "Evaluation of FGFR3 as a Therapeutic Target in Head and Neck Squamous Cell Carcinoma," Targ. Oncol., 2016, 11: 631-642.

(56) References Cited

OTHER PUBLICATIONS

Wang et al., "The fibroblast growth factor receptor-4 Arg388 allele is associated with prostate cancer initiation and progression," Clin Cancer Res. 2004, 10:6169-6178.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 2017, 1-10.
Ware et al., "Rapidly Acquired Resistance to EFGR Tyrosine Kinase Inhibitors in NSCLC Cell Lines through De-Repression of FGFR2 andFGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Williams et al., "Oncogenic FGFR3 gene fusions in bladder cancer," Hum Mol Genet, 2013, 22:795-803.
Wu, "Urothelial Tumorigenesis: A Tale Of Divergent Pathways," Nature Reviews, Sep. 2005, 5: 713-725.
Wuts et al., "Greene's Protective Groups in Organic Synthesis," 4th Ed., 2006, Chapter 7, 696-926.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 Is Efficacious in a Newly Developed Fibroblast Growth Factor Receptor 3-Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.
Yu et al., "Analysis of the Biochemical Mechanisms for the Endocrine Actions of Fibroblast Growth Factor-23," Endocrinology, Nov. 2005, 146(11): 4647-4656.
Yu et al., "FGFR-4 Arg(3)(8)(8) enhances prostate cancer progression via extracellular signal-related kinase and serum response factor signaling," Clin Cancer Res., Jul. 2011, 17:4355-4366.
Ying et al., "Genome-wide screening for genetic alterations in esophageal cancer by aCGH identifies 11q13 amplification oncogenes associated with nodal metastasis," PLoS One, Jun. 25, 2012, 7:e39797.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.
Zhang et al., "Enhanced FGFR signalling predisposes pancreatic cancer to the effect of a potent FGFR inhibitor in preclinical models," British Journal of Cancer, 2014, 110: 320-329.
Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.
Zhang et al., "Receptor Specificity of the Fibroblast Growth Factor Family," Journal of Biological Chemistiy, Jun. 2006, 281(23): 15694-15700.

Zhang et al., "Translating the therapeutic potential of AZD4547 in FGFR 1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.
Arai et al., "Fibroblast growth factor receptor 2 tyrosine kinase fusions define a unique molecular subtype of cholangiocarcinoma," Hepatology, 2014, 59(4): 1427-1434.
Argentina Office Action in Argentina Application No. 20130102068, dated Jul. 17, 2020, 10 pages.
Atzrodt et al., "The Renaissance of H/D Exchange," Angew Chem Int Ed., 2007, 7744-7765.
Chilean Office Action in Chilean Application No. 3439-2019, dated Feb. 10, 2021, 26 pages.
Chinese Office Action in Chinese Application No. 201910023729.3, dated Mar. 3, 2021, 15 pages.
Ciappetti and Geithlen "Molecular Variations Based on Isosteric Replacements," The Practice of Medicinal Chemistry, 2008, Chapter 15, pp. 290-341.
Cordovilla et al., "The Stille Reaction, 38 Years Later," ACS Catal., Apr. 17, 2015, 5(5):3040-3053.
Drueke et al., "Phosphate binders in CKD: bad news or good news?," Journal of the American Society of Nephrology, Aug. 2012, 23(8): 1277-1280.
European Office Action in European Application No. 18733045.1, dated Jan. 11, 2021, 5 pages.
European Office Action in European Application No. 20192679.7, dated Feb. 11, 2021, 7 pages.
FDA.gov, "FDA grants accelerated approval to pemigatinib for cholangiocarcinoma with an FGFR2 rearrangement or fusion," Apr. 20, 2020, [Retrieved on Apr. 27, 2021], retrieved from URL <https://www.fda.gov/drugs/resources-information-approved-drugs/fda-grants-accelerated-approval-pemigatinib-cholangiocarcinoma-fgfr2-rearrangement-or-fusion>, 2 pages.
Fricker, "Metal based drugs: from serendipity to design," Dalton Transactions, 2007, 43:4903-4917.
Fricker, "The therapeutic application of lanthanides," Chemical Society Reviews, 2006, 35(6):524-533.
Fu et al., "Intratumoral inorganic phosphate deprivation: A new anticancer strategy," Medical Hypotheses, Feb. 2020, 135:109497.
Fun et al., "2-7(7,8-Diphenyl-1H-imidazo[4,5-f]-quinoxalin-2-yl)phenol methanol disolvate," Acta Crystallographica Section E Structure Reports Online, 2008, 64(9):o1741-o1742.
Gallo et al., "Functions of Fibroblast Growth Factor Receptors in cancer defined by novel translocations and mutations," Cytokine & Growth Factor Reviews, 2015, 26(4):425-449.
Haas et al., "Recent Developments in Negishi Cross-Coupling Reactions," ACS Catal., 2016, 6(3):4540-1552.
International Preliminary Report on Patentability in International Application No. PCT/US2019/030578, dated Nov. 10, 2020, 14 pages.
International Preliminary Report on Patentability in International Application No. PCT/US2019/030633, dated Nov. 10, 2020, 10 pages.

(56) References Cited

OTHER PUBLICATIONS

International Search Report and Written Opinion in International Application No. PCT/US2020/041104, dated Sep. 4, 2020, 14 pages.
International Search Report and Written Opinion in International Appln. No. PCT/US2020/063064, dated Feb. 12, 2021, 13 pages.
International Search Report and Written Opinion in International Appln. No. PCT/US2020/063038, dated Mar. 15, 2021, 16 pages.
International Search Report in International Application No. PCT/US2020/053436, dated Dec. 4, 2020, 15 pages.
International Search Report in Written Opinion in International Application No. PCT/US2020/055547, dated Jan. 11, 2021, 13 pages.
International Search Report in Written Opinion in International Application No. PCT/US2021/013438, dated Apr. 20, 2021, 16 pages.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Korean Office Action in Korean Application No. 10-2015-7032502, dated Sep. 9, 2020, 16 pages.
Korean Office Action in Korean Application No. 10-2020-7021884, dated Oct. 28, 2020, 15 pages.
Kotha et al., "Recent applications of the Suzuki-Miyaura cross-coupling reaction in organic synthesis," Tetrahedron, 2002, 58:9633-9695.
Novelli, "Fosrenol (TM) reduces damaging high levels of phosphate in end-stage kidney disease patients," EurekAlert!, Nov. 2, 2002 [retrieved on Dec. 1, 2020], retrieved from URL <https://www.eurekalert.org/pub_releases/2002-11/pn-fr110202.php>, 4 pages.
Peruvian Office Action in Peruvian Application No. 1424, dated Mar. 12, 2021, 13 pages.
Philippine Office Action in the Philippine Application No. 1/2017/501483, dated Aug. 31, 2020, 4 pages.
Peruvian Office Action in Peruvian Application No. 1429, dated Mar. 19, 2021, 12 pages.
Rowe et al., "Handbook of Pharmaceutical Additives," The Pharmaceutical Press and the American Pharmaceutical Association, 2009, 3rd ed..
STN International Search Report for CAS RN 2380276-25-3, dated Nov. 20, 2019, 11 pages.
STN Search Report, dated Sep. 11, 2019, 31 pages.
Surry et al., "Dialkylbiaryl Phosphines in Pd-Catalyzed Amination: A User's Guide," Chem Sci., 2011, 2(1):27-50.
Vogt et al., "FGF23 and phosphate cardiovascular toxins in ckd," Toxins, Nov. 6, 2019, 11(11):647.
Xu et al. "Design, synthesis and biological evaluation of deuterated nintedanib for improving pharmacokinetic properties," J Label Compd Radiopharm., 2015, 58(7):308-312.
Zhang et al., "Recent progress in therapeutic and diagnostic applications of lanthanides," Mini-Reviews in Medicinal Chemistry, 2011, 11(8):678-694.
Casey et al., "Translating in vivo metabolomic analysis of succinate dehydrogenase deficient tumours into clinical utility," JCO Precis Oncol., Mar. 29, 2018, 2:1-12.
European Office Action in European Application No. 19724676.2, dated Aug. 26, 2021, 5 pages.
Goyal et al., "Polyclonal Secondary FGFR2 Mutations Drive Acquired Resistance to FGFR Inhibition in Patients with FGFR2 Fusion-Positive Cholangiocarcinoma," Cancer Discov., 2016, 7(3):252-263.
Anonymous, "In Vitro Metabolism- and Transporter- Mediated Drug-Drug Interaction Studies Guidance for Industry", Clinical Pharmacology, Oct. 2017, 47 pages.
Argentina Office Action in Argentina Application No. 20140101651, dated Jul. 29, 2021, 9 pages.
Australian Office Action in Australian Application No. 2018272013, dated Sep. 2, 2021, 4 pages.
Australian Office Action in Australian Application No. 2020250211, dated Sep. 13, 2021, 4 pages.
Australian Office Action in Australian Application No. 2020270520, dated Dec. 16, 2021, 4 pages.
Cherukupalli et al., "An insight on synthetic and medicinal aspects of pyrazolo[1,5-a]pyrimidine scaffold," European Journal of Medicinal Chemistry, Nov. 10, 2016, 126:298-352.
Chinese Office Action in Chinese Application No. 201910023729.3, dated Sep. 8, 2021, 11 pages.
Colombian Opposition in Colombian Application No. NC 2021/0004568, dated Apr. 15, 2021, 21 pages.
Ecuador Office Action in Ecuador Application No. IEPI-2015-1225, dated Dec. 30, 2021, 21 pages.
Eurasian Office Action in Eurasian Application No. 202091923, dated Jul. 27, 2021, 6 pages (English Translation).
Eurasian Office Action in Eurasian Application No. 201992794, dated Sep. 17, 2021, 7 pages.
European Office Action in European Application No. 16715139.8, dated May 18, 2021, 9 pages.
European Office Action in European Application No. 19724670.5, dated Nov. 9, 2021, 4 pages.
Ezzat et al., "Dual Inhibition of RET and FGFR4 Restrains Medullary Thyroid Cancer Cell Growth," Clinical Cancer Research, 2005, 11:1336-1341.
International Preliminary Report on Patentability in International Application No. PCT/US2020/021313, dated Aug. 25, 2021, 11 pages.
International Preliminary Report on Patentability in International Application No. PCT/US2020/041104, dated Jan. 11, 2022, 7 pages.
International Search Report and Written Opinion in International Application No. PCT/US2020/021313, dated Jun. 26, 2020, 19 pages.
International Search Report and Written Opinion in International Application No. PCT/US2020/055735, dated Dec. 15, 2020, 16 pages.
Japanese Office Action in Japanese Application No. 2020-069604, dated Nov. 15, 2021, 7 pages.
Ji et al., "Embase abstract: Modeling and simulation as gating for clinical pharmacology studies of INCB054828," 119th Annual Meeting of the American Society for Clinical Pharmacology and Therapeutics, Mar. 1, 2018, 2 pages.
Khojasteh et al., "Chemical inhibitors of cytochrome P450 isoforms in human liver microsomes: a re-evaluation of P450 isoform selectivity," Eur J Drug Metab Pharmacokinet., Mar. 2011, 36:1-16.
Korean Office Action in Korean Application No. 10-2021-7018897, dated Oct. 1, 2021, 15 pages.
Korean Office Action in Korean Application No. 10-2020-7021884, dated Oct. 25, 2021, 6 pages.
Philippine Office Action in Philippine Application No. 1/2015/502383, dated Nov. 11, 2021, 4 pages.
Philippine Office Action in Philippine Application No. 1/2019/502810, dated Dec. 7, 2021, 4 pages.
sigmaaldrich.com, "4-Chloro-1H-pyrrolo[2,3-b]pyridine-5-carbaldehyde," CAS # 958230-19-8, [retrieved on Feb. 4, 2021] retrieved from URL <https://www.sigmaaldrich.com/catalog/product/aldrich/ade000976?lang=en&region=US>, 2 pages.
Staerk et al., "Pan-Src Family Kinase Inhibitors Replace Sox2 during the Direct Reprogramming of Somatic Cells," Angewandte Chem., Jun. 14, 2011, 50(25):5734-5736.
Taiwan Office Action in Taiwan Application No. 109132389, dated Aug. 23, 2021, 4 pages.
Ukraine Office Action in Ukraine Application No. a201801562, dated Jul. 28, 2021, 9 pages.
Ukraine Office Action in Ukraine Application No. a 2019 12195, dated Nov. 11, 2021, 7 pages.
Verstovsek et al., "Interim Results from Fight-203, a Phase 2, Open-Label, Multicenter Study Evaluating the Efficacy and Safety of Pemigatinib (INCB054828) in Patients with Myeloid/Lymphoid Neoplasms with Rearrangement of Fibroblast Growth Factor Receptor 1 (FGFR1)," Blood, Nov. 29, 2018, retrieved from URL <https://ashpublications.org/blood/article/132/Supplement%201/690/266005/Interim-Results-from-Fight203-a-Phase-2-0penLabel>, 132(Supplement 1):690.
Walsky and Obach, "Validated assays for human cytochrome P450 activities," Drug Metab Dispos., 2004, 32(6):647-660.

(56) References Cited

OTHER PUBLICATIONS

Walsky et al., "Evaluation of 227 drugs for in vitro inhibition of cytochrome P450 2B6," J Clin Pharmacol., Dec. 2006, 46(12): 1426-1438.

Ye et al., "Combination of the FGFR4 inhibitor PD173074 and 5-fluorouracil reduces proliferation and promotes apoptosis in gastric cancer," Oncol Rep., Dec. 2013, 30(6):2777-2784.

* cited by examiner

SOLID FORMS OF AN FGFR INHIBITOR AND PROCESSES FOR PREPARING THE SAME

FIELD OF THE INVENTION

This application relates to solid forms of a Fibroblast Growth Factor Receptors (FGFR) inhibitor, including methods of preparation thereof, and intermediates in the preparation thereof, which are useful in the treatment of FGFR mediated disease such as cancer.

BACKGROUND OF THE INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005).

Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook Pharmacology & Therapeutics, 2010; Turner and Grose, Nature Reviews Cancer, 2010). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achondroplasia and craniosynostosis syndromes. The FGFR4-FGF19 signaling axis, specifically, has been implicated in the pathogenesis of a number of cancers including hepatocellular carcinoma (Heinzle et al., Cur. Pharm. Des. 2014, 20:2881). Ectopic expression of FGF19 in transgenic mice was shown to lead to tumor formation in the liver and a neutralizing antibody to FGF19 was found to inhibit tumor growth in mice. In addition, overexpression of FGFR4 has been observed in a multiple tumor types including hepatocellular carcinoma, colorectal, breast, pancreatic, prostate, lung, and thyroid cancers. Furthermore, activating mutations in FGFR4 have been reported in rhabdomyosarcoma (Taylor et al. JCI 2009, 119:3395).

Inhibitors of FGFR are currently being developed for the treatment of cancer. For example, the molecule 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one and other small molecule inhibitors of FGFR are reported in e.g., US Publication Nos.: 2012/0165305; 2014-0045814; 2013-0338134; 2014/0171405; 2014/0315902; 2016/0115164; 2016/0244448; 2016/0244449; and 2016-0244450. Accordingly, there is a need for new solid forms of FGFR-inhibiting molecules for preparing pharmaceutically useful formulations and dosage forms with suitable properties related to, for example, facilitating the manufacture of safe, effective, and high quality drug products.

SUMMARY OF THE INVENTION

Provided herein are solid forms of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one ("Compound 1").

Provided herein are also pharmaceutical compositions, which include the solid forms as described herein, and one or more pharmaceutically acceptable carriers or excipients.

The present disclosure also provides methods of inhibiting FGFR enzymes using the solid forms as described herein.

The present disclosure also provides therapeutic methods of using the solid forms as described herein. The present disclosure also provides uses of the solid forms described herein in the manufacture of a medicament for use in therapy. The present disclosure also provides the solid forms described herein for use in therapy.

Provided herein are also processes for preparing 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one and its solid forms as described herein.

Provided herein are also intermediates useful for the preparation of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one and its solid forms described herein.

Provided herein is also a method of treating cholangiocarcinoma in a patient in need thereof comprising administering to the patient a therapeutically effective amount of Compound 1. Also provided is a method of treating myeloid/lymphoid neoplasms (e.g., 8p11 myeloproliferative syndrome) in a patient in need thereof comprising administering to the patient a therapeutically effective amount of Compound 1. Further, provided herein is a method of increasing survival or progression-free survival in a patient that has cholangiocarcinoma, wherein the cholangiocarcinoma is characterized by an FGFR2 fusion, comprising administering Compound 1 to the patient.

DETAILED DESCRIPTION

Figure 1:
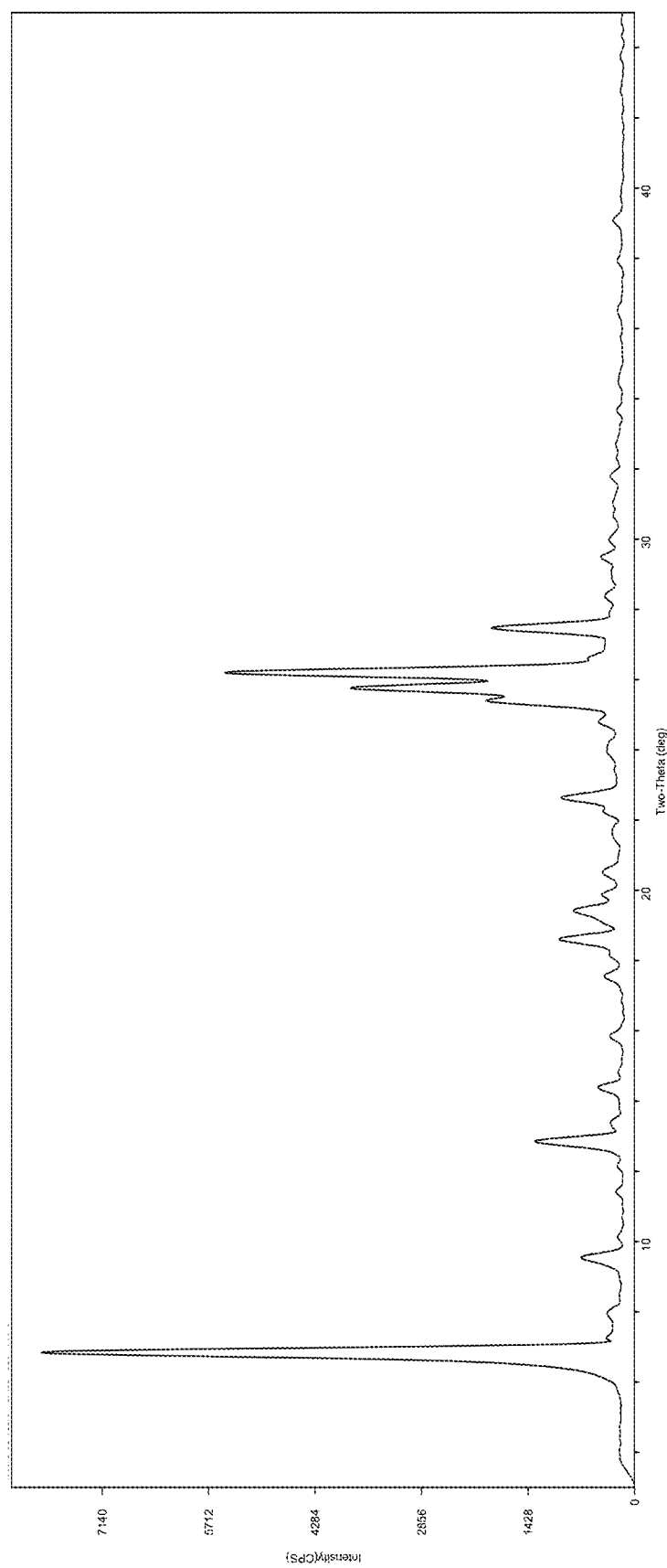
FIG. 1 shows an X-ray powder diffraction (XRPD) pattern of Compound 1, Form I.

The present disclosure is directed to, inter alia, solid forms, including crystalline forms and amorphous forms, of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one (Compound 1), and processes and intermediates for preparing the compound. The structure of Compound 1 is shown below.

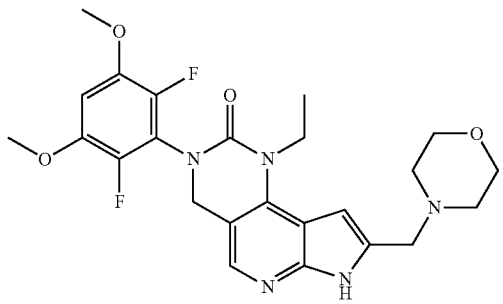

Compound 1

Compound 1 is described in U.S. Pat. No. 9,611,267, the entirety of which is incorporated herein by reference.

Compound 1 can be isolated as one or more solid forms. The solid forms (e.g., crystalline forms) described herein can have certain advantages, for example, they may have desirable properties, such as ease of handling, ease of processing, storage stability, and ease of purification. Moreover, the crystalline forms can be useful for improving the performance characteristics of a pharmaceutical product such as dissolution profile, shelf-life and bioavailability As used herein, and unless otherwise specified, the term "about", when used in connection with a numeric value or range of values which is provided to describe a particular solid form (e.g., a specific temperature or temperature range, such as describing a melting, dehydration, or glass transition; a mass change, such as a mass change as a function of temperature or humidity; a solvent or water content, in terms of, for example, mass or a percentage; or a peak position, such as in analysis by, for example, $^{13}$C NMR, DSC, TGA and XRPD), indicate that the value or range of values may deviate to an extent deemed reasonable to one of ordinary skill in the art while still describing the particular solid form. Specifically, the term "about", when used in this context, indicates that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form. The term "about", when used in reference to a degree 2-theta value refers to +/−0.2 degrees 2-theta.

As used herein, the phrase "solid form" refers to a compound provided herein in either an amorphous state or a crystalline state ("crystalline form" or "crystalline solid" or "crystalline solid form"), whereby a compound provided herein in a crystalline state may optionally include solvent or water within the crystalline lattice, for example, to form a solvated or hydrated crystalline form. In some embodiments, the compound provided herein is in a crystalline state as described herein.

As used herein, the term "peak" or "characteristic peak" refers to an XRPD reflection having a relative height/intensity of at least about 3% of the maximum peak height/intensity.

As used herein, the term "crystalline" or "crystalline form" refers to a crystalline solid form of a chemical compound, including, but not limited to, a single-component or multiple-component crystal form, e.g., including solvates, hydrates, clathrates, and a co-crystal. For example, crystalline means having a regularly repeating and/or ordered arrangement of molecules, and possessing a distinguishable crystal lattice. The term "crystalline form" is meant to refer to a certain lattice configuration of a crystalline substance. Different crystalline forms of the same substance typically have different crystalline lattices (e.g., unit cells), typically have different physical properties attributed to their different crystalline lattices, and in some instances, have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the crystalline form as well as help determine stability and solvent/water content.

Different crystalline forms of a particular substance, such as Compound 1 as described herein, can include both anhydrous forms of that substance and solvated/hydrated forms of that substance, where each of the anhydrous forms and solvated/hydrated forms are distinguished from each other by different XRPD patterns, or other solid state characterization methods, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters used, the sample mounting procedure, and the particular instrument employed. In some instances, new peaks may be observed or existing peaks may disappear, depending on the type of the machine or the settings (for example, whether a Ni filter is used or not). As used herein, the term "peak" refers to a reflection having a relative height/intensity of at least about 3% or at least about 4% of the maximum peak height/intensity. Moreover, instrument variation and other factors can affect the 2-theta values. Thus, peak assignments, such as those reported herein, can vary by plus or minus about 0.2° (2-theta) and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures is understood to accommodate such variation.

Crystalline forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, exposure to moisture, grinding and solvent-drop grinding.

As used herein, the term "amorphous" or "amorphous form" is intended to mean that the substance, component, or product in question is not crystalline as determined, for instance, by XRPD or where the substance, component, or product in question, for example is not birefringent when viewed microscopically. For example, amorphous means essentially without regularly repeating arrangement of molecules or lacks the long range order of a crystal, i.e., amorphous form is non-crystalline. An amorphous form does not display a defined x-ray diffraction pattern with sharp maxima. In certain embodiments, a sample comprising an amorphous form of a substance may be substantially free of other amorphous forms and/or crystalline forms. For example, an amorphous substance can be identified by an XRPD spectrum having an absence of reflections.

As used herein, the term "substantially amorphous" means a majority of the weight of a sample or preparation of Compound 1 is amorphous and the remainder of the sample is a crystalline form of the same compound. In some embodiments, a substantially amorphous sample has less than about 5% crystallinity (e.g., about 95% of the non-crystalline form of the same compound), less than about 4% crystallinity (e.g., about 96% of the non-crystalline form of the same compound), less than about 3% crystallinity (e.g., about 97% of the non-crystalline form of the same compound), less than about 2% crystallinity (e.g., about 98% of the non-crystalline form of the same compound), less than about 1% crystallinity (e.g., about 99% of the non-crystalline form of the same compound), or about 0% crystallinity (e.g., about 100% of the non-crystalline form of the same compound). In some embodiments, the term "fully amorphous" means less than about 99% or about 0% crystallinity.

Compound 1 can be prepared in batches referred to as batches, samples, or preparations. The batches, samples, or preparations can include Compound 1 in any of the crystalline or non-crystalline forms described herein, including hydrated and non-hydrated forms, and mixtures thereof.

Compounds provided herein (e.g., Compound 1) can also include all isotopes of atoms occurring in the intermediates or final compounds. Isotopes include those atoms having the same atomic number but different mass numbers. For example, isotopes of hydrogen include tritium and deuterium. One or more constituent atoms of the compounds provided herein can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

In some embodiments, Compound 1 is substantially isolated. The term "substantially isolated" is meant that the compound is at least partially or substantially separated from the environment in which it was formed or detected. Partial separation can include, e.g., a composition enriched in the compound, salts, hydrates, solvates, or solid forms provided herein. Substantial separation can include compositions containing at least about 50%, at least about 60%, at least about 70%, at least about 80%, at least about 90%, at least about 95%, at least about 97%, or at least about 99% by weight of the compound, salts, hydrates, solvates, or solid forms provided herein.

The term "hydrate," as used herein, is meant to refer to a solid form of Compound 1 that includes water. The water in a hydrate can be present in a stoichiometric amount with respect to the amount of salt in the solid, or can be present in varying amounts, such as can be found in connection with channel hydrates.

As used herein, the term "substantially" when referring to a characteristic figure of a crystal form, such as an XRPD pattern, a DSC thermogram, a TGA thermogram, or the like, means that a subject figure may be non-identical to the reference depicted herein, but it falls within the limits of experimental error and thus may be deemed as derived from the same crystal form as disclosed herein, as judged by a person of ordinary skill in the art.

As used herein, the term "substantially crystalline," means a majority of the weight of a sample or preparation of Compound 1 is crystalline and the remainder of the sample is a non-crystalline form (e.g., amorphous form) of the same compound. In some embodiments, a substantially crystalline sample has at least about 95% crystallinity (e.g., about 5% of the non-crystalline form of the same compound), at least about 96% crystallinity (e.g., about 4% of the non-crystalline form of the same compound), at least about 97% crystallinity (e.g., about 3% of the non-crystalline form of the same compound), at least about 98% crystallinity (e.g., about 2% of the non-crystalline form of the same compound), at least about 99% crystallinity (e.g., about 1% of the non-crystalline form of the same compound), or about 100% crystallinity (e.g., about 0% of the non-crystalline form of the same compound). In some embodiments, the term "fully crystalline" means at least about 99% or about 100% crystallinity.

As used herein, the term "% crystallinity" or "crystalline purity," means percentage of a crystalline form in a preparation or sample which may contain other forms such as an amorphous form of the same compound, or at least one other crystalline form of the compound, or mixtures thereof. In some embodiments, the crystalline forms can be isolated with a purity of at least about 80%, about 85%, about 90%, about 95%, about 96%, about 97%, about 98%, or about 99%. In some embodiments, the crystalline forms can be isolated with a purity greater than about 99%.

As used herein, the term "reacting" is used as known in the art and generally refers to the bringing together of chemical reagents in such a manner so as to allow their interaction at the molecular level to achieve a chemical or physical transformation. In some embodiments, the reacting involves at least two reagents, wherein one or more molar equivalents of second reagent are used with respect to the first reagent. In some embodiments, the reacting step of a synthetic process may involve one or more substances in addition to the reagents such as solvent and/or a catalyst. The reacting steps of the processes described herein can be conducted for a time and under conditions suitable for preparing the identified product.

As used herein, the terms "converting" with respect to changing an intermediate or starting reagent or material in a chemical reaction refers to subjecting the intermediate or starting reagent or material to the suitable reagents and conditions (e.g., temperature, time, solvent, etc.) to effect certain changes (e.g., breaking or formation of a chemical bond) to generate the desired product.

Compound 1 can be prepared in various crystalline forms including, e.g., Form I, Form II, Form II-a, Form III, Form IV, Form V, Form VI, Form VII, Form VIII, Form VIIIa, Form IX, Form X, Form XI, Form XII, Form XIII, Form XIII-a, Form XIV, Form XV, Form XVI, Form XVII, Form XVIII, Form XIX, Form XX, Form XXI, Form XXII, Form XXIII, Form XXIV, Form XXV or Form XXVI. In some embodiments, the solid form of Compound 1 is amorphous.

Compound 1 Form I

Provided herein is a solid form of Compound 1 which is crystalline, referred to as Form I, which is described below in the Examples.

In some embodiments, Form I has at least one characteristic XRPD peaks selected from about 6.8, about 12.9, about 25.4, about 25.8, about 26.2 and about 27.5 degrees 2-theta.

In some embodiments, Form I has at least two characteristic XRPD peaks selected from about 6.8, about 12.9, about 25.4, about 25.8, about 26.2 and about 27.5 degrees 2-theta.

In some embodiments, Form I has at least three characteristic XRPD peaks selected from about 6.8, about 12.9, about 25.4, about 25.8, about 26.2 and about 27.5 degrees 2-theta.

In some embodiments, Form I has at least one characteristic XRPD peak selected from about 6.8, about 9.6, about 12.9, about 18.6, about 19.4, about 22.6, about 25.4, about 25.8, about 26.2, and about 27.5 degrees 2-theta.

In some embodiments, Form I has at least two characteristic XRPD peaks selected from about 6.8, about 9.6, about 12.9, about 18.6, about 19.4, about 22.6, about 25.4, about 25.8, about 26.2, and about 27.5 degrees 2-theta.

In some embodiments, Form I has at least three characteristic XRPD peaks selected from about 6.8, about 9.6, about 12.9, about 18.6, about 19.4, about 22.6, about 25.4, about 25.8, about 26.2, and about 27.5 degrees 2-theta.

In some embodiments, Form I has an XRPD pattern with characteristic peaks as substantially shown in FIG. 1.

Figure 2:
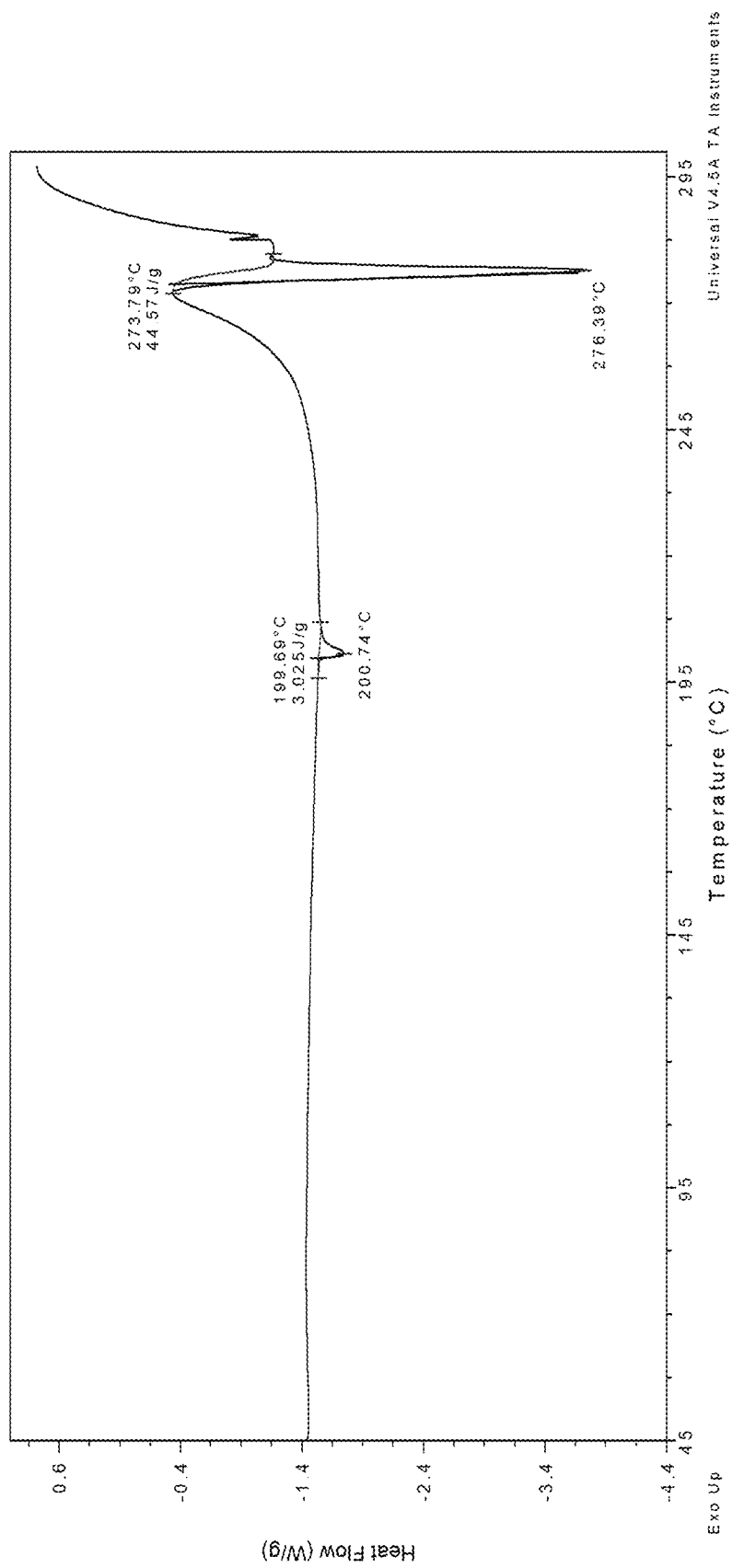
FIG. 2 shows a differential scanning calorimetry (DSC) thermogram of Compound 1, Form I.
Figure 3:
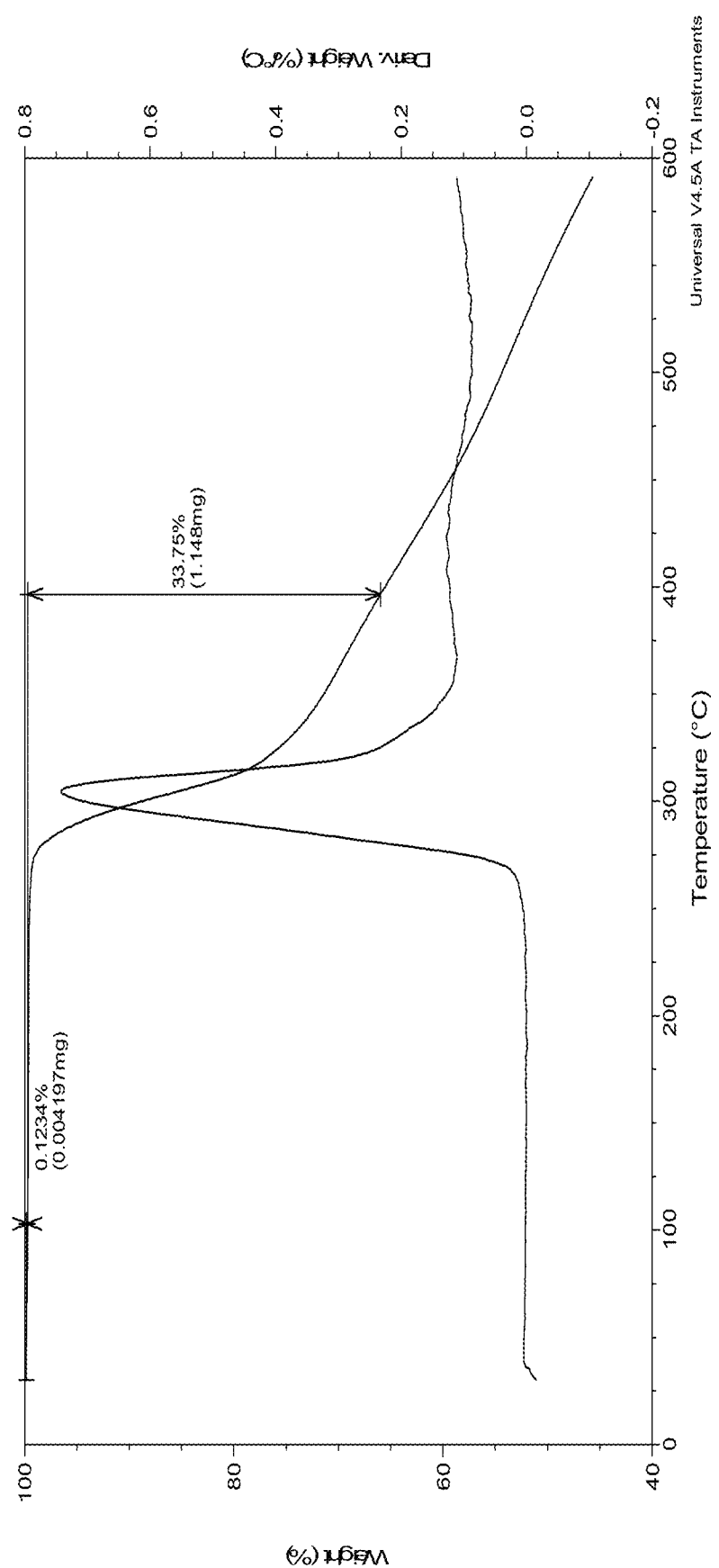
FIG. 3 shows a thermogravimetric analysis (TGA) thermogram of Compound 1, Form I.

In some embodiments, Form I exhibits a DSC thermogram having endotherm peaks at temperatures of about 201° C. and 276° C. In some embodiments, Form I exhibits a DSC thermogram having an endotherm peak at a temperature of about 201° C. In some embodiments, Form I exhibits a DSC thermogram having an endotherm peak at a temperature of about 276° C. In some embodiments, Form I has a DSC thermogram substantially as depicted in FIG. 2. In some embodiments, Form I has a TGA thermogram substantially as depicted in FIG. 3.

In some embodiments, Form I has at least one characteristic XRPD peaks selected from about 6.8, about 12.9, about 25.4, about 25.8, about 26.2 and about 27.5 degrees 2-theta; and Form I exhibits a DSC thermogram having endotherm peaks at temperatures of about 201° C. and 276° C.

Provided herein are also processes for preparing Form I of Compound 1 comprising recrystallizing Compound 1 in a solvent. In some embodiments, the solvent is a mixture of dichloromethane and methyl t-butyl ether. In some embodiments, the process for preparing Form I of Compound 1 comprises recrystallizing Compound 1 from a mixture of dichloromethane and methyl t-butyl ether. In some embodiments, the recrystallizing comprises a) heating a solution of Compound 1 in a mixture of dichloromethane and methyl t-butyl ether to an elevated temperature for a first period of time and b) cooling to a reduced temperature for a second period of time. In some embodiments, the elevated temperature is ≥30° C., ≥35° C., ≥36° C., ≥39° C., or ≥40° C. In certain embodiments, the first period of time is between 5 and 6 h. In some embodiments, the first period of time is greater than 5 h. In some embodiments, the reduced temperature is ambient temperature. In some embodiments, the reduced temperature is about 23° C. In some embodiments, the second period of time is between 10 and 11 hours. In some embodiments, the second period of time is longer than 5, 8, or 10 hours. In some embodiments, the second period of time is 10.5 h.

In some embodiments, Form I can be isolated with a purity of at least about 80%, about 85%, about 90%, about 95%, about 96%, about 97%, about 98%, or about 99%. In some embodiments, Form I can be isolated with a purity greater than about 99%.

Compound 1 Form II

Provided herein is a solid form of Compound 1 having Form II, which is described below in the Examples.

In some embodiments, Form II has at least one characteristic XRPD peaks selected from about 6.8, about 9.5, about 12.8, about 13.3 and about 25.8 degrees 2-theta.

In some embodiments, Form II has at least two characteristic XRPD peaks selected from about 6.8, about 9.5, about 12.8, about 13.3 and about 25.8 degrees 2-theta.

In some embodiments, Form II has at least three characteristic XRPD peaks selected from about 6.8, about 9.5, about 12.8, about 13.3 and about 25.8 degrees 2-theta.

In some embodiments, Form II has at least one characteristic XRPD peak selected from about 6.8, about 9.5, about 12.8, about 13.3, about 19.0, about 20.5, about 22.6, about 25.8, about 26.2, and about 27.4 degrees 2-theta.

In some embodiments, Form II has at least two characteristic XRPD peaks selected from about 6.8, about 9.5, about 12.8, about 13.3, about 19.0, about 20.5, about 22.6, about 25.8, about 26.2, and about 27.4 degrees 2-theta.

In some embodiments, Form II has at least three characteristic XRPD peaks selected from about 6.8, about 9.5, about 12.8, about 13.3, about 19.0, about 20.5, about 22.6, about 25.8, about 26.2, and about 27.4 degrees 2-theta.

Figure 4:
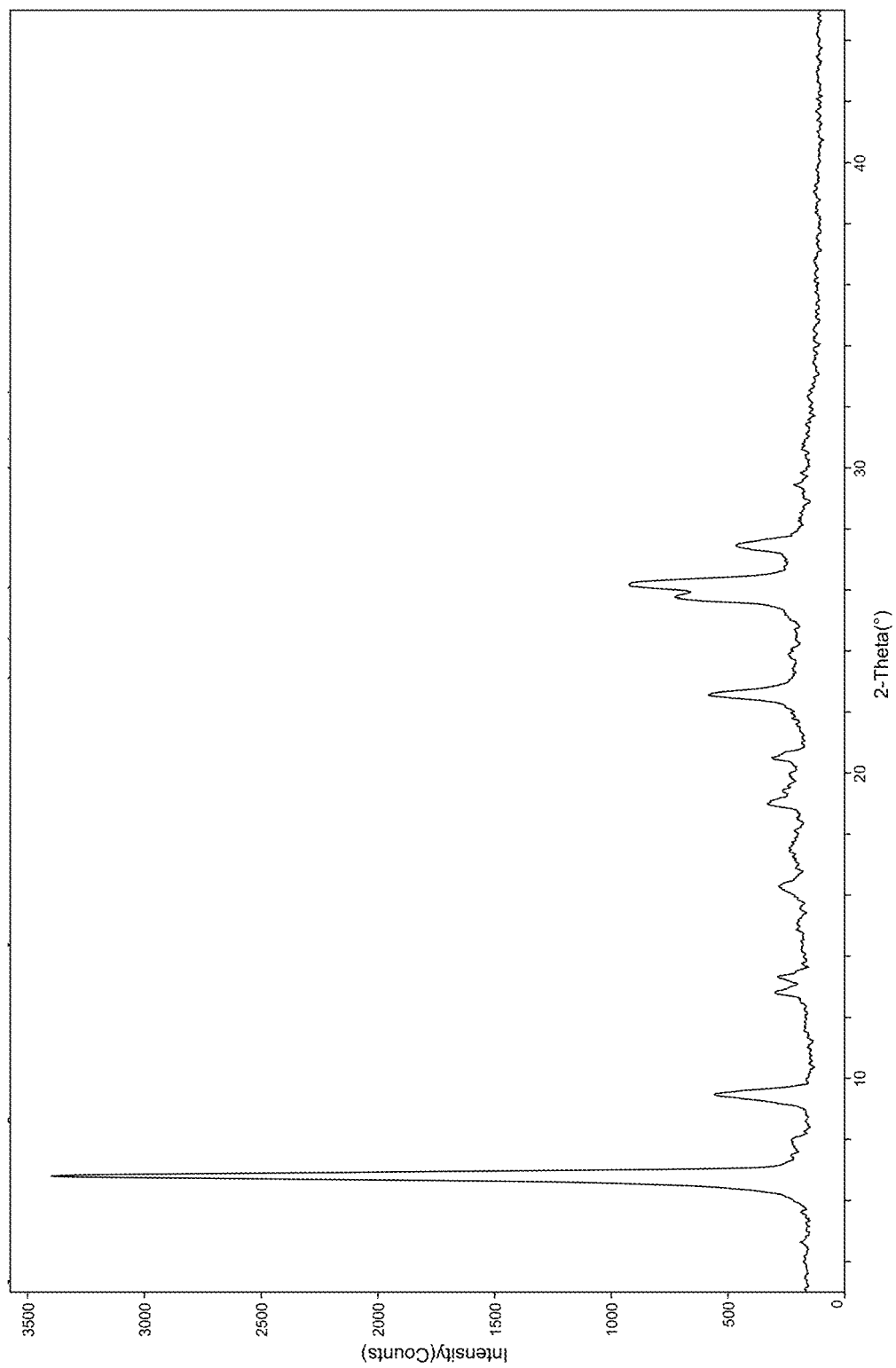
FIG. 4 shows an XRPD pattern of Compound 1, Form II.

In some embodiments, Form II has an XRPD pattern with characteristic peaks as substantially shown in FIG. 4.

Figure 5:
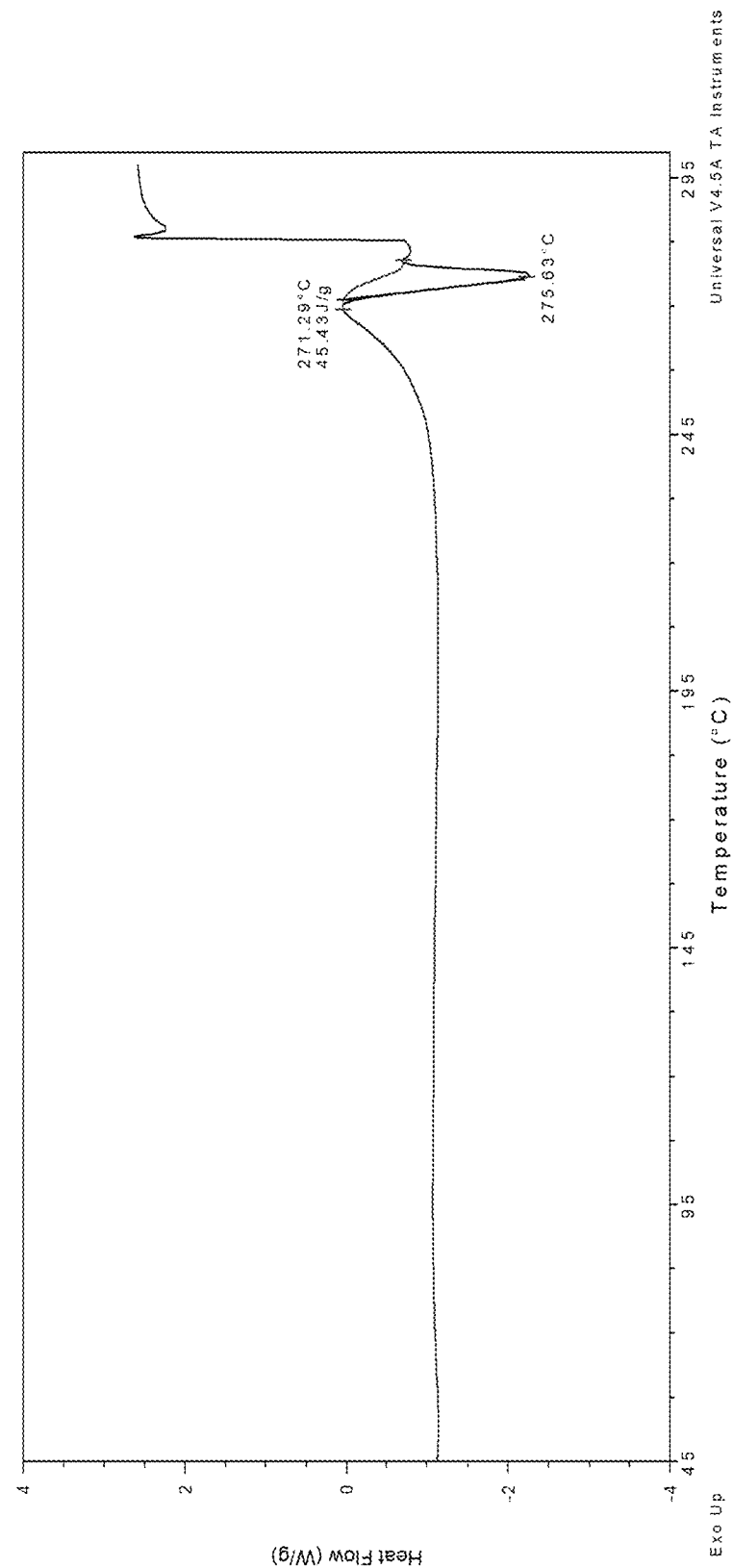
FIG. 5 shows a DSC thermogram of Compound 1, Form II.
Figure 6:
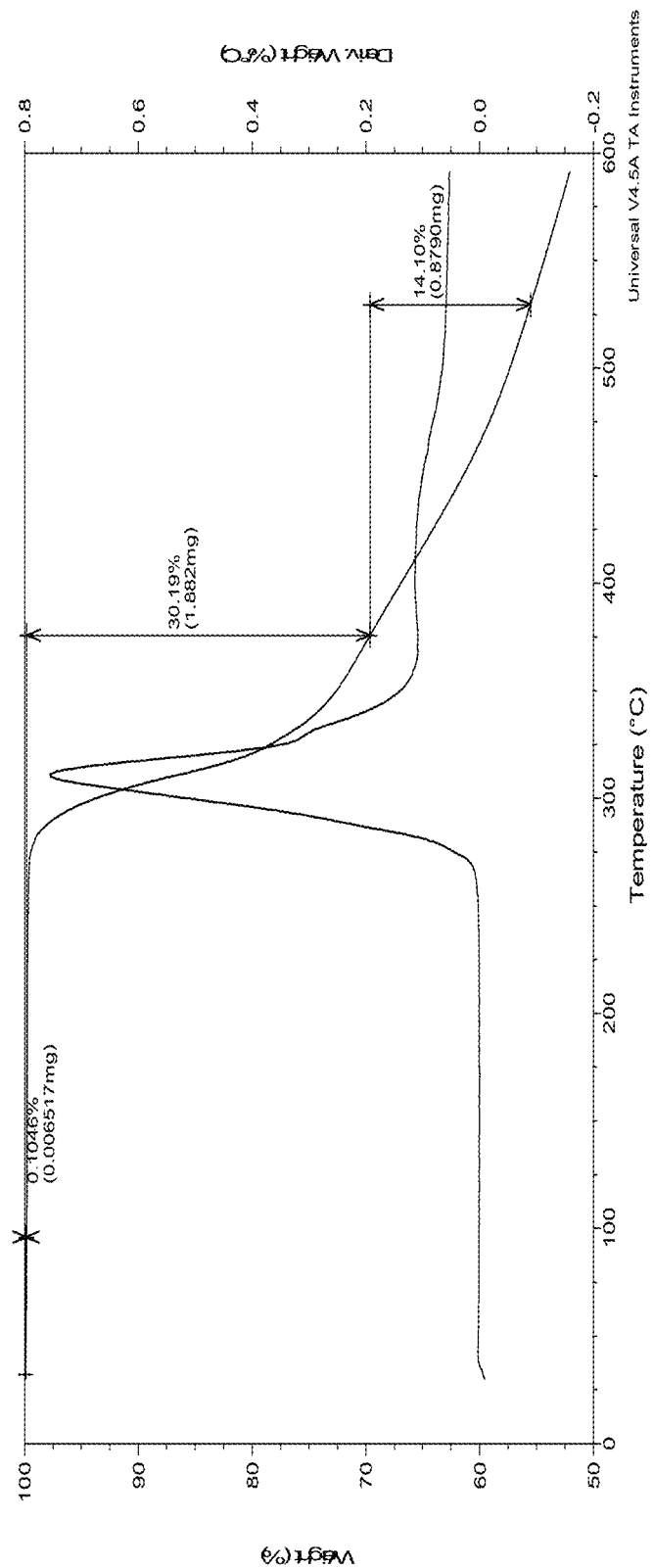
FIG. 6 shows a TGA thermogram of Compound 1, Form II.

In some embodiments, Form II exhibits a DSC thermogram having an endotherm peak at a temperature of about 276° C. In some embodiments, Form II has a DSC thermogram substantially as depicted in FIG. 5. In some embodiments, Form II has a TGA thermogram substantially as depicted in FIG. 6.

In some embodiments, Form II has at least one characteristic XRPD peaks selected from about 6.8, about 9.5, about 12.8, about 13.3 and about 25.8 degrees 2-theta; and Form II exhibits a DSC thermogram having an endotherm peak at a temperature of about 276° C.

Provided herein are also processes for preparing Form II of Compound 1 comprising evaporating a saturated solution of Compound 1, Form I in dichloromethane at 50±1° C.

In some embodiments, Form II can be isolated with a purity of at least about 80%, about 85%, about 90%, about 95%, about 96%, about 97%, about 98%, or about 99%. In some embodiments, Form I can be isolated with a purity greater than about 99%.

Compound 1 Form II-a

Provided herein is a solid form of Compound 1 having Form II-a, which is described below in the Examples.

In some embodiments, Form II-a has at least one characteristic XRPD peaks selected from about 6.9, about 9.4, about 13.3, about 16.3, and about 19.9 degrees 2-theta.

In some embodiments, Form II-a has at least two characteristic XRPD peaks selected from about 6.9, about 9.4, about 13.3, about 16.3, and about 19.9 degrees 2-theta.

In some embodiments, Form II-a has at least three characteristic XRPD peaks selected from about 6.9, about 9.4, about 13.3, about 16.3, and about 19.9 degrees 2-theta.

In some embodiments, Form II-a has at least one characteristic XRPD peak selected from about 6.9, about 9.4, about 12.9, about 13.3, about 16.3, about 17.5, about 19.0, about 19.9, about 22.5, and about 26.1 degrees 2-theta.

In some embodiments, Form II-a has at least two characteristic XRPD peaks selected from about 6.9, about 9.4, about 12.9, about 13.3, about 16.3, about 17.5, about 19.0, about 19.9, about 22.5, and about 26.1 degrees 2-theta.

In some embodiments, Form II-a has at least three characteristic XRPD peaks selected from about 6.9, about 9.4, about 12.9, about 13.3, about 16.3, about 17.5, about 19.0, about 19.9, about 22.5, and about 26.1 degrees 2-theta.

Figure 7:
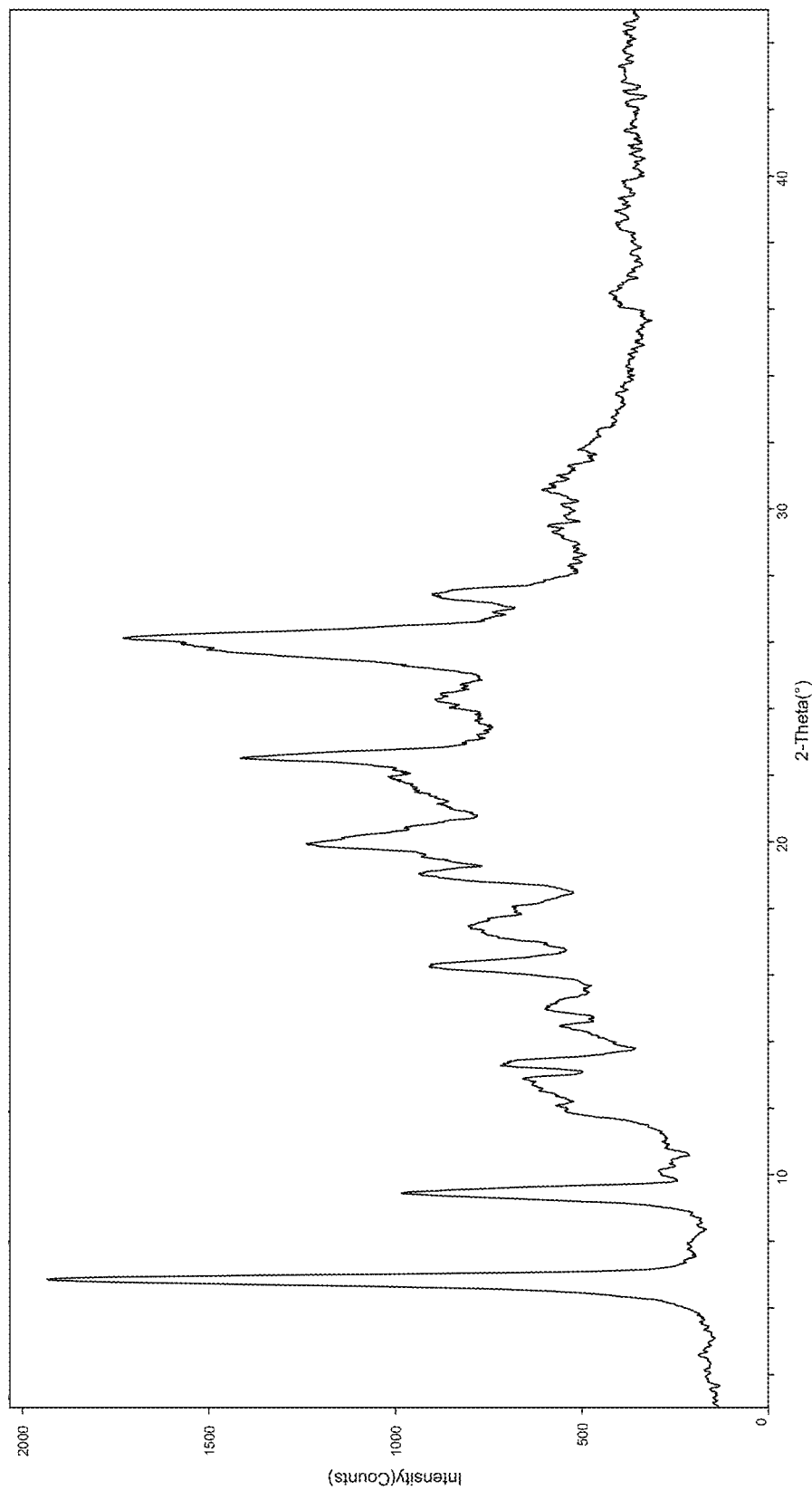
FIG. 7 shows an XRPD pattern of Compound 1, Form IIa.

In some embodiments, Form II-a has an XRPD pattern with characteristic peaks as substantially shown in FIG. 7.

Figure 8:
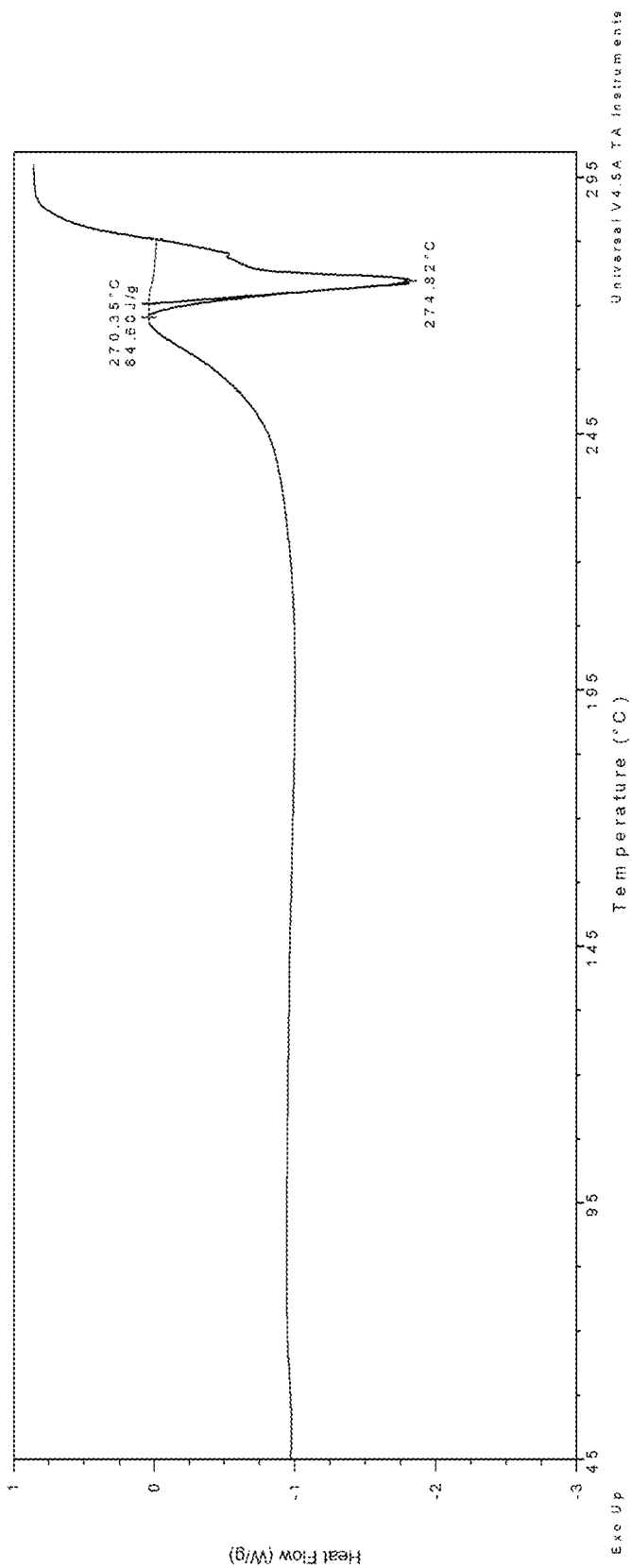
FIG. 8 shows a DSC thermogram of Compound 1, Form IIa.
Figure 9:
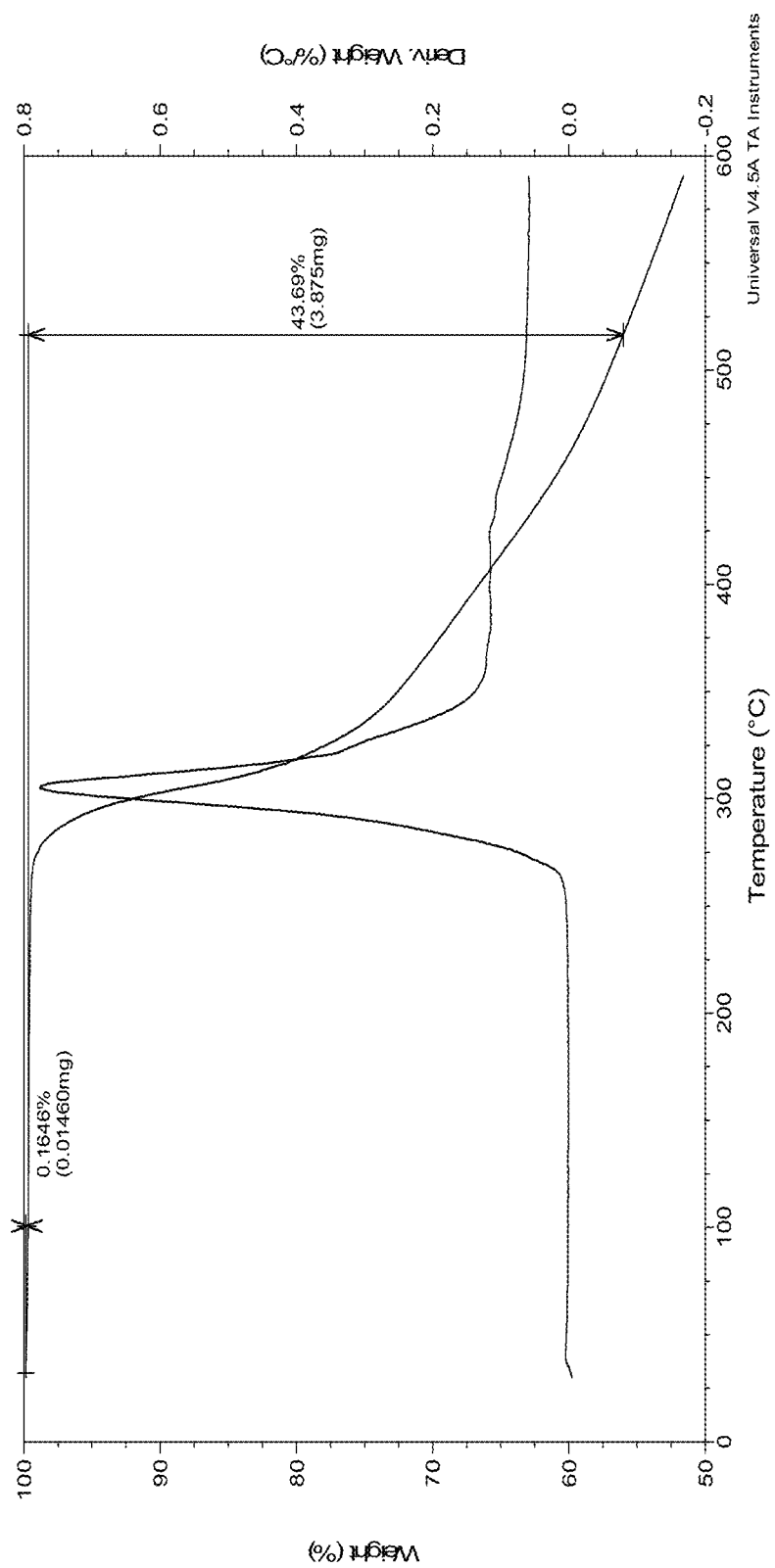
FIG. 9 shows a TGA thermogram of Compound 1, Form IIa.

In some embodiments, Form II-a exhibits a DSC thermogram having an endotherm peak at a temperature of about 275° C. In some embodiments, Form II-a has a DSC thermogram substantially as depicted in FIG. 8. In some embodiments, Form II-a has a TGA thermogram substantially as depicted in FIG. 9.

In some embodiments, Form II-a has at least one characteristic XRPD peaks selected from about 6.9, about 9.4, about 13.3, about 16.3, and about 19.9 degrees 2-theta; and Form II-a exhibits a DSC thermogram having an endotherm peak at a temperature of about 275° C.

Provided herein are also processes for preparing Form II-a of Compound 1 comprising evaporating a solution of Compound 1, Form I in dichloromethane at 25±1° C.

In some embodiments, Form II-a can be isolated with a purity of at least about 80%, about 85%, about 90%, about 95%, about 96%, about 97%, about 98%, or about 99%. In some embodiments, Form I can be isolated with a purity greater than about 99%.

Compound 1 Form III

Provided herein is a solid form of Compound 1 having Form III, which is described below in the Examples.

In some embodiments, Form III has at least one characteristic XRPD peaks selected from about 3.5, about 13.9, about 15.0, about 15.3, about 16.8, and about 18.6.

In some embodiments, Form III has at least two characteristic XRPD peaks selected from about 3.5, about 13.9, about 15.0, about 15.3, about 16.8, and about 18.6.

In some embodiments, Form III has at least three characteristic XRPD peaks selected from about 3.5, about 13.9, about 15.0, about 15.3, about 16.8, and about 18.6.

In some embodiments, Form III has at least one characteristic XRPD peak selected from about 3.5, about 6.7, about 8.5, about 13.9, about 15.0, about 15.3, about 16.8, about 18.6, about 19.3, about 21.5, about 22.9, about 24.2, and about 25.9 degrees 2-theta.

In some embodiments, Form III has at least two characteristic XRPD peaks selected from about 3.5, about 6.7, about 8.5, about 13.9, about 15.0, about 15.3, about 16.8, about 18.6, about 19.3, about 21.5, about 22.9, about 24.2, and about 25.9 degrees 2-theta.

In some embodiments, Form III has at least three characteristic XRPD peaks selected from about 3.5, about 6.7, about 8.5, about 13.9, about 15.0, about 15.3, about 16.8, about 18.6, about 19.3, about 21.5, about 22.9, about 24.2, and about 25.9 degrees 2-theta.

Figure 10:
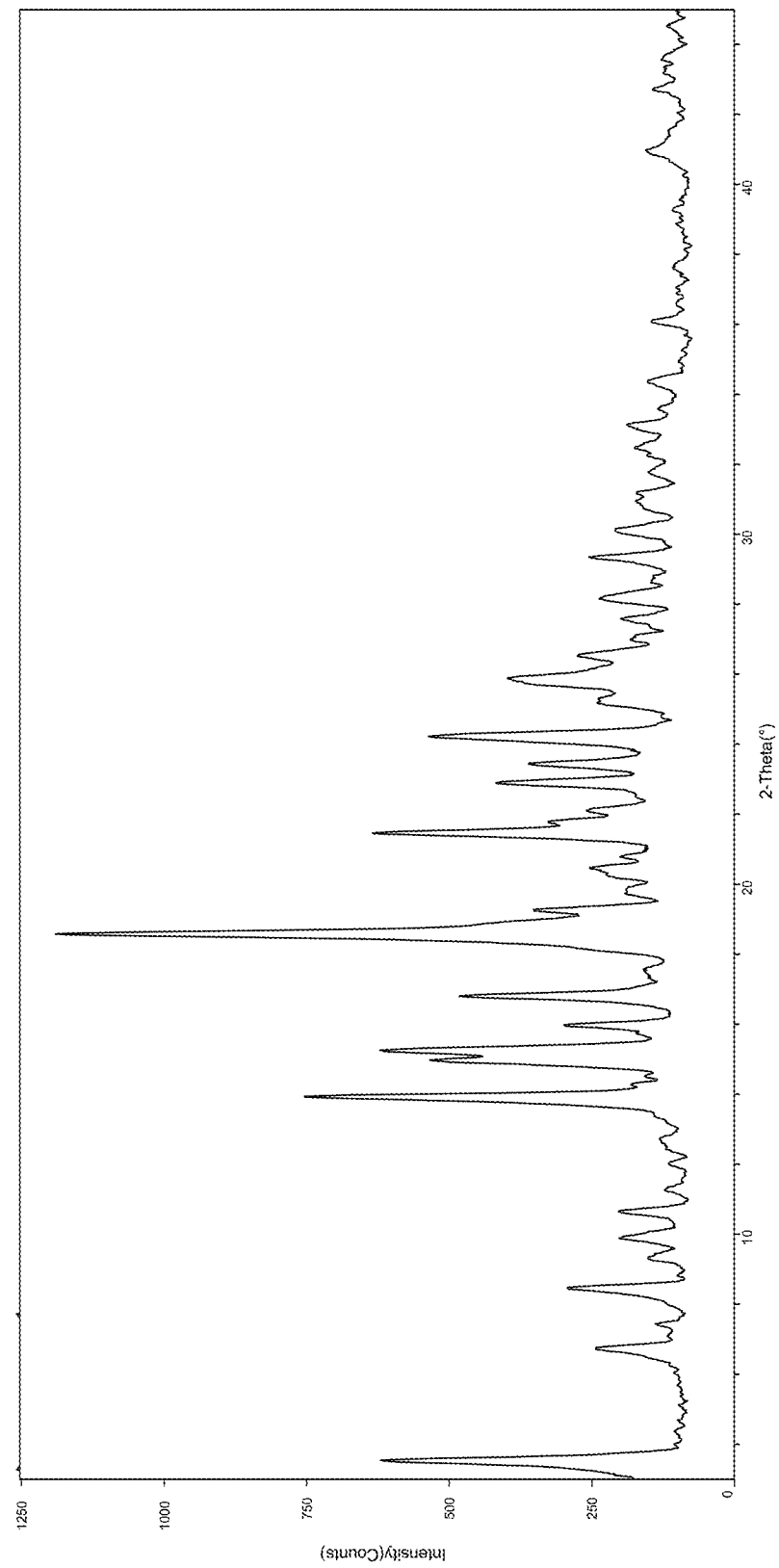
FIG. 10 shows an XRPD pattern of Compound 1, Form III.

In some embodiments, Form III has an XRPD pattern with characteristic peaks as substantially shown in FIG. 10.

Figure 11:
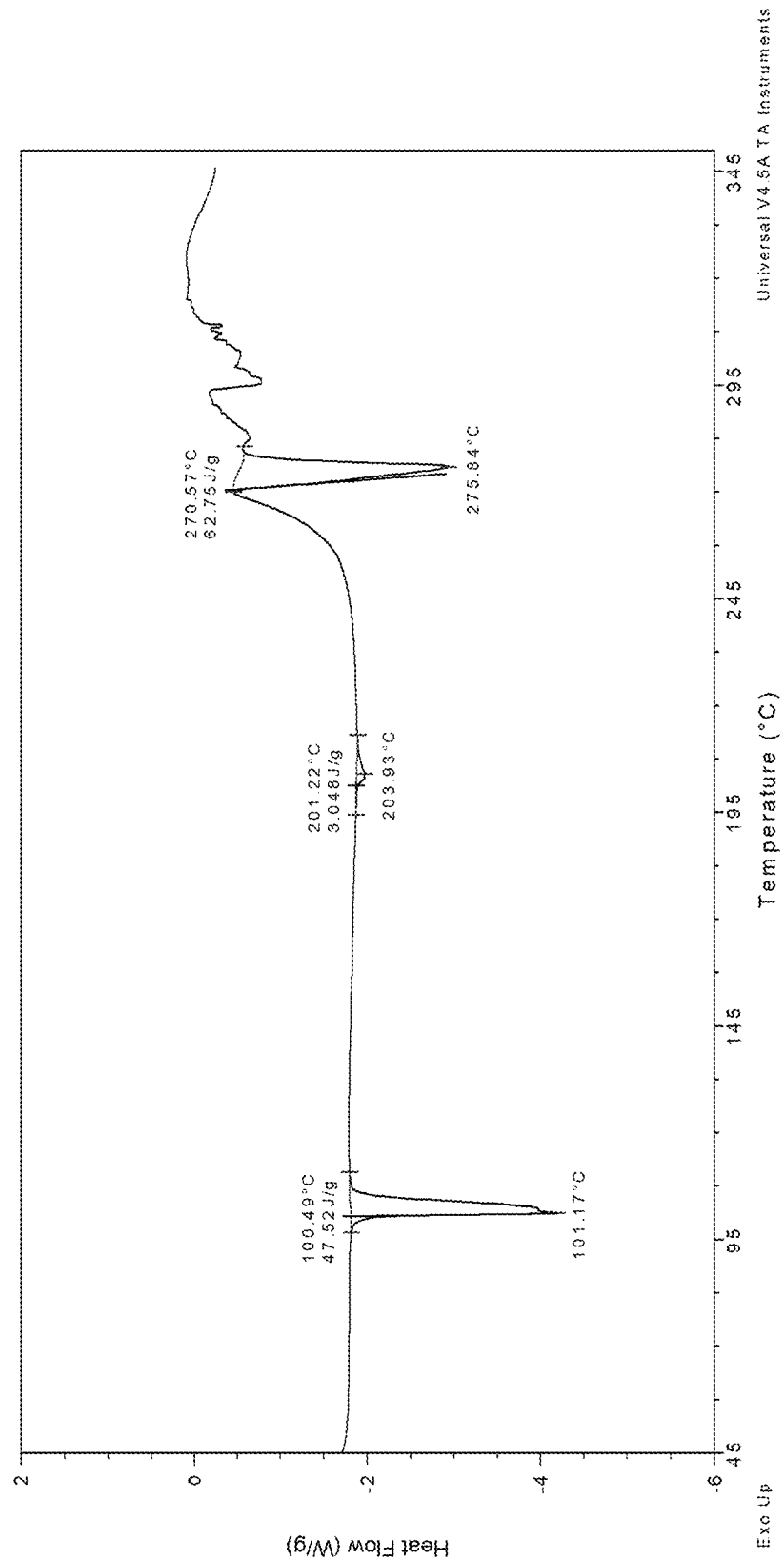
FIG. 11 shows a DSC thermogram of Compound 1, Form III.
Figure 12:
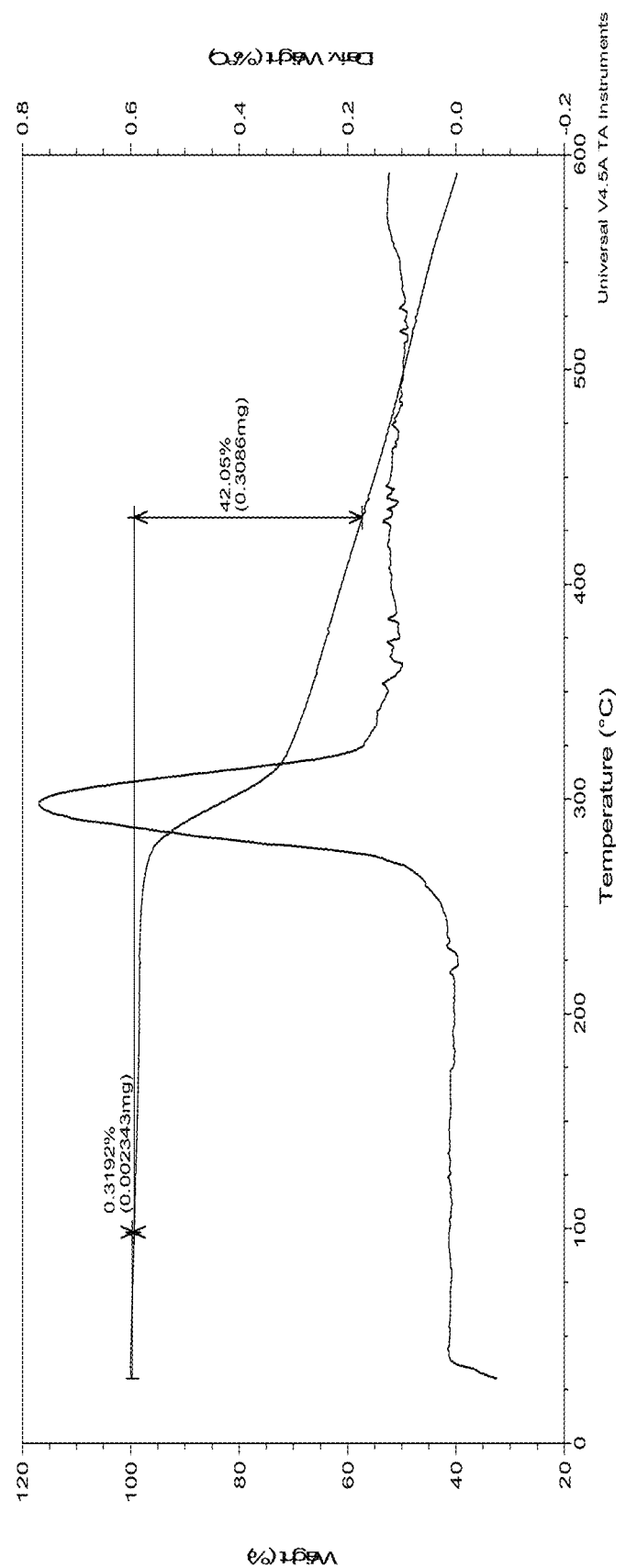
FIG. 12 shows a TGA thermogram of Compound 1, Form III.

In some embodiments, Form III exhibits a DSC thermogram having endotherm peaks at temperatures of about 101° C., 204° C., and 276° C. In some embodiments, Form III exhibits a DSC thermogram having an endotherm peak at a temperature of about 101° C. In some embodiments, Form III exhibits a DSC thermogram having an endotherm peak at a temperature of about 204° C. In some embodiments, Form III exhibits a DSC thermogram having an endotherm peak at a temperature of about 276° C. In some embodiments, Form III has a DSC thermogram substantially as depicted in FIG. 11. In some embodiments, Form III has a TGA thermogram substantially as depicted in FIG. 12.

In some embodiments, Form III has at least one characteristic XRPD peaks selected from about 3.5, about 13.9, about 15.0, about 15.3, about 16.8, and about 18.6; and Form III exhibits a DSC thermogram having endotherm peaks at temperatures of about 101° C., 204° C., and 276° C.

Provided herein are also processes for preparing Form III of Compound 1 comprising adding Compound 1, Form I to a solution of Compound 1, Form I in 1,4-dioxane, stirring at 25±1° C. for 2 days, and removing the supernatant by centrifugation.

In some embodiments, Form III can be isolated with a purity of at least about 80%, about 85%, about 90%, about 95%, about 96%, about 97%, about 98%, or about 99%. In some embodiments, Form I can be isolated with a purity greater than about 99%.

Compound 1 Form IV

Provided herein is a solid form of Compound 1 having Form IV, which is described below in the Examples.

In some embodiments, Form IV has at least one characteristic XRPD peaks selected from about 10.1, about 13.0, about 14.0, about 18.4, about 22.2, about 24.3, and about 26.4 degrees 2-theta.

In some embodiments, Form IV has at least two characteristic XRPD peaks selected from about 10.1, about 13.0, about 14.0, about 18.4, about 22.2, about 24.3, and about 26.4 degrees 2-theta.

In some embodiments, Form IV has at least three characteristic XRPD peaks selected from about 10.1, about 13.0, about 14.0, about 18.4, about 22.2, about 24.3, and about 26.4 degrees 2-theta.

In some embodiments, Form IV has at least one characteristic XRPD peak selected from about 10.1, about 13.0, about 14.0, about 15.6, about 17.3, about 18.4, about 20.2, about 21.4, about 22.2, about 22.7, about 24.3, about 26.4 and about 26.8 degrees 2-theta.

In some embodiments, Form IV has at least two characteristic XRPD peaks selected from about 10.1, about 13.0, about 14.0, about 15.6, about 17.3, about 18.4, about 20.2, about 21.4, about 22.2, about 22.7, about 24.3, about 26.4 and about 26.8 degrees 2-theta.

In some embodiments, Form IV has at least three characteristic XRPD peaks selected from about 10.1, about 13.0, about 14.0, about 15.6, about 17.3, about 18.4, about 20.2, about 21.4, about 22.2, about 22.7, about 24.3, about 26.4 and about 26.8 degrees 2-theta.

Figure 13:
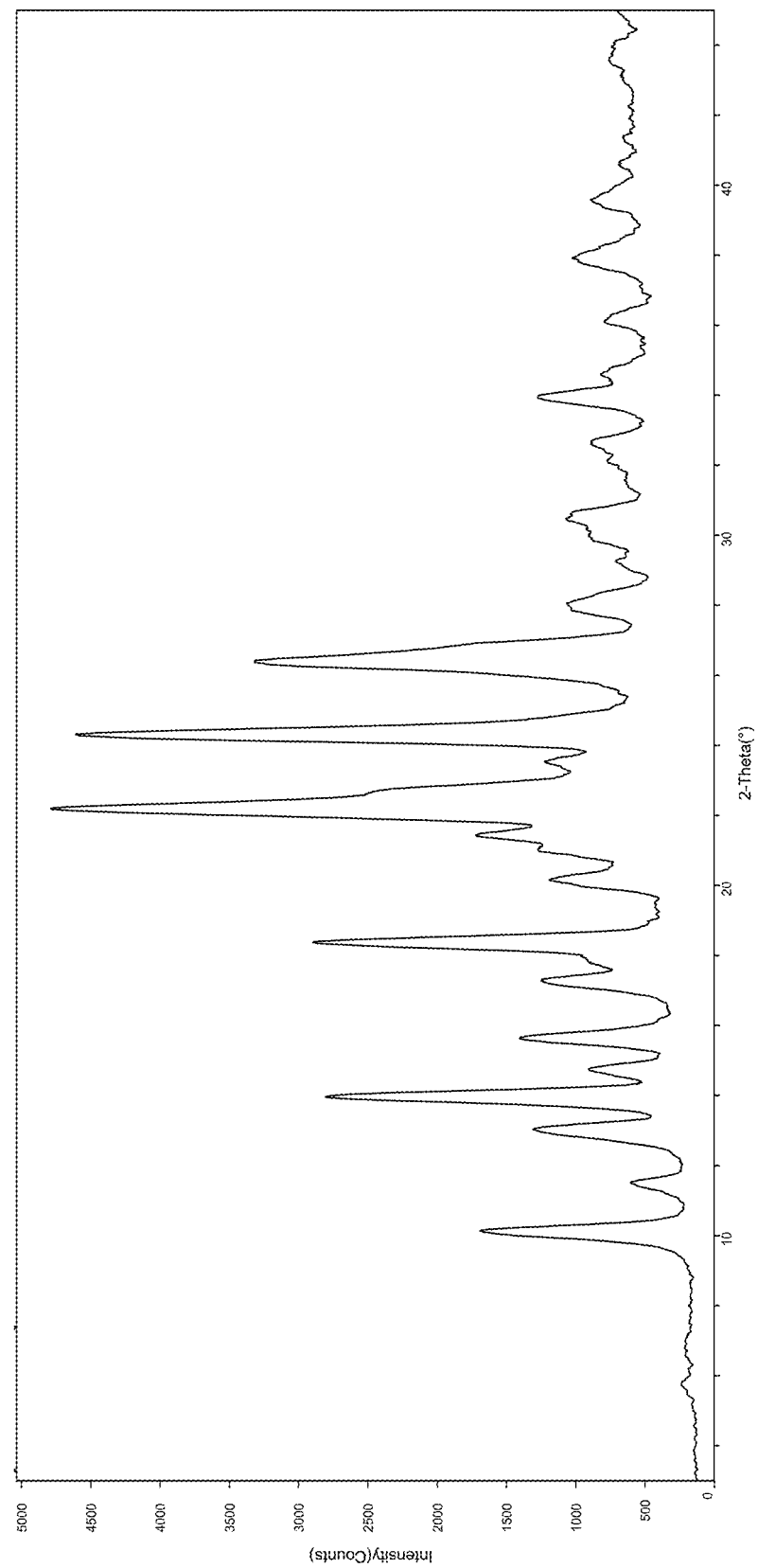
FIG. 13 shows an XRPD pattern of Compound 1, Form IV.

In some embodiments, Form IV has an XRPD pattern with characteristic peaks as substantially shown in FIG. 13.

Figure 14:
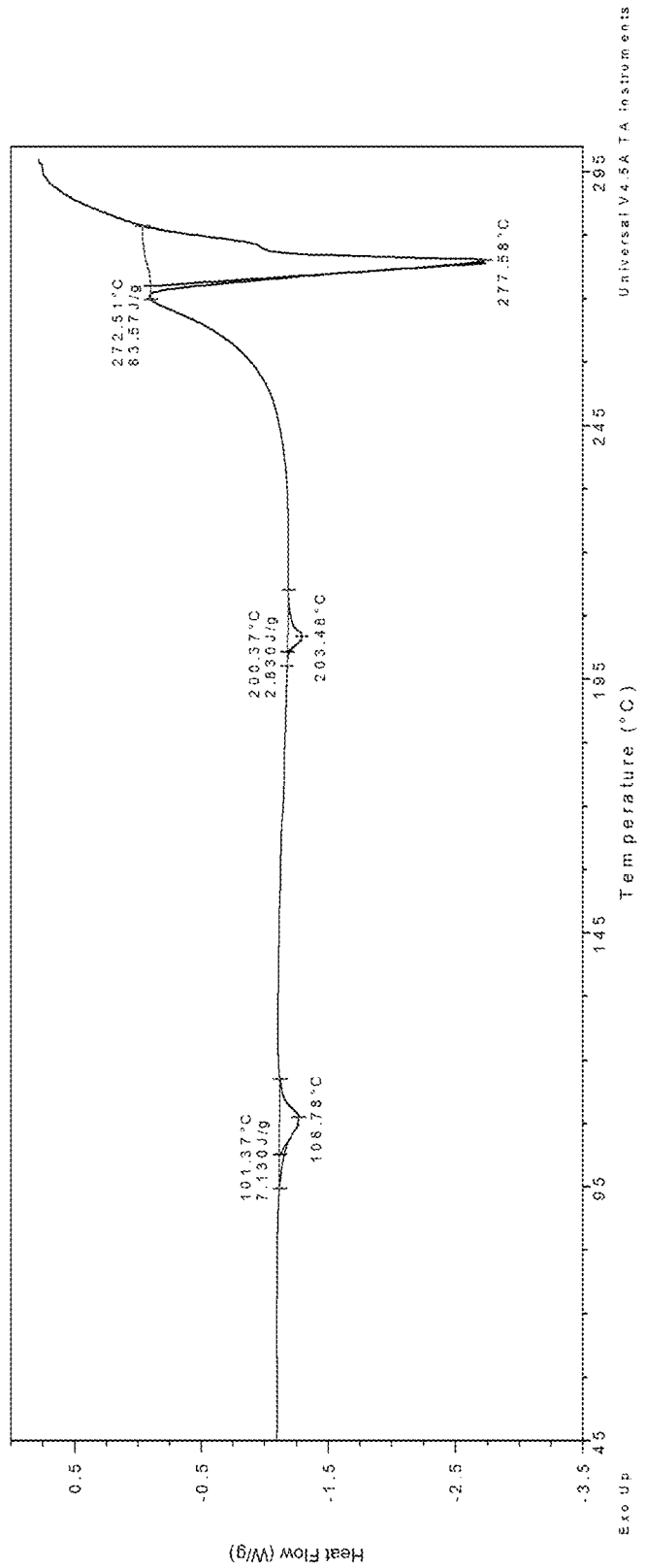
FIG. 14 shows a DSC thermogram of Compound 1, Form IV.
Figure 15:
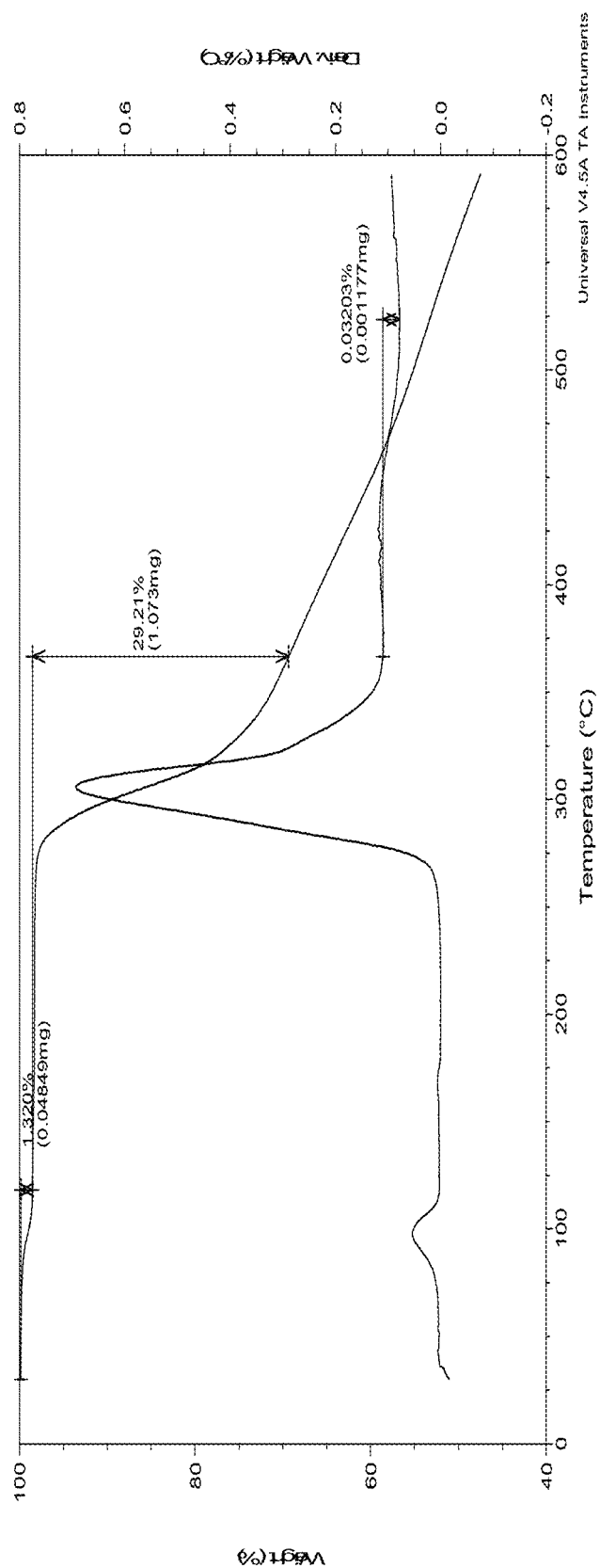
FIG. 15 shows a TGA thermogram of Compound 1, Form IV.

In some embodiments, Form IV exhibits a DSC thermogram having endotherm peaks at temperatures of about 109° C., 203° C., and 278° C. In some embodiments, Form IV exhibits a DSC thermogram having an endotherm peak at a temperature of about 109° C. In some embodiments, Form IV exhibits a DSC thermogram having an endotherm peak at a temperature of about 203° C. In some embodiments, Form IV exhibits a DSC thermogram having an endotherm peak at a temperature of about 278° C. In some embodiments, Form IV has a DSC thermogram substantially as depicted in FIG. 14. In some embodiments, Form IV has a TGA thermogram substantially as depicted in FIG. 15.

In some embodiments, Form IV has at least one characteristic XRPD peaks selected from about 10.1, about 13.0, about 14.0, about 18.4, about 22.2, about 24.3, and about 26.4 degrees 2-theta; and Form IV exhibits a DSC thermogram having endotherm peaks at temperatures of about 109° C., 203° C., and 278° C.

Provided herein are also processes for preparing Form IV of Compound 1 comprising adding Compound 1, Form I to a cloudy solution of Compound 1, Form I in 1,4-dioxane, and stirring at 25±1° C. for 6 days.

In some embodiments, Form IV can be isolated with a purity of at least about 80%, about 85%, about 90%, about 95%, about 96%, about 97%, about 98%, or about 99%. In some embodiments, Form I can be isolated with a purity greater than about 99%.

Compound 1 Form V

Provided herein is a solid form of Compound 1 having Form V, which is described below in the Examples.

In some embodiments, Form V has at least one characteristic XRPD peak selected from about 7.4, about 14.8, about 21.3, about 22.0, and about 22.3 degrees 2-theta.

In some embodiments, Form V has at least two characteristic XRPD peaks selected from about 7.4, about 14.8, about 21.3, about 22.0, and about 22.3 degrees 2-theta.

In some embodiments, Form V has at least three characteristic XRPD peaks selected from about 7.4, about 14.8, about 21.3, about 22.0, and about 22.3 degrees 2-theta.

Figure 16:
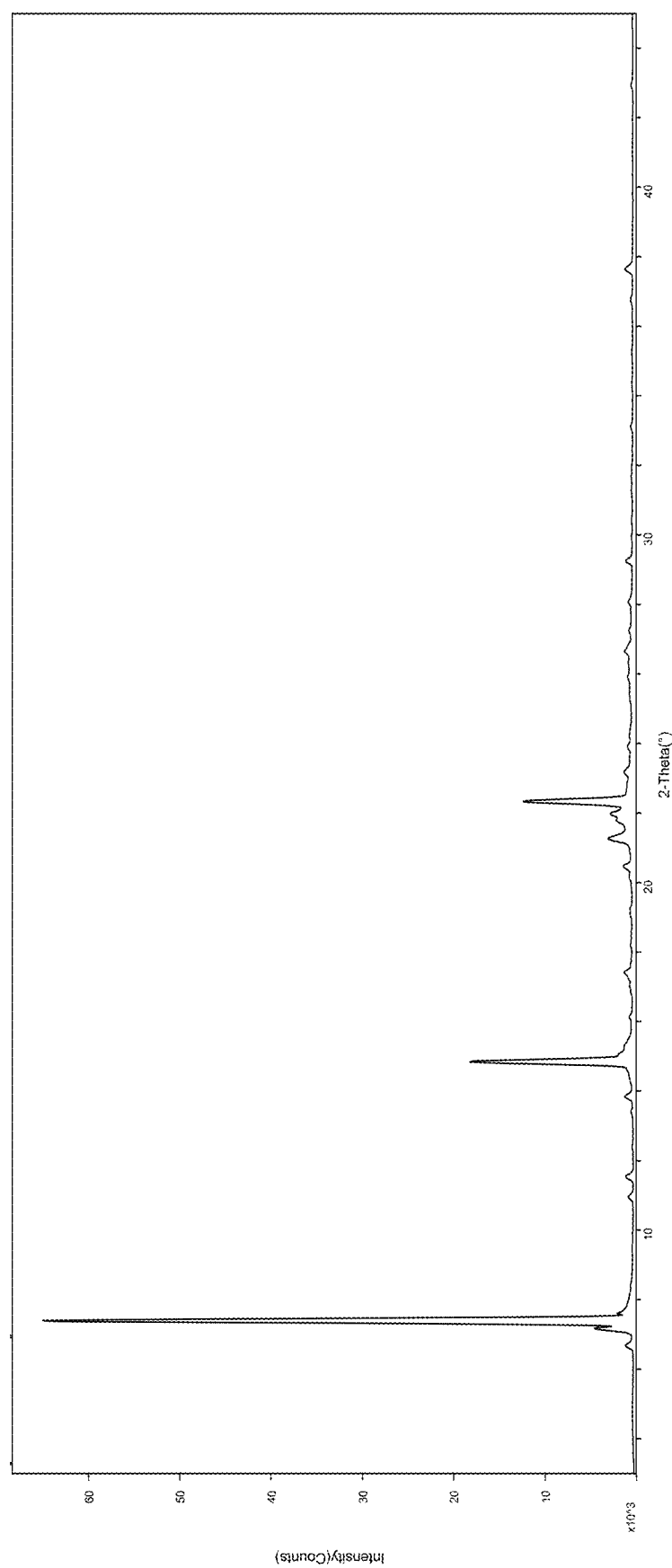
FIG. 16 shows an XRPD pattern of Compound 1, Form V.

In some embodiments, Form V has an XRPD pattern with characteristic peaks as substantially shown in FIG. 16.

Figure 17:
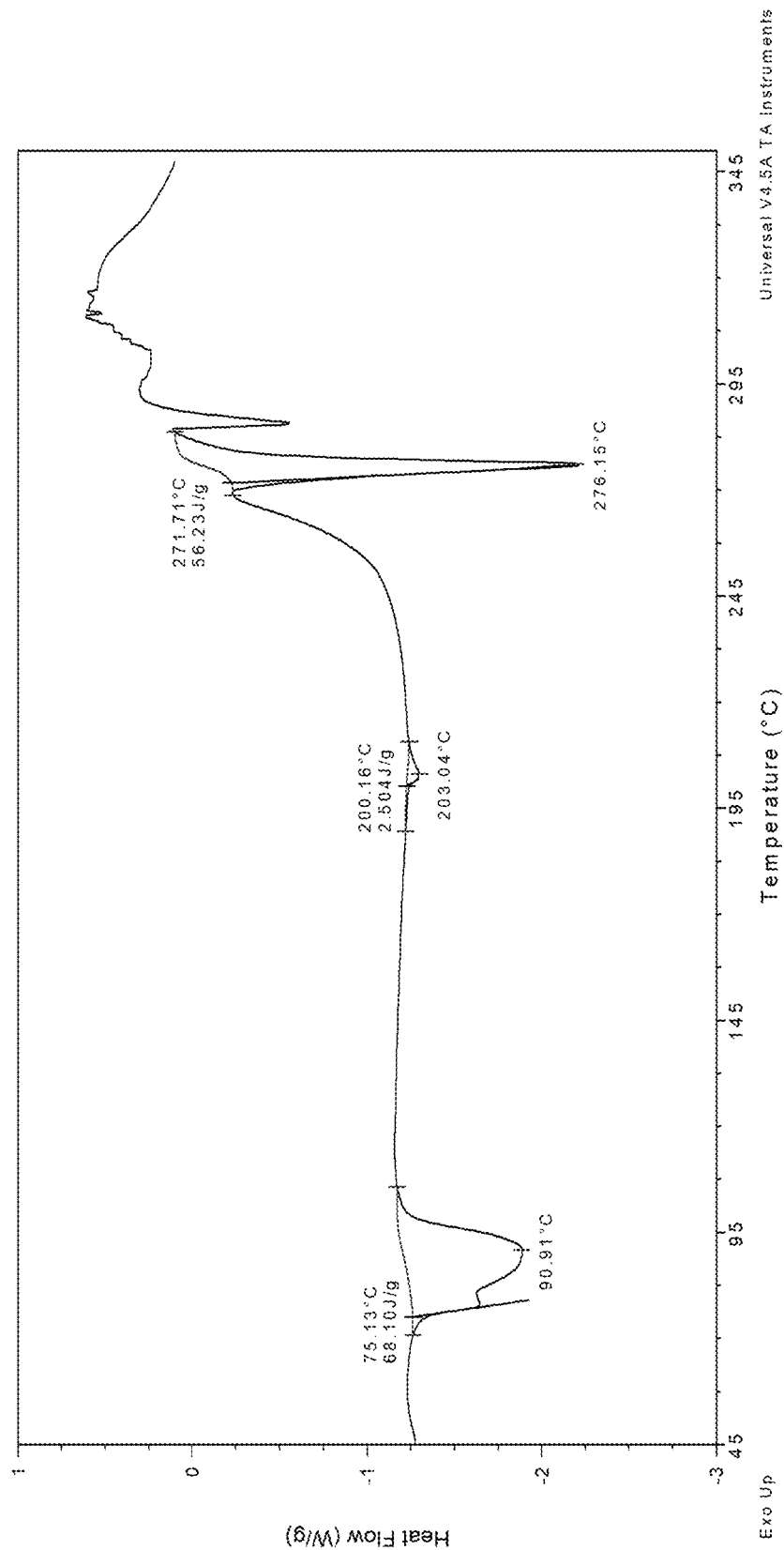
FIG. 17 shows a DSC thermogram of Compound 1, Form V.

In some embodiments, Form V exhibits a DSC thermogram having endotherm peaks at temperatures of about 91° C., 203° C., and 276° C. In some embodiments, Form V exhibits a DSC thermogram having an endotherm peak at a temperature of about 91° C. In some embodiments, Form V exhibits a DSC thermogram having an endotherm peak at a temperature of about 203° C. In some embodiments, Form V exhibits a DSC thermogram having an endotherm peak at a temperature of about 276° C. In some embodiments, Form V has a DSC thermogram substantially as depicted in FIG. 17.

In some embodiments, Form V has at least one characteristic XRPD peak selected from about 7.4, about 14.8, about 21.3, about 22.0, and about 22.3 degrees 2-theta; and Form V exhibits a DSC thermogram having endotherm peaks at temperatures of about 91° C., 203° C., and 276° C.

Provided herein are also processes for preparing Form V of Compound 1 comprising allowing a saturated solution of Compound 1, Form I in 1,4-dioxane to rest for more than 30 days.

In some embodiments, Form V can be isolated with a purity of at least about 80%, about 85%, about 90%, about 95%, about 96%, about 97%, about 98%, or about 99%. In some embodiments, Form I can be isolated with a purity greater than about 99%.

Compound 1 Form VI

Provided herein is a solid form of Compound 1 having Form VI, which is described below in the Examples.

In some embodiments, Form VI has at least one characteristic XRPD peaks selected from about 9.1, about 9.5, about 14.4, about 17.6, about 18.6, about 19.9, and about 22.3 degrees 2-theta.

In some embodiments, Form VI has at least two characteristic XRPD peaks selected from about 9.1, about 9.5, about 14.4, about 17.6, about 18.6, about 19.9, and about 22.3 degrees 2-theta.

In some embodiments, Form VI has at least three characteristic XRPD peaks selected from about 9.1, about 9.5, about 14.4, about 17.6, about 18.6, about 19.9, and about 22.3 degrees 2-theta.

In some embodiments, Form VI has at least one characteristic XRPD peak selected from about 7.8, about 9.1, about 9.5, about 10.2, about 11.4, about 12.1, about 13.4, about 14.4, about 15.9, about 17.6, about 18.6, about 19.2, about 19.9, about 22.3, about 22.7, about 25.4, and about 26.2 degrees 2-theta.

In some embodiments, Form VI has at least two characteristic XRPD peaks selected from about 7.8, about 9.1, about 9.5, about 10.2, about 11.4, about 12.1, about 13.4, about 14.4, about 15.9, about 17.6, about 18.6, about 19.2, about 19.9, about 22.3, about 22.7, about 25.4, and about 26.2 degrees 2-theta.

In some embodiments, Form VI has at least three characteristic XRPD peaks selected from about 7.8, about 9.1, about 9.5, about 10.2, about 11.4, about 12.1, about 13.4, about 14.4, about 15.9, about 17.6, about 18.6, about 19.2, about 19.9, about 22.3, about 22.7, about 25.4, and about 26.2 degrees 2-theta.

Figure 18:
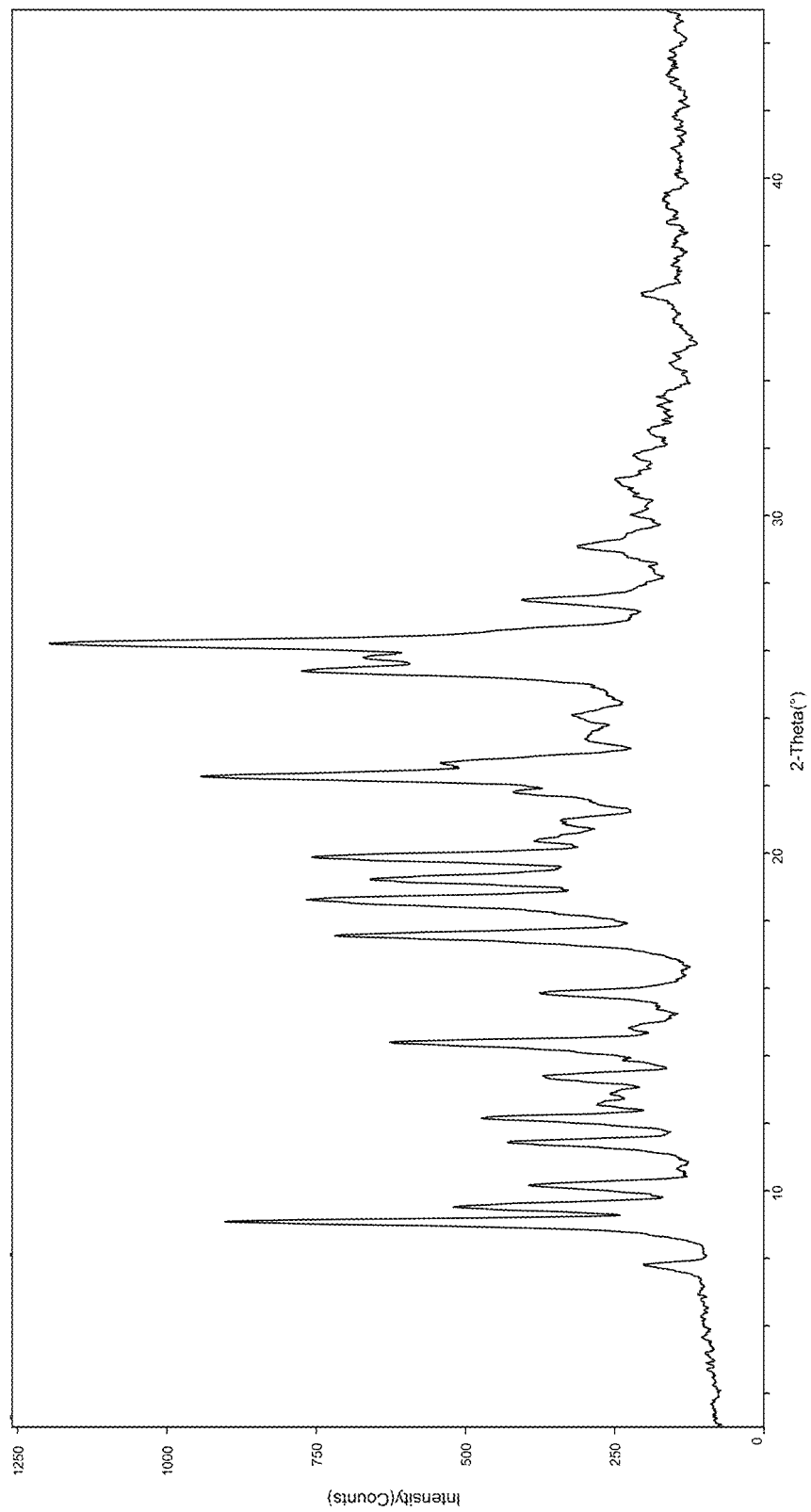
FIG. 18 shows an XRPD pattern of Compound 1, Form VI.

In some embodiments, Form VI has an XRPD pattern with characteristic peaks as substantially shown in FIG. 18.

Figure 19:
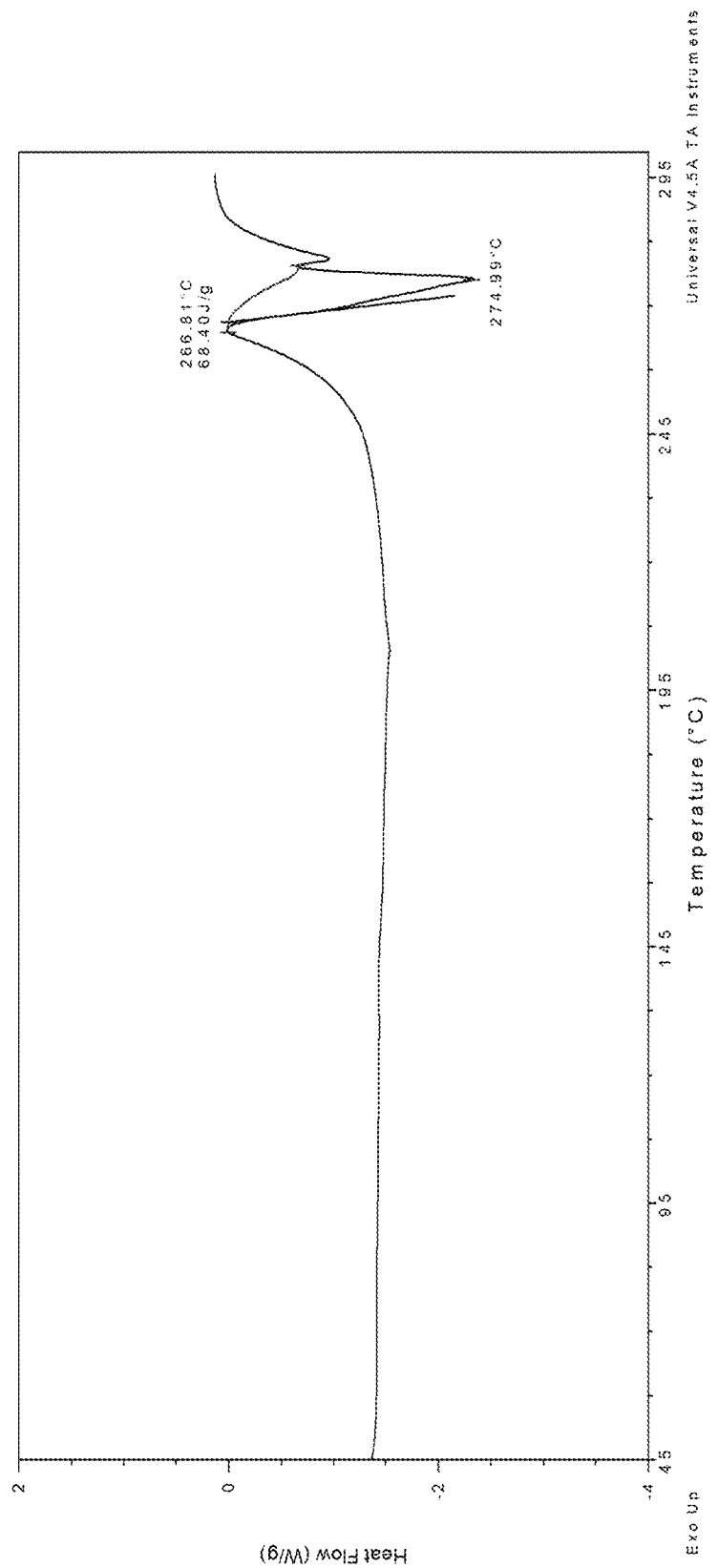
FIG. 19 shows a DSC thermogram of Compound 1, Form VI.
Figure 20:
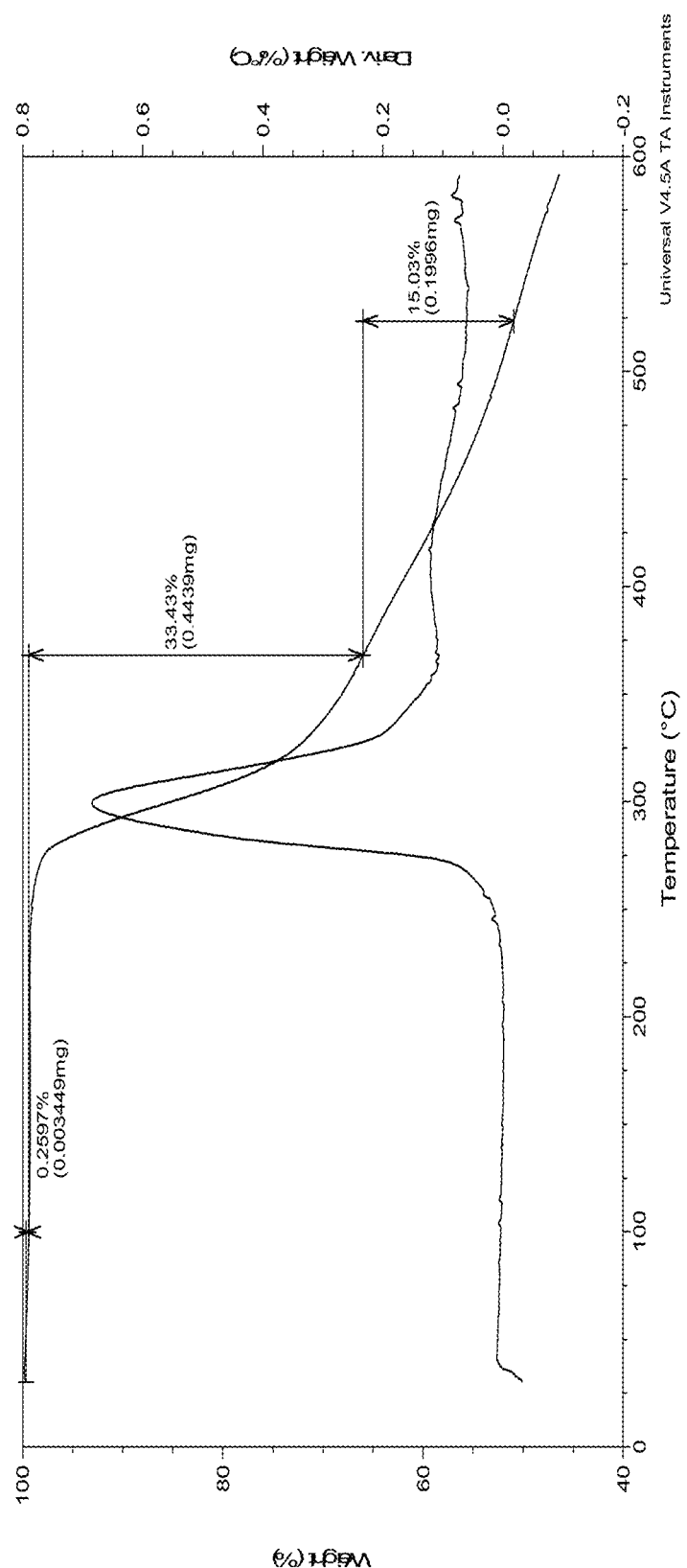
FIG. 20 shows a TGA thermogram of Compound 1, Form VI.

In some embodiments, Form VI exhibits a DSC thermogram having an endotherm peak at a temperature of about 275° C. In some embodiments, Form VI has a DSC thermogram substantially as depicted in FIG. 19. In some embodiments, Form VI has a TGA thermogram substantially as depicted in FIG. 20.

In some embodiments, Form VI has at least one characteristic XRPD peaks selected from about 9.1, about 9.5, about 14.4, about 17.6, about 18.6, about 19.9, and about 22.3 degrees 2-theta; and Form VI exhibits a DSC thermogram having an endotherm peak at a temperature of about 275° C.

Provided herein are also processes for preparing Form VI of Compound 1 comprising adding Compound 1, Form I to a cloudy solution of Compound 1 prepared in methanol, and stirring at 25±1° C. for 3 days.

In some embodiments, Form VI can be isolated with a purity of at least about 80%, about 85%, about 90%, about 95%, about 96%, about 97%, about 98%, or about 99%. In some embodiments, Form I can be isolated with a purity greater than about 99%.

Compound 1 Form VII

Provided herein is a solid form of Compound 1 having Form VII, which is described below in the Examples.

In some embodiments, Form VII has at least one characteristic XRPD peaks selected from about 9.8, about 15.4, about 18.8, about 19.6, and about 20.1 degrees 2-theta.

In some embodiments, Form VII has at least two characteristic XRPD peaks selected from about 9.8, about 15.4, about 18.8, about 19.6, and about 20.1 degrees 2-theta.

In some embodiments, Form VII has at least three characteristic XRPD peaks selected from about 9.8, about 15.4, about 18.8, about 19.6, and about 20.1 degrees 2-theta.

In some embodiments, Form VII has at least one characteristic XRPD peak selected from about 8.2, about 9.8, about 15.4, about 17.9, about 18.8, about 19.6, about 20.1, about 21.1, about 22.3, and about 24.3 degrees 2-theta.

In some embodiments, Form VII has at least two characteristic XRPD peaks selected from about 8.2, about 9.8, about 15.4, about 17.9, about 18.8, about 19.6, about 20.1, about 21.1, about 22.3, and about 24.3 degrees 2-theta.

In some embodiments, Form VII has at least three characteristic XRPD peaks selected from about 8.2, about 9.8, about 15.4, about 17.9, about 18.8, about 19.6, about 20.1, about 21.1, about 22.3, and about 24.3 degrees 2-theta.

Figure 21:
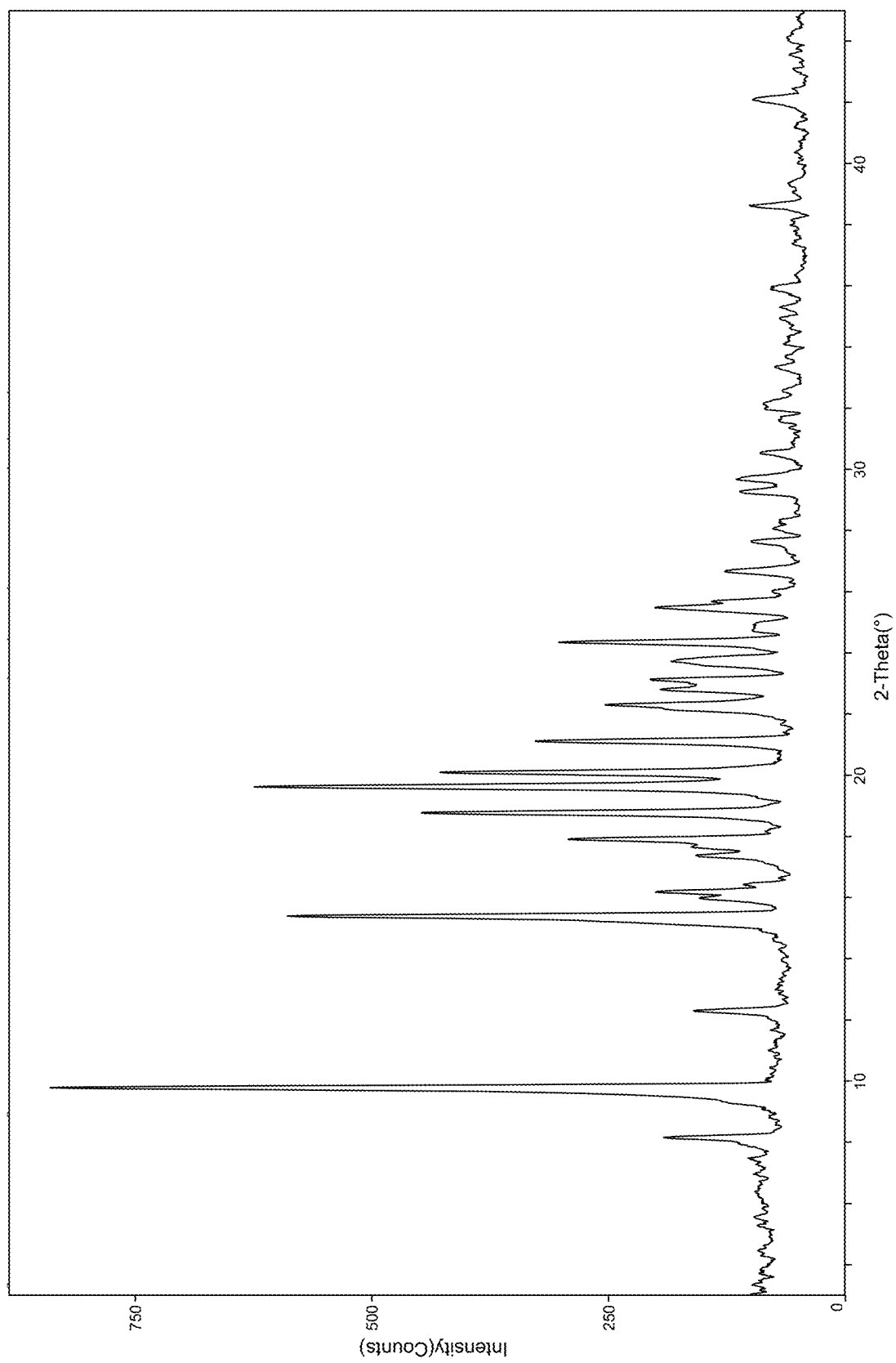
FIG. 21 shows an XRPD pattern of Compound 1, Form VII.

In some embodiments, Form VII has an XRPD pattern with characteristic peaks as substantially shown in FIG. 21.

Figure 22:
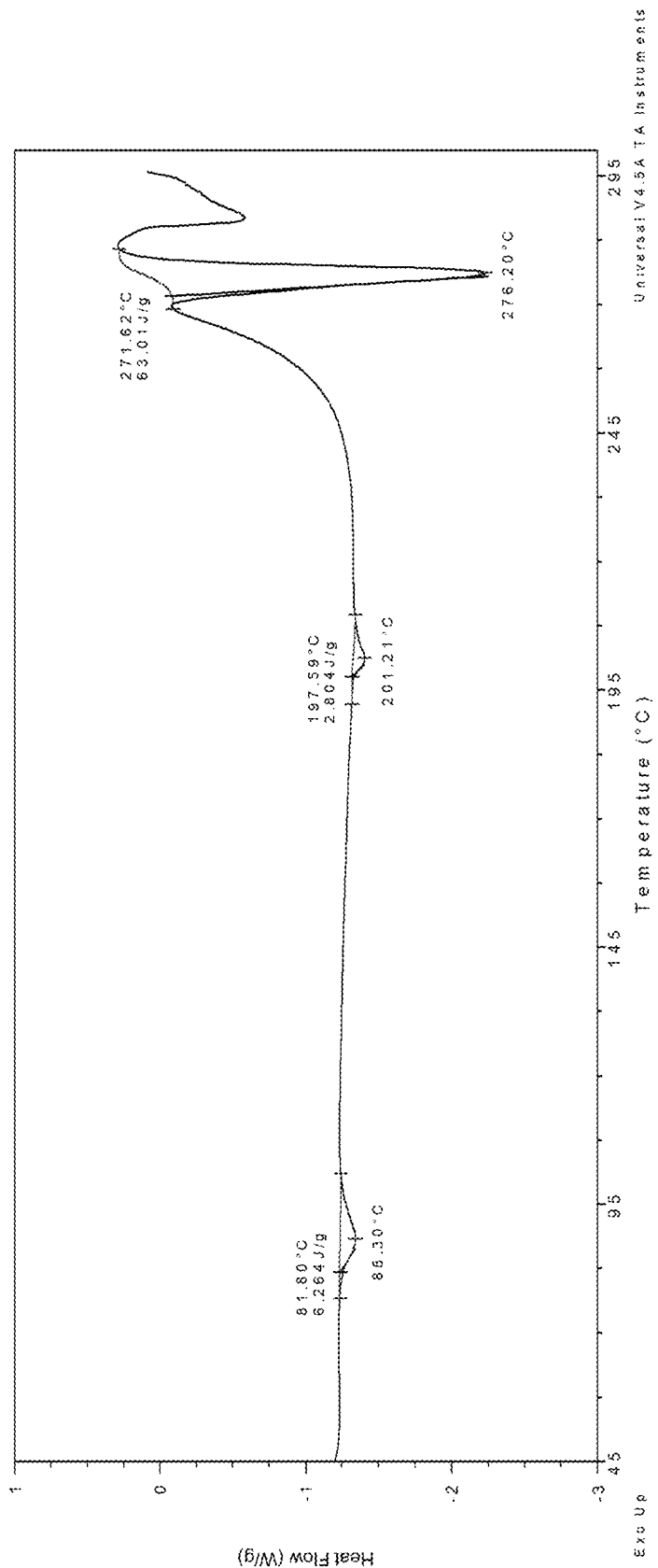
FIG. 22 shows a DSC thermogram of Compound 1, Form VII.
Figure 23:
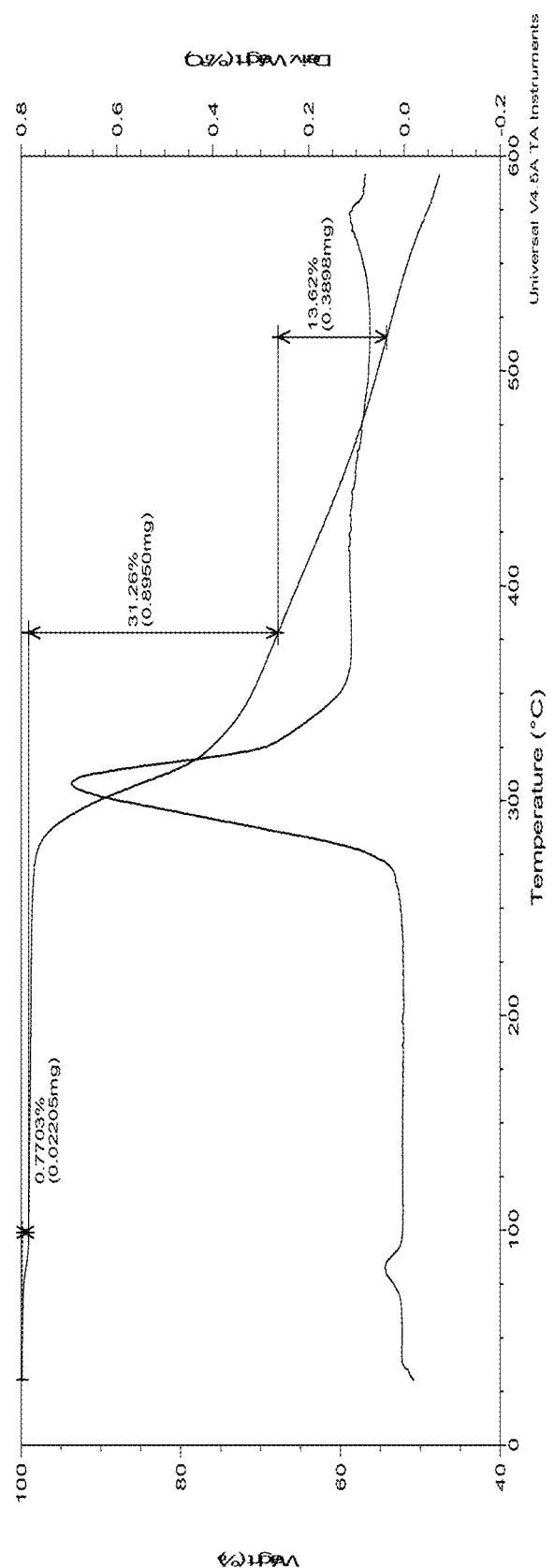
FIG. 23 shows a TGA thermogram of Compound 1, Form VII.

In some embodiments, Form VII exhibits a DSC thermogram having endotherm peaks at temperatures of about 88° C., 201° C., and 276° C. In some embodiments, Form VII exhibits a DSC thermogram having an endotherm peak at a temperature of about 88° C. In some embodiments, Form VII exhibits a DSC thermogram having an endotherm peak at a temperature of about 201° C. In some embodiments, Form VII exhibits a DSC thermogram having an endotherm peak at a temperature of about 276° C. In some embodiments, Form VII has a DSC thermogram substantially as depicted in FIG. 22. In some embodiments, Form VII has a TGA thermogram substantially as depicted in FIG. 23.

In some embodiments, Form VII has at least one characteristic XRPD peaks selected from about 9.8, about 15.4, about 18.8, about 19.6, and about 20.1 degrees 2-theta; and Form VII exhibits a DSC thermogram having endotherm peaks at temperatures of about 88° C., 201° C., and 276° C.

Provided herein are also processes for preparing Form VII of Compound 1 comprising adding Compound 1, Form I to a cloudy solution of Compound 1, Form I prepared in methyl isobutyl ketone, and stirring at 25±1° C. for 3 days.

In some embodiments, Form VII can be isolated with a purity of at least about 80%, about 85%, about 90%, about 95%, about 96%, about 97%, about 98%, or about 99%. In some embodiments, Form I can be isolated with a purity greater than about 99%.

Compound 1 Form VIII

Provided herein is a solid form of Compound 1 having Form VIII, which is described below in the Examples.

In some embodiments, Form VIII has at least one characteristic XRPD peaks selected from about 9.1, about 16.7, about 18.2, about 18.6, and about 20.2 degrees 2-theta.

In some embodiments, Form VIII has at least two characteristic XRPD peaks selected from about 9.1, about 16.7, about 18.2, about 18.6, and about 20.2 degrees 2-theta.

In some embodiments, Form VIII has at least three characteristic XRPD peaks selected from about 9.1, about 16.7, about 18.2, about 18.6, and about 20.2 degrees 2-theta.

In some embodiments, Form VIII has at least one characteristic XRPD peak selected from about 9.1, about 15.2, about 16.7, about 18.2, about 18.6, about 20.2, about 22.5, about 24.6, about 26.8, and about 29.8 degrees 2-theta.

In some embodiments, Form VIII has at least two characteristic XRPD peaks selected from about 9.1, about 15.2, about 16.7, about 18.2, about 18.6, about 20.2, about 22.5, about 24.6, about 26.8, and about 29.8 degrees 2-theta.

In some embodiments, Form VIII has at least three characteristic XRPD peaks selected from about 9.1, about 15.2, about 16.7, about 18.2, about 18.6, about 20.2, about 22.5, about 24.6, about 26.8, and about 29.8 degrees 2-theta.

Figure 24:
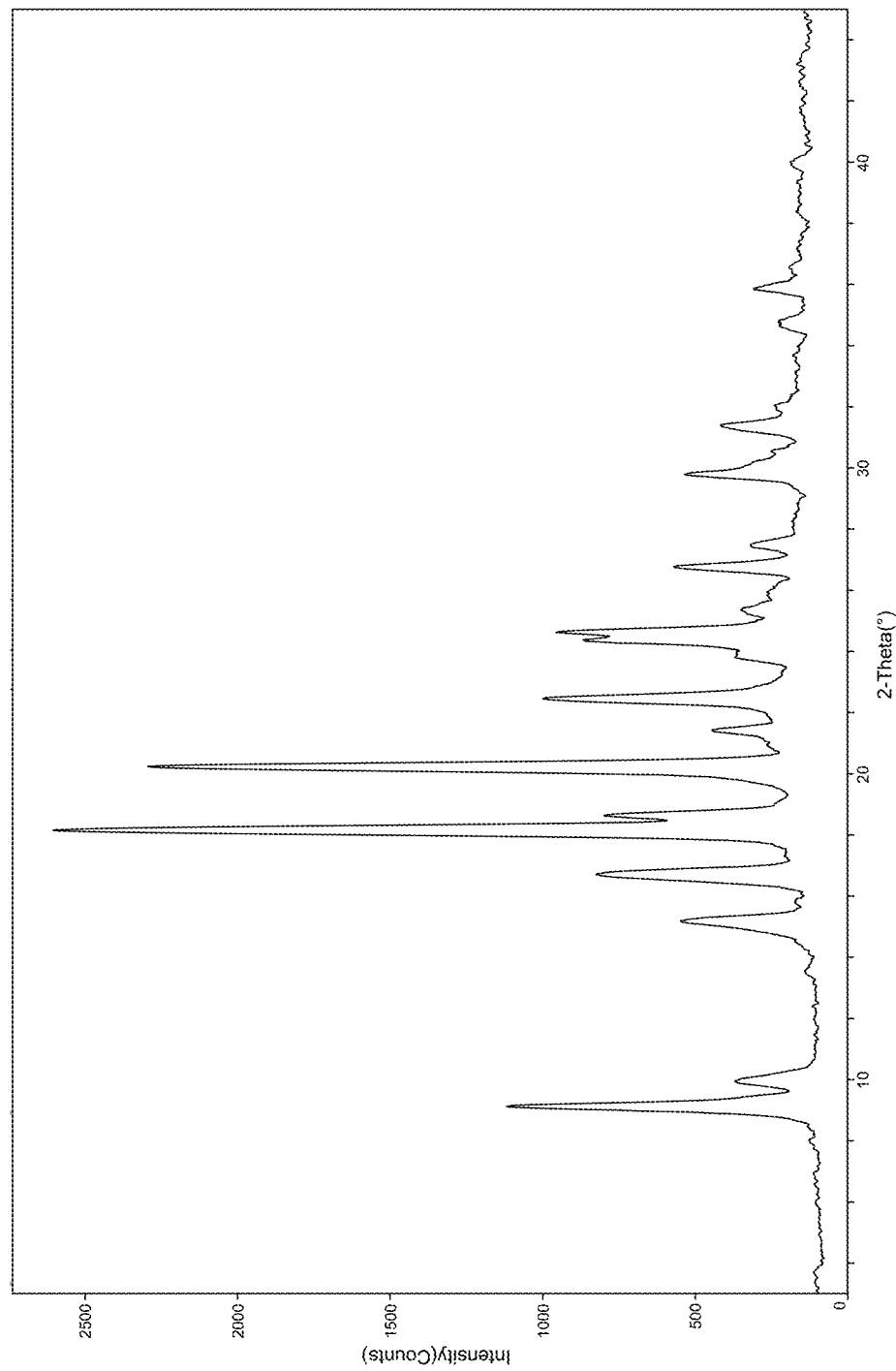
FIG. 24 shows an XRPD pattern of Compound 1, Form VIII.

In some embodiments, Form VIII has an XRPD pattern with characteristic peaks as substantially shown in FIG. 24.

Figure 25:
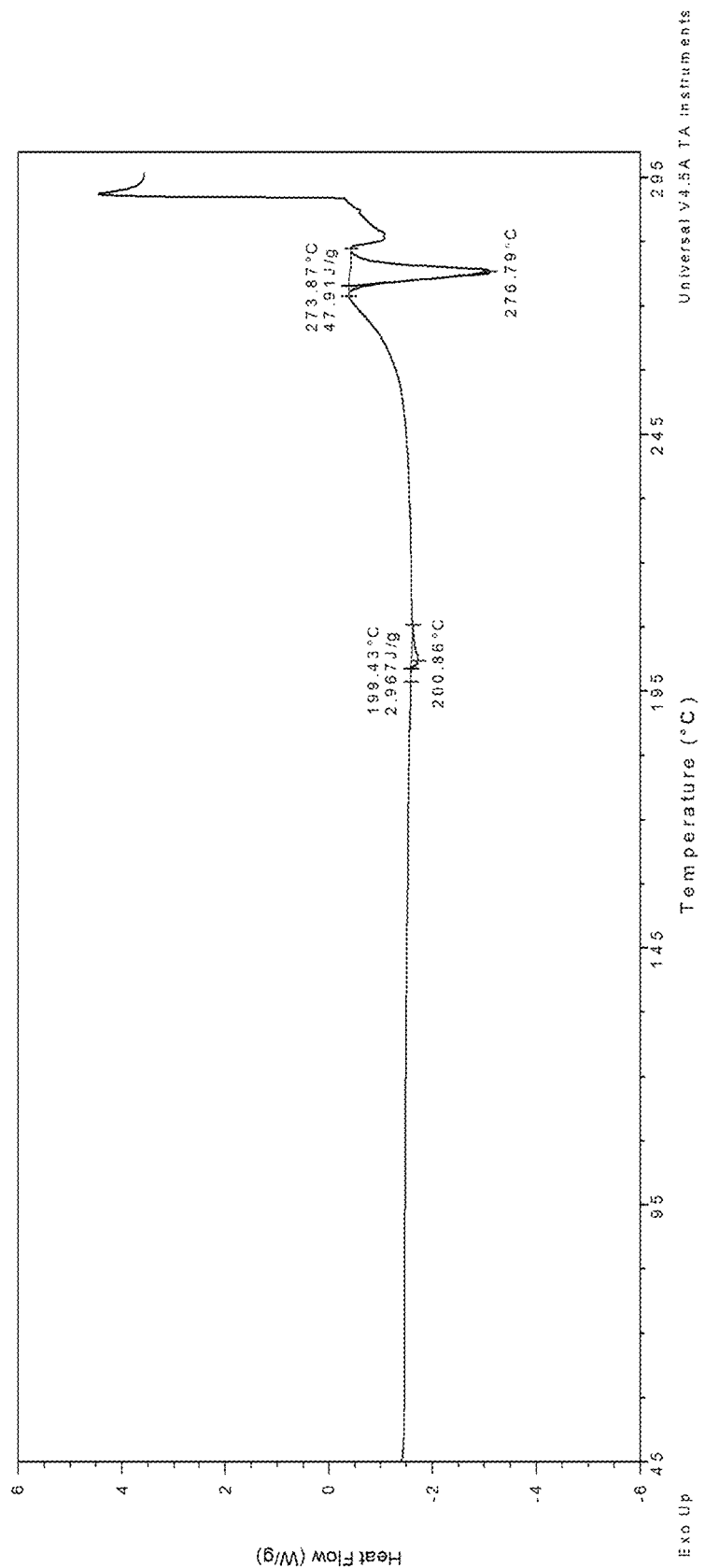
FIG. 25 shows a DSC thermogram of Compound 1, Form VIII.
Figure 26:
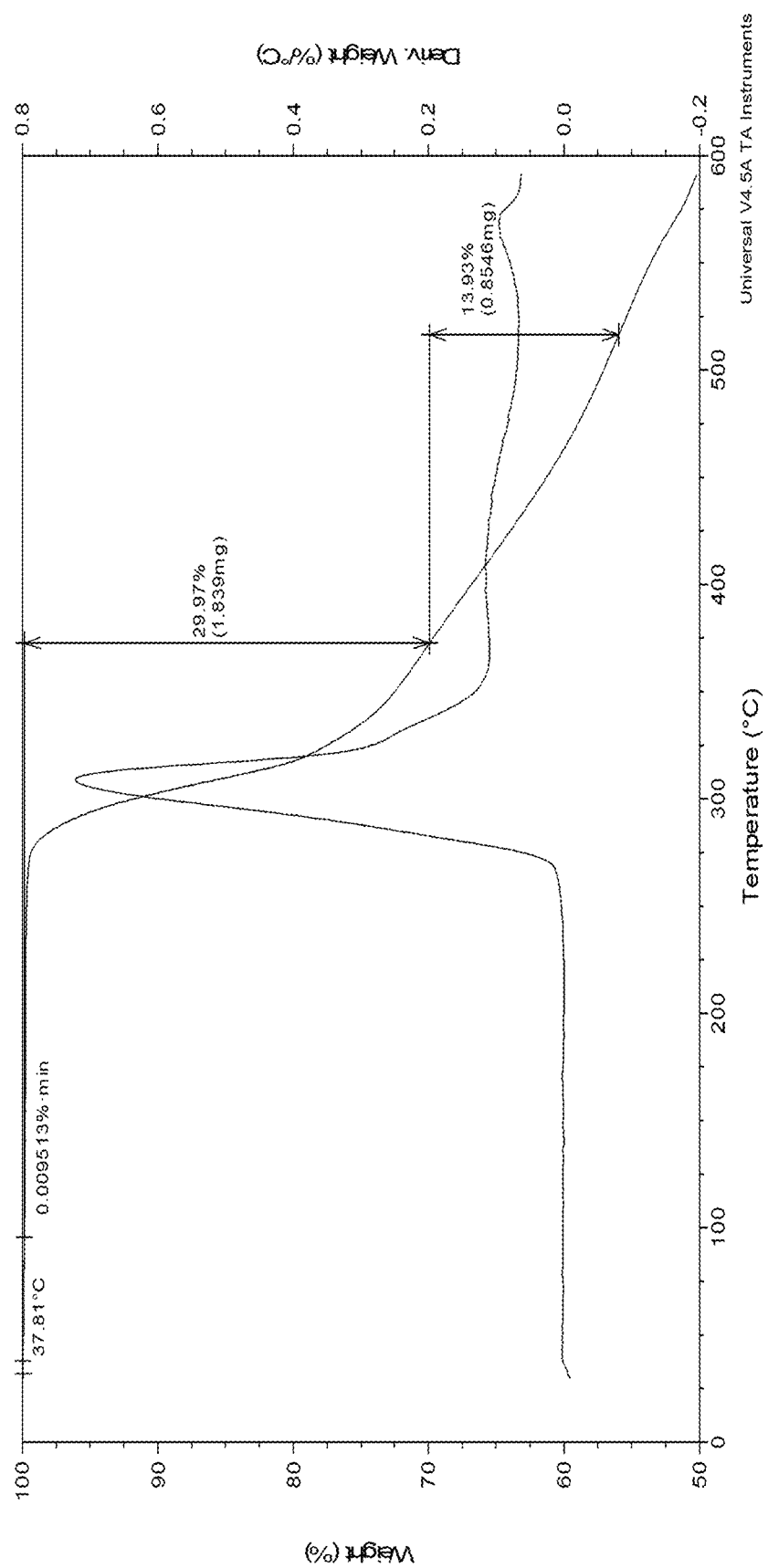
FIG. 26 shows a TGA thermogram of Compound 1, Form VIII.

In some embodiments, Form VIII exhibits a DSC thermogram having endotherm peaks at temperatures of about 201° C., and 277° C. In some embodiments, Form VIII exhibits a DSC thermogram having an endotherm peak at a temperature of about 201° C. In some embodiments, Form VIII exhibits a DSC thermogram having an endotherm peak at a temperature of about 277° C. In some embodiments, Form VIII has a DSC thermogram substantially as depicted in FIG. 25. In some embodiments, Form VIII has a TGA thermogram substantially as depicted in FIG. 26.

In some embodiments, Form VIII has at least one characteristic XRPD peaks selected from about 9.1, about 16.7, about 18.2, about 18.6, and about 20.2 degrees 2-theta; and Form VIII exhibits a DSC thermogram having endotherm peaks at temperatures of about 201° C., and 277° C.

Provided herein are also processes for preparing Form VIII of Compound 1 comprising adding Compound 1, Form I to a solution of Compound 1 in acetone, and stirring at 25±1° C. for 3 days.

In some embodiments, Form VIII can be isolated with a purity of at least about 80%, about 85%, about 90%, about 95%, about 96%, about 97%, about 98%, or about 99%. In some embodiments, Form I can be isolated with a purity greater than about 99%.

Compound 1 Form VIII-a

Provided herein is a solid form of Compound 1 having Form VIII-a, which is described below in the Examples.

In some embodiments, Form VIII-a has at least one characteristic XRPD peaks selected from about 8.9, about 16.2, about 18.0, about 18.4, about 19.9, and about 21.1 degrees 2-theta.

In some embodiments, Form VIII-a has at least two characteristic XRPD peaks selected from about 8.9, about 16.2, about 18.0, about 18.4, about 19.9, and about 21.1 degrees 2-theta.

In some embodiments, Form VIII-a has at least three characteristic XRPD peaks selected from about 8.9, about 16.2, about 18.0, about 18.4, about 19.9, and about 21.1 degrees 2-theta.

In some embodiments, Form VIII-a has at least one characteristic XRPD peak selected from about 8.9, about 16.2, about 18.0, about 18.4, about 19.9, about 21.1, about 22.0, about 23.5, about 24.1, about 24.3, and about 29.5 degrees 2-theta.

In some embodiments, Form VIII-a has at least two characteristic XRPD peaks selected from about 8.9, about 16.2, about 18.0, about 18.4, about 19.9, about 21.1, about 22.0, about 23.5, about 24.1, about 24.3, and about 29.5 degrees 2-theta.

In some embodiments, Form VIII-a has at least three characteristic XRPD peaks selected from about 8.9, about 16.2, about 18.0, about 18.4, about 19.9, about 21.1, about 22.0, about 23.5, about 24.1, about 24.3, and about 29.5 degrees 2-theta.

Figure 27:
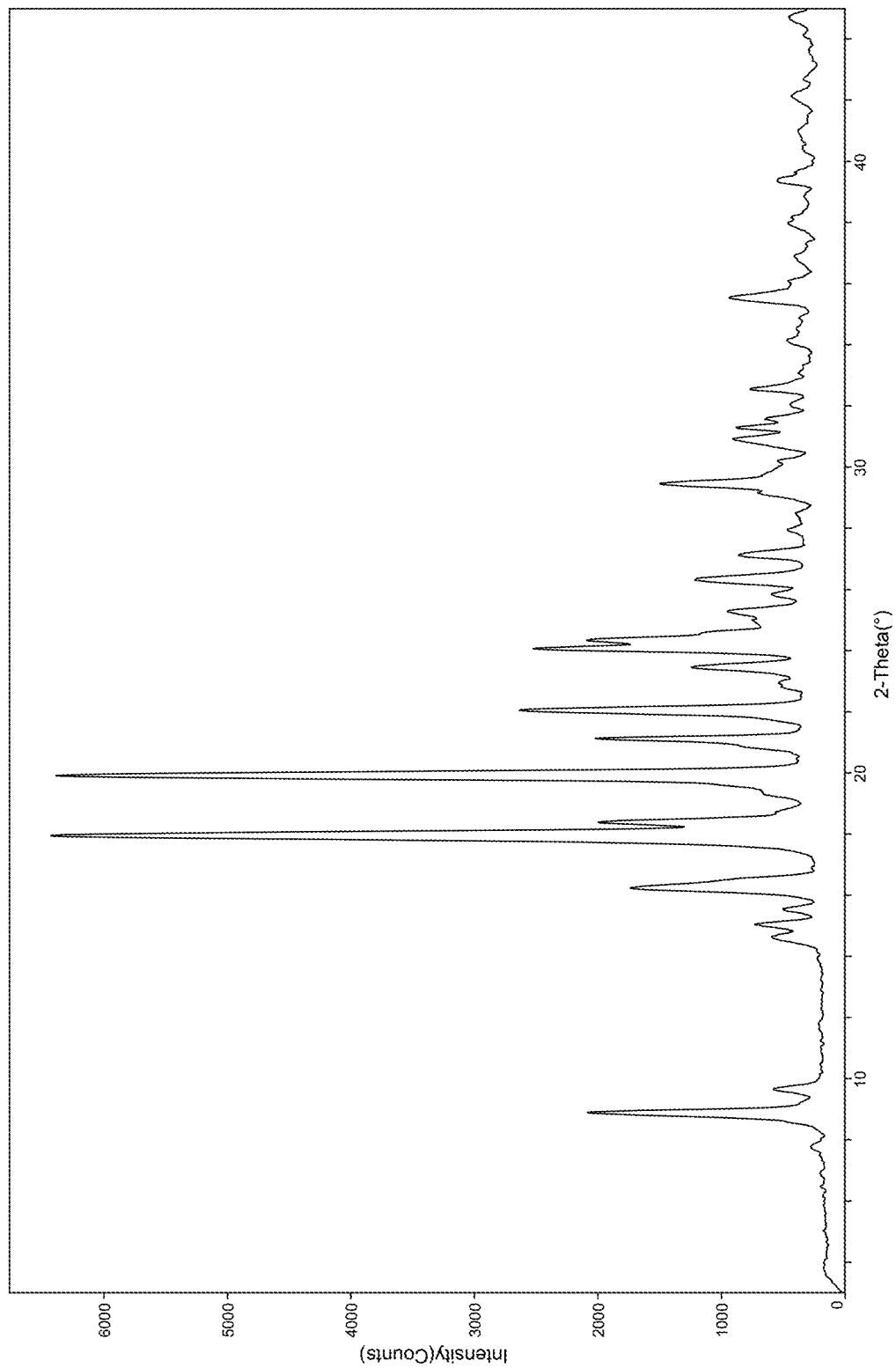
FIG. 27 shows an XRPD pattern of Compound 1, Form VIIIa.

In some embodiments, Form VIII-a has an XRPD pattern with characteristic peaks as substantially shown in FIG. 27.

Provided herein are also processes for preparing Form VIII-a of Compound 1 comprising adding Compound 1, Form I to a cloudy solution of Compound 1 in methyl ethyl ketone, and stirring at 50±1° C. for 3 days.

In some embodiments, Form VIII-a can be isolated with a purity of at least about 80%, about 85%, about 90%, about 95%, about 96%, about 97%, about 98%, or about 99%. In some embodiments, Form I can be isolated with a purity greater than about 99%.

Compound 1 Form IX

Provided herein is a solid form of Compound 1 having Form IX, which is described below in the Examples.

In some embodiments, Form IX has at least one characteristic XRPD peaks selected from about 8.5, about 9.2, about 12.1, about 14.6, about 15.6, about 18.6, about 22.4, and about 22.9 degrees 2-theta.

In some embodiments, Form IX has at least two characteristic XRPD peaks selected from about 8.5, about 9.2, about 12.1, about 14.6, about 15.6, about 18.6, about 22.4, and about 22.9 degrees 2-theta.

In some embodiments, Form IX has at least three characteristic XRPD peaks selected from about 8.5, about 9.2, about 12.1, about 14.6, about 15.6, about 18.6, about 22.4, and about 22.9 degrees 2-theta.

In some embodiments, Form IX has at least one characteristic XRPD peak selected from about 8.5, about 9.2, about 12.1, about 13.9, about 14.6, about 15.6, about 16.8, about 18.6, about 19.3, about 22.4, about 22.9, about 24.6, and about 31.4 degrees 2-theta.

In some embodiments, Form IX has at least two characteristic XRPD peaks selected from about 8.5, about 9.2, about 12.1, about 13.9, about 14.6, about 15.6, about 16.8, about 18.6, about 19.3, about 22.4, about 22.9, about 24.6, and about 31.4 degrees 2-theta.

In some embodiments, Form IX has at least three characteristic XRPD peaks selected from about 8.5, about 9.2, about 12.1, about 13.9, about 14.6, about 15.6, about 16.8, about 18.6, about 19.3, about 22.4, about 22.9, about 24.6, and about 31.4 degrees 2-theta.

Figure 28:
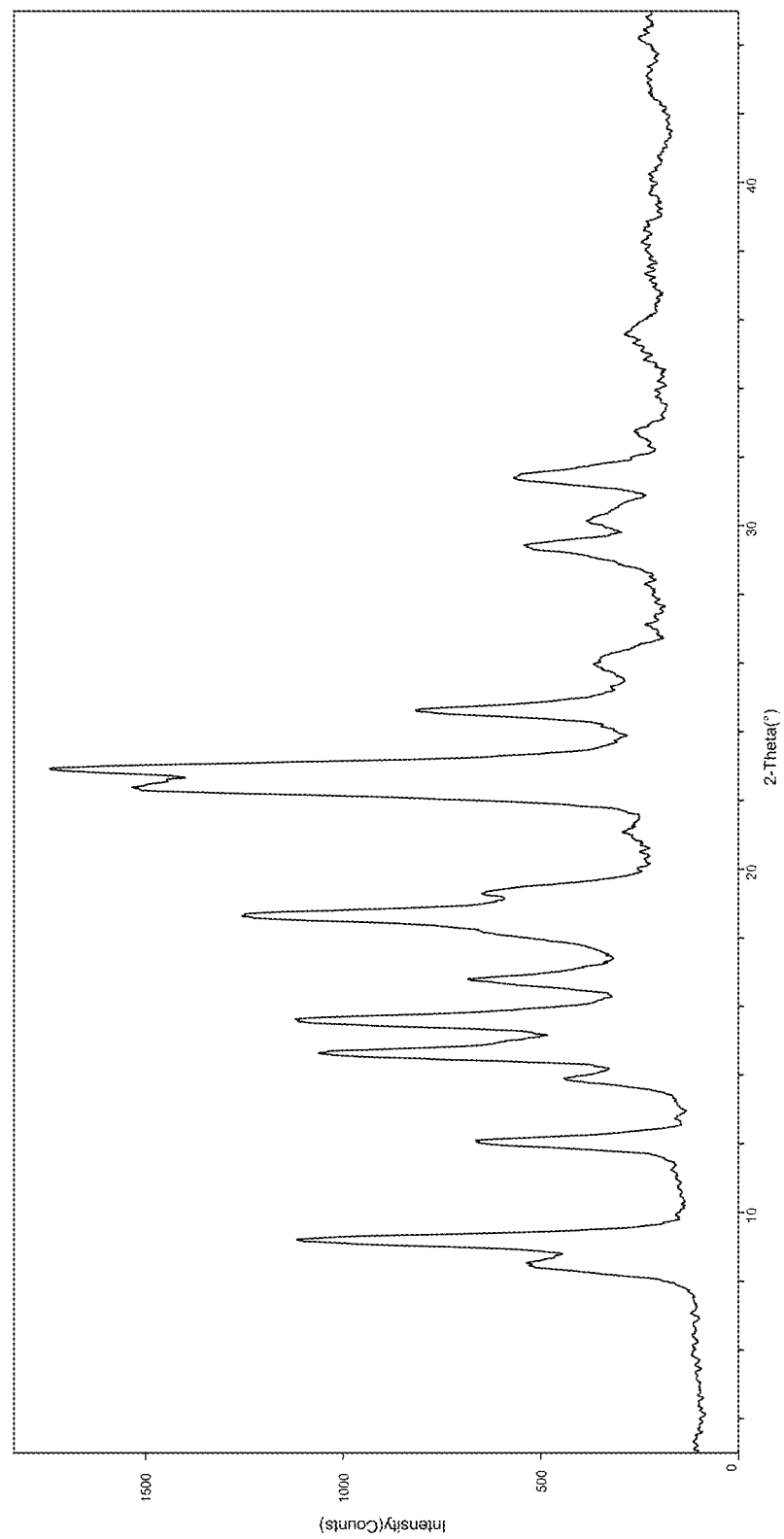
FIG. 28 shows an XRPD pattern of Compound 1, Form IX.

In some embodiments, Form IX has an XRPD pattern with characteristic peaks as substantially shown in FIG. 28.

Figure 29:
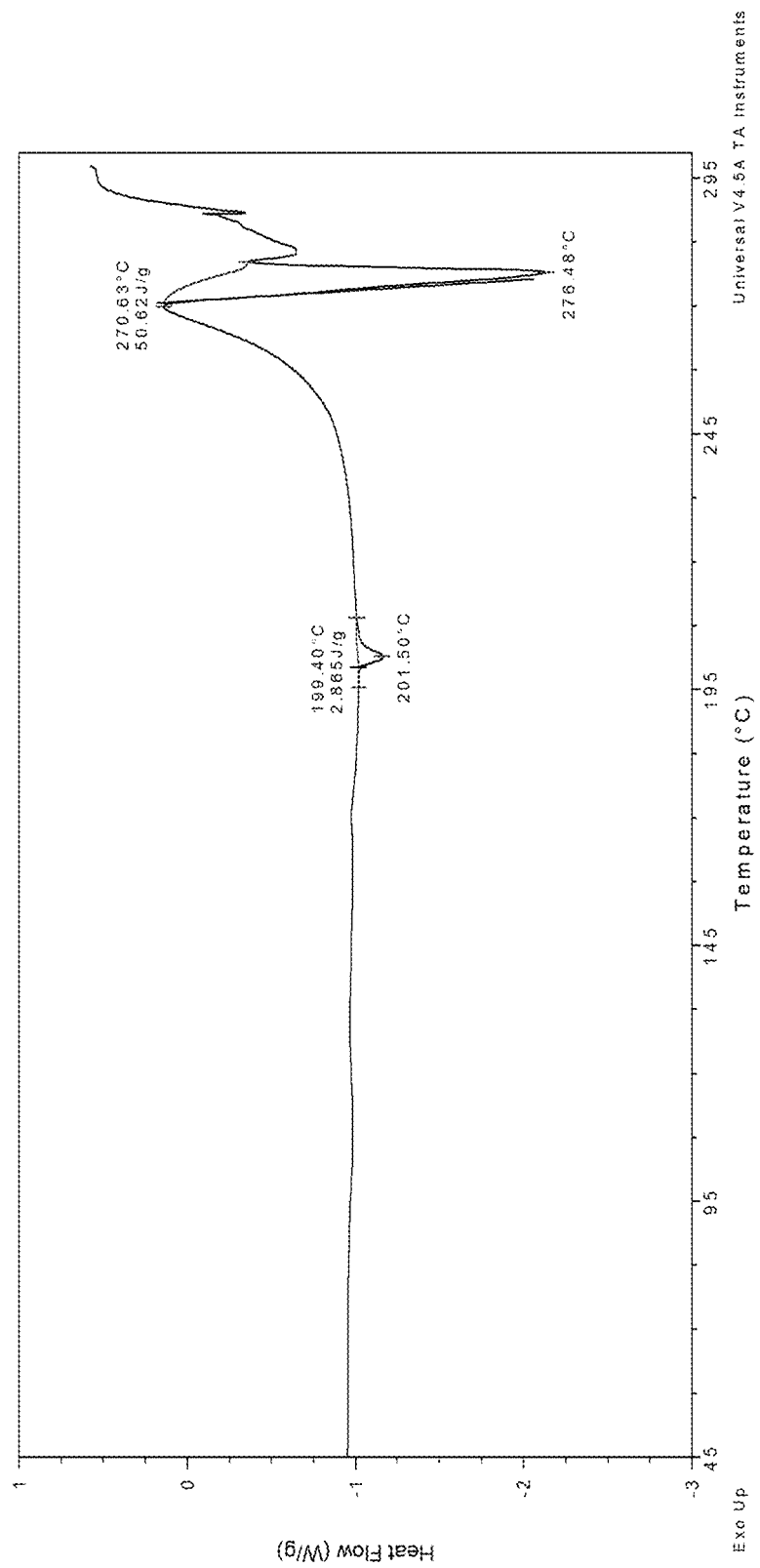
FIG. 29 shows a DSC thermogram of Compound 1, Form IX.
Figure 30:
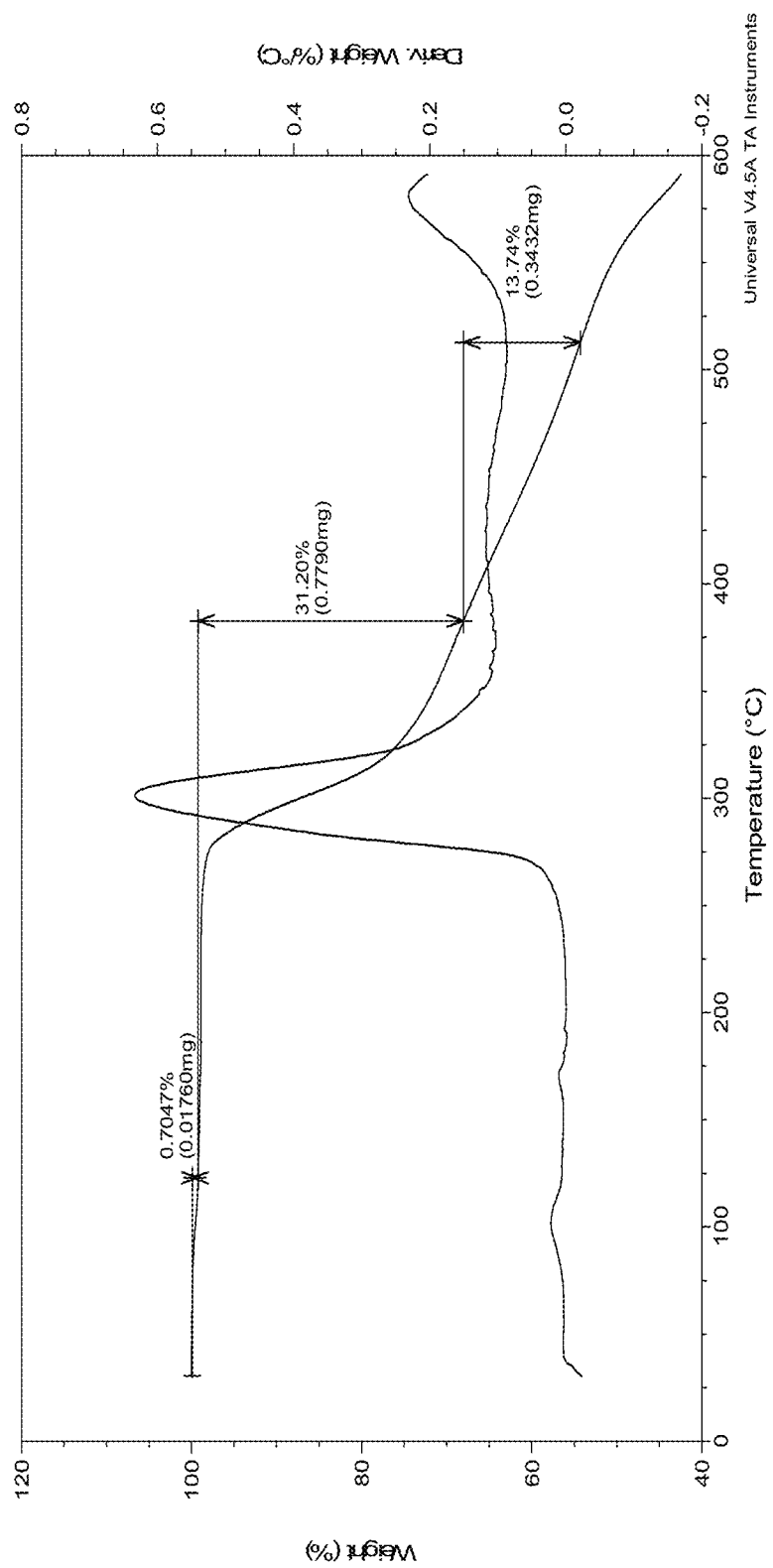
FIG. 30 shows a TGA thermogram of Compound 1, Form IX.

In some embodiments, Form IX exhibits a DSC thermogram having endotherm peaks at temperatures of about 201° C., and 276° C. In some embodiments, Form IX exhibits a DSC thermogram having an endotherm peak at a temperature of about 201° C. In some embodiments, Form IX exhibits a DSC thermogram having an endotherm peak at a temperature of about 276° C. In some embodiments, Form IX has a DSC thermogram substantially as depicted in FIG. 29. In some embodiments, Form IX has a TGA thermogram substantially as depicted in FIG. 30.

In some embodiments, Form IX has at least one characteristic XRPD peaks selected from about 8.5, about 9.2, about 12.1, about 14.6, about 15.6, about 18.6, about 22.4, and about 22.9 degrees 2-theta; and Form IX exhibits a DSC thermogram having endotherm peaks at temperatures of about 201° C., and 276° C.

Provided herein are also processes for preparing Form IX of Compound 1 comprising adding Compound 1, Form I to a cloudy solution of Compound 1, Form I in methyl t-butyl ether, and stirring at 25±1° C. for 3 days.

In some embodiments, Form IX can be isolated with a purity of at least about 80%, about 85%, about 90%, about 95%, about 96%, about 97%, about 98%, or about 99%. In some embodiments, Form I can be isolated with a purity greater than about 99%.

Compound 1 Form X

Provided herein is a solid form of Compound 1 having Form X, which is described below in the Examples.

In some embodiments, Form X has at least one characteristic XRPD peaks selected from about 10.1, about 14.6, about 15.4, about 15.7, about 18.1, and about 22.3 degrees 2-theta.

In some embodiments, Form X has at least two characteristic XRPD peaks selected from about 10.1, about 14.6, about 15.4, about 15.7, about 18.1, and about 22.3 degrees 2-theta.

In some embodiments, Form X has at least three characteristic XRPD peaks selected from about 10.1, about 14.6, about 15.4, about 15.7, about 18.1, and about 22.3 degrees 2-theta. In some embodiments, Form X has at least one characteristic XRPD peak selected from about 4.9, about 10.1, about 11.3, about 14.6, about 15.4, about 15.7, about 17.2, about 18.1, about 19.5, about 20.0, about 22.3, about 23.8, about 25.3, about 25.7, and about 26.3 degrees 2-theta.

In some embodiments, Form X has at least two characteristic XRPD peaks selected from about 4.9, about 10.1, about 11.3, about 14.6, about 15.4, about 15.7, about 17.2, about 18.1, about 19.5, about 20.0, about 22.3, about 23.8, about 25.3, about 25.7, and about 26.3 degrees 2-theta.

In some embodiments, Form X has at least three characteristic XRPD peaks selected from about 4.9, about 10.1, about 11.3, about 14.6, about 15.4, about 15.7, about 17.2, about 18.1, about 19.5, about 20.0, about 22.3, about 23.8, about 25.3, about 25.7, and about 26.3 degrees 2-theta.

Figure 31:
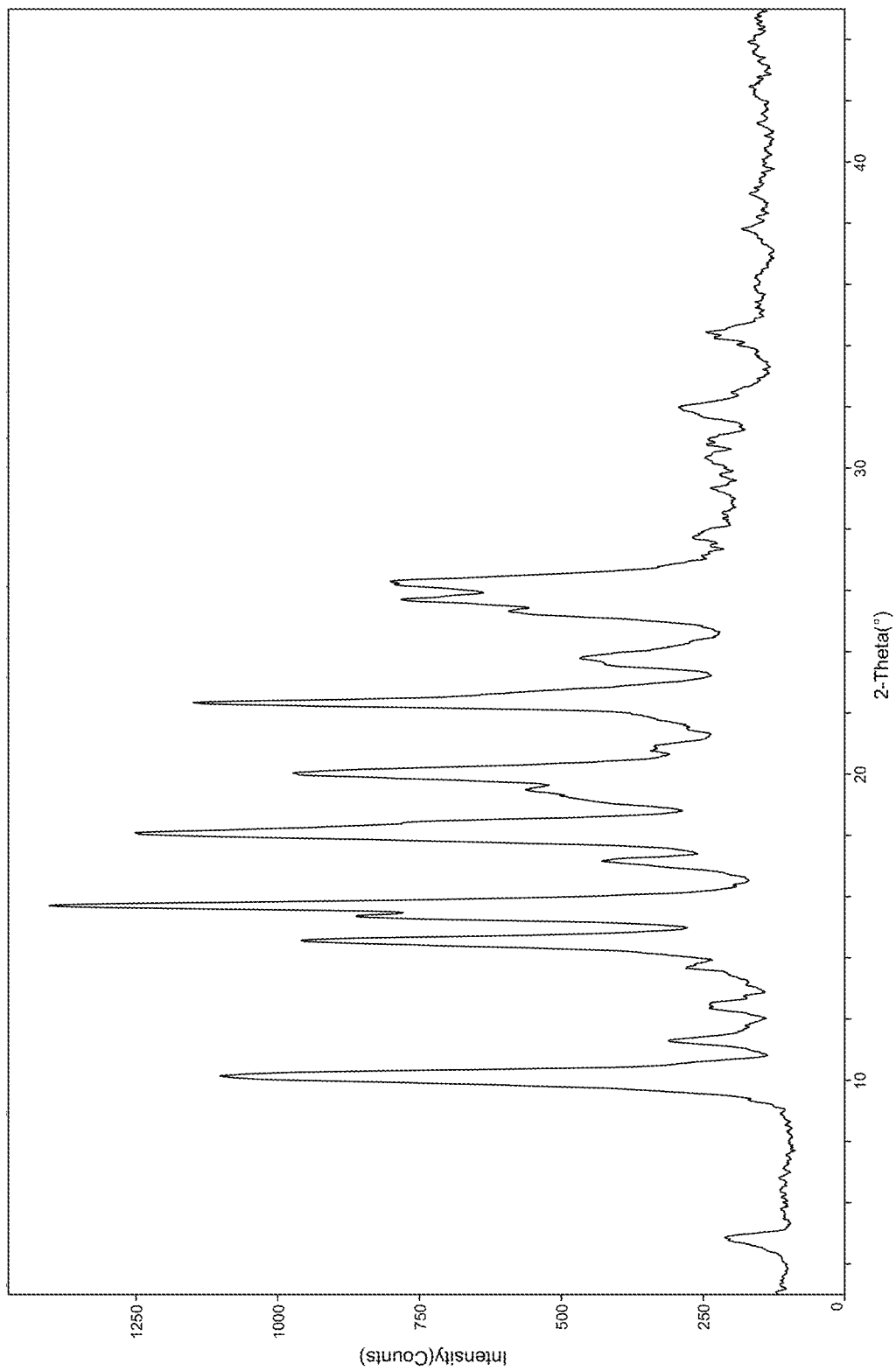
FIG. 31 shows an XRPD pattern of Compound 1, Form X.

In some embodiments, Form X has an XRPD pattern with characteristic peaks as substantially shown in FIG. 31.

In some embodiments, Form X exhibits a DSC thermogram having endotherm peaks at temperatures of about 202° C., and 276° C. In some embodiments, Form X exhibits a DSC thermogram having an endotherm peak at a temperature of about 202° C. In some embodiments, Form X exhibits a DSC thermogram having an endotherm peak at a temperature of about 276° C.

Figure 32:
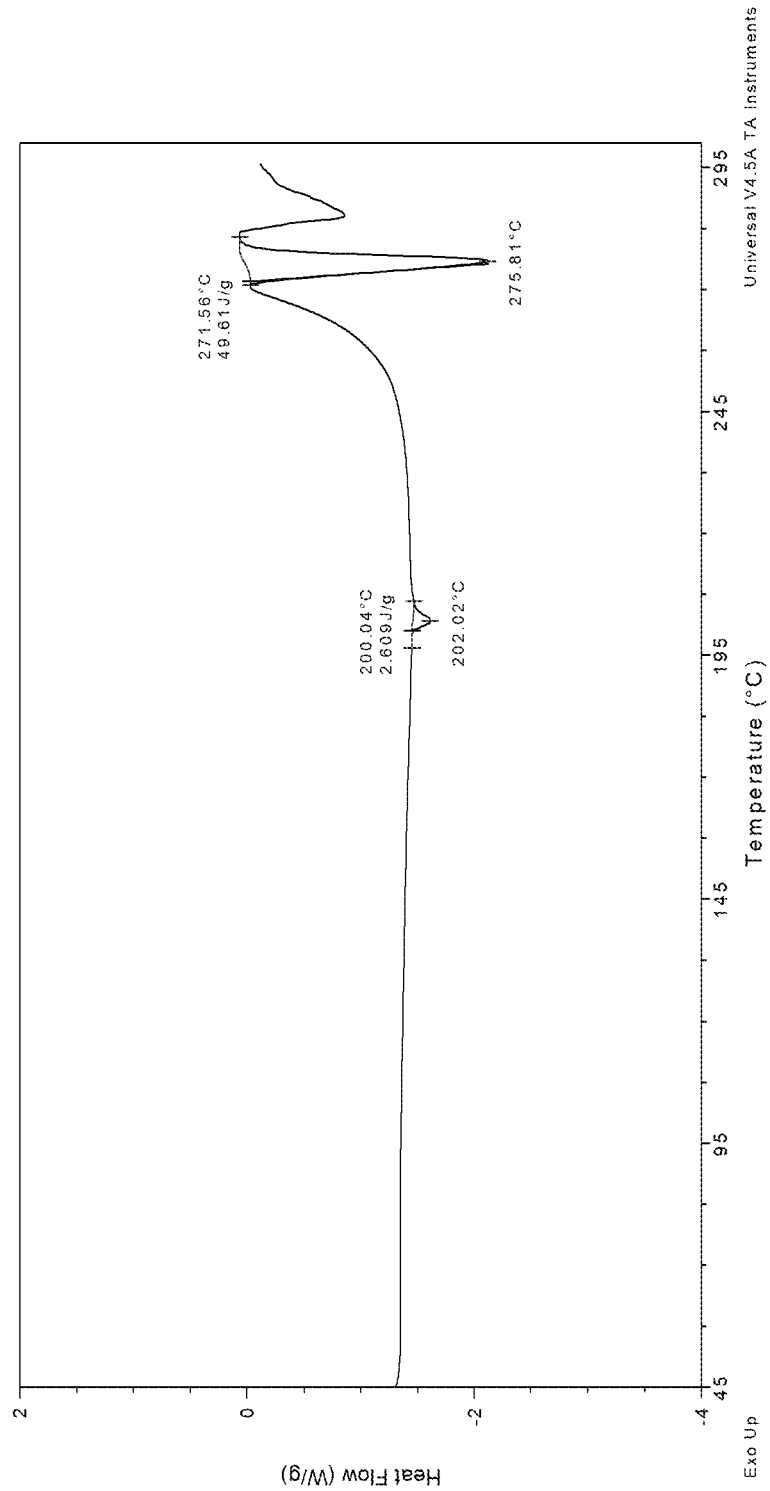
FIG. 32 shows a DSC thermogram of Compound 1, Form X.
Figure 33:
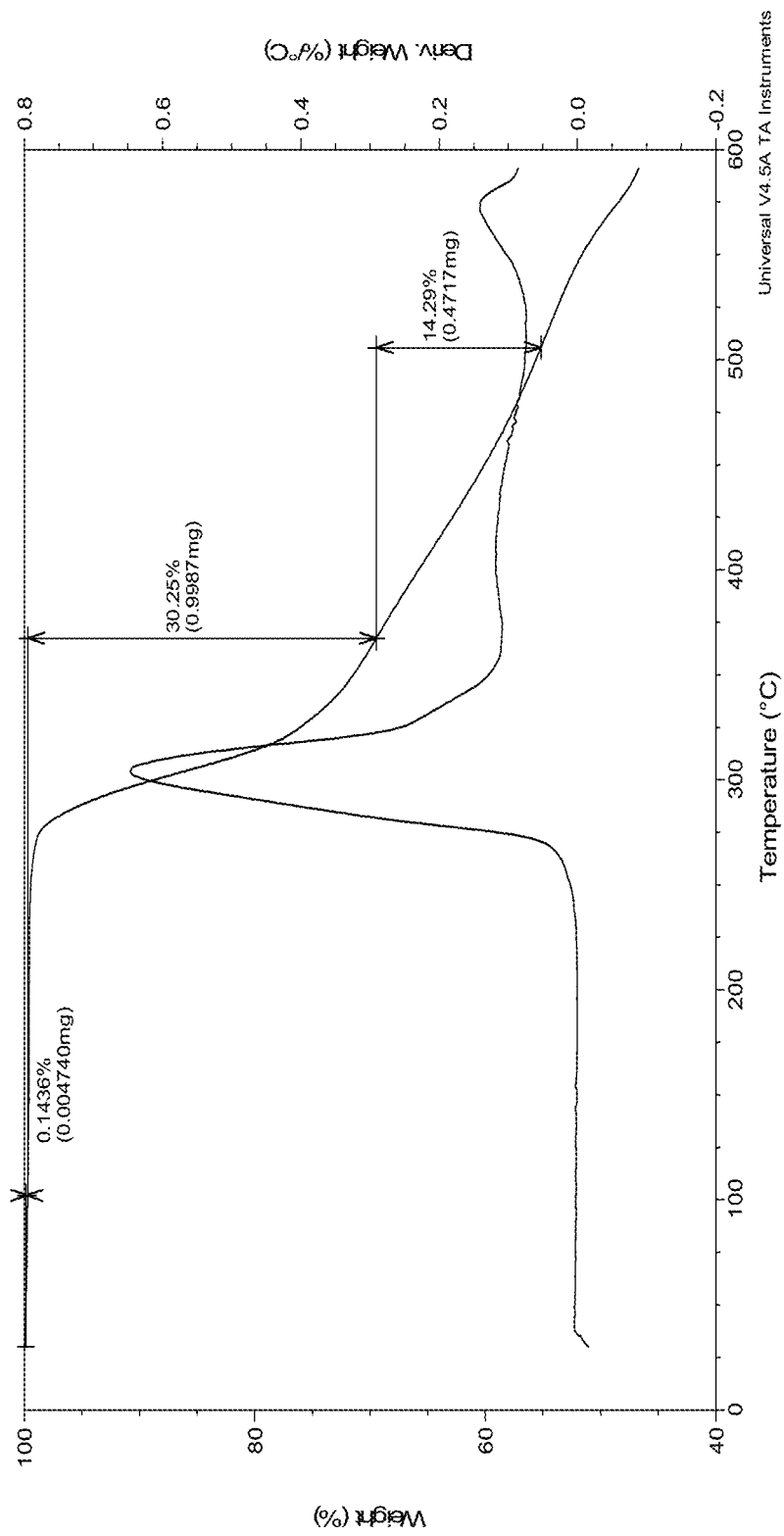
FIG. 33 shows a TGA thermogram of Compound 1, Form X.

In some embodiments, Form X has a DSC thermogram substantially as depicted in FIG. 32. In some embodiments, Form X has a TGA thermogram substantially as depicted in FIG. 33.

In some embodiments, Form X has at least one characteristic XRPD peaks selected from about 10.1, about 14.6, about 15.4, about 15.7, about 18.1, and about 22.3 degrees 2-theta; and Form X exhibits a DSC thermogram having endotherm peaks at temperatures of about 202° C., and 276° C.

Provided herein are also processes for preparing Form X of Compound 1 comprising adding Compound 1, Form I to a cloudy solution of Compound 1, Form I in ethyl acetate, and stirring at 25±1° C. for 3 days.

In some embodiments, Form X can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XI

Provided herein is a solid form of Compound 1 having Form XI, which is described below in the Examples.

In some embodiments, Form XI has at least one characteristic XRPD peaks selected from about 3.9, about 7.5, about 13.0, about 17.3, about 21.4, and about 22.8 degrees 2-theta.

In some embodiments, Form XI has at least two characteristic XRPD peaks selected from about 3.9, about 7.5, about 13.0, about 17.3, about 21.4, and about 22.8 degrees 2-theta.

In some embodiments, Form XI has at least three characteristic XRPD peaks selected from about 3.9, about 7.5, about 13.0, about 17.3, about 21.4, and about 22.8 degrees 2-theta.

In some embodiments, Form XI has at least one characteristic XRPD peak selected from about 3.9, about 4.3, about 7.5, about 13.0, about 13.7, about 15.0, about 16.5, about 17.3, about 19.1, about 19.9, about 21.4, about 22.2, about 22.8, about 25.2, and about 26.9 degrees 2-theta.

In some embodiments, Form XI has at least two characteristic XRPD peaks selected from about 3.9, about 4.3, about 7.5, about 13.0, about 13.7, about 15.0, about 16.5, about 17.3, about 19.1, about 19.9, about 21.4, about 22.2, about 22.8, about 25.2, and about 26.9 degrees 2-theta.

In some embodiments, Form XI has at least three characteristic XRPD peaks selected from about 3.9, about 4.3, about 7.5, about 13.0, about 13.7, about 15.0, about 16.5, about 17.3, about 19.1, about 19.9, about 21.4, about 22.2, about 22.8, about 25.2, and about 26.9 degrees 2-theta.

Figure 34:
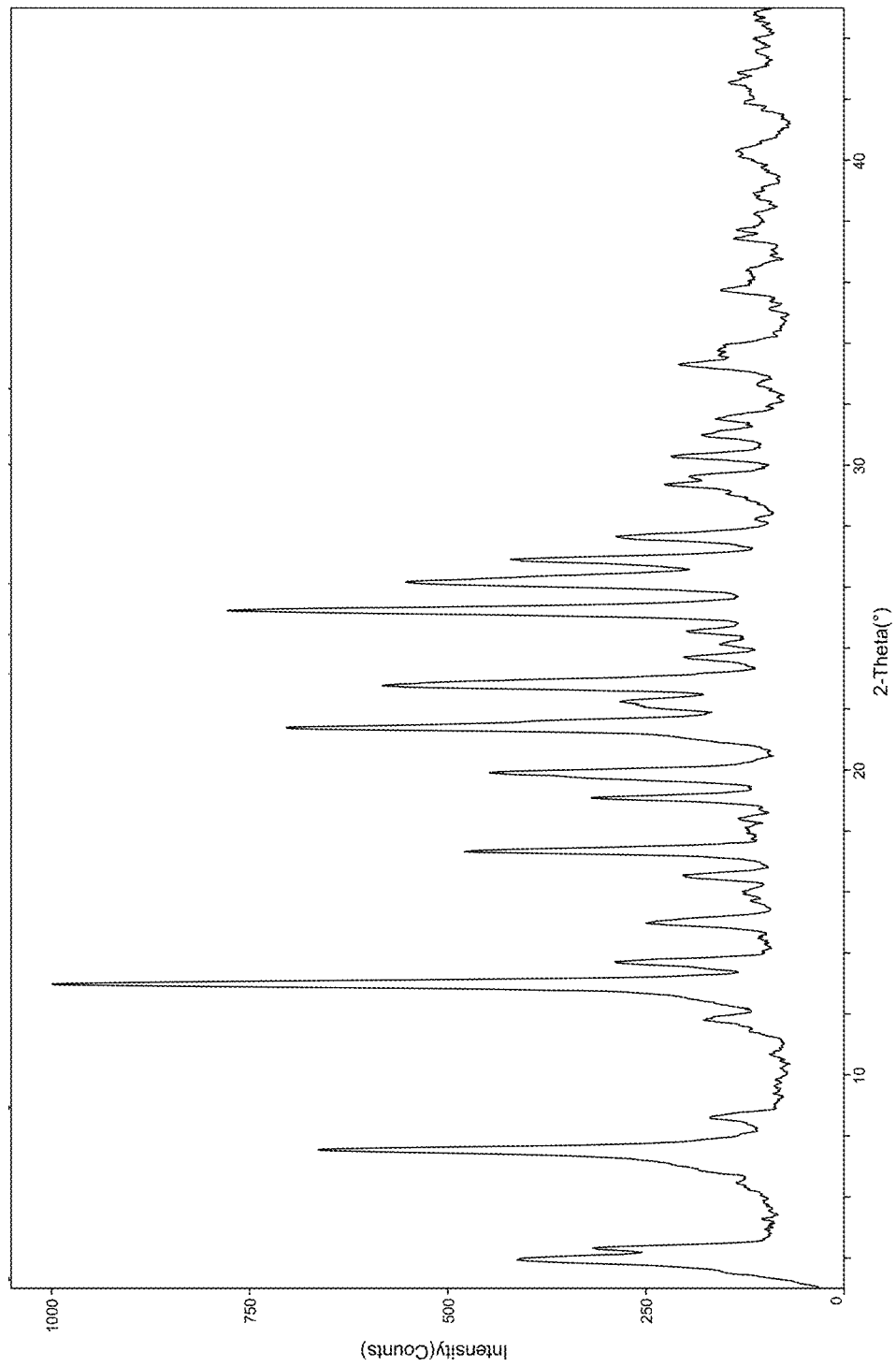
FIG. 34 shows an XRPD pattern of Compound 1, Form XI.

In some embodiments, Form XI has an XRPD pattern with characteristic peaks as substantially shown in FIG. 34.

Figure 35:
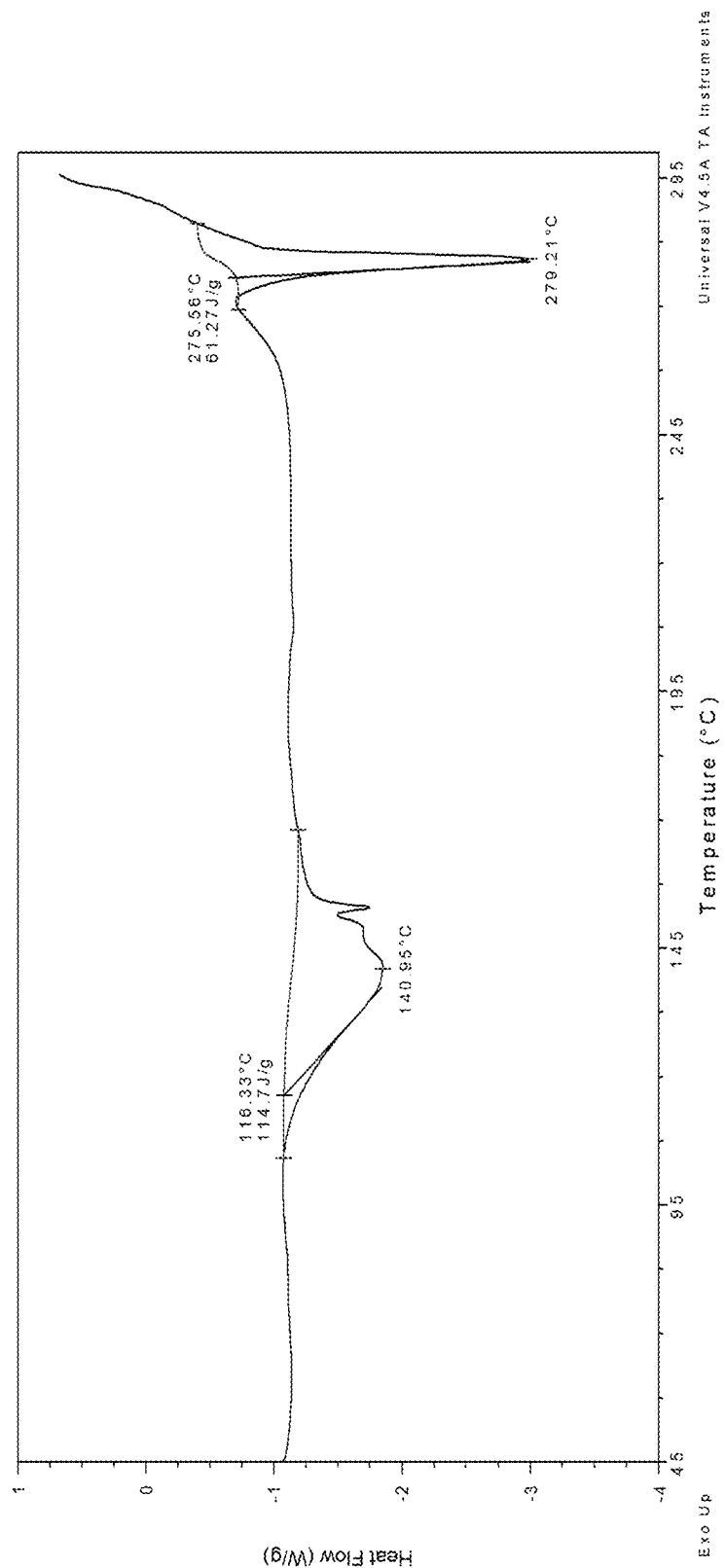
FIG. 35 shows a DSC thermogram of Compound 1, Form XI.
Figure 36:
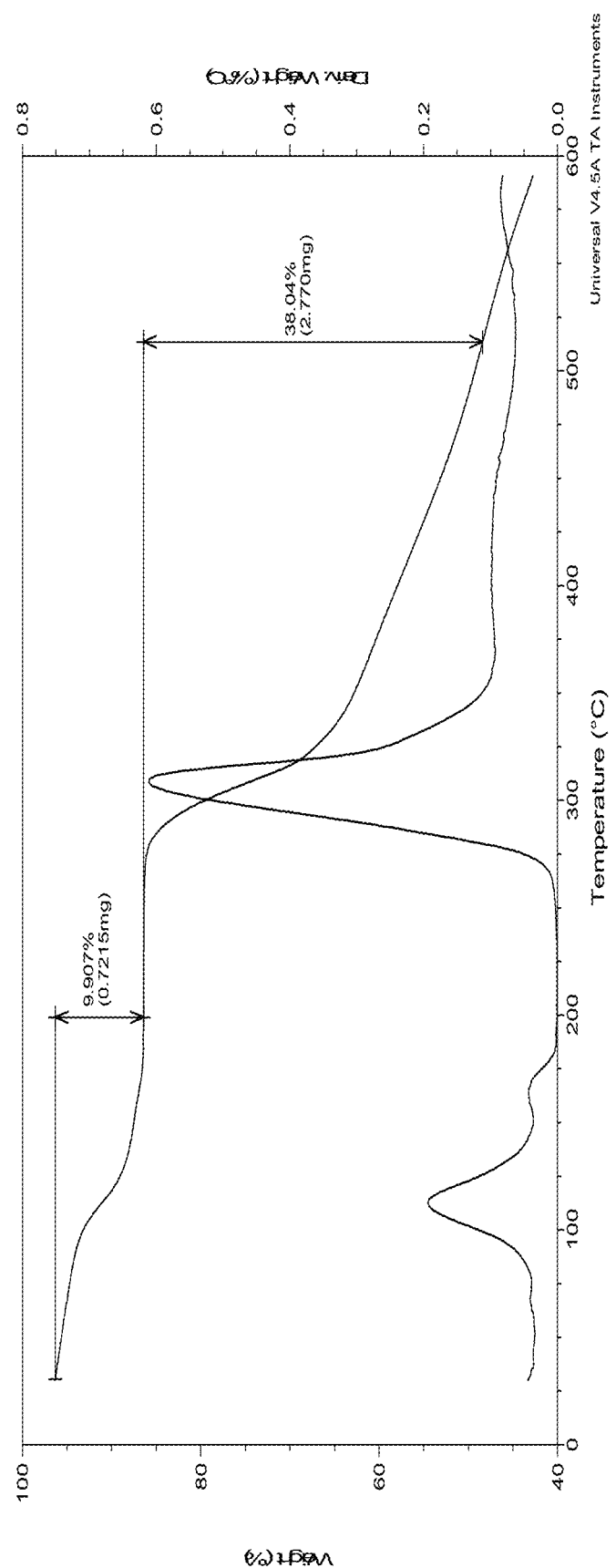
FIG. 36 shows a TGA thermogram of Compound 1, Form XI.

In some embodiments, Form XI exhibits a DSC thermogram having endotherm peaks at temperatures of about 141° C., and 279° C. In some embodiments, Form XI exhibits a DSC thermogram having an endotherm peak at a temperature of about 141° C. In some embodiments, Form XI exhibits a DSC thermogram having an endotherm peak at a temperature of about 279° C. In some embodiments, Form XI has a DSC thermogram substantially as depicted in FIG. 35. In some embodiments, Form XI has a TGA thermogram substantially as depicted in FIG. 36.

In some embodiments, Form XI has at least one characteristic XRPD peaks selected from about 3.9, about 7.5, about 13.0, about 17.3, about 21.4, and about 22.8 degrees 2-theta; and Form XI exhibits a DSC thermogram having endotherm peaks at temperatures of about 141° C., and 279° C.

Provided herein are also processes for preparing Form XI of Compound 1 comprising adding Compound 1, Form I to a 5 mL cloudy solution of Compound 1, Form I in ethyl formate, and stirring at 25±1° C. for 3 days.

In some embodiments, Form XI can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XII

Provided herein is a solid form of Compound 1 having Form XII, which is described below in the Examples.

In some embodiments, Form XII has at least one characteristic XRPD peaks selected from about 7.5, about 14.1, about 17.3, about 18.3, about 22.1, and about 22.7 degrees 2-theta.

In some embodiments, Form XII has at least two characteristic XRPD peaks selected from about 7.5, about 14.1, about 17.3, about 18.3, about 22.1, and about 22.7 degrees 2-theta.

In some embodiments, Form XII has at least three characteristic XRPD peaks selected from about 7.5, about 14.1, about 17.3, about 18.3, about 22.1, and about 22.7 degrees 2-theta.

In some embodiments, Form XII has at least one characteristic XRPD peak selected from about 3.9, about 7.5, about 9.8, about 11.5, about 12.9, about 14.1, about 17.3, about 18.3, about 22.1, about 22.7, about 24.3, about 26.3, and about 26.9 degrees 2-theta.

In some embodiments, Form XII has at least two characteristic XRPD peaks selected from about 3.9, about 7.5, about 9.8, about 11.5, about 12.9, about 14.1, about 17.3, about 18.3, about 22.1, about 22.7, about 24.3, about 26.3, and about 26.9 degrees 2-theta.

In some embodiments, Form XII has at least three characteristic XRPD peaks selected from about 3.9, about 7.5, about 9.8, about 11.5, about 12.9, about 14.1, about 17.3, about 18.3, about 22.1, about 22.7, about 24.3, about 26.3, and about 26.9 degrees 2-theta.

Figure 37:
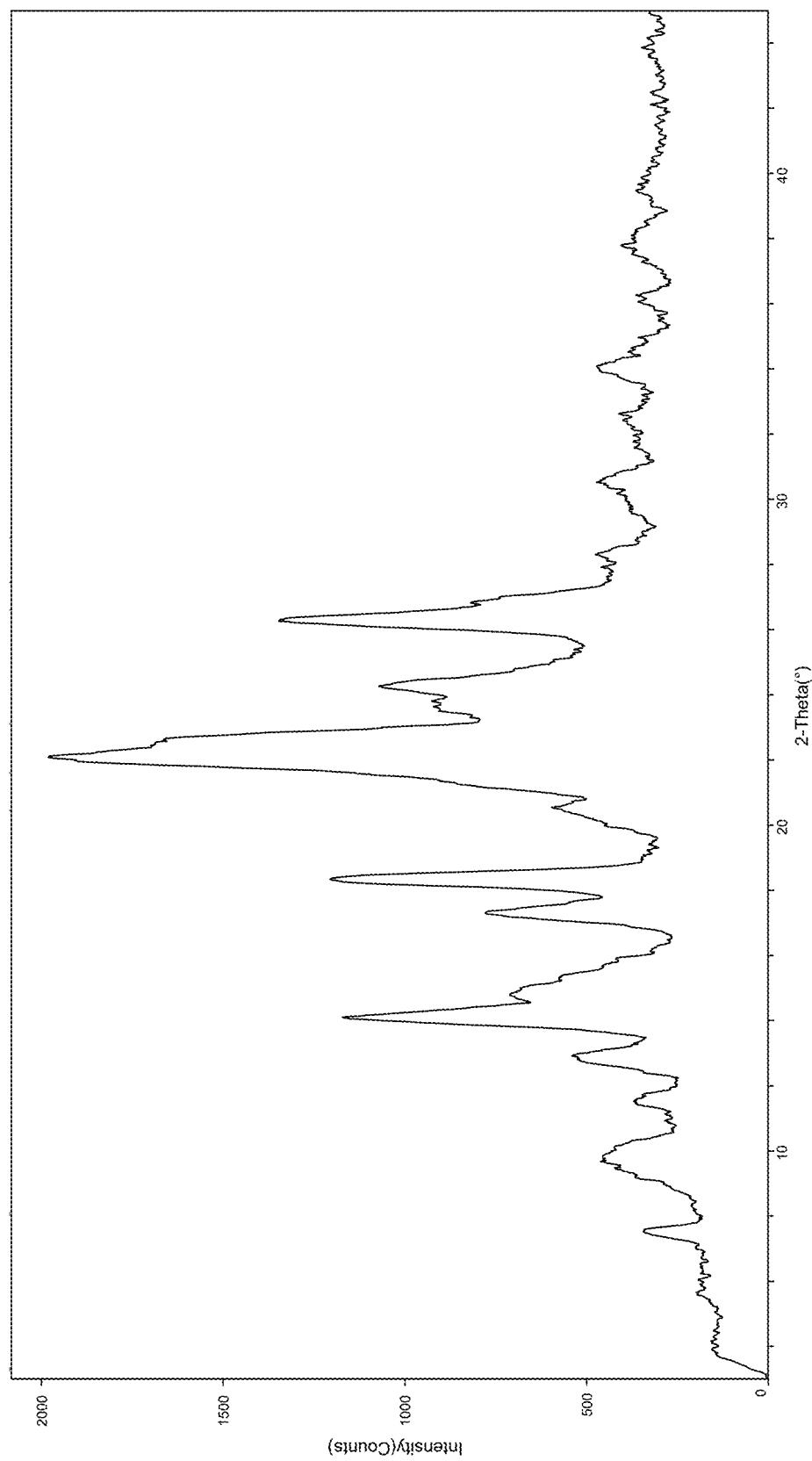
FIG. 37 shows an XRPD pattern of Compound 1, Form XII.

In some embodiments, Form XII has an XRPD pattern with characteristic peaks as substantially shown in FIG. 37.

Figure 38:
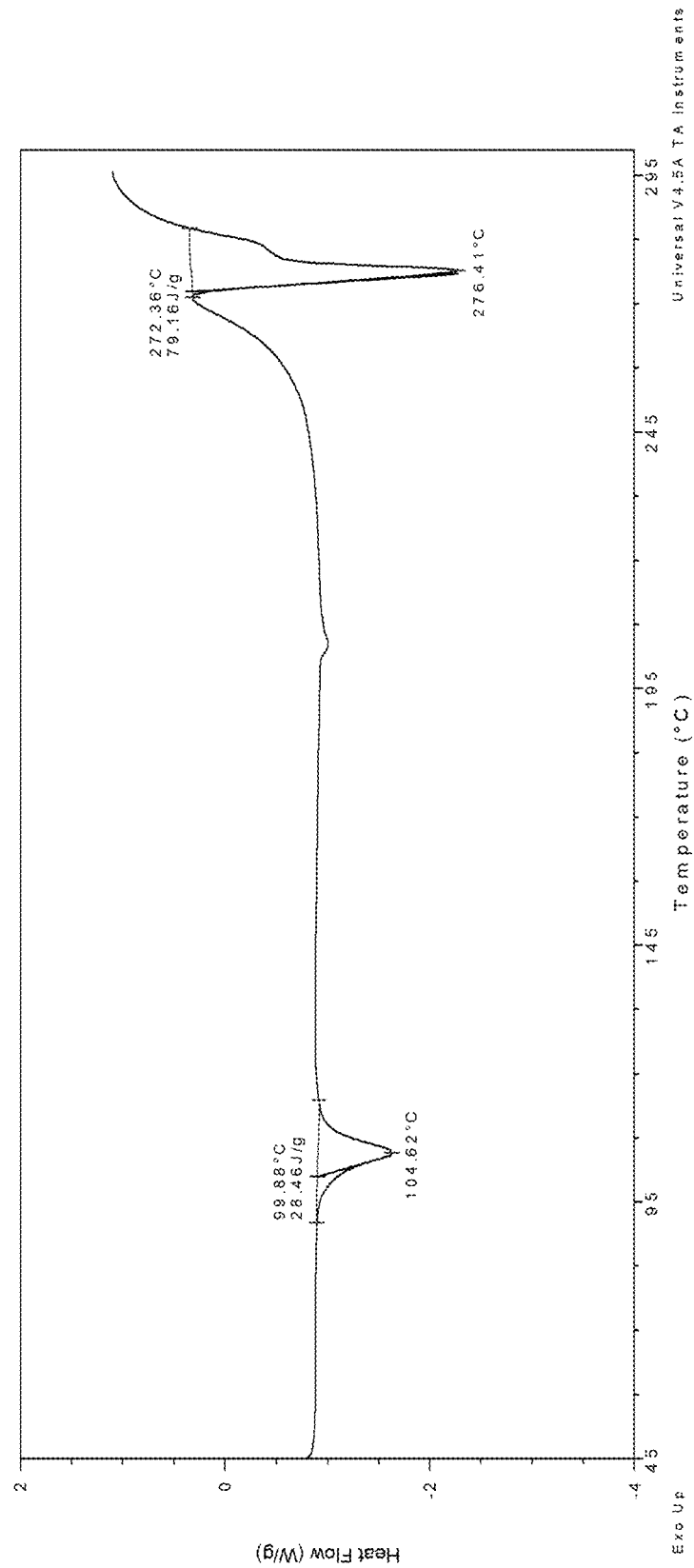
FIG. 38 shows a DSC thermogram of Compound 1, Form XII.
Figure 39:
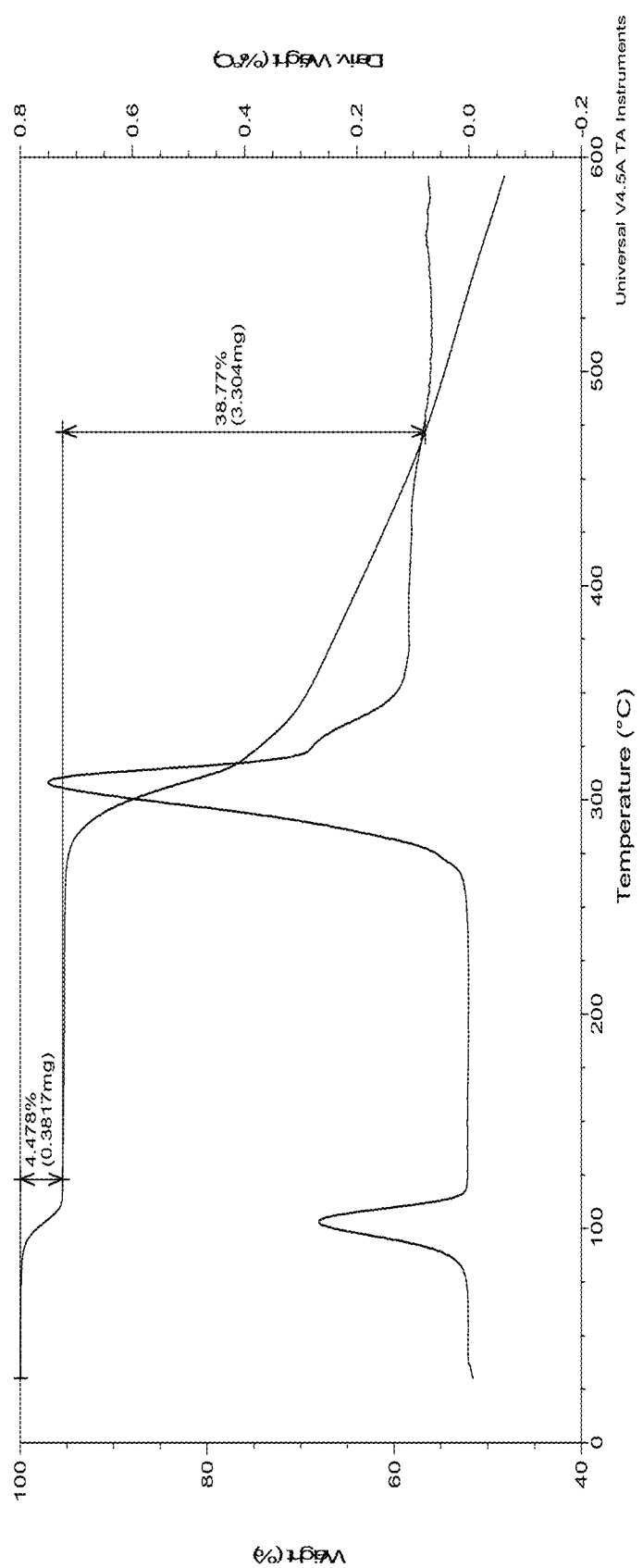
FIG. 39 shows a TGA thermogram of Compound 1, Form XII.

In some embodiments, Form XII exhibits a DSC thermogram having endotherm peaks at temperatures of about 105° C., and 276° C. In some embodiments, Form XII exhibits a DSC thermogram having an endotherm peak at a temperature of about 105° C. In some embodiments, Form XII exhibits a DSC thermogram having an endotherm peak at a temperature of about 276° C. In some embodiments, Form XII has a DSC thermogram substantially as depicted in FIG. 38. In some embodiments, Form XII has a TGA thermogram substantially as depicted in FIG. 39.

In some embodiments, Form XII has at least one characteristic XRPD peaks selected from about 7.5, about 14.1, about 17.3, about 18.3, about 22.1, and about 22.7 degrees 2-theta; and Form XII exhibits a DSC thermogram having endotherm peaks at temperatures of about 105° C., and 276° C.

Provided herein are also processes for preparing Form XII of Compound 1 comprising adding Compound 1, Form I to a cloudy solution of Compound 1, Form I prepared in 1,4-dioxane, and stirring at 50±1° C. for 2 days.

In some embodiments, Form XII can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XIII

Provided herein is a solid form of Compound 1 having Form XIII, which is described below in the Examples.

In some embodiments, Form XIII has at least one characteristic XRPD peaks selected from about 7.7, about 15.2, about 15.7, about 21.9, about 23.1, and about 26.1 degrees 2-theta.

In some embodiments, Form XIII has at least two characteristic XRPD peaks selected from about 7.7, about 15.2, about 15.7, about 21.9, about 23.1, and about 26.1 degrees 2-theta.

In some embodiments, Form XIII has at least three characteristic XRPD peaks selected from about 7.7, about 15.2, about 15.7, about 21.9, about 23.1, and about 26.1 degrees 2-theta.

In some embodiments, Form XIII has at least one characteristic XRPD peak selected from about 4.0, about 7.7, about 10.9, about 11.6, about 14.2, about 15.2, about 15.7, about 17.8, about 19.0, about 21.9, about 22.2, about 23.1, about 25.6, and about 26.1 degrees 2-theta.

In some embodiments, Form XIII has at least two characteristic XRPD peaks selected from about 4.0, about 7.7, about 10.9, about 11.6, about 14.2, about 15.2, about 15.7, about 17.8, about 19.0, about 21.9, about 22.2, about 23.1, about 25.6, and about 26.1 degrees 2-theta.

In some embodiments, Form XIII has at least three characteristic XRPD peaks selected from about 4.0, about 7.7, about 10.9, about 11.6, about 14.2, about 15.2, about 15.7, about 17.8, about 19.0, about 21.9, about 22.2, about 23.1, about 25.6, and about 26.1 degrees 2-theta.

Figure 40:
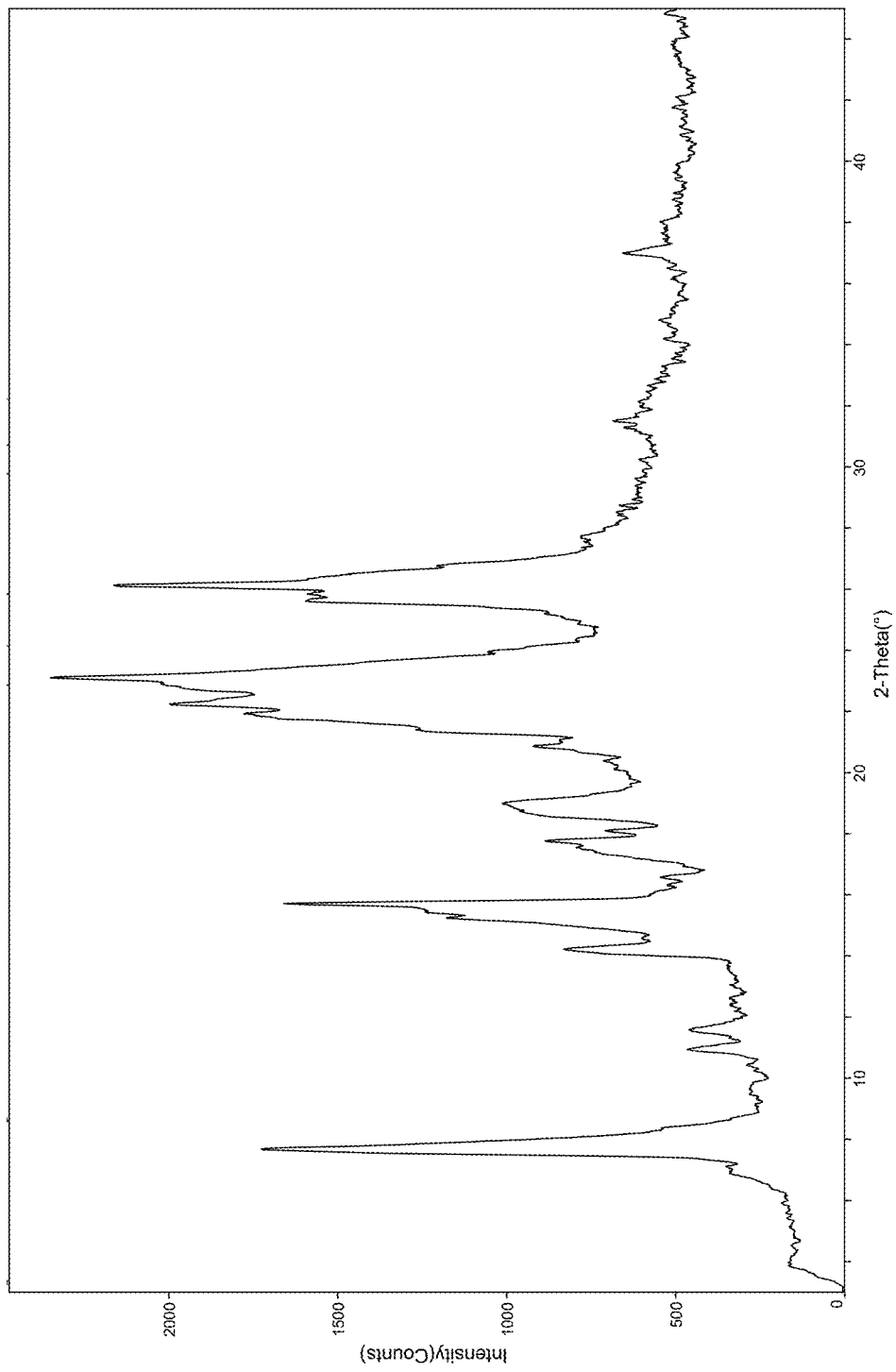
FIG. 40 shows an XRPD pattern of Compound 1, Form XIII.

In some embodiments, Form XIII has an XRPD pattern with characteristic peaks as substantially shown in FIG. 40.

Figure 41:
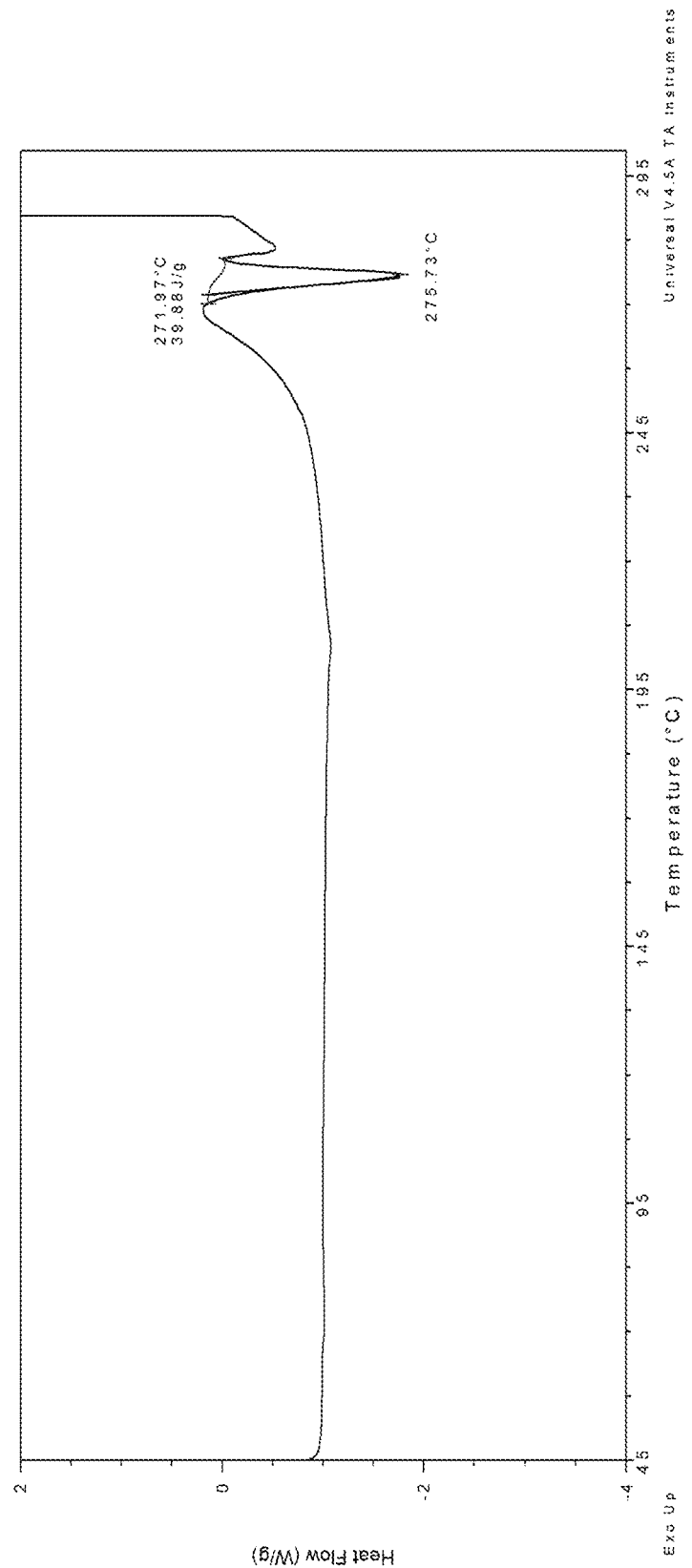
FIG. 41 shows a DSC thermogram of Compound 1, Form XIII.
Figure 42:
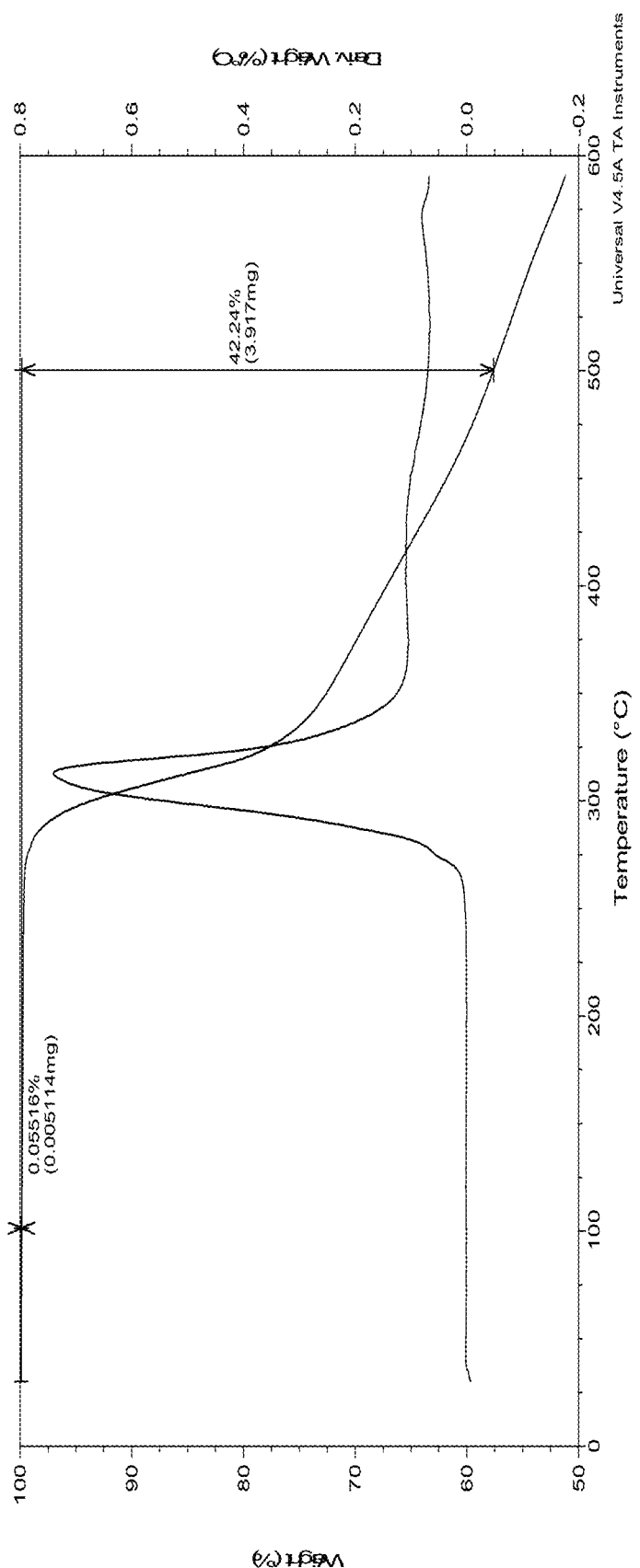
FIG. 42 shows a TGA thermogram of Compound 1, Form XIII.

In some embodiments, Form XIII exhibits a DSC thermogram having an endotherm peak at a temperature of about 276° C. In some embodiments, Form XIII has a DSC thermogram substantially as depicted in FIG. 41. In some embodiments, Form XIII has a TGA thermogram substantially as depicted in FIG. 42.

In some embodiments, Form XIII has at least two characteristic XRPD peaks selected from about 7.7, about 15.2, about 15.7, about 21.9, about 23.1, and about 26.1 degrees 2-theta; and Form XIII exhibits a DSC thermogram having an endotherm peak at a temperature of about 276° C.

Provided herein are also processes for preparing Form XIII of Compound 1, Form I comprising adding Compound 1, Form I to a cloudy solution of Compound 1 in THF, and stirring at 50±1° C. for 2 days.

In some embodiments, Form XIII can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XII-a

Provided herein is a solid form of Compound 1 having Form XIII-a, which is described below in the Examples.

In some embodiments, Form XIII-a has at least one characteristic XRPD peaks selected from about 6.9, about 7.7, about 10.4, about 15.2, about 21.5, and about 26.2 degrees 2-theta.

In some embodiments, Form XIII-a has at least two characteristic XRPD peaks selected from about 6.9, about 7.7, about 10.4, about 15.2, about 21.5, and about 26.2 degrees 2-theta.

In some embodiments, Form XIII-a has at least three characteristic XRPD peaks selected from about 6.9, about 7.7, about 10.4, about 15.2, about 21.5, and about 26.2 degrees 2-theta.

In some embodiments, Form XIII-a has at least one characteristic XRPD peak selected from about 6.9, about 7.7, about 8.3, about 10.4, about 10.9, about 12.1, about 14.4, about 15.2, about 18.6, about 19.7, about 21.5, about 22.3, about 22.6, and about 26.2 degrees 2-theta.

In some embodiments, Form XIII-a has at least two characteristic XRPD peaks selected from about 6.9, about 7.7, about 8.3, about 10.4, about 10.9, about 12.1, about 14.4, about 15.2, about 18.6, about 19.7, about 21.5, about 22.3, about 22.6, and about 26.2 degrees 2-theta.

In some embodiments, Form XIII-a has at least three characteristic XRPD peaks selected from about 6.9, about 7.7, about 8.3, about 10.4, about 10.9, about 12.1, about 14.4, about 15.2, about 18.6, about 19.7, about 21.5, about 22.3, about 22.6, and about 26.2 degrees 2-theta.

Figure 43:
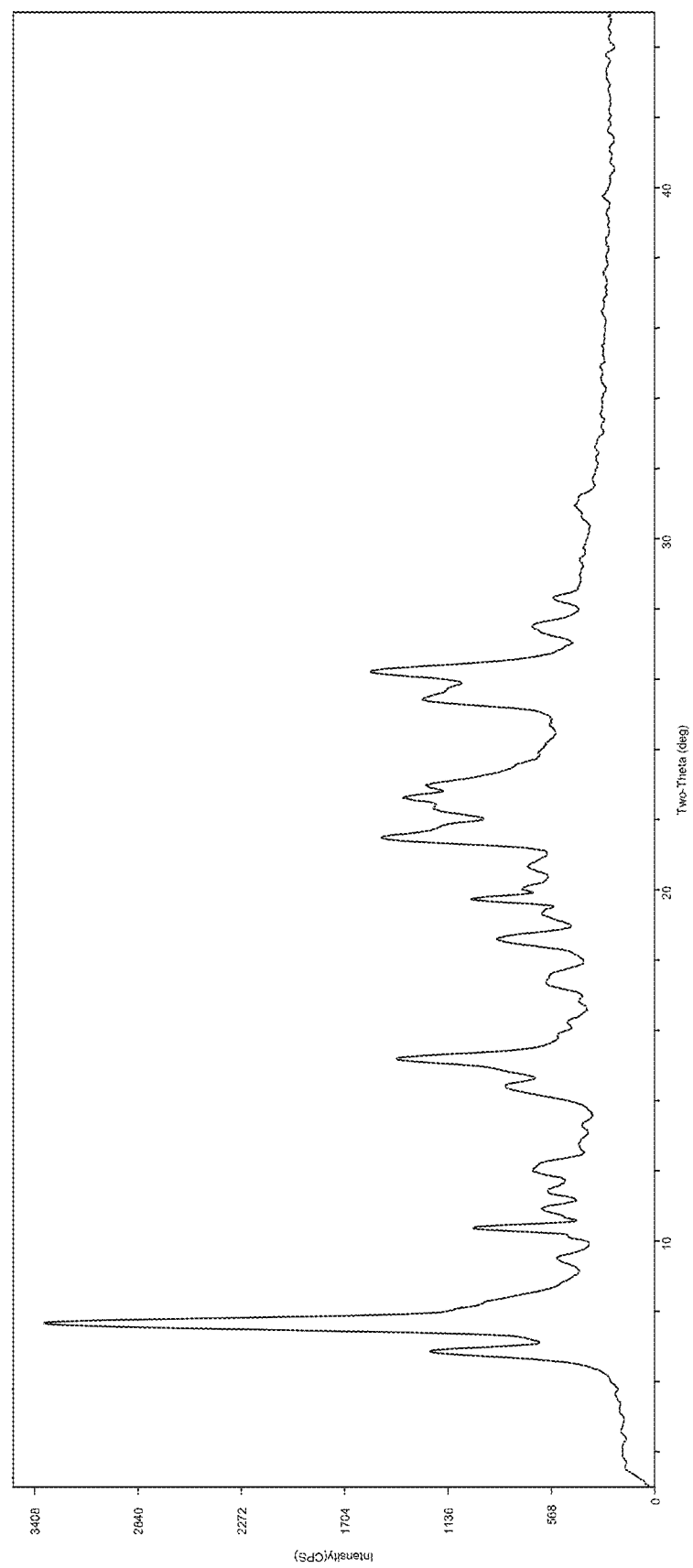
FIG. 43 shows an XRPD pattern of Compound 1, Form XIIIa.

In some embodiments, Form XIII-a has an XRPD pattern with characteristic peaks as substantially shown in FIG. 43.

Figure 44:
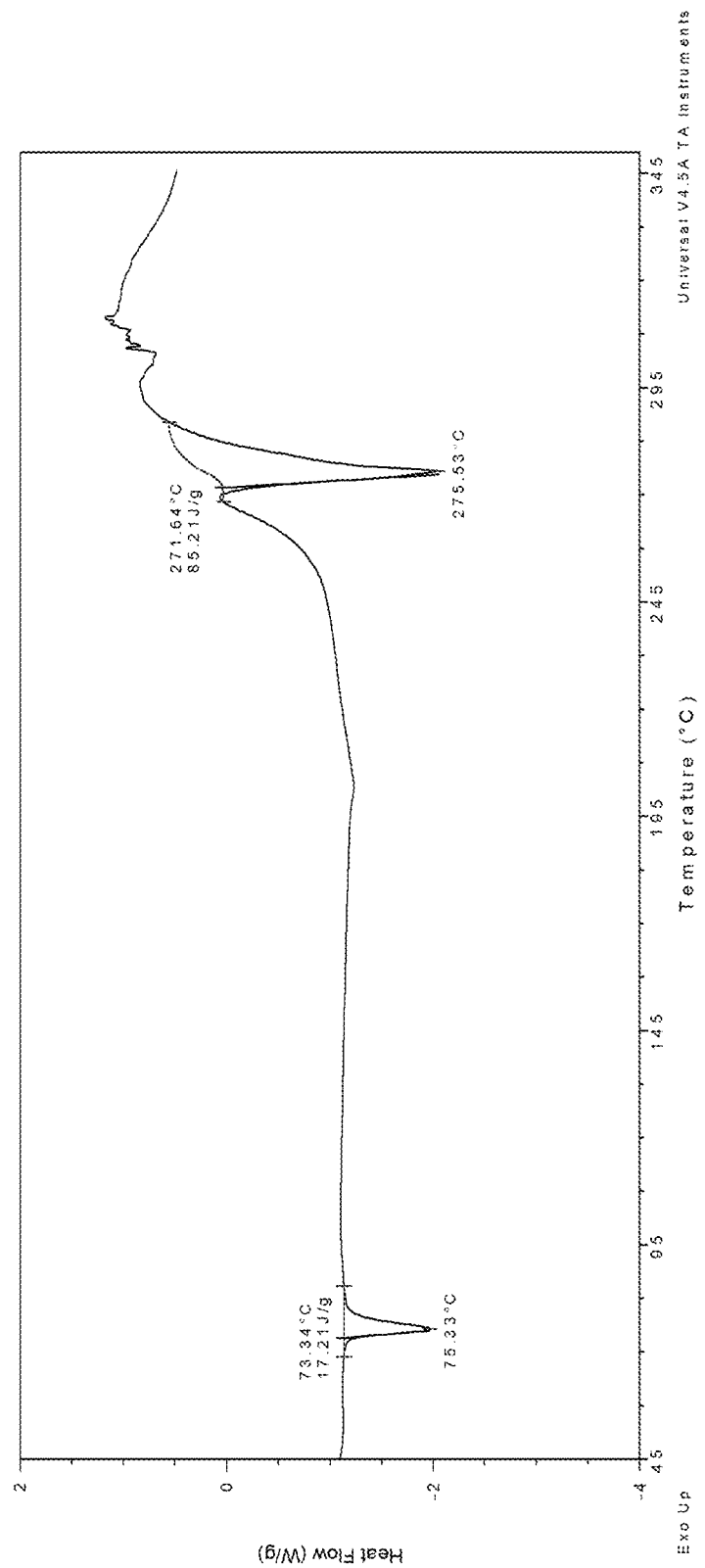
FIG. 44 shows a DSC thermogram of Compound 1, Form XIIIa.

In some embodiments, Form XIII-a exhibits a DSC thermogram having endotherm peaks at temperatures of about 75° C. and 276° C. In some embodiments, Form XIII-a exhibits a DSC thermogram having an endotherm peak at a temperature of about 75° C. In some embodiments, Form XIII-a exhibits a DSC thermogram having an endotherm peak at a temperature of about 276° C. In some embodiments, Form XIII-a has a DSC thermogram substantially as depicted in FIG. 44.

In some embodiments, Form XIII-a has at least one characteristic XRPD peaks selected from about 6.9, about 7.7, about 10.4, about 15.2, about 21.5, and about 26.2 degrees 2-theta; and Form XIII-a exhibits a DSC thermogram having endotherm peaks at temperatures of about 75° C. and 276° C.

Provided herein are also processes for preparing Form XIII-a of Compound 1 comprising cooling a saturated solution of Compound 1, Form I in THF to −20° C., and holding the temperature at −20° C. for a period of time (e.g., 3 h).

In some embodiments, Form XIII-a can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XIV

Provided herein is a solid form of Compound 1 having Form XIV, which is described below in the Examples.

In some embodiments, Form XIV has at least one characteristic XRPD peaks selected from about 7.0, about 14.1, about 16.1, about 20.0, about 22.0, and about 25.8 degrees 2-theta.

In some embodiments, Form XIV has at least two characteristic XRPD peaks selected from about 7.0, about 14.1, about 16.1, about 20.0, about 22.0, and about 25.8 degrees 2-theta.

In some embodiments, Form XIV has at least three characteristic XRPD peaks selected from about 7.0, about 14.1, about 16.1, about 20.0, about 22.0, and about 25.8 degrees 2-theta.

In some embodiments, Form XIV has at least one characteristic XRPD peak selected from about 7.0, about 8.6, about 9.2, about 9.6, about 10.3, about 11.5, about 12.2, about 14.1, about 14.5, about 16.1, about 17.6, about 18.3, about 18.7, about 19.3, about 20.0, about 22.0, about 22.3, about 22.9, and about 25.8 degrees 2-theta.

In some embodiments, Form XIV has at least two characteristic XRPD peaks selected from about 7.0, about 8.6, about 9.2, about 9.6, about 10.3, about 11.5, about 12.2, about 14.1, about 14.5, about 16.1, about 17.6, about 18.3, about 18.7, about 19.3, about 20.0, about 22.0, about 22.3, about 22.9, and about 25.8 degrees 2-theta.

In some embodiments, Form XIV has at least three characteristic XRPD peaks selected from about 7.0, about 8.6, about 9.2, about 9.6, about 10.3, about 11.5, about 12.2, about 14.1, about 14.5, about 16.1, about 17.6, about 18.3, about 18.7, about 19.3, about 20.0, about 22.0, about 22.3, about 22.9, and about 25.8 degrees 2-theta.

Figure 45:
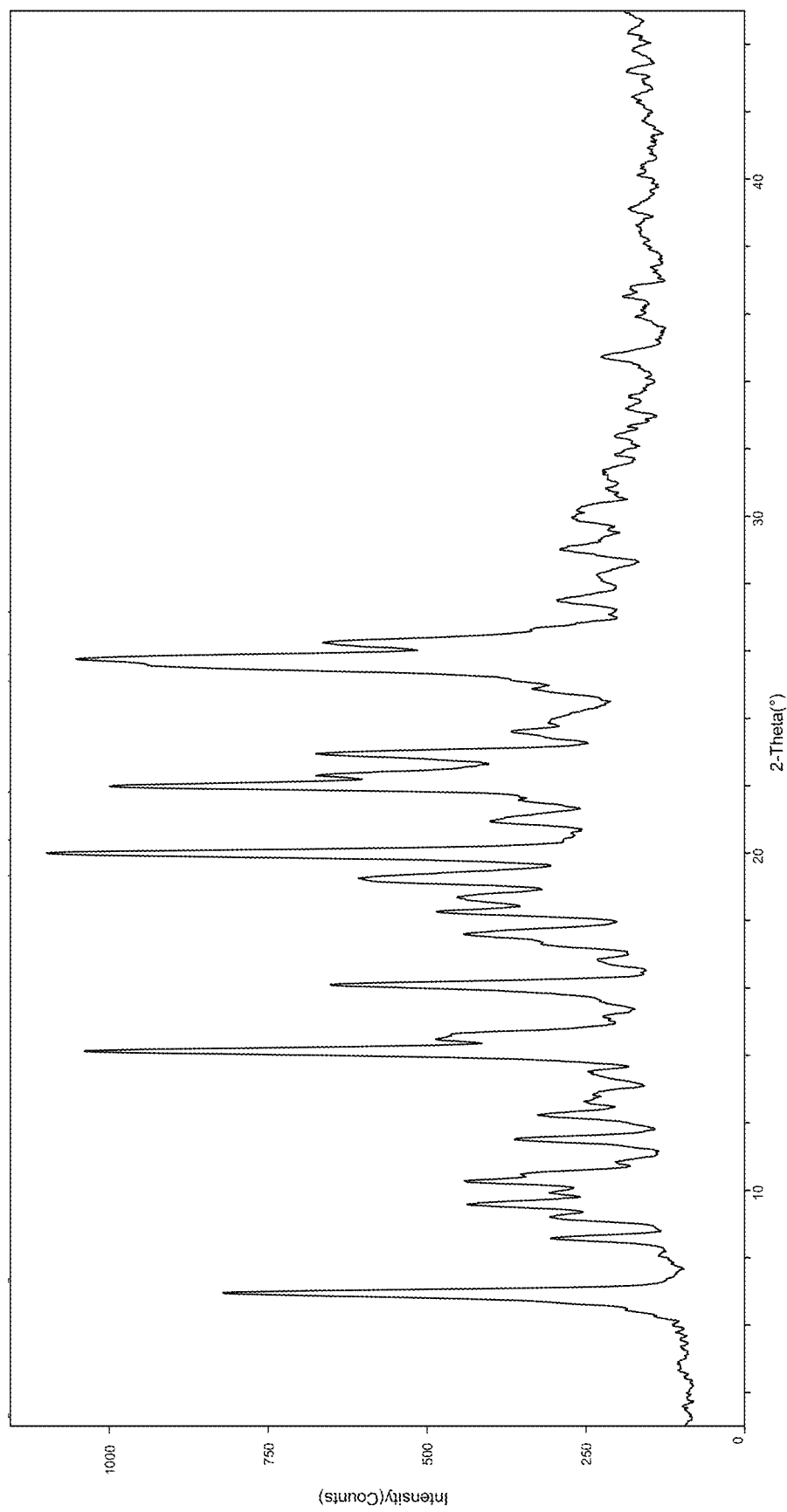
FIG. 45 shows an XRPD pattern of Compound 1, Form XIV.

In some embodiments, Form XIV has an XRPD pattern with characteristic peaks as substantially shown in FIG. 45.

Figure 46:
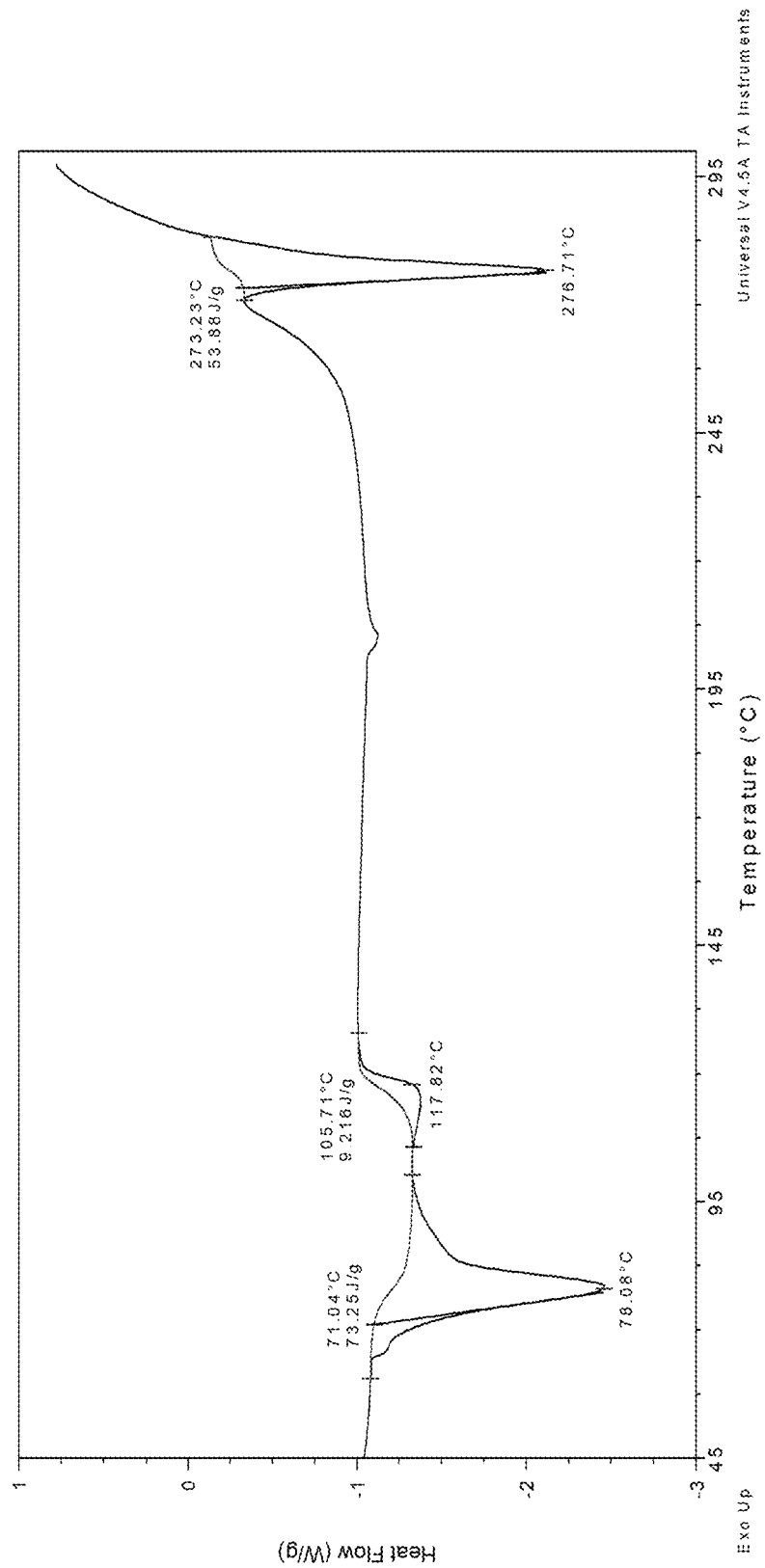
FIG. 46 shows a DSC thermogram of Compound 1, Form XIV.
Figure 47:
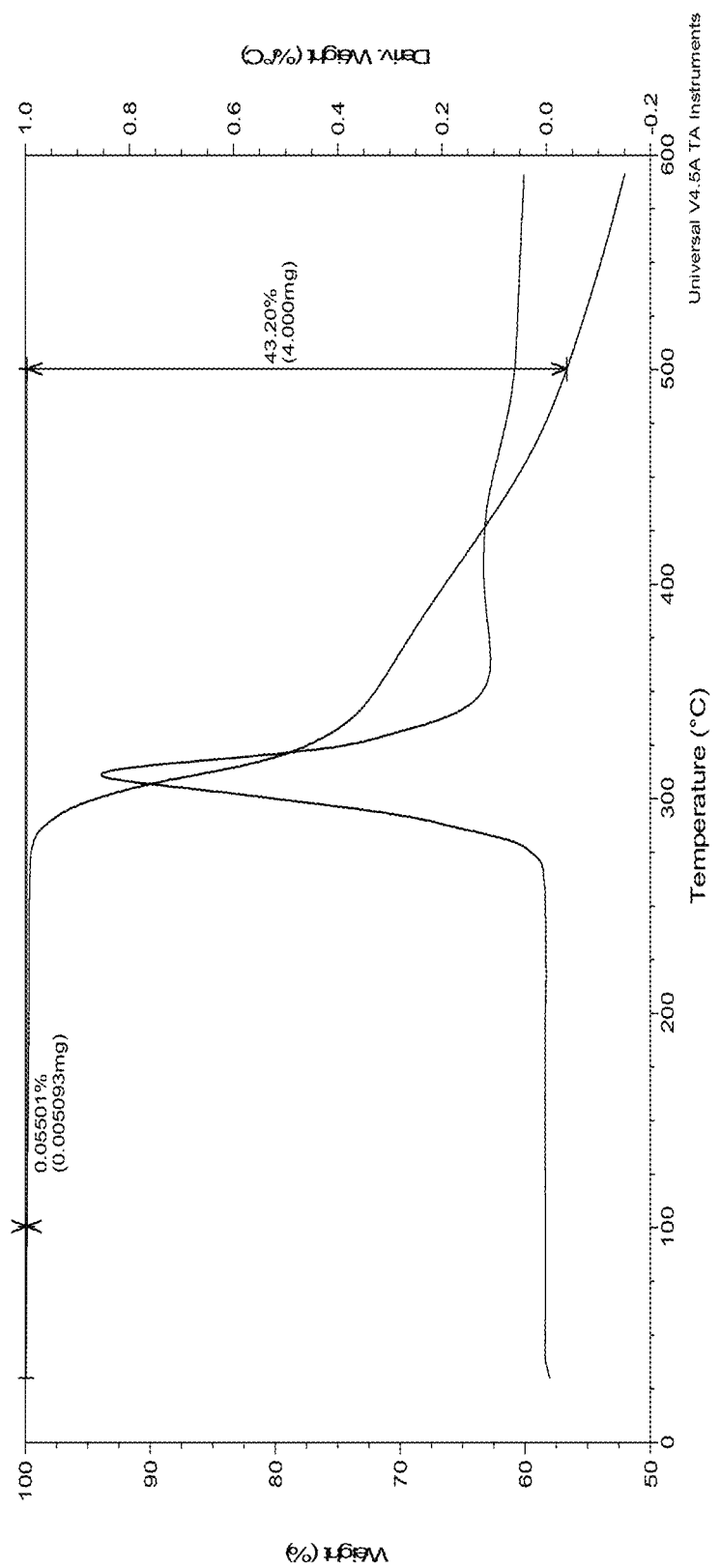
FIG. 47 shows a TGA thermogram of Compound 1, Form XIV.

In some embodiments, Form XIV exhibits a DSC thermogram having endotherm peaks at temperatures of about 78° C., 118° C., and 277° C. In some embodiments, Form XIV exhibits a DSC thermogram having an endotherm peak at a temperature of about 78° C. In some embodiments, Form XIV exhibits a DSC thermogram having an endotherm peak at a temperature of about 118° C. In some embodiments, Form XIV exhibits a DSC thermogram having an endotherm peak at a temperature of about 277° C. In some embodiments, Form XIV has a DSC thermogram substantially as depicted in FIG. 46. In some embodiments, Form XIV has a TGA thermogram substantially as depicted in FIG. 47.

In some embodiments, Form XIV has at least one characteristic XRPD peaks selected from about 7.0, about 14.1, about 16.1, about 20.0, about 22.0, and about 25.8 degrees 2-theta; and Form XIV exhibits a DSC thermogram having endotherm peaks at temperatures of about 78° C., 118° C., and 277° C.

Provided herein are also processes for preparing Form XIV of Compound 1 comprising evaporating a saturated solution of Compound, Form I 1 in DMF at 25±1° C.

In some embodiments, Form XIV can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XV

Provided herein is a solid form of Compound 1 having Form XV, which is described below in the Examples.

In some embodiments, Form XV has at least one characteristic XRPD peaks selected from about 8.9, about 9.2, about 15.6, about 18.5, and about 22.4.

In some embodiments, Form XV has at least two characteristic XRPD peaks selected from about 8.9, about 9.2, about 15.6, about 18.5, and about 22.4.

In some embodiments, Form XV has at least three characteristic XRPD peaks selected from about 8.9, about 9.2, about 15.6, about 18.5, and about 22.4.

In some embodiments, Form XV has at least one characteristic XRPD peak selected from about 3.9, about 8.9, about 9.2, about 15.6, about 16.6, about 18.5, about 20.3, about 21.4, about 21.8, about 22.4, about 24.5, about 24.9, about 30.0, and about 31.1 degrees 2-theta.

In some embodiments, Form XV has at least two characteristic XRPD peaks selected from about 3.9, about 8.9, about 9.2, about 15.6, about 16.6, about 18.5, about 20.3, about 21.4, about 21.8, about 22.4, about 24.5, about 24.9, about 30.0, and about 31.1 degrees 2-theta.

In some embodiments, Form XV has at least three characteristic XRPD peaks selected from about 3.9, about 8.9, about 9.2, about 15.6, about 16.6, about 18.5, about 20.3, about 21.4, about 21.8, about 22.4, about 24.5, about 24.9, about 30.0, and about 31.1 degrees 2-theta.

Figure 48:
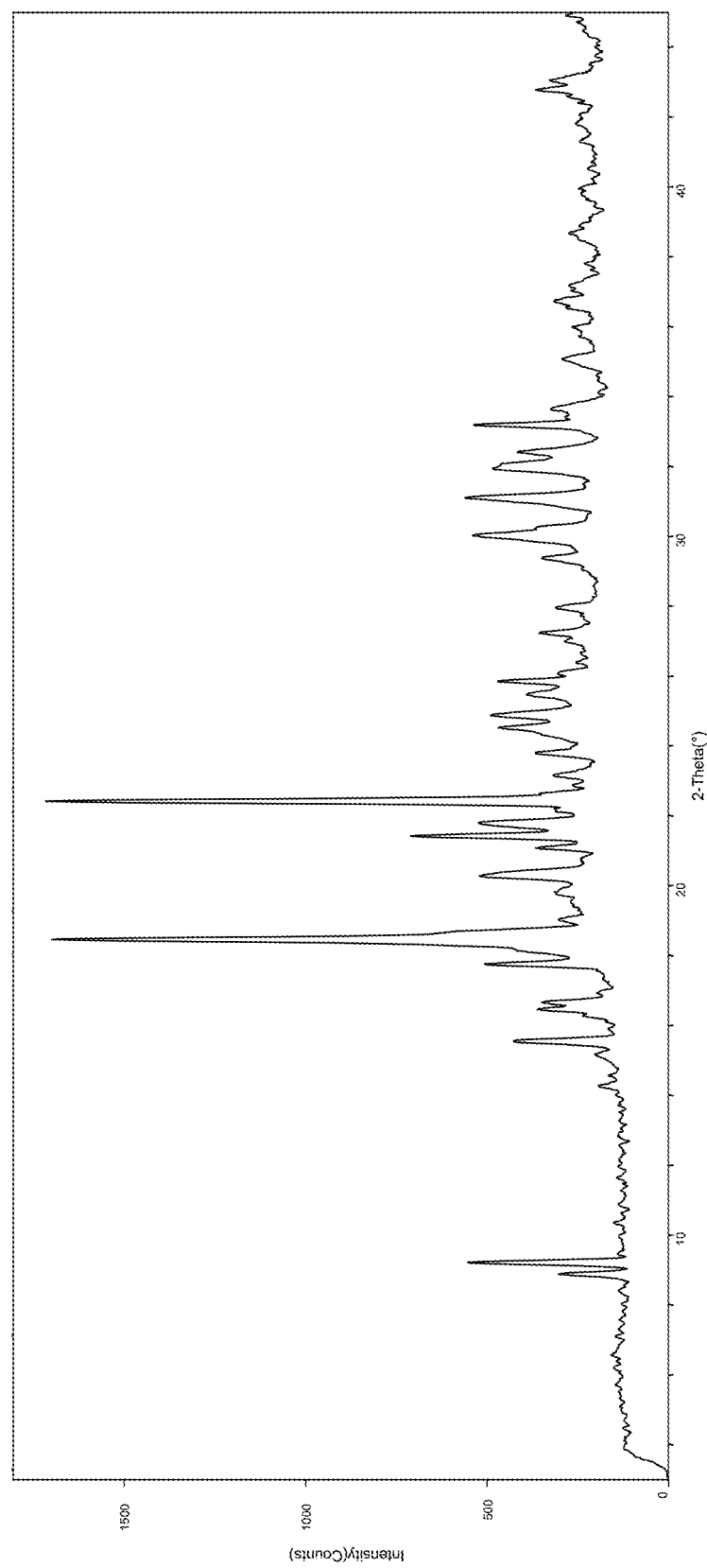
FIG. 48 shows an XRPD pattern of Compound 1, Form XV.

In some embodiments, Form XV has an XRPD pattern with characteristic peaks as substantially shown in FIG. 48.

Figure 49:
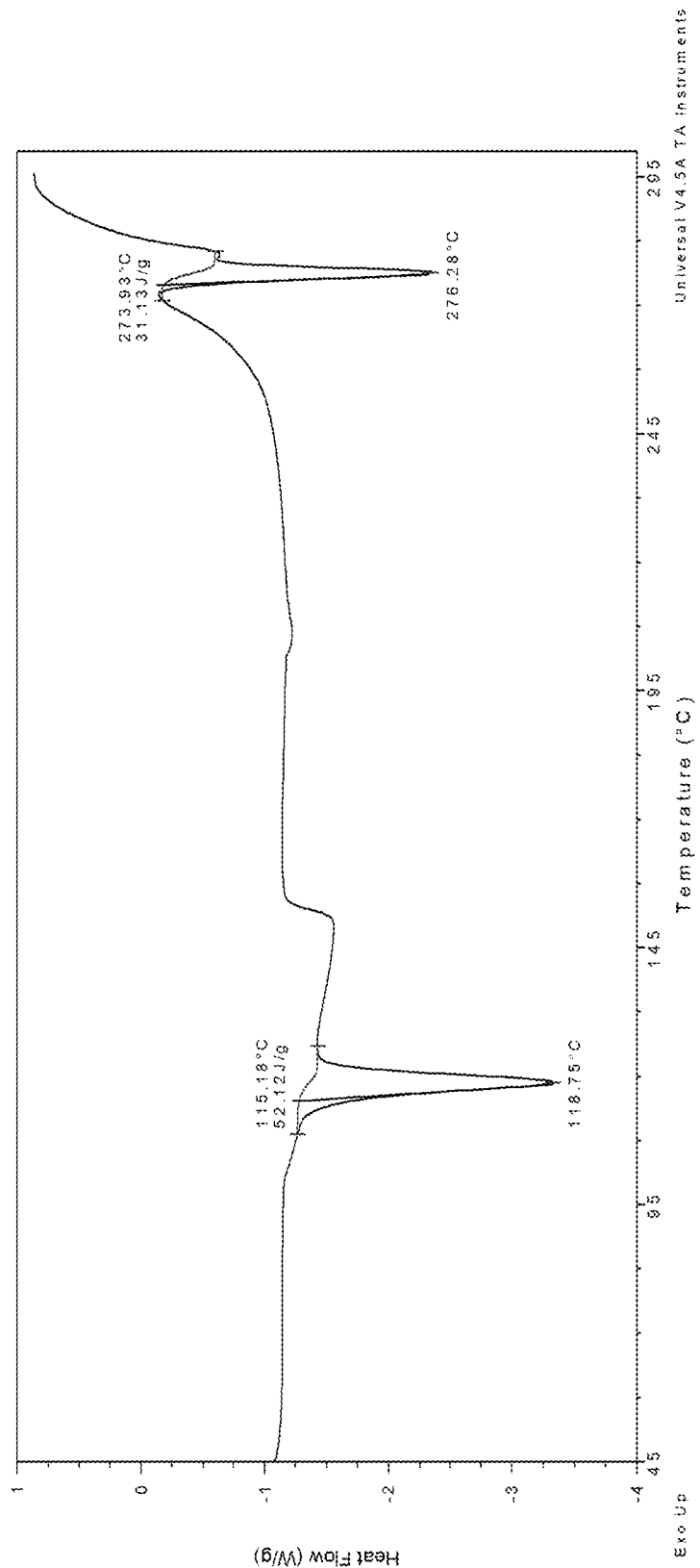
FIG. 49 shows a DSC thermogram of Compound 1, Form XV.
Figure 50:
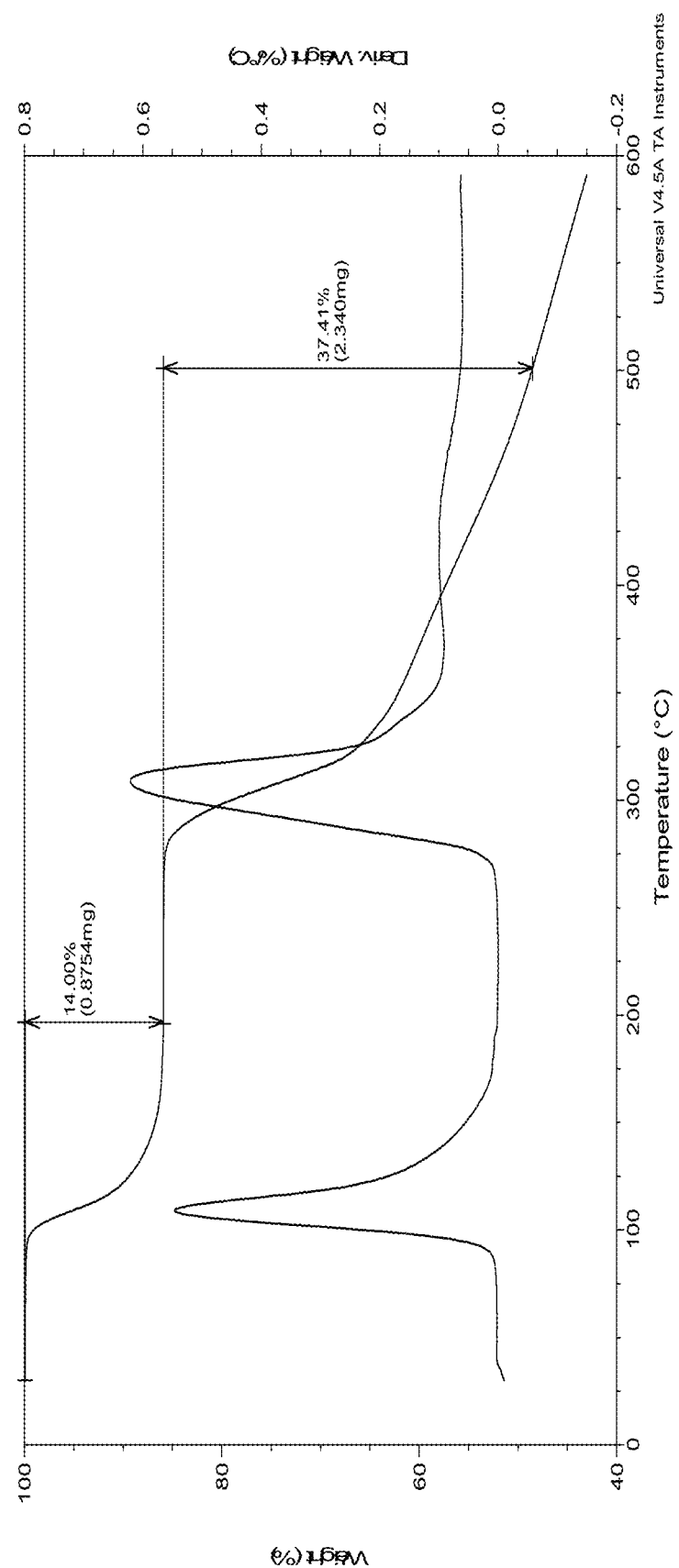
FIG. 50 shows a TGA thermogram of Compound 1, Form XV.

In some embodiments, Form XV exhibits a DSC thermogram having endotherm peaks at temperatures of about 119° C. and 276° C. In some embodiments, Form XV exhibits a DSC thermogram having an endotherm peak at a temperature of about 119° C. In some embodiments, Form XV exhibits a DSC thermogram having an endotherm peak at a temperature of about 276° C. In some embodiments, Form XV has a DSC thermogram substantially as depicted in FIG. 49. In some embodiments, Form XV has a TGA thermogram substantially as depicted in FIG. 50.

In some embodiments, Form XV has at least one characteristic XRPD peaks selected from about 8.9, about 9.2, about 15.6, about 18.5, and about 22.4; and Form XV exhibits a DSC thermogram having endotherm peaks at temperatures of about 119° C. and 276° C.

Provided herein are also processes for preparing Form XV of Compound 1 comprising evaporating a saturated solution of Compound 1, Form I in DMSO at 25±1° C.

In some embodiments, Form XV can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XVI

Provided herein is a solid form of Compound 1 having Form XVI, which is described below in the Examples.

In some embodiments, Form XVI has at least one characteristic XRPD peaks selected from about 6.8, about 10.7, about 14.0, about 14.9, about 16.0, and about 19.9.

In some embodiments, Form XVI has at least two characteristic XRPD peaks selected from about 6.8, about 10.7, about 14.0, about 14.9, about 16.0, and about 19.9.

In some embodiments, Form XVI has at least three characteristic XRPD peaks selected from about 6.8, about 10.7, about 14.0, about 14.9, about 16.0, and about 19.9.

In some embodiments, Form XVI has at least one characteristic XRPD peak selected from about 6.8, about 9.4, about 10.7, about 14.0, about 14.9, about 16.0, about 17.5, about 18.5, about 19.2, about 19.9, about 22.2, about 23.5, about 24.5, about 25.4, about 25.7, about 26.1, and about 30.2 degrees 2-theta.

In some embodiments, Form XVI has at least two characteristic XRPD peaks selected from about 6.8, about 9.4, about 10.7, about 14.0, about 14.9, about 16.0, about 17.5, about 18.5, about 19.2, about 19.9, about 22.2, about 23.5, about 24.5, about 25.4, about 25.7, about 26.1, and about 30.2 degrees 2-theta.

In some embodiments, Form XVI has at least three characteristic XRPD peaks selected from about 6.8, about 9.4, about 10.7, about 14.0, about 14.9, about 16.0, about 17.5, about 18.5, about 19.2, about 19.9, about 22.2, about 23.5, about 24.5, about 25.4, about 25.7, about 26.1, and about 30.2 degrees 2-theta.

Figure 51:
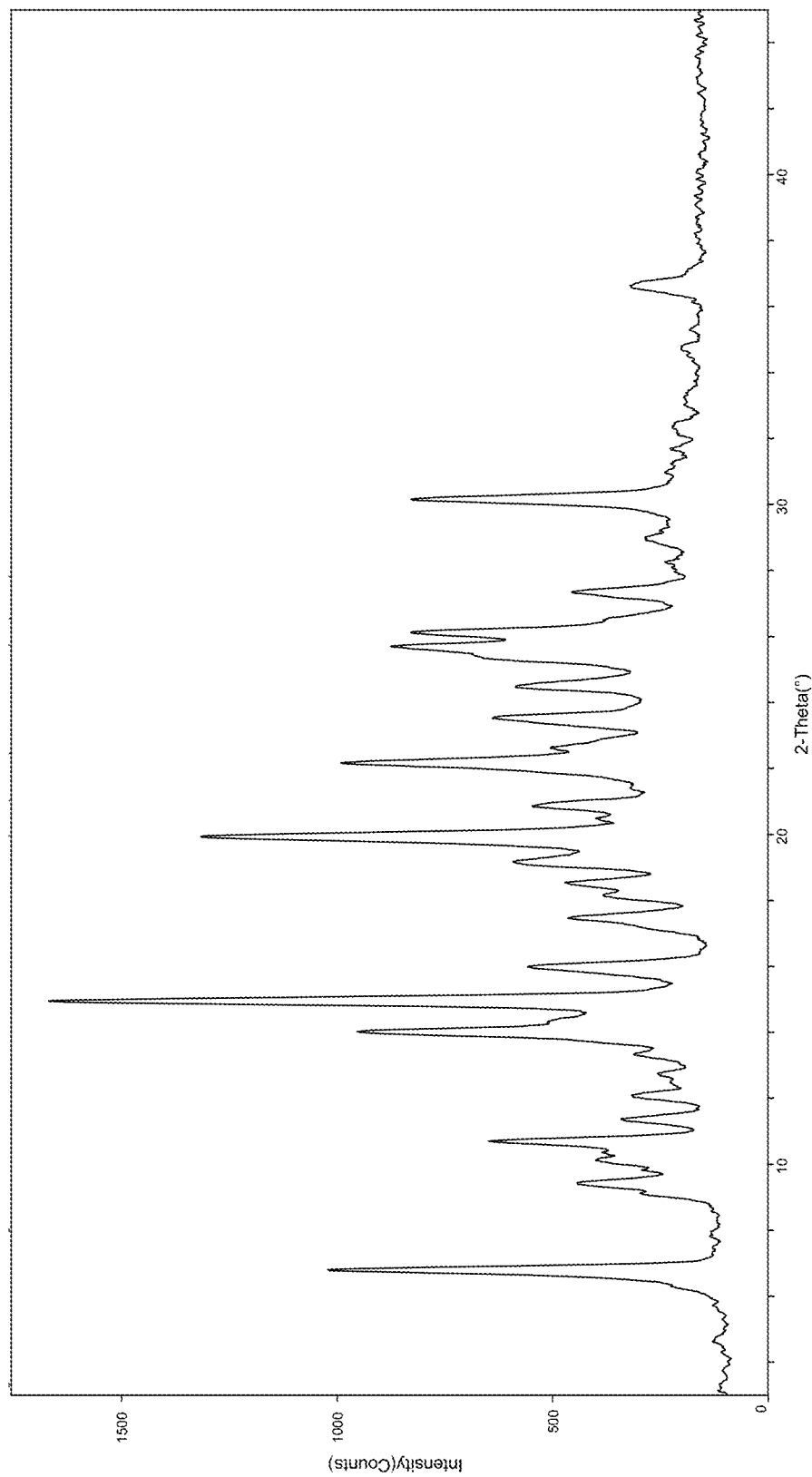
FIG. 51 shows an XRPD pattern of Compound 1, Form XVI.

In some embodiments, Form XVI has an XRPD pattern with characteristic peaks as substantially shown in FIG. 51.

Figure 52:
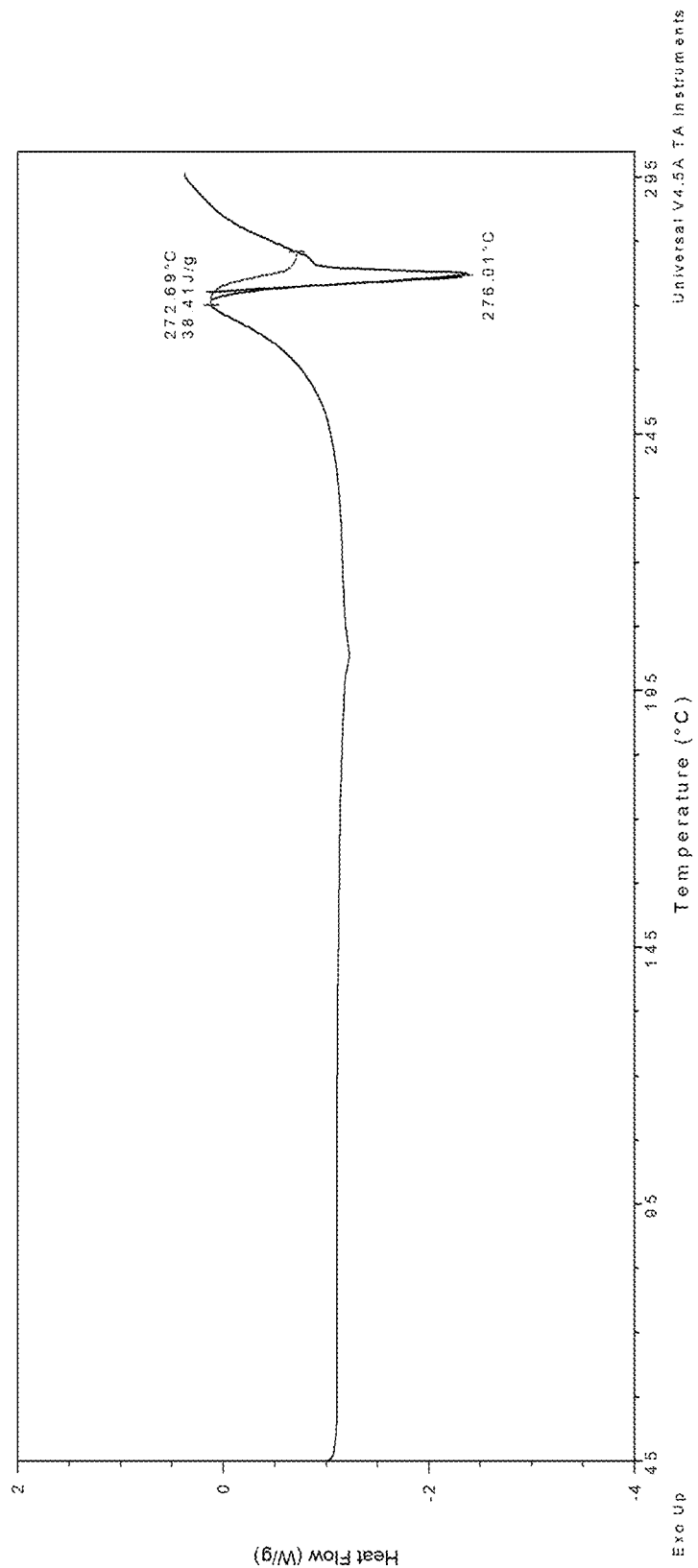
FIG. 52 shows a DSC thermogram of Compound 1, Form XVI.
Figure 53:
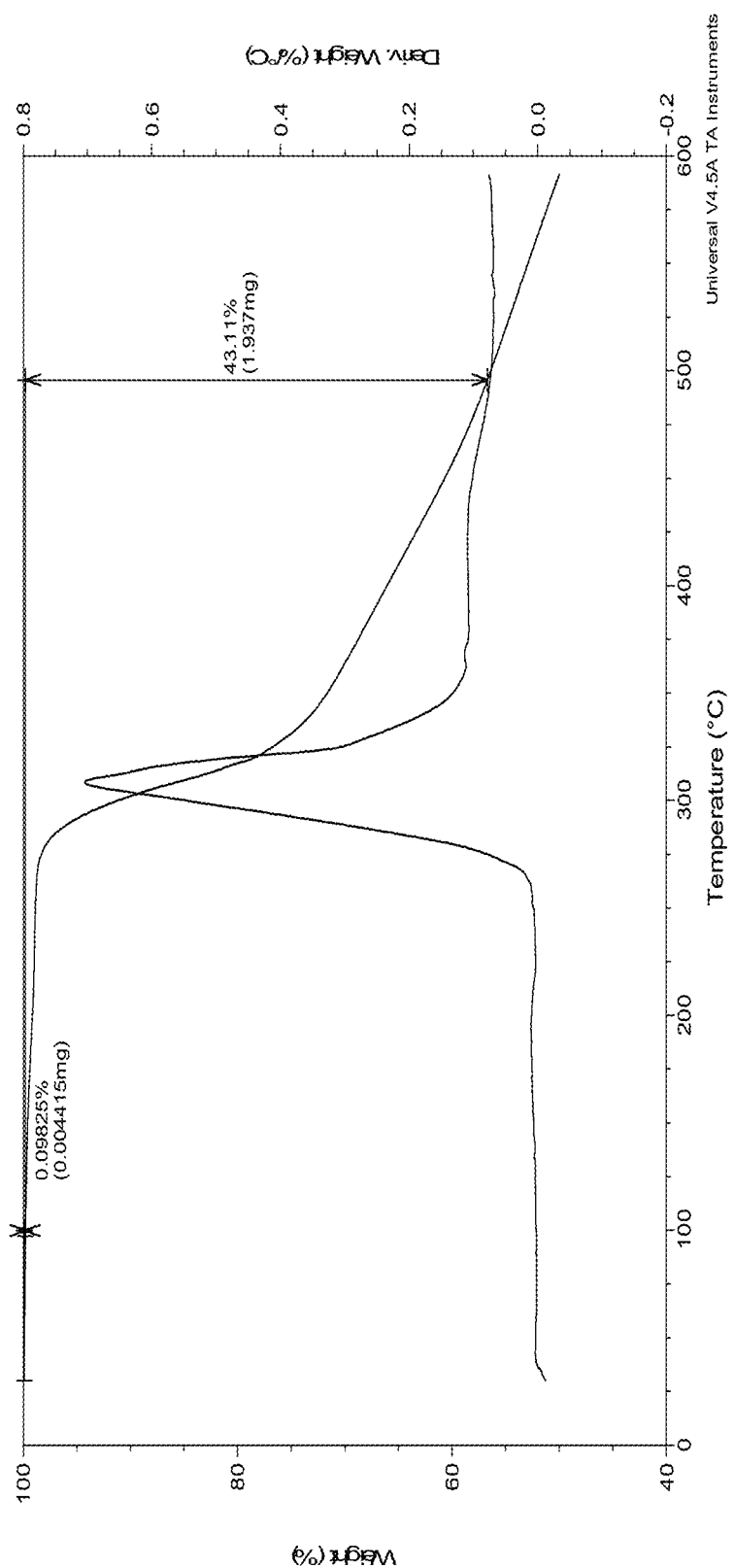
FIG. 53 shows a TGA thermogram of Compound 1, Form XVI.

In some embodiments, Form XVI exhibits a DSC thermogram having an endotherm peak at a temperature of about 276° C. In some embodiments, Form XVI has a DSC thermogram substantially as depicted in FIG. 52. In some embodiments, Form XVI has a TGA thermogram substantially as depicted in FIG. 53.

In some embodiments, Form XVI has at least one characteristic XRPD peaks selected from about 6.8, about 10.7, about 14.0, about 14.9, about 16.0, and about 19.9; and Form XVI exhibits a DSC thermogram having an endotherm peak at a temperature of about 276° C.

Provided herein are also processes for preparing Form XVI of Compound 1 comprising evaporating a saturated solution of Compound 1, Form I in THF at 50±1° C.

In some embodiments, Form XVI can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XVII

Provided herein is a solid form of Compound 1 having Form XVII, which is described below in the Examples.

In some embodiments, Form XVII has at least one characteristic XRPD peak selected from about 15.7, about 18.1, about 18.4, and about 32.2 degrees 2-theta.

In some embodiments, Form XVII has at least two characteristic XRPD peaks selected from about 15.7, about 18.1, about 18.4, and about 32.2 degrees 2-theta.

In some embodiments, Form XVII has at least three characteristic XRPD peaks selected from about 15.7, about 18.1, about 18.4, and about 32.2 degrees 2-theta.

Figure 54:
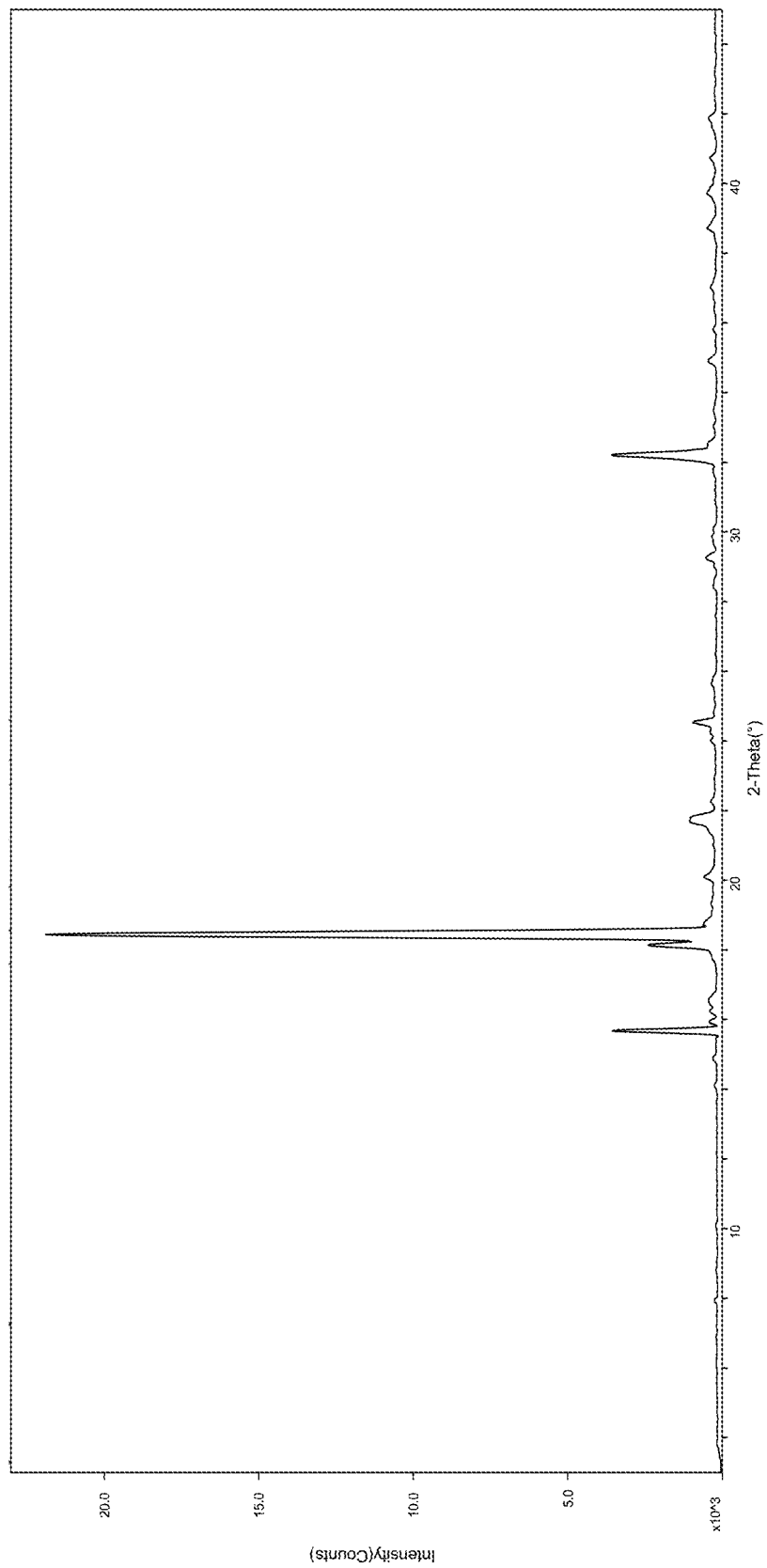
FIG. 54 shows an XRPD pattern of Compound 1, Form XVII.

In some embodiments, Form XVII has an XRPD pattern with characteristic peaks as substantially shown in FIG. 54.

Figure 55:
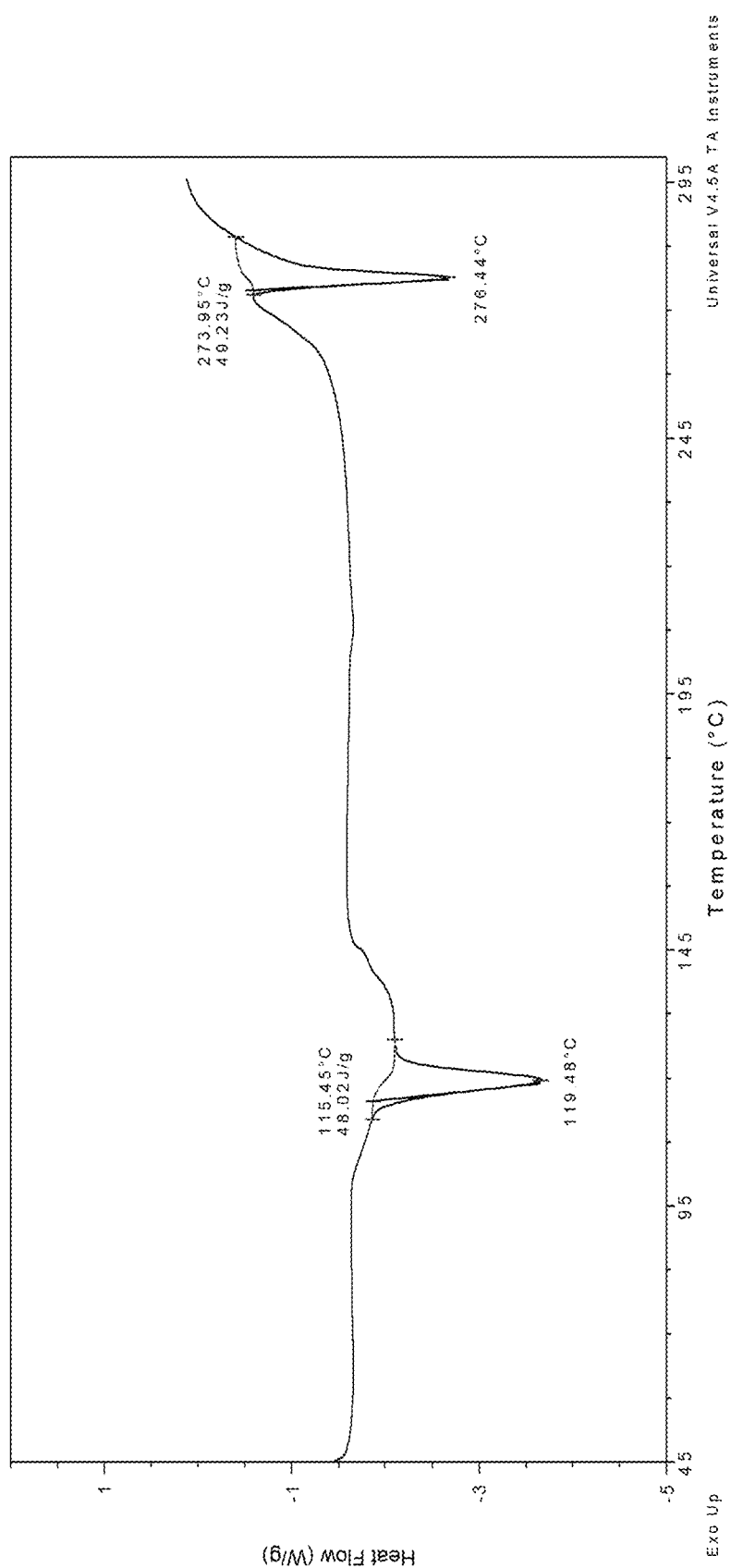
FIG. 55 shows a DSC thermogram of Compound 1, Form XVII.
Figure 56:
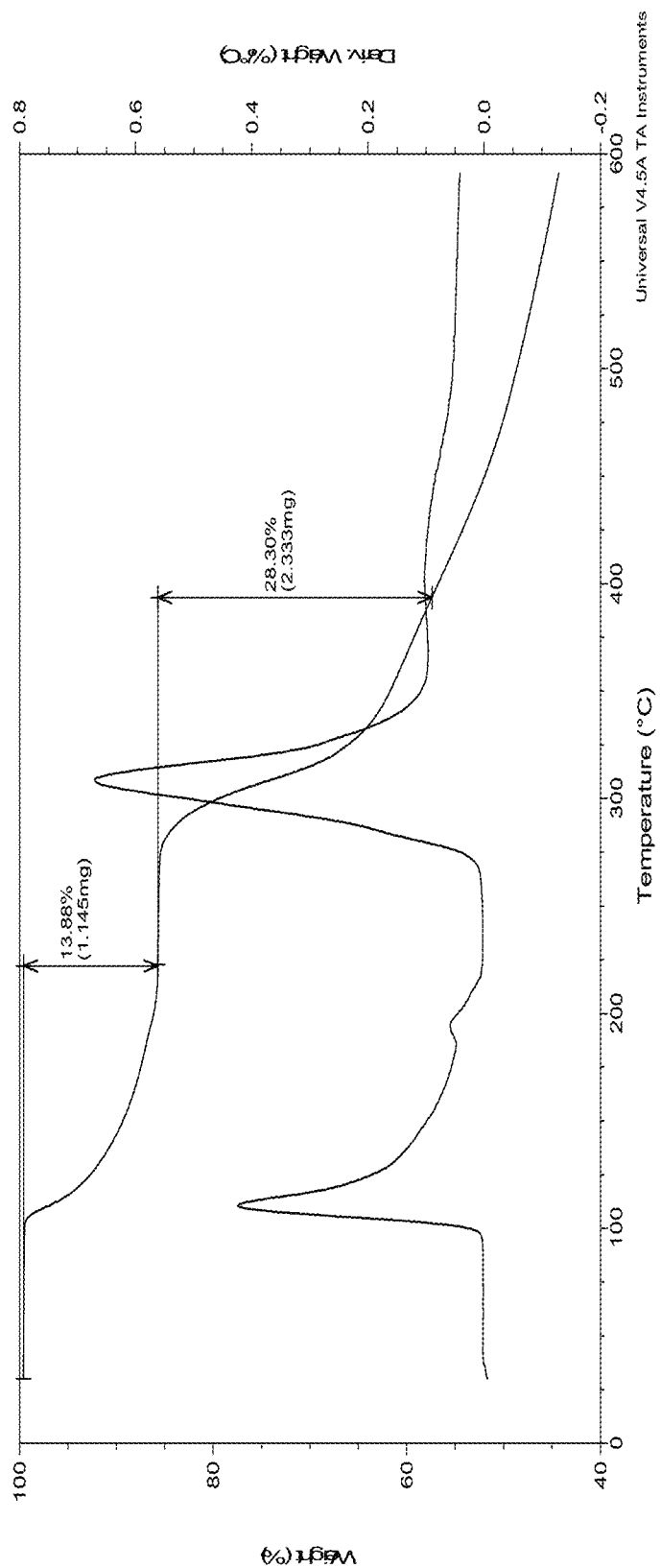
FIG. 56 shows a TGA thermogram of Compound 1, Form XVII.

In some embodiments, Form XVII exhibits a DSC thermogram having endotherm peaks at temperatures of about 119° C. and 276° C. In some embodiments, Form XVII exhibits a DSC thermogram having an endotherm peak at a temperature of about 119° C. In some embodiments, Form XVII exhibits a DSC thermogram having an endotherm peak at a temperature of about 276° C. In some embodiments, Form XVII has a DSC thermogram substantially as depicted in FIG. 55. In some embodiments, Form XVII has a TGA thermogram substantially as depicted in FIG. 56.

In some embodiments, Form XVII has at least one characteristic XRPD peak selected from about 15.7, about 18.1, about 18.4, and about 32.2 degrees 2-theta; and Form XVII exhibits a DSC thermogram having endotherm peaks at temperatures of about 119° C. and 276° C.

Provided herein are also processes for preparing Form XVII of Compound 1 comprising evaporating a saturated solution of Compound 1, Form I in DMSO at 50±1° C.

In some embodiments, Form XVII can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XVIII

Provided herein is a solid form of Compound 1 having Form XVIII, which is described below in the Examples.

In some embodiments, Form XVIII has at least one characteristic XRPD peaks selected from about 9.4, about 14.6, about 16.2, about 17.5, about 18.8, about 22.3, and about 22.7 degrees 2-theta.

In some embodiments, Form XVIII has at least two characteristic XRPD peaks selected from about 9.4, about 14.6, about 16.2, about 17.5, about 18.8, about 22.3, and about 22.7 degrees 2-theta.

In some embodiments, Form XVIII has at least three characteristic XRPD peaks selected from about 9.4, about 14.6, about 16.2, about 17.5, about 18.8, about 22.3, and about 22.7 degrees 2-theta.

In some embodiments, Form XVIII has at least one characteristic XRPD peak selected from about 6.8, about 9.4, about 10.3, about 11.9, about 12.6, about 13.4, about 14.6, about 16.2, about 17.5, about 18.3, about 18.8, about 20.8, about 22.3, about 22.7, and about 25.4 degrees 2-theta.

In some embodiments, Form XVIII has at least two characteristic XRPD peaks selected from about 6.8, about 9.4, about 10.3, about 11.9, about 12.6, about 13.4, about 14.6, about 16.2, about 17.5, about 18.3, about 18.8, about 20.8, about 22.3, about 22.7, and about 25.4 degrees 2-theta.

In some embodiments, Form XVIII has at least three characteristic XRPD peaks selected from about 6.8, about 9.4, about 10.3, about 11.9, about 12.6, about 13.4, about 14.6, about 16.2, about 17.5, about 18.3, about 18.8, about 20.8, about 22.3, about 22.7, and about 25.4 degrees 2-theta.

Figure 57:
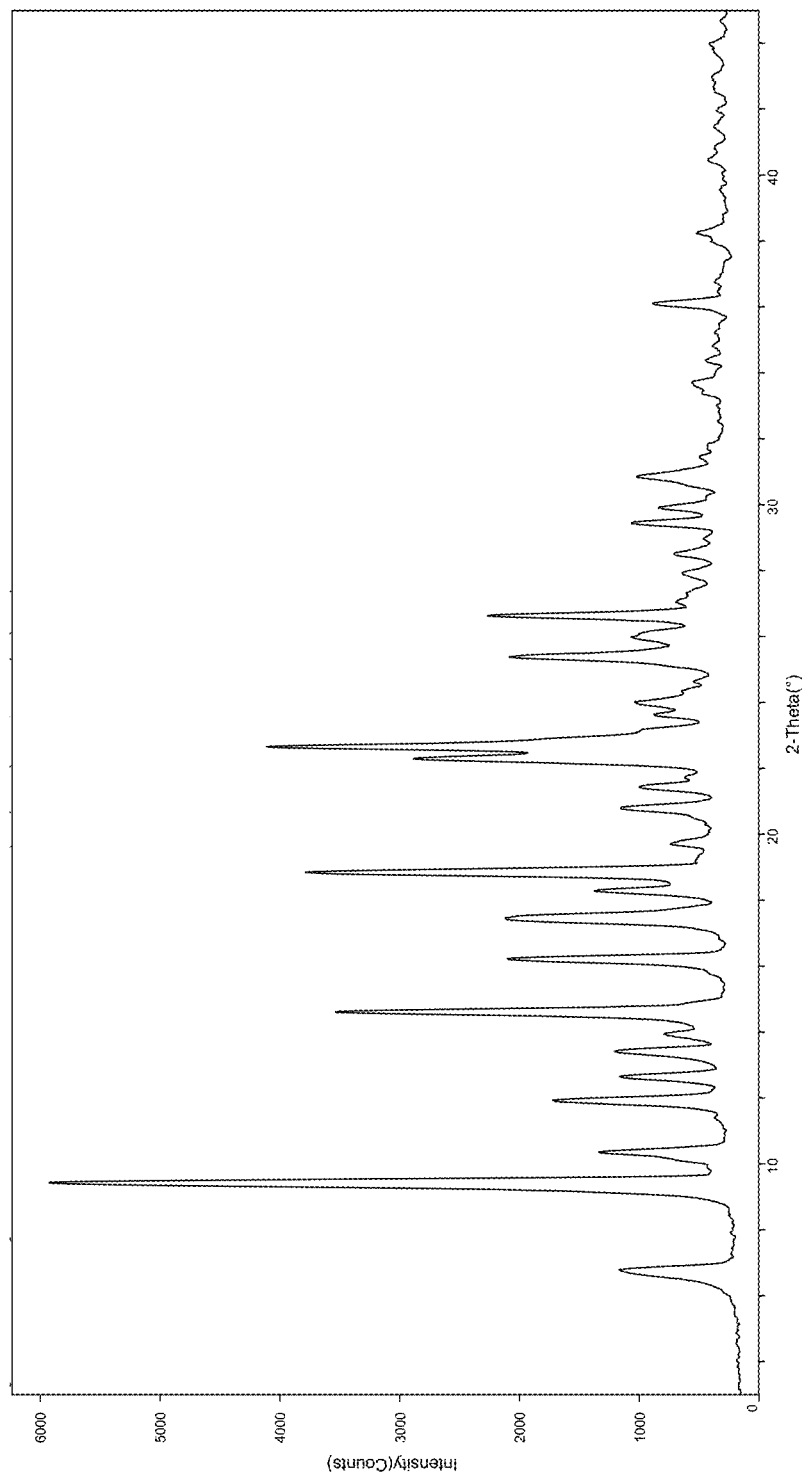
FIG. 57 shows an XRPD pattern of Compound 1, Form XVIII.

In some embodiments, Form XVIII has an XRPD pattern with characteristic peaks as substantially shown in FIG. 57.

Figure 58:
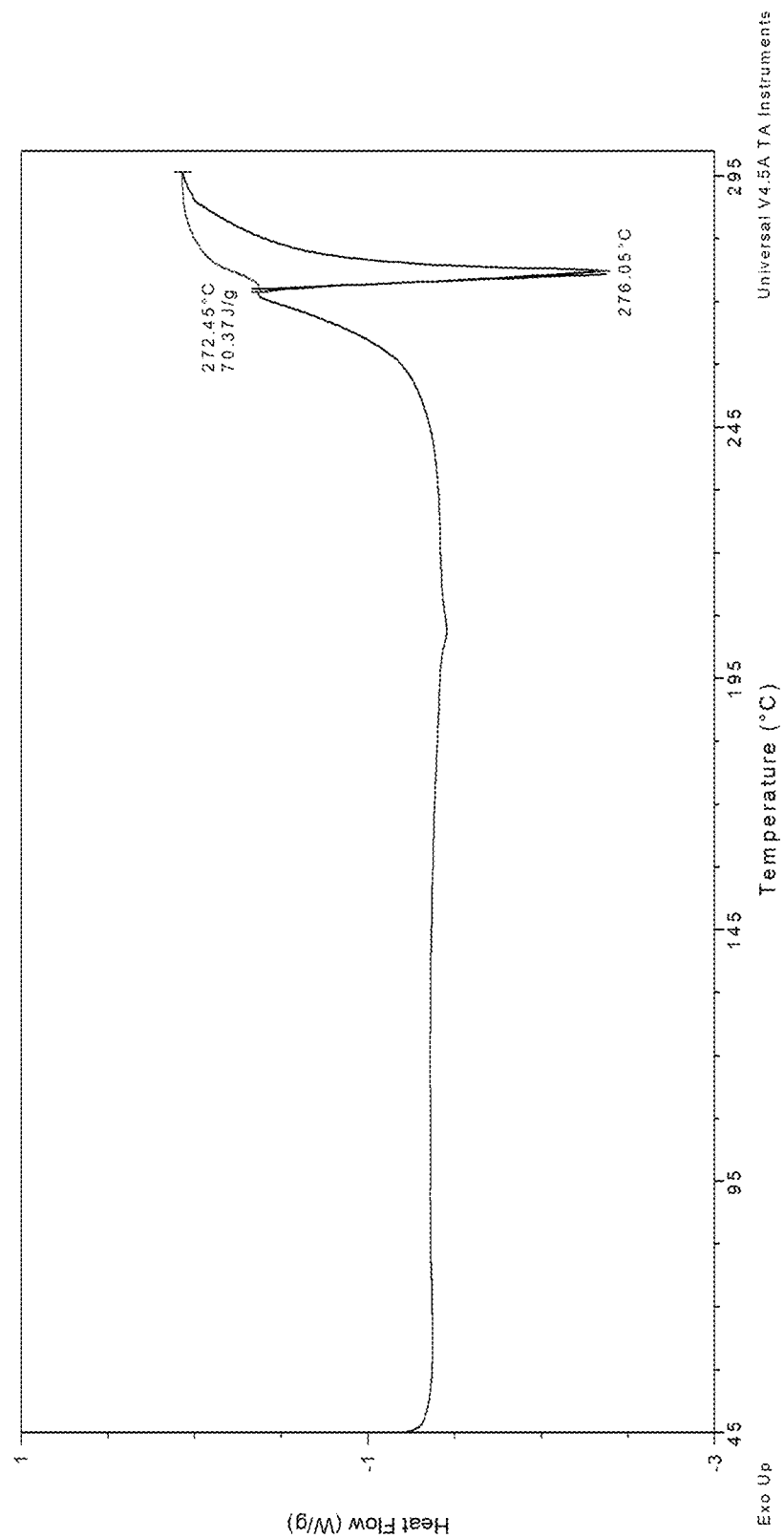
FIG. 58 shows a DSC thermogram of Compound 1, Form XVIII.
Figure 59:
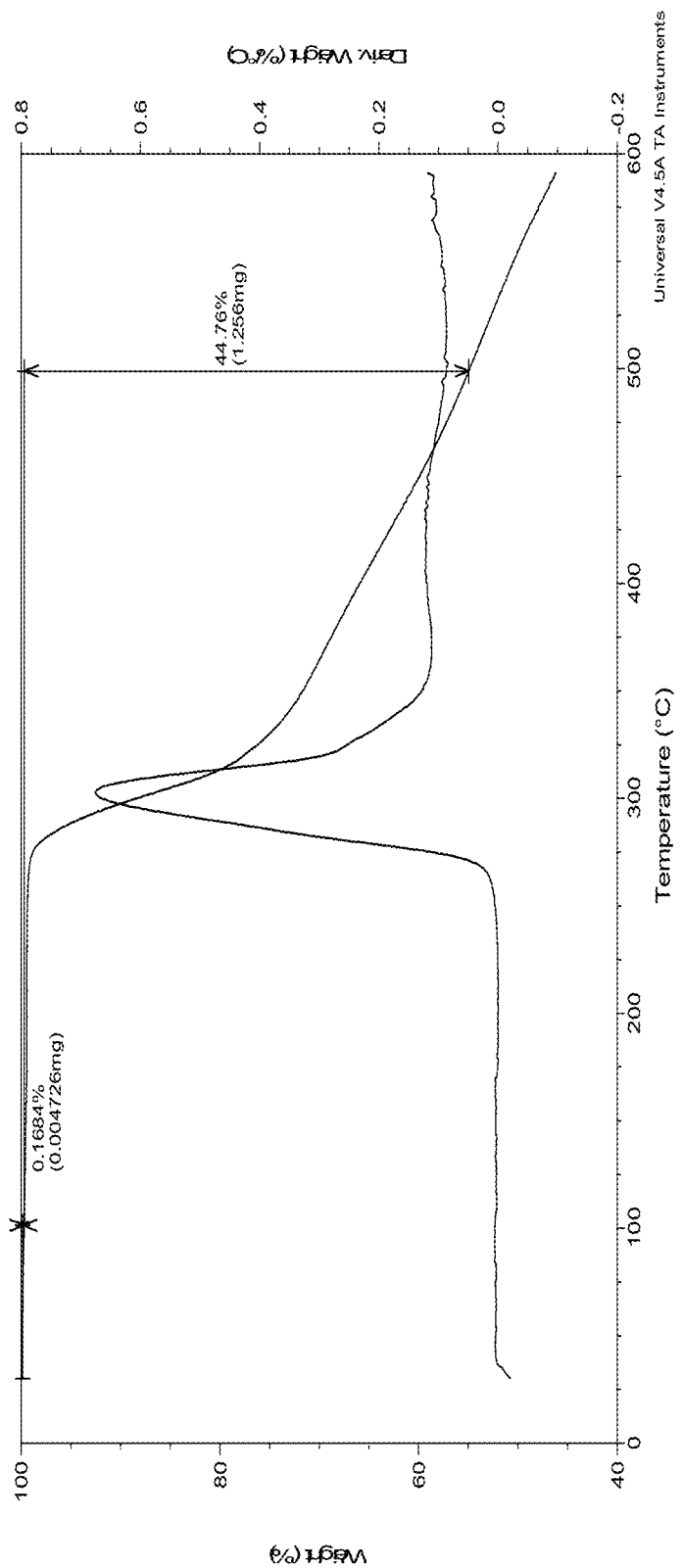
FIG. 59 shows a TGA thermogram of Compound 1, Form XVIII.

In some embodiments, Form XVIII exhibits a DSC thermogram having an endotherm peak at a temperatures of about 276° C. In some embodiments, Form XVIII has a DSC thermogram substantially as depicted in FIG. 58. In some embodiments, Form XVIII has a TGA thermogram substantially as depicted in FIG. 59.

In some embodiments, Form XVIII has at least one characteristic XRPD peaks selected from about 9.4, about 14.6, about 16.2, about 17.5, about 18.8, about 22.3, and about 22.7 degrees 2-theta; and Form XVIII exhibits a DSC thermogram having an endotherm peak at a temperatures of about 276° C.

Provided herein are also processes for preparing Form XVIII of Compound 1 comprising adding hexane to a saturated solution of Compound 1, Form I in chloroform.

In some embodiments, Form XVIII can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XIX

Provided herein is a solid form of Compound 1 having Form XIX, which is described below in the Examples.

In some embodiments, Form XIX has at least one characteristic XRPD peaks selected from about 6.7, about 10.0, about 17.4, about 18.0, about 20.2, and about 21.4 degrees 2-theta.

In some embodiments, Form XIX has at least two characteristic XRPD peaks selected from about 6.7, about 10.0, about 17.4, about 18.0, about 20.2, and about 21.4 degrees 2-theta.

In some embodiments, Form XIX has at least three characteristic XRPD peaks selected from about 6.7, about 10.0, about 17.4, about 18.0, about 20.2, and about 21.4 degrees 2-theta.

In some embodiments, Form XIX has at least one characteristic XRPD peak selected from about 3.9, about 6.7, about 9.4, about 10.0, about 13.6, about 17.4, about 18.0, about 20.2, about 21.4, about 22.1, and about 25.0 degrees 2-theta.

In some embodiments, Form XIX has at least two characteristic XRPD peaks selected from about 3.9, about 6.7, about 9.4, about 10.0, about 13.6, about 17.4, about 18.0, about 20.2, about 21.4, about 22.1, and about 25.0 degrees 2-theta.

In some embodiments, Form XIX has at least three characteristic XRPD peaks selected from about 3.9, about 6.7, about 9.4, about 10.0, about 13.6, about 17.4, about 18.0, about 20.2, about 21.4, about 22.1, and about 25.0 degrees 2-theta.

Figure 60:
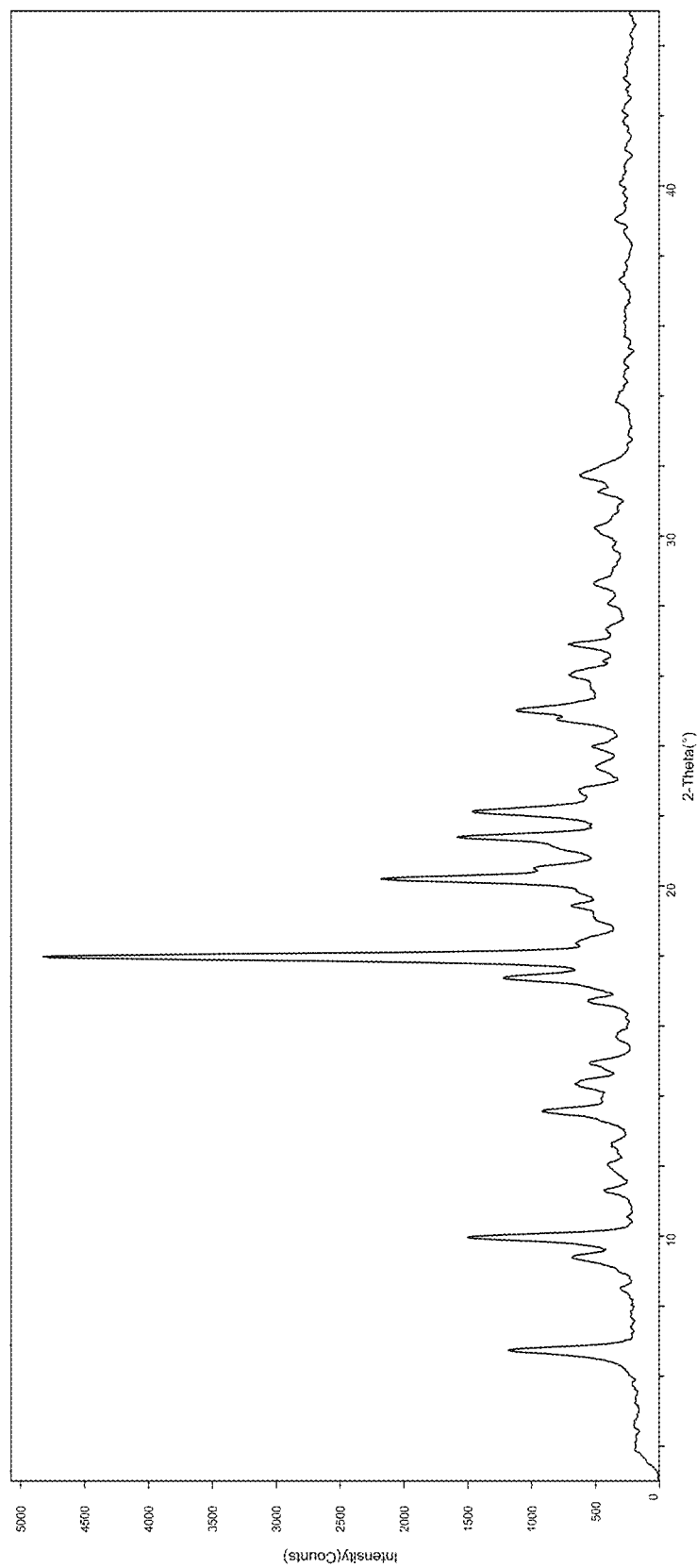
FIG. 60 shows an XRPD pattern of Compound 1, Form XIX.

In some embodiments, Form XIX has an XRPD pattern with characteristic peaks as substantially shown in FIG. 60.

Figure 61:
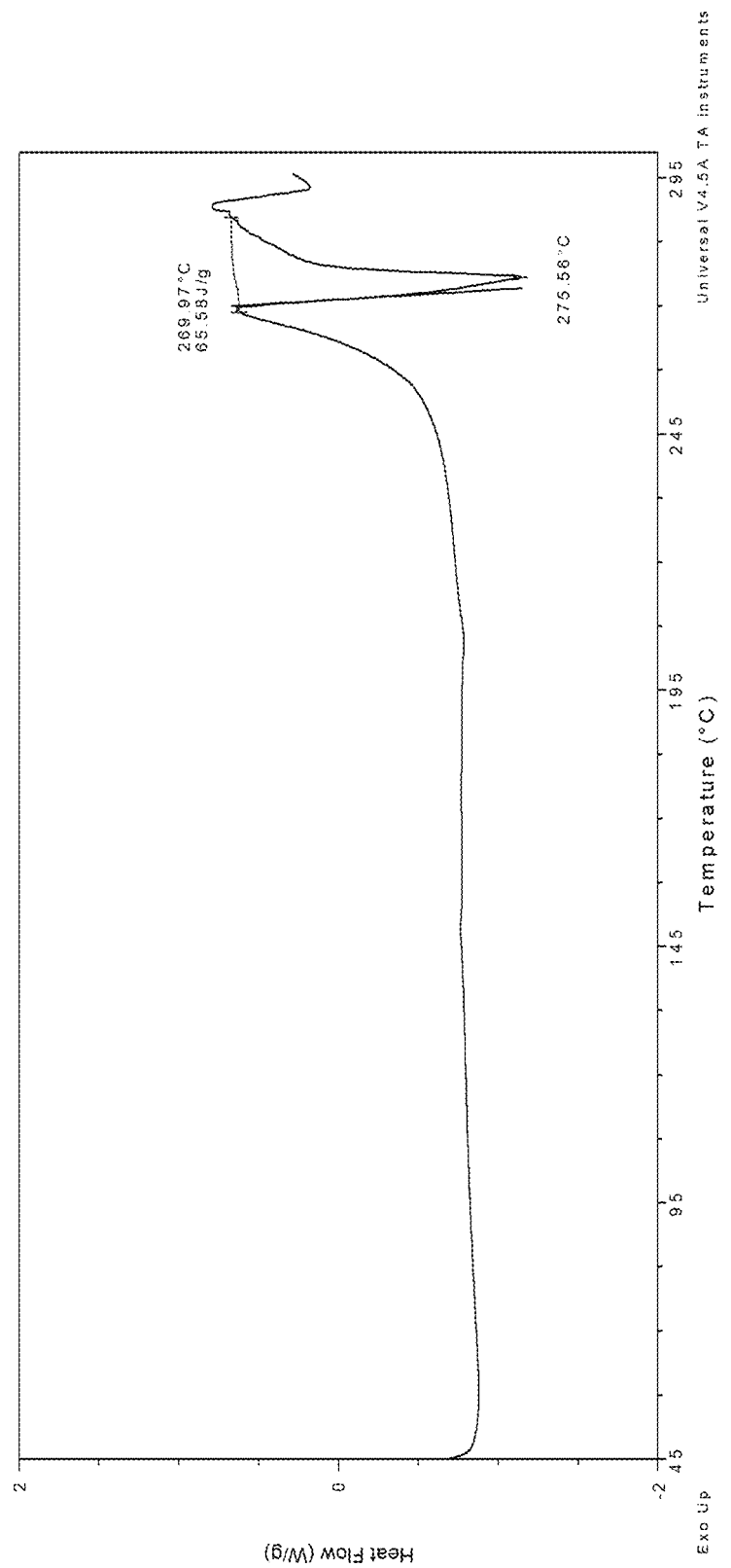
FIG. 61 shows a DSC thermogram of Compound 1, Form XIX.
Figure 62:
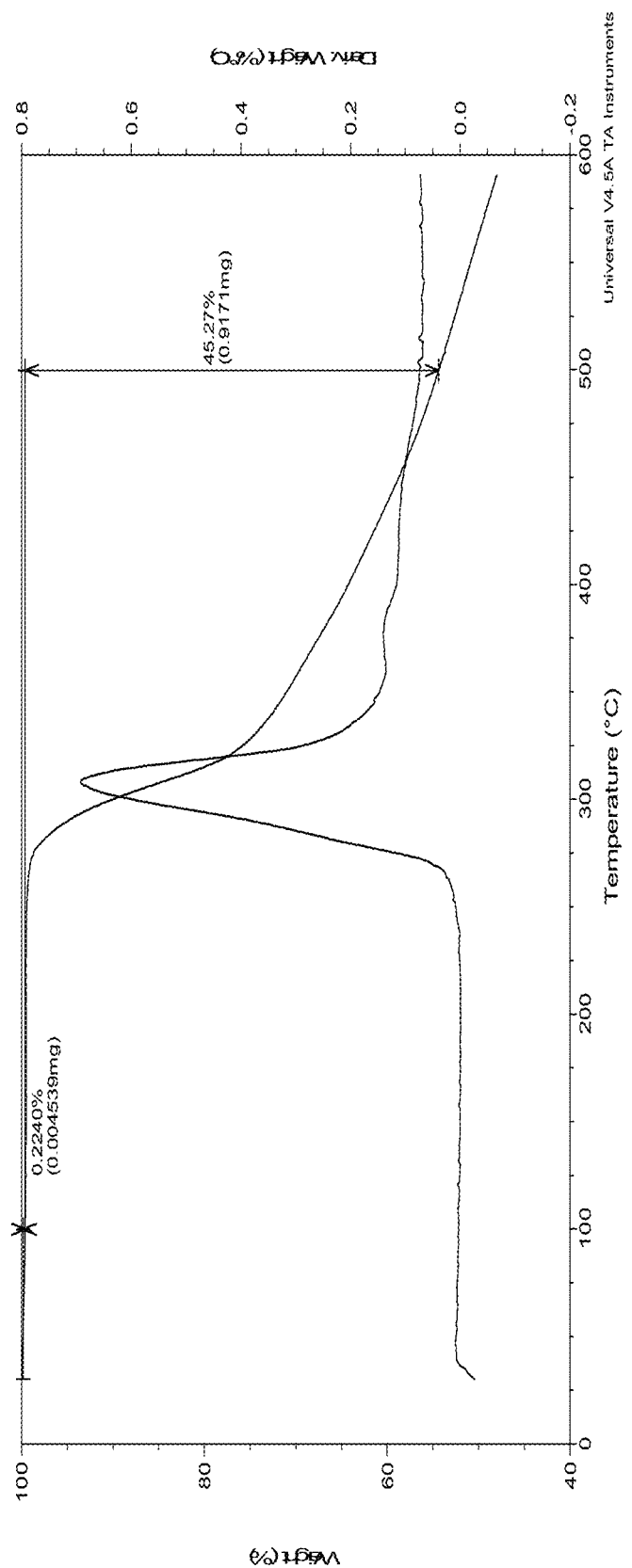
FIG. 62 shows a TGA thermogram of Compound 1, Form XIX.

In some embodiments, Form XIX exhibits a DSC thermogram having an endotherm peak at a temperature of about 276° C. In some embodiments, Form XIX has a DSC thermogram substantially as depicted in FIG. 61. In some embodiments, Form XIX has a TGA thermogram substantially as depicted in FIG. 62.

In some embodiments, Form XIX has at least one characteristic XRPD peaks selected from about 6.7, about 10.0, about 17.4, about 18.0, about 20.2, and about 21.4 degrees 2-theta; and Form XIX exhibits a DSC thermogram having an endotherm peak at a temperature of about 276° C.

Provided herein are also processes for preparing Form XIX of Compound 1 comprising adding methanol to a saturated solution of Compound 1, Form I in dichloromethane.

In some embodiments, Form XIX can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XX

Provided herein is a solid form of Compound 1 having Form XX, which is described below in the Examples.

In some embodiments, Form XX has at least one characteristic XRPD peaks selected from about 9.2, about 14.7, about 18.6, about 22.5, and about 23.0.

In some embodiments, Form XX has at least two characteristic XRPD peaks selected from about 9.2, about 14.7, about 18.6, about 22.5, and about 23.0.

In some embodiments, Form XX has at least three characteristic XRPD peaks selected from about 9.2, about 14.7, about 18.6, about 22.5, and about 23.0.

In some embodiments, Form XX has at least one characteristic XRPD peak selected from about 9.2, about 14.7, about 15.6, about 18.6, about 22.3, about 22.5, about 23.0, about 24.7, and about 29.5 degrees 2-theta.

In some embodiments, Form XX has at least two characteristic XRPD peaks selected from about 9.2, about 14.7, about 15.6, about 18.6, about 22.3, about 22.5, about 23.0, about 24.7, and about 29.5 degrees 2-theta.

In some embodiments, Form XX has at least three characteristic XRPD peaks selected from about 9.2, about 14.7, about 15.6, about 18.6, about 22.3, about 22.5, about 23.0, about 24.7, and about 29.5 degrees 2-theta.

Figure 63:
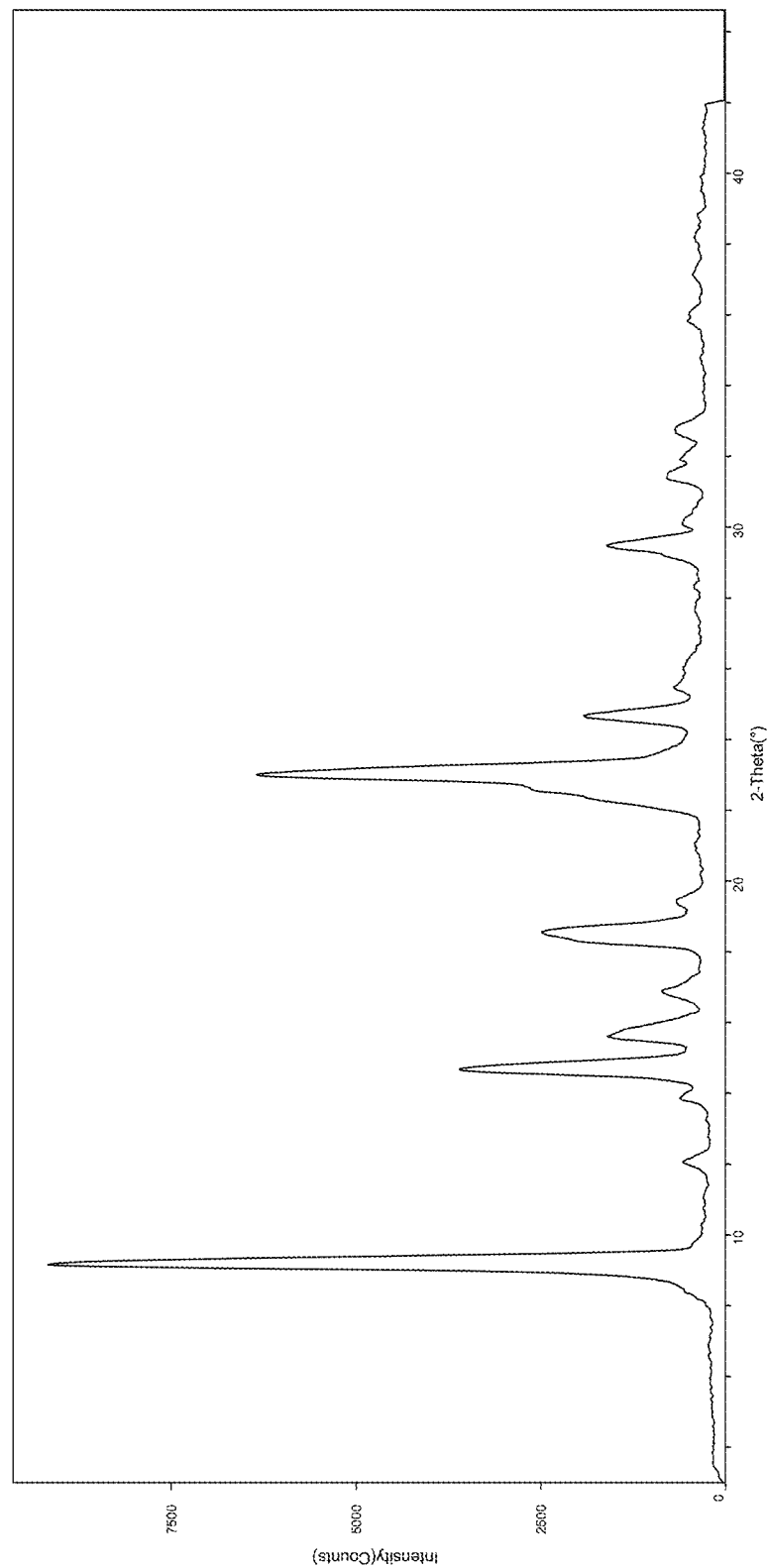
FIG. 63 shows an XRPD pattern of Compound 1, Form XX.

In some embodiments, Form XX has an XRPD pattern with characteristic peaks as substantially shown in FIG. 63.

Figure 64:
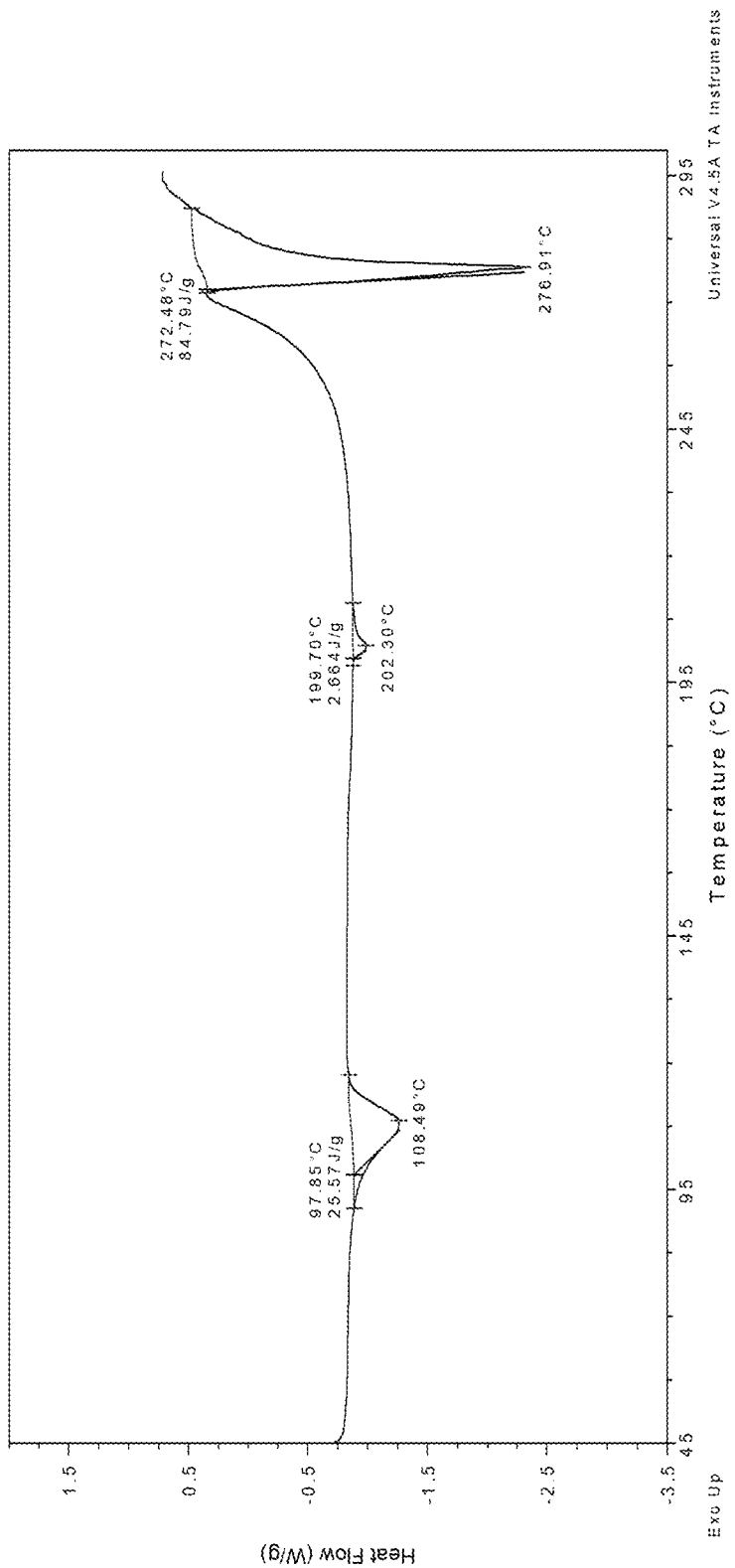
FIG. 64 shows a DSC thermogram of Compound 1, Form XX.
Figure 65:
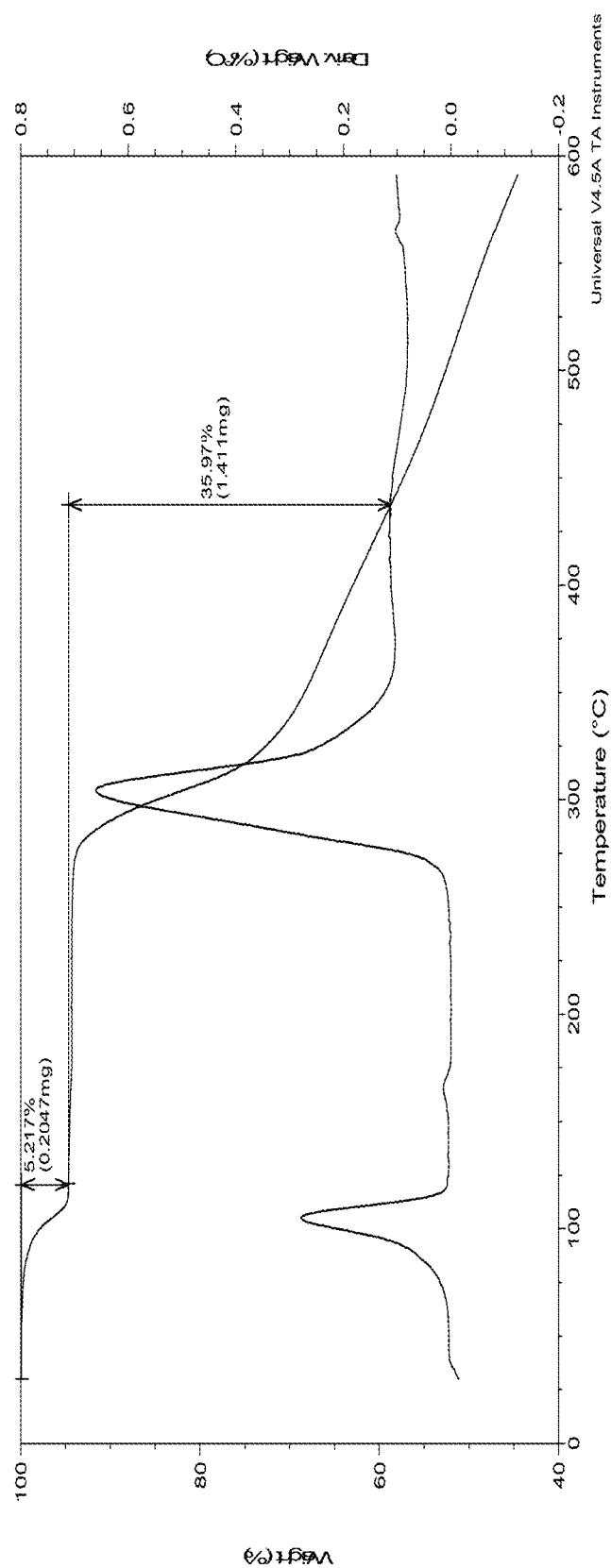
FIG. 65 shows a TGA thermogram of Compound 1, Form XX.

In some embodiments, Form XX exhibits a DSC thermogram having endotherm peaks at temperatures of about 108° C., 202° C., and 277° C. In some embodiments, Form XX exhibits a DSC thermogram having an endotherm peak at a temperature of about 108° C. In some embodiments, Form XX exhibits a DSC thermogram having an endotherm peak at a temperature of about 202° C. In some embodiments, Form XX exhibits a DSC thermogram having an endotherm peak at a temperature of about 277° C. In some embodiments, Form XX has a DSC thermogram substantially as depicted in FIG. 64. In some embodiments, Form XX has a TGA thermogram substantially as depicted in FIG. 65.

In some embodiments, Form XX has at least one characteristic XRPD peaks selected from about 9.2, about 14.7, about 18.6, about 22.5, and about 23.0; and Form XX exhibits a DSC thermogram having endotherm peaks at temperatures of about 108° C., 202° C., and 277° C.

Provided herein are also processes for preparing Form XX of Compound 1 comprising adding a saturated solution of Compound 1, Form I in dichloromethane to methyl t-butyl ether.

In some embodiments, Form XX can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XXI

Provided herein is a solid form of Compound 1 having Form XXI, which is described below in the Examples.

In some embodiments, Form XXI has at least one characteristic XRPD peaks selected from about 10.3, about 14.2, about 20.7, about 22.6, about 24.2, and about 27.1 degrees 2-theta.

In some embodiments, Form XXI has at least two characteristic XRPD peaks selected from about 10.3, about 14.2, about 20.7, about 22.6, about 24.2, and about 27.1 degrees 2-theta.

In some embodiments, Form XXI has at least three characteristic XRPD peaks selected from about 10.3, about 14.2, about 20.7, about 22.6, about 24.2, and about 27.1 degrees 2-theta.

In some embodiments, Form XXI has at least one characteristic XRPD peak selected from about 3.9, about 6.5, about 10.3, about 13.2, about 14.2, about 17.5, about 19.4, about 20.7, about 22.6, about 24.2, and about 27.1 degrees 2-theta.

In some embodiments, Form XXI has at least two characteristic XRPD peaks selected from about 3.9, about 6.5, about 10.3, about 13.2, about 14.2, about 17.5, about 19.4, about 20.7, about 22.6, about 24.2, and about 27.1 degrees 2-theta.

In some embodiments, Form XXI has at least three characteristic XRPD peaks selected from about 3.9, about 6.5, about 10.3, about 13.2, about 14.2, about 17.5, about 19.4, about 20.7, about 22.6, about 24.2, and about 27.1 degrees 2-theta.

Figure 66:
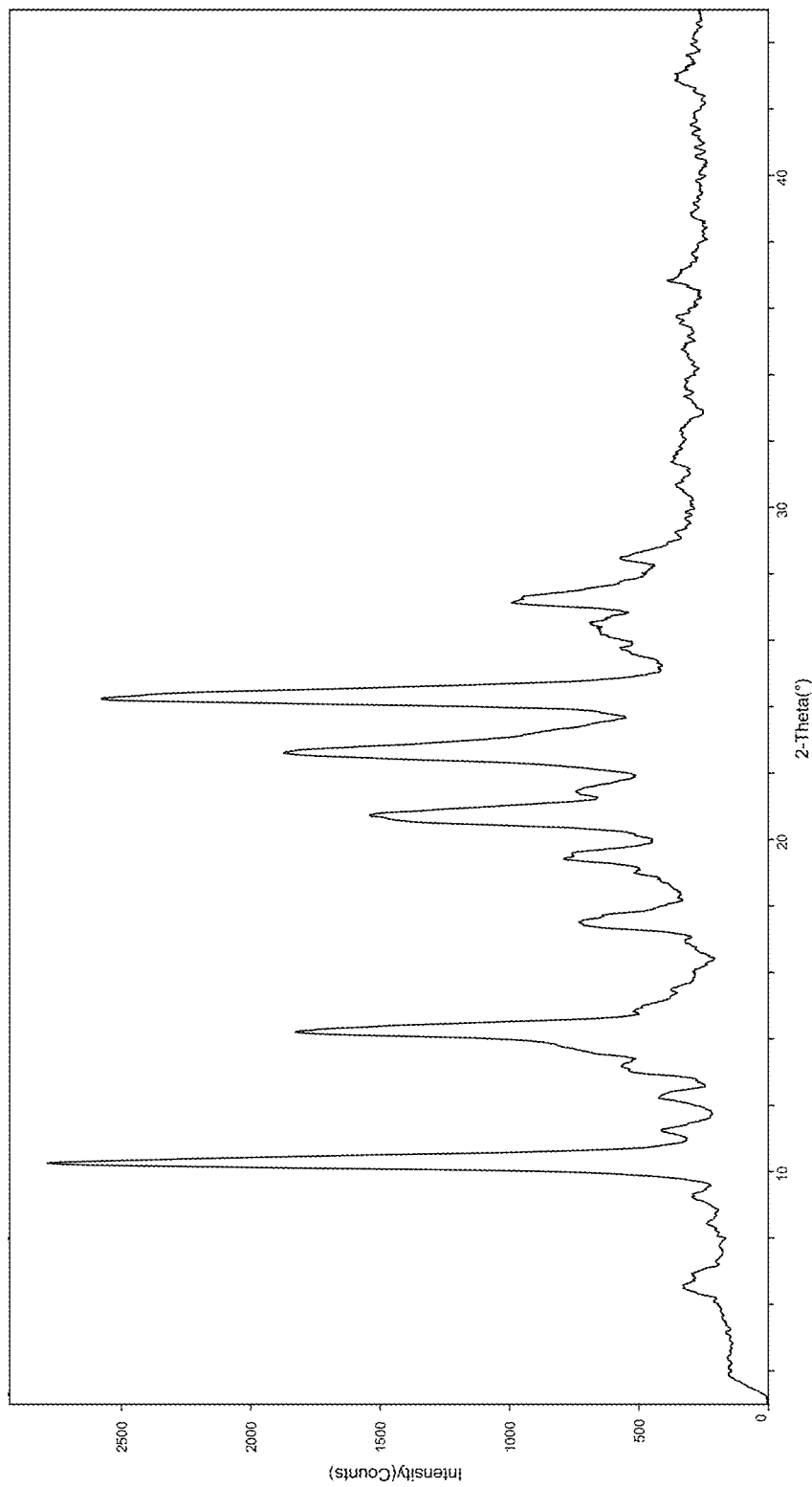
FIG. 66 shows an XRPD pattern of Compound 1, Form XXI.

In some embodiments, Form XXI has an XRPD pattern with characteristic peaks as substantially shown in FIG. 66.

Figure 67:
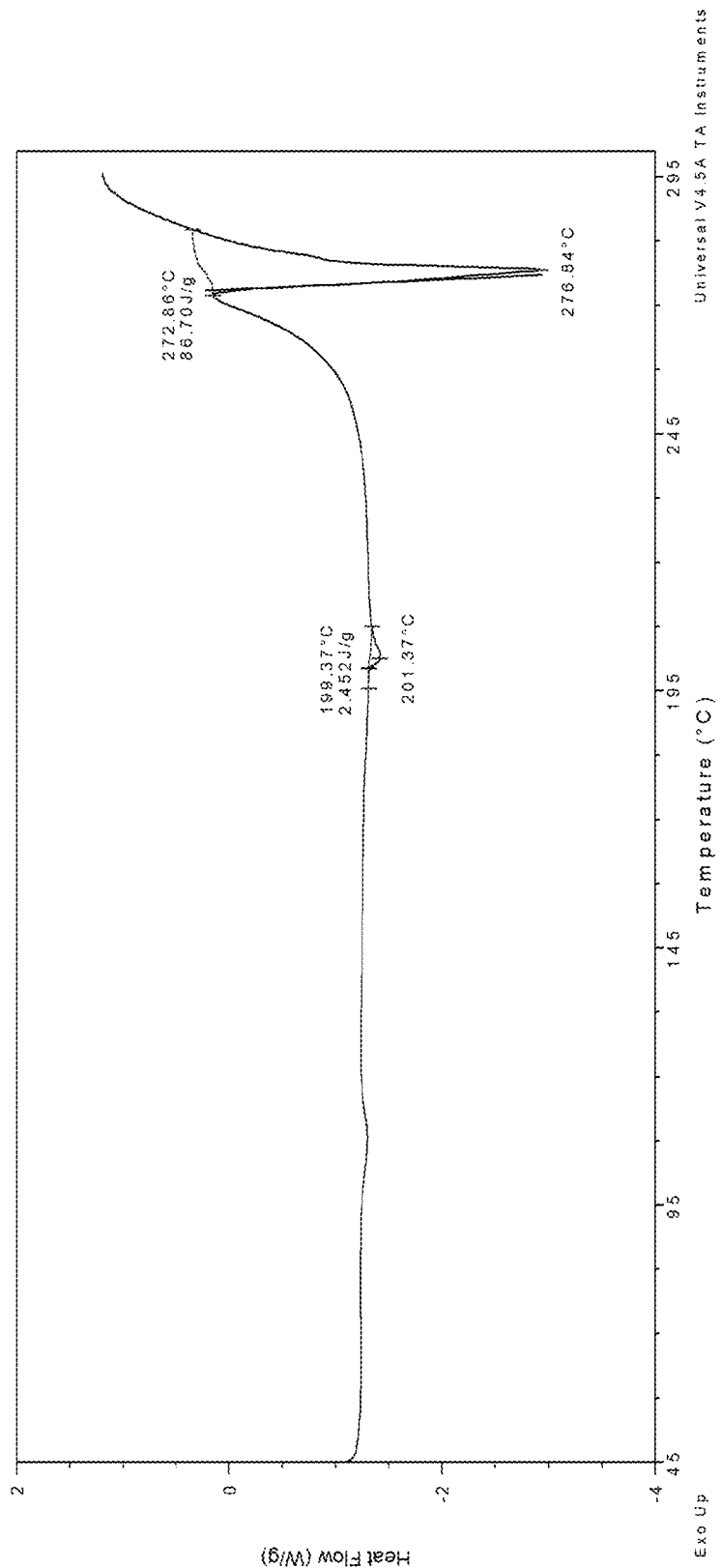
FIG. 67 shows a DSC thermogram of Compound 1, Form XXI.

In some embodiments, Form XXI exhibits a DSC thermogram having endotherm peaks at temperatures of about 201° C., and 277° C. In some embodiments, Form XXI exhibits a DSC thermogram having an endotherm peak at a temperature of about 201° C. In some embodiments, Form XXI exhibits a DSC thermogram having an endotherm peak at a temperature of about 277° C. In some embodiments, Form XXI has a DSC thermogram substantially as depicted in FIG. 67.

In some embodiments, Form XXI has at least two characteristic XRPD peaks selected from about 10.3, about 14.2, about 20.7, about 22.6, about 24.2, and about 27.1 degrees 2-theta; and Form XXI exhibits a DSC thermogram having endotherm peaks at temperatures of about 201° C., and 277° C.

Provided herein are also processes for preparing Form XXI of Compound 1 comprising adding a saturated solution of Compound 1, Form I in dichloromethane to toluene.

In some embodiments, Form XXI can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XXII

Provided herein is a solid form of Compound 1 having Form XXII, which is described below in the Examples.

In some embodiments, Form XXII has at least one characteristic XRPD peaks selected from about 6.8, about 9.4, about 10.1, about 11.4, about 12.1, about 14.3, about 17.5, about 18.5, and about 22.2 degrees 2-theta.

In some embodiments, Form XXII has at least two characteristic XRPD peaks selected from about 6.8, about 9.4, about 10.1, about 11.4, about 12.1, about 14.3, about 17.5, about 18.5, and about 22.2 degrees 2-theta.

In some embodiments, Form XXII has at least three characteristic XRPD peaks selected from about 6.8, about 9.4, about 10.1, about 11.4, about 12.1, about 14.3, about 17.5, about 18.5, and about 22.2 degrees 2-theta.

In some embodiments, Form XXII has at least one characteristic XRPD peak selected from about 6.8, about 9.4, about 10.1, about 11.4, about 12.1, about 13.3, about 14.3, about 15.8, about 17.5, about 18.0, about 18.5, about 19.2, about 19.8, about 22.2, about 25.3, and about 26.1 degrees 2-theta.

In some embodiments, Form XXII has at least two characteristic XRPD peaks selected from about 6.8, about 9.4, about 10.1, about 11.4, about 12.1, about 13.3, about 14.3, about 15.8, about 17.5, about 18.0, about 18.5, about 19.2, about 19.8, about 22.2, about 25.3, and about 26.1 degrees 2-theta.

In some embodiments, Form XXII has at least three characteristic XRPD peaks selected from about 6.8, about 9.4, about 10.1, about 11.4, about 12.1, about 13.3, about 14.3, about 15.8, about 17.5, about 18.0, about 18.5, about 19.2, about 19.8, about 22.2, about 25.3, and about 26.1 degrees 2-theta.

Figure 68:
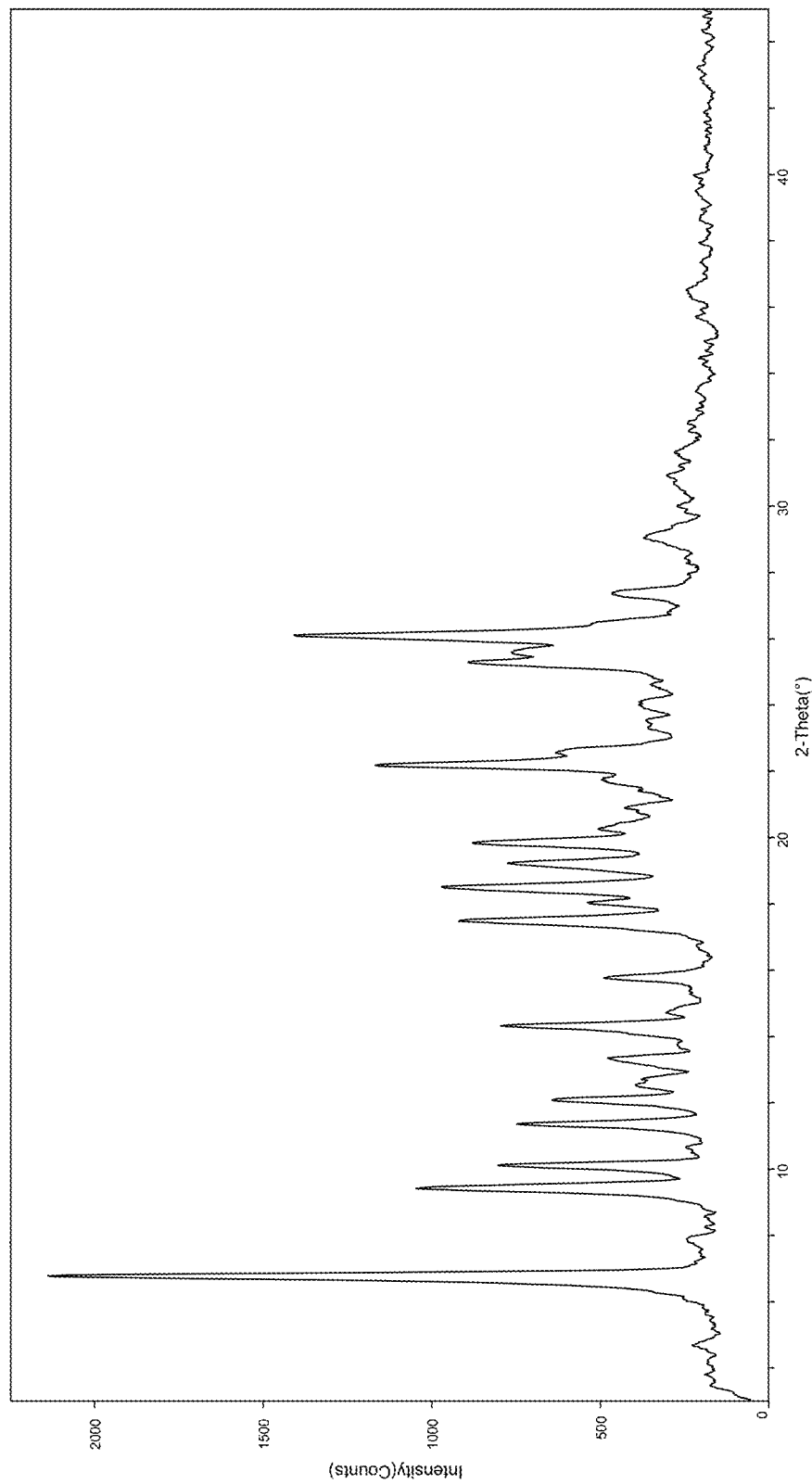
FIG. 68 shows an XRPD pattern of Compound 1, Form XXII.

In some embodiments, Form XXII has an XRPD pattern with characteristic peaks as substantially shown in FIG. 68.

Figure 69:
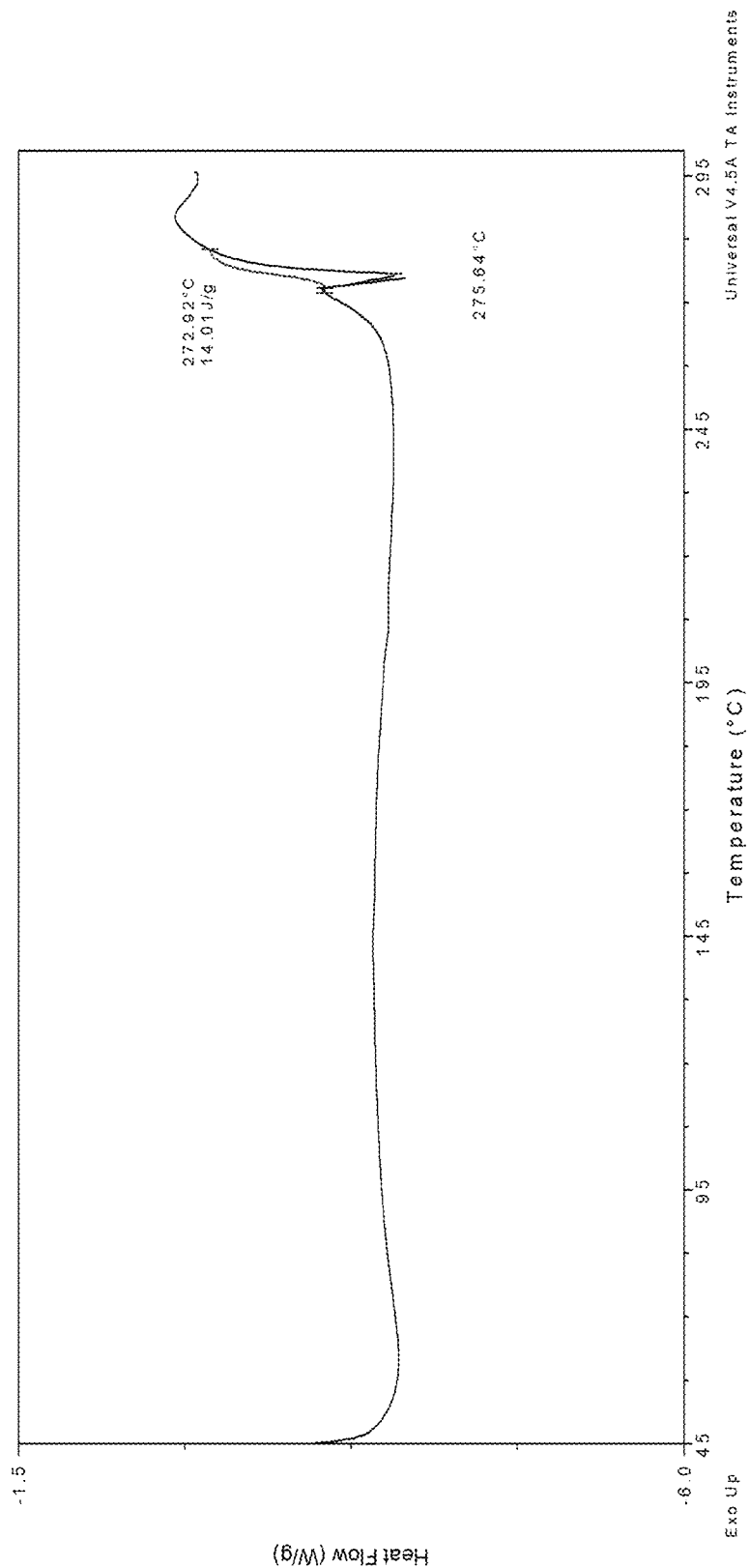
FIG. 69 shows a DSC thermogram of Compound 1, Form XXII.

In some embodiments, Form XXII exhibits a DSC thermogram having an endotherm peak at a temperature of about 276° C. In some embodiments, Form XXII has a DSC thermogram substantially as depicted in FIG. 69.

In some embodiments, Form XXII has at least one characteristic XRPD peaks selected from about 6.8, about 9.4, about 10.1, about 11.4, about 12.1, about 14.3, about 17.5, about 18.5, and about 22.2 degrees 2-theta; and Form XXII exhibits a DSC thermogram having an endotherm peak at a temperature of about 276° C.

Provided herein are also processes for preparing Form XXII of Compound 1 comprising adding a saturated solution of Compound 1, Form I in dichloromethane to methanol.

In some embodiments, Form XXII can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XXIII

Provided herein is a solid form of Compound 1 having Form XXIII, which is described below in the Examples.

In some embodiments, Form XXIII has at least one characteristic XRPD peaks selected from about 12.0, about 12.7, about 21.0, about 24.9, and about 25.6 degrees 2-theta.

In some embodiments, Form XXIII has at least two characteristic XRPD peaks selected from about 12.0, about 12.7, about 21.0, about 24.9, and about 25.6 degrees 2-theta.

In some embodiments, Form XXIII has at least three characteristic XRPD peaks selected from about 12.0, about 12.7, about 21.0, about 24.9, and about 25.6 degrees 2-theta.

In some embodiments, Form XXIII has at least one characteristic XRPD peak selected from about 12.0, about 12.7, about 13.2, about 14.3, about 18.9, about 19.6, about 21.0, about 24.9, and about 25.6 degrees 2-theta.

In some embodiments, Form XXIII has at least two characteristic XRPD peaks selected from about 12.0, about 12.7, about 13.2, about 14.3, about 18.9, about 19.6, about 21.0, about 24.9, and about 25.6 degrees 2-theta.

In some embodiments, Form XXIII has at least three characteristic XRPD peaks selected from about 12.0, about 12.7, about 13.2, about 14.3, about 18.9, about 19.6, about 21.0, about 24.9, and about 25.6 degrees 2-theta.

Figure 70:
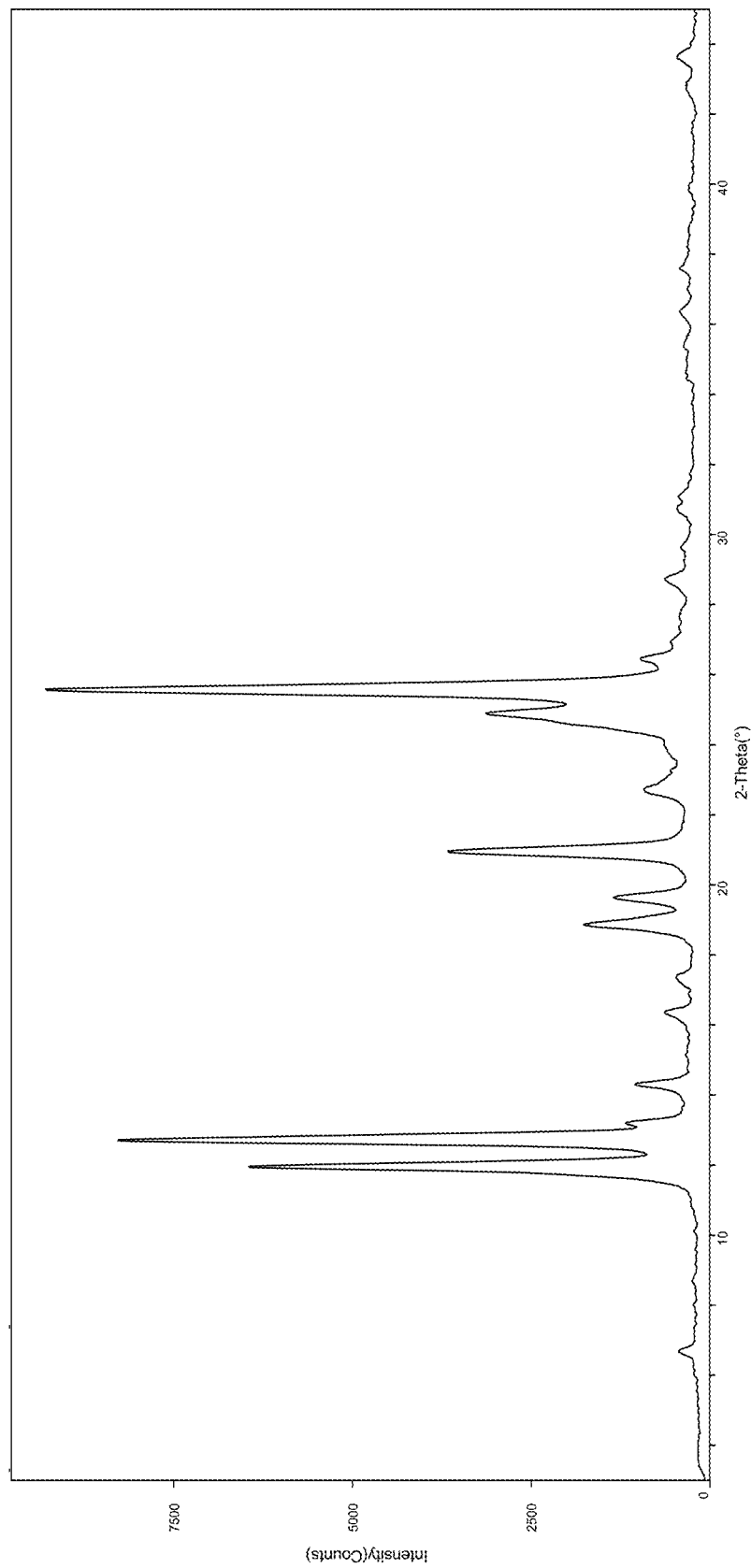
FIG. 70 shows an XRPD pattern of Compound 1, Form XXIII.

In some embodiments, Form XXIII has an XRPD pattern with characteristic peaks as substantially shown in FIG. 70.

Figure 71:
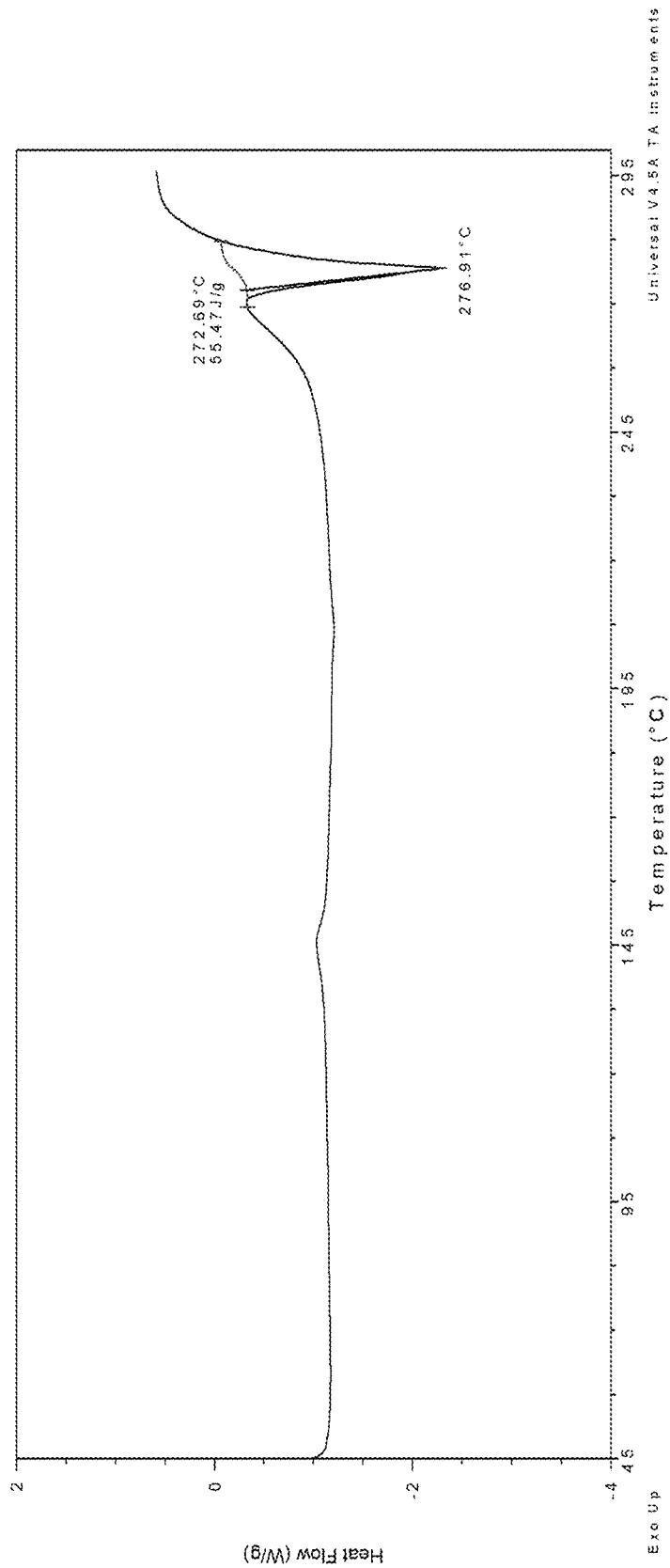
FIG. 71 shows a DSC thermogram of Compound 1, Form XXIII.
Figure 72:
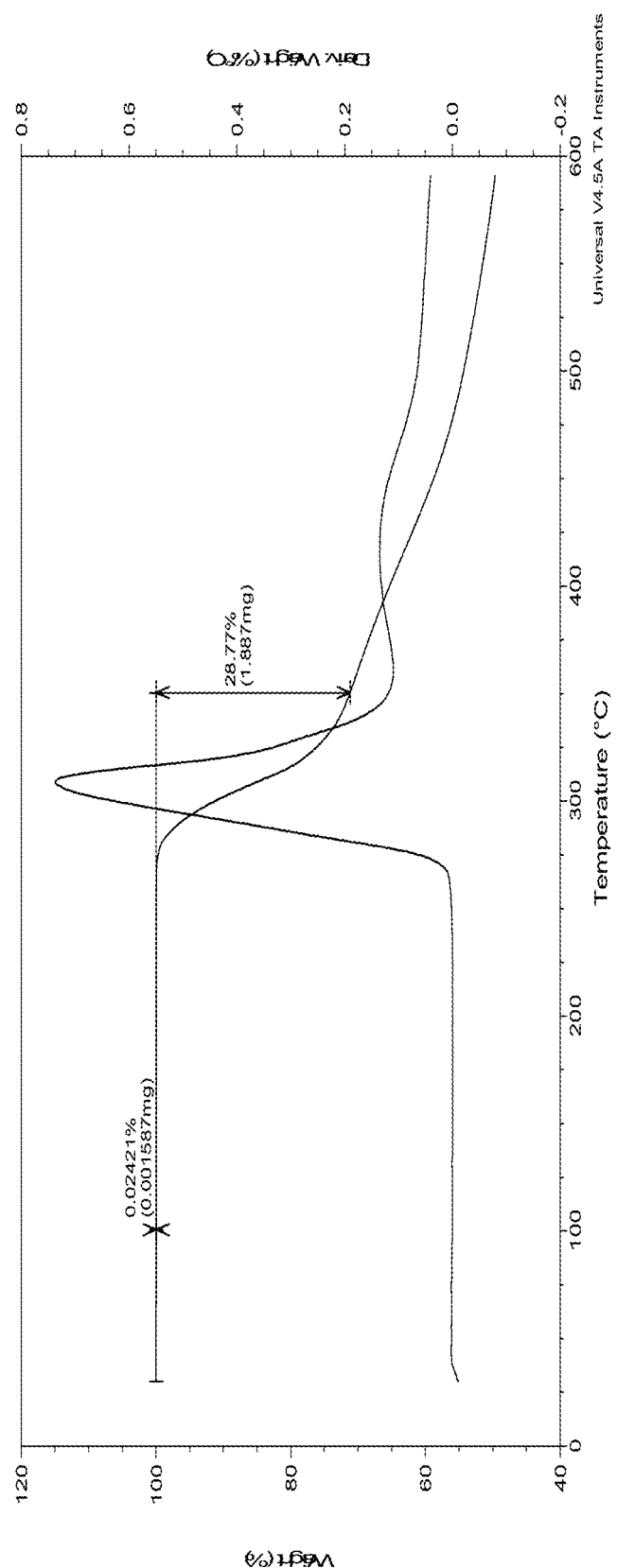
FIG. 72 shows a TGA thermogram of Compound 1, Form XXIII.

In some embodiments, Form XXIII exhibits a DSC thermogram having an endotherm peak at a temperature of about 277° C. In some embodiments, Form XXIII has a DSC thermogram substantially as depicted in FIG. 71. In some embodiments, Form XXIII has a TGA thermogram substantially as depicted in FIG. 72.

In some embodiments, Form XXIII has at least one characteristic XRPD peaks selected from about 12.0, about 12.7, about 21.0, about 24.9, and about 25.6 degrees 2-theta; and Form XXIII exhibits a DSC thermogram having an endotherm peak at a temperature of about 277° C.

Provided herein are also processes for preparing Form XXIII of Compound 1 comprising cooling a 10 mL of saturated solution of Compound 1, Form I in dichloromethane to −20° C., and holding the temperature at −20° C. for 3 h.

In some embodiments, Form XXIII can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XXIV

Provided herein is a solid form of Compound 1 having Form XXIV, which is described below in the Examples.

In some embodiments, Form XXIV has at least one characteristic XRPD peaks selected from about 8.6, about 15.6, about 18.1, about 20.4, about 22.2, about 22.9, about 24.2, and about 25.5 degrees 2-theta.

In some embodiments, Form XXIV has at least two characteristic XRPD peaks selected from about 8.6, about 15.6, about 18.1, about 20.4, about 22.2, about 22.9, about 24.2, and about 25.5 degrees 2-theta.

In some embodiments, Form XXIV has at least three characteristic XRPD peaks selected from about 8.6, about 15.6, about 18.1, about 20.4, about 22.2, about 22.9, about 24.2, and about 25.5 degrees 2-theta.

In some embodiments, Form XXIV has at least one characteristic XRPD peak selected from about 8.6, about 9.7, about 13.8, about 15.6, about 17.4, about 18.1, about 19.4, about 20.4, about 22.2, about 22.9, about 24.2, about 25.5, about 26.0, about 27.5, and about 27.9 degrees 2-theta.

In some embodiments, Form XXIV has at least two characteristic XRPD peaks selected from about 8.6, about 9.7, about 13.8, about 15.6, about 17.4, about 18.1, about 19.4, about 20.4, about 22.2, about 22.9, about 24.2, about 25.5, about 26.0, about 27.5, and about 27.9 degrees 2-theta.

In some embodiments, Form XXIV has at least three characteristic XRPD peaks selected from about 8.6, about 9.7, about 13.8, about 15.6, about 17.4, about 18.1, about 19.4, about 20.4, about 22.2, about 22.9, about 24.2, about 25.5, about 26.0, about 27.5, and about 27.9 degrees 2-theta.

Figure 73:
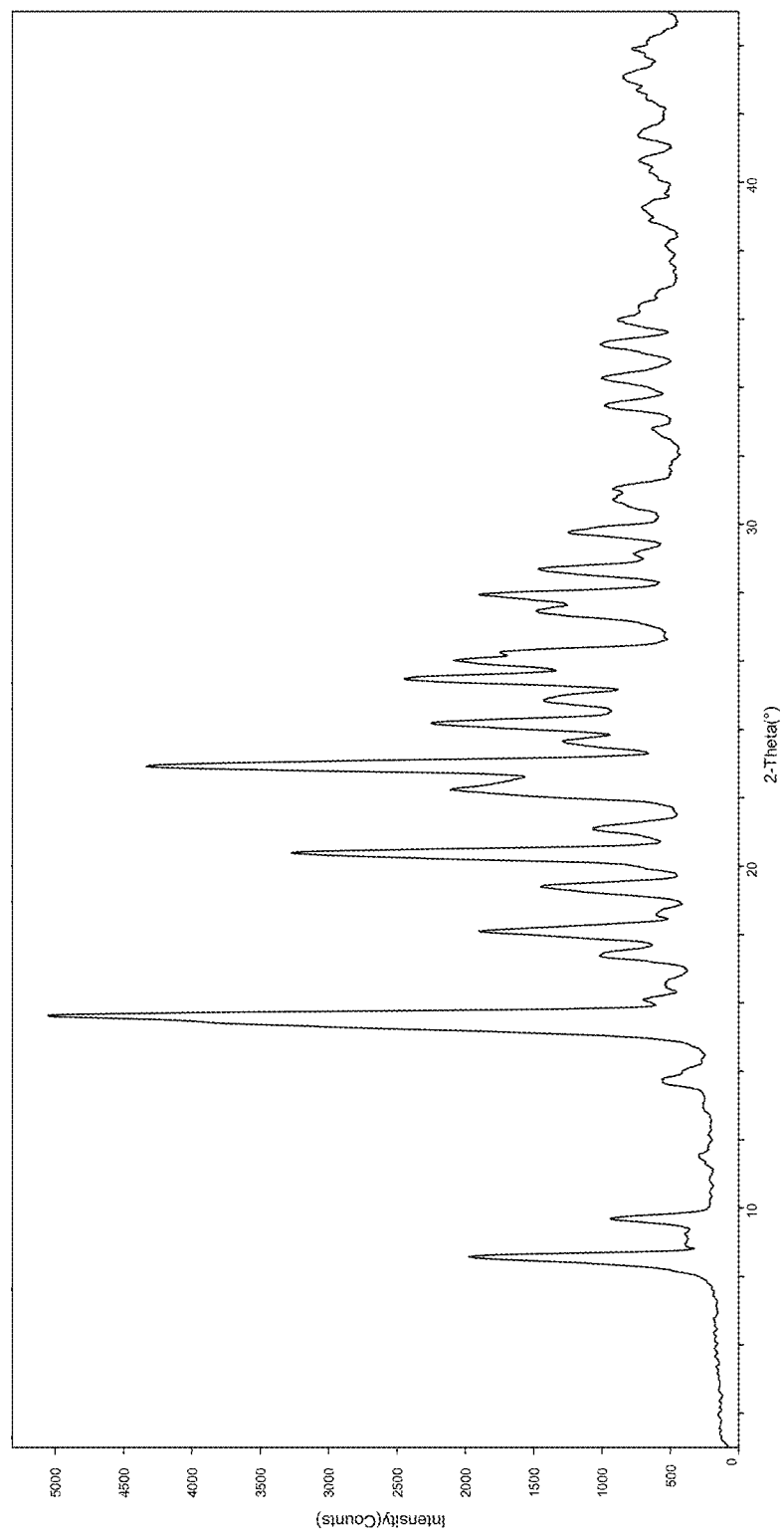
FIG. 73 shows an XRPD pattern of Compound 1, Form XXIV.

In some embodiments, Form XXIV has an XRPD pattern with characteristic peaks as substantially shown in FIG. 73.

Figure 74:
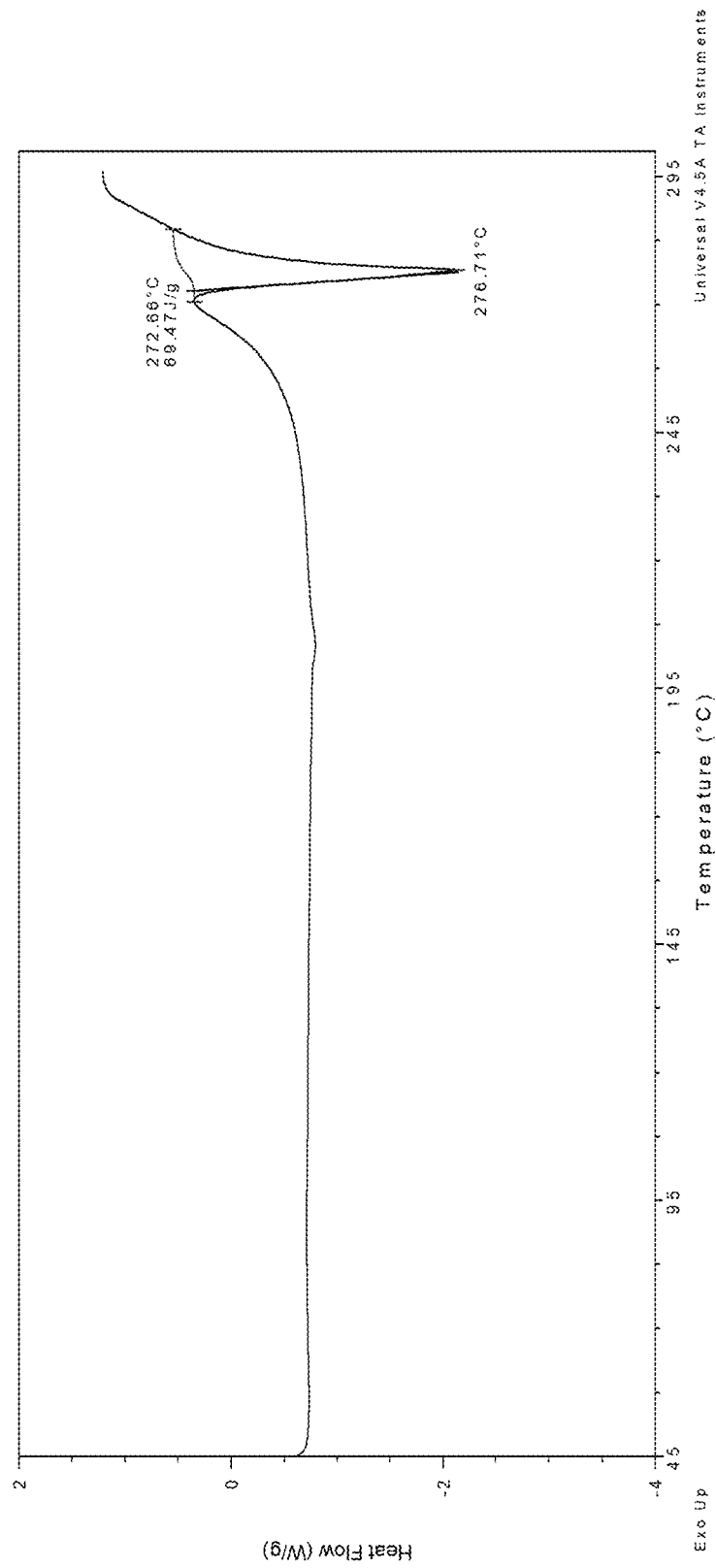
FIG. 74 shows a DSC thermogram of Compound 1, Form XXIV.
Figure 75:
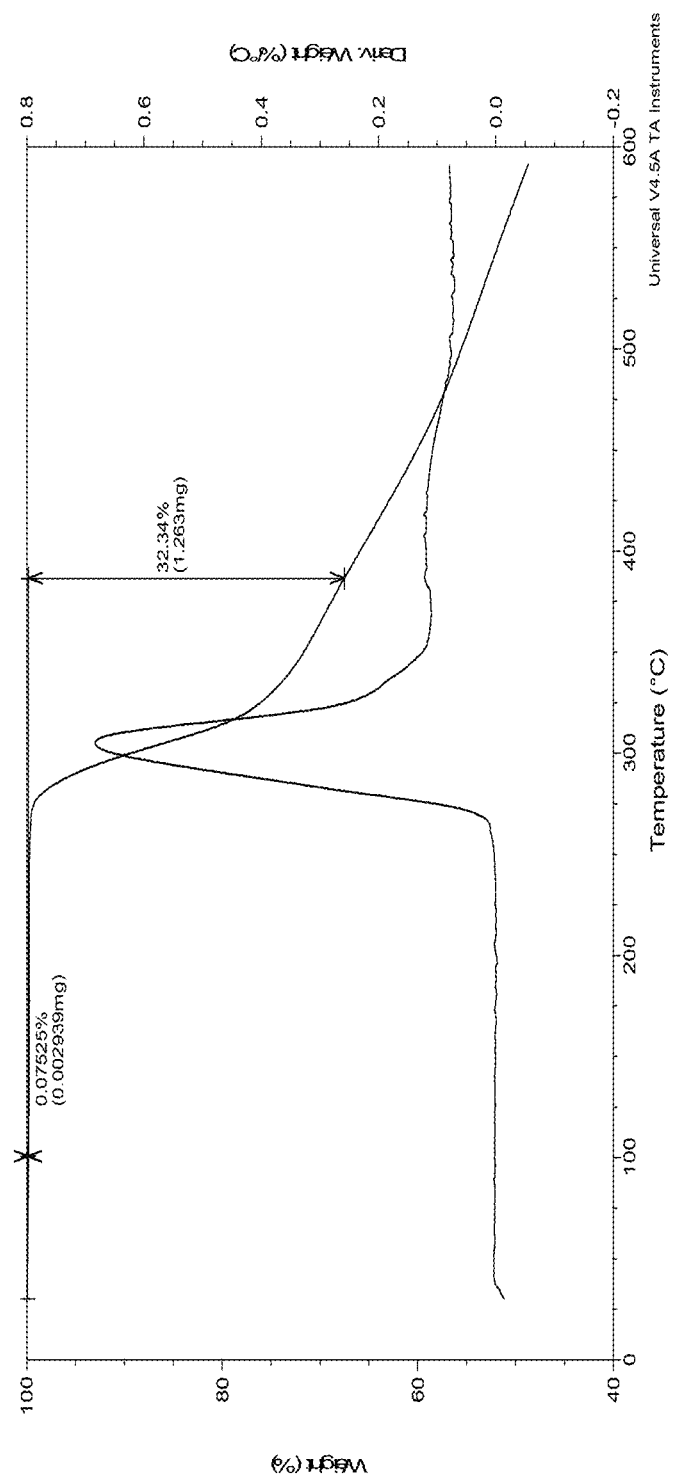
FIG. 75 shows a TGA thermogram of Compound 1, Form XXIV.

In some embodiments, Form XXIV exhibits a DSC thermogram having an endotherm peak at a temperature of about 277° C. In some embodiments, Form XXIV has a DSC thermogram substantially as depicted in FIG. 74. In some embodiments, Form XXIV has a TGA thermogram substantially as depicted in FIG. 75.

In some embodiments, Form XXIV has at least one characteristic XRPD peaks selected from about 8.6, about 15.6, about 18.1, about 20.4, about 22.2, about 22.9, about 24.2, and about 25.5 degrees 2-theta; and Form XXIV exhibits a DSC thermogram having an endotherm peak at a temperature of about 277° C.

Provided herein are also processes for preparing Form XXIV of Compound 1 comprising cycling a saturated solution of Compound 1, Form I in DMF between 5-50° C. for a period of time (e.g., at least three days or at least 72 hours).

In some embodiments, Form XXIV can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XXV

Provided herein is a solid form of Compound 1 having Form XXV, which is described below in the Examples.

In some embodiments, Form XXV has at least one characteristic XRPD peaks selected from about 16.6, about 18.4, about 20.4, about 22.4, about 24.4, about 24.9 and about 29.9 degrees 2-theta.

In some embodiments, Form XXV has at least two characteristic XRPD peaks selected from about 16.6, about 18.4, about 20.4, about 22.4, about 24.4, about 24.9 and about 29.9 degrees 2-theta.

In some embodiments, Form XXV has at least three characteristic XRPD peaks selected from about 16.6, about 18.4, about 20.4, about 22.4, about 24.4, about 24.9 and about 29.9 degrees 2-theta.

In some embodiments, Form XXV has at least one characteristic XRPD peak selected from about 16.6, about 18.4, about 20.4, about 21.7, about 22.4, about 24.4, about 24.9, about 25.7, about 29.9, about 31.9, about 35.8, and about 38.9 degrees 2-theta.

In some embodiments, Form XXV has at least two characteristic XRPD peaks selected from about 16.6, about 18.4, about 20.4, about 21.7, about 22.4, about 24.4, about 24.9, about 25.7, about 29.9, about 31.9, about 35.8, and about 38.9 degrees 2-theta.

In some embodiments, Form XXV has at least three characteristic XRPD peaks selected from about 16.6, about 18.4, about 20.4, about 21.7, about 22.4, about 24.4, about 24.9, about 25.7, about 29.9, about 31.9, about 35.8, and about 38.9 degrees 2-theta.

Figure 76:
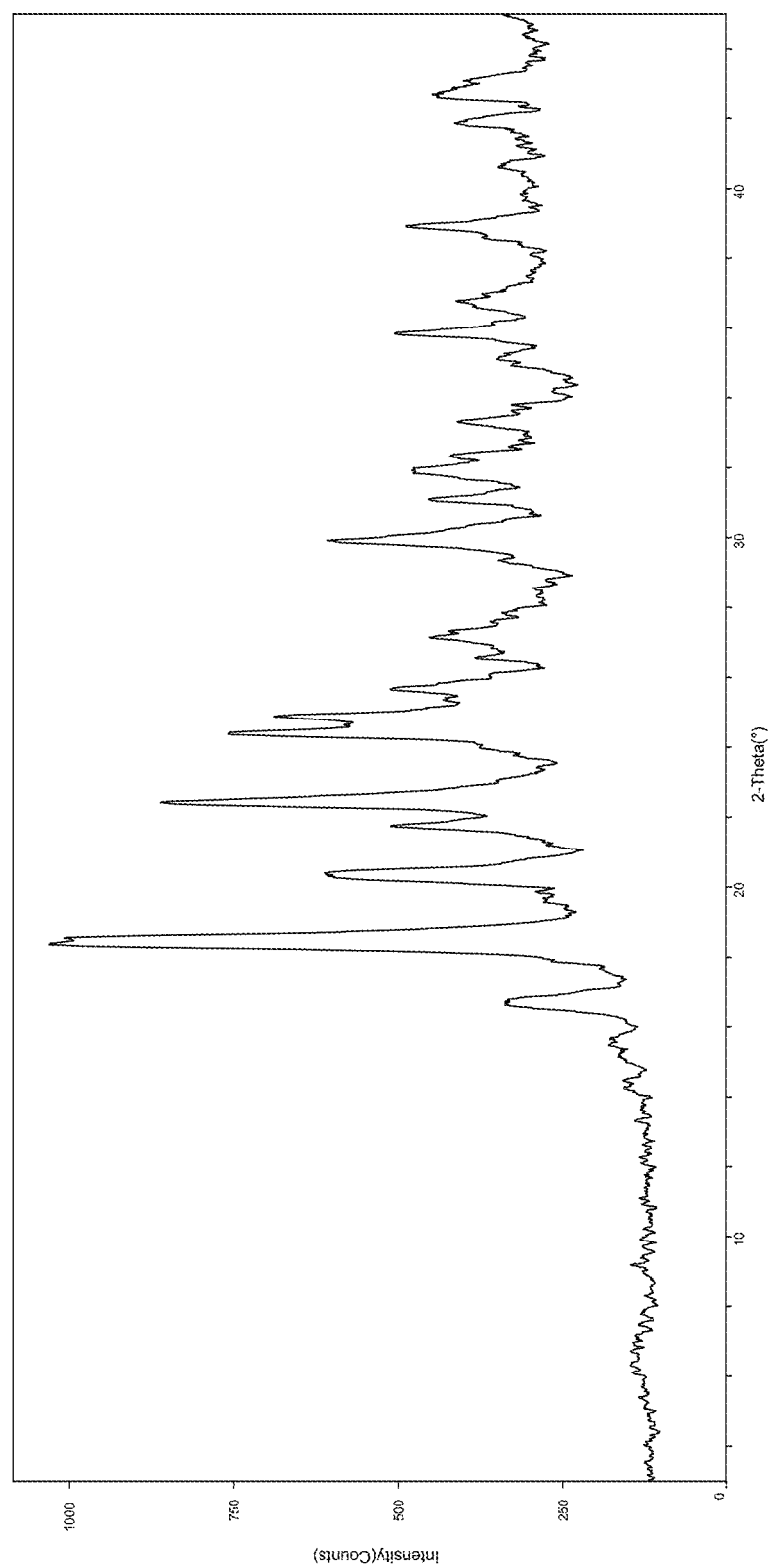
FIG. 76 shows an XRPD pattern of Compound 1, Form XXV.

In some embodiments, Form XXV has an XRPD pattern with characteristic peaks as substantially shown in FIG. 76.

Figure 77:
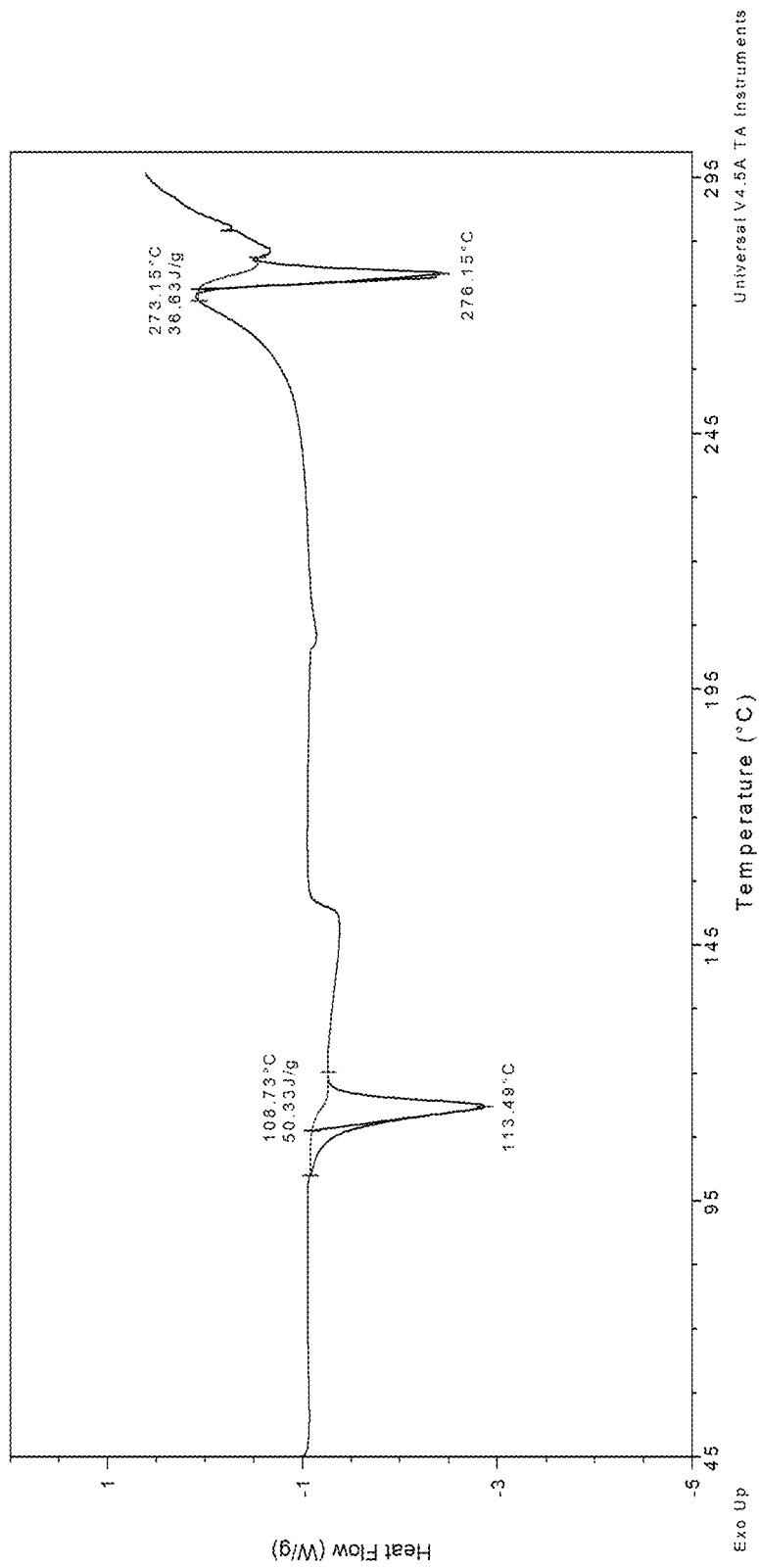
FIG. 77 shows a DSC thermogram of Compound 1, Form XXV.

In some embodiments, Form XXV exhibits a DSC thermogram having endotherm peaks at temperatures of about 113° C. and 276° C. In some embodiments, Form XXV exhibits a DSC thermogram having an endotherm peak at a temperature of about 113° C. In some embodiments, Form XXV exhibits a DSC thermogram having an endotherm peak at a temperature of about 276° C. In some embodiments, Form XXIV has a DSC thermogram substantially as depicted in FIG. 77.

In some embodiments, Form XXV has at least one characteristic XRPD peaks selected from about 16.6, about 18.4, about 20.4, about 22.4, about 24.4, about 24.9 and about 29.9 degrees 2-theta; and Form XXV exhibits a DSC thermogram having endotherm peaks at temperatures of about 113° C. and 276° C.

Provided herein are also processes for preparing Form XXV of Compound 1 comprising cycling a saturated solution of Compound 1, Form I in DMSO between 5-50° C. for a period of time (e.g., at least three days or at least 72 hours).

In some embodiments, Form XXV can be isolated with a purity of at least about 80%, about 85%, about 90%, about 95%, about 96%, about 97%, about 98%, or about 99%. In some embodiments, Form I can be isolated with a purity greater than about 99%.

Compound 1 Form XXVI

Provided herein is a solid form of Compound 1 having Form XXVI, which is described below in the Examples.

In some embodiments, Form XXVI has at least one characteristic XRPD peaks selected from about 6.8, about 9.9, about 19.9, and about 26.1 degrees 2-theta.

In some embodiments, Form XXVI has at least two characteristic XRPD peaks selected from about 6.8, about 9.9, about 19.9, and about 26.1 degrees 2-theta.

In some embodiments, Form XXVI has at least three characteristic XRPD peaks selected from about 6.8, about 9.9, about 19.9, and about 26.1 degrees 2-theta.

In some embodiments, Form XXVI has at least one characteristic XRPD peak selected from about 6.8, about 9.4, about 9.9, about 10.6, about 19.9, about 25.7, about 26.1, and about 27.4 degrees 2-theta.

In some embodiments, Form XXVI has at least two characteristic XRPD peaks selected from about 6.8, about 9.4, about 9.9, about 10.6, about 19.9, about 25.7, about 26.1, and about 27.4 degrees 2-theta.

In some embodiments, Form XXVI has at least three characteristic XRPD peaks selected from about 6.8, about 9.4, about 9.9, about 10.6, about 19.9, about 25.7, about 26.1, and about 27.4 degrees 2-theta.

Figure 78:
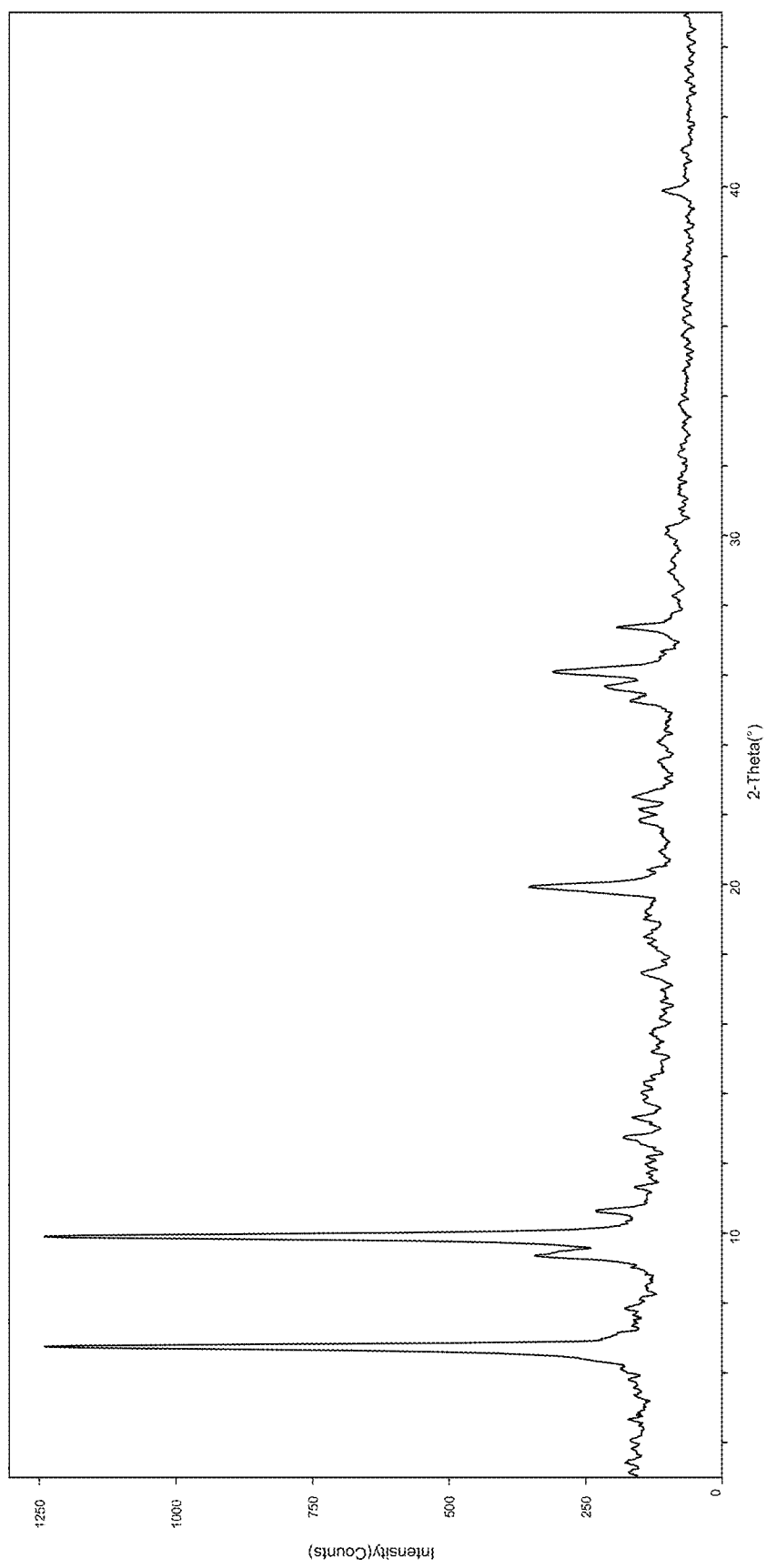
FIG. 78 shows an XRPD pattern of Compound 1, Form XXVI.

In some embodiments, Form XXVI has an XRPD pattern with characteristic peaks as substantially shown in FIG. 78.

Provided herein are also processes for preparing Form XXVI of Compound 1 comprising drying Compound 1, Form V under vacuum at 50° C. for a period of time (e.g., 3 days).

In some embodiments, Form XXVI can be isolated with a purity of at least about 80%, about 85%, about 90%, about 95%, about 96%, about 97%, about 98%, or about 99%. In some embodiments, Form I can be isolated with a purity greater than about 99%.

Process for Preparation of Compound 1

The present application further provides a process of preparing Compound 1, where the process can be suitable for scale up. A process of preparing Compound 1 is described in U.S. Pat. No. 9,611,267, the entirety of which is incorporated herein by reference.

The present invention provides a process of making Compound 1 having the formula:

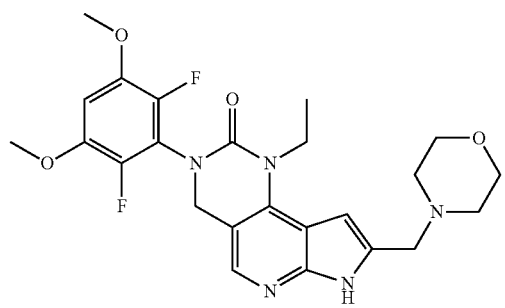

Compound 1 or a salt thereof, comprising a) deprotecting Compound F8 having the formula:

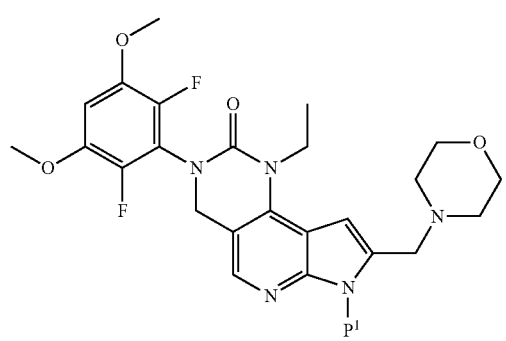

Compound F8 or a salt thereof, wherein $P^1$ is an amino protecting group. In some embodiments, $P^1$ is arylsulfonyl. In some embodiments, $P^1$ is phenylsulphonyl or toluenesulfonyl.

In some embodiments, the deprotecting in step a) comprises reacting Compound F8 with a suitable deprotecting agent. In some embodiments, the deprotecting comprises treating with base. In some embodiments, the base is sodium hydroxide or potassium hydroxide. In some embodiments, the base is aqueous sodium hydroxide or aqueous potassium hydroxide. In some embodiments, the aqueous base is a 1 M solution of the base. In some embodiments, the deprotection is carried out in a suitable solvent at a temperature of 70-90° C. (e.g., 80° C.). In some embodiments, the suitable solvent is 1,4-dioxane. In some embodiments, the base is present in $\geq 2$, $\geq 3$, or $\geq 4$ molar equivalents relative to the compound of Formula II.

In some embodiments, Compound 1 and Compound F8 are, preferably, in their non-salt forms.

In some embodiments, Compound F8, or a salt thereof, is produced by a process comprising b) reacting Compound F7 having the formula:

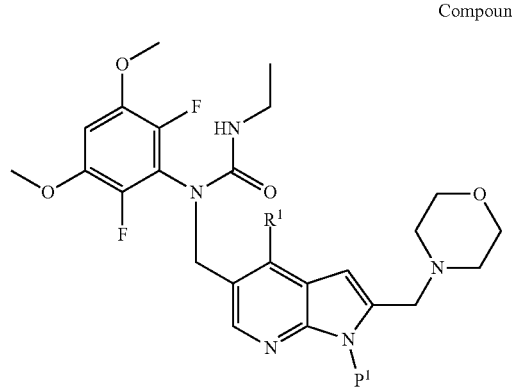

Compound F7 or a salt thereof, wherein $R^1$ is Cl, Br, or I, with a base.

In some embodiments, Compound F7 and Compound F8 are, preferably, in their non-salt forms.

In some embodiments, the base in step b) is lithium hexamethyldisilazide ("LHMDS"), sodium hexamethyldisilazide ("NHMDS"), potassium hexamethyldisilazide ("KHMDS"), or lithium diisopropyl amide ("LDA"). In some embodiments, the reaction of Compound F7 and the base is carried out in THF at ambient temperature.

In some embodiments, Compound F7, or a salt thereof, is produced by a process comprising c) reacting Compound F6 having the formula:

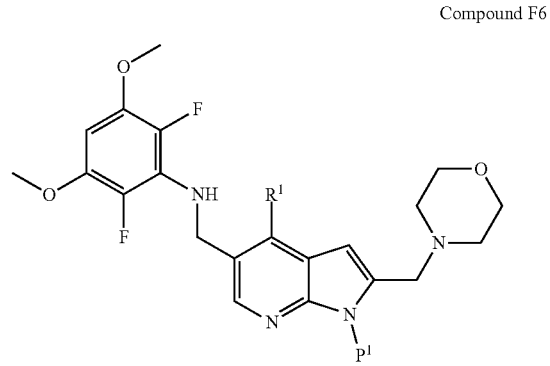

Compound F6 or a salt thereof, with ethyl isocyanate.

In some embodiments, the process further comprises purifying Compound F7. In some embodiments, the purifying comprises mixing compound F7 with a first organic solvent at an elevated temperature to produce a first mixture; filtering the first mixture to produce a first solid; mixing the first solid with water to produce a second mixture; filtering the second mixture to produce a second solid; and mixing the second solid with a second organic solvent. In certain embodiments, the first organic solvent is acetonitrile and the second organic solvent is heptane.

In some embodiments, the reacting in step c) is carried out in the presence of an acid. In some embodiments, the acid is methanesulfonic acid, toluenesulfonic acid, or HCl.

In some embodiments, the reaction of Compound F6 with ethyl isocyanate is carried out in acetonitrile at ambient temperature.

In some embodiments, Compound F6, or a salt thereof, is produced by a process comprising d) reacting Compound F4 having the formula:

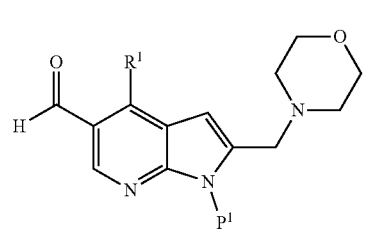

Compound F4 or a salt thereof, with Compound F5 having the formula:

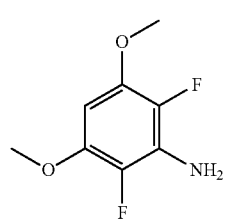

Compound F5 or a salt thereof, in the presence of a Lewis acid and a reducing agent, wherein $P^1$ is an amino protecting group and $R^1$ is Cl, Br or I.

In some embodiments, Compound F4 and Compound F5 are, preferably, in their non-salt forms.

In some embodiments, the Lewis acid in step d) is chlorotrimethylsilane. In some embodiments, the reducing agent is borane-THF complex ("BH$_3$-THF").

In some embodiments, the reaction of Compound F4 and Compound F5 is carried out in DMF at room temperature.

In some embodiments, Compound F4, or a salt thereof, is produced by a process comprising e) reacting Compound F3 having the formula:

Compound F3

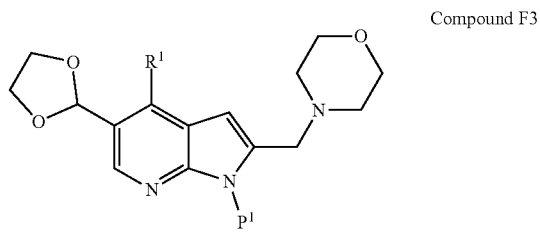

or a salt thereof, with an acid. In some embodiments, P$^1$ is an amino protecting group. In some embodiments, R$^1$ is Cl, Br, or I.

In some embodiments, Compound F3 and Compound F4 are, preferably, in their non-salt forms.

In some embodiments, the acid in step e) is an aqueous acid. In some embodiments, the acid is HCl or sulfuric acid. In some embodiments, the acid is aqueous HCl or aqueous sulfuric acid.

In some embodiments, the reaction of a Compound F3 is carried out in dichloromethane at room temperature.

In some embodiments, Compound F3, or a salt thereof, is produced by a process comprising f) reacting Compound F2 having the formula:

Compound F2

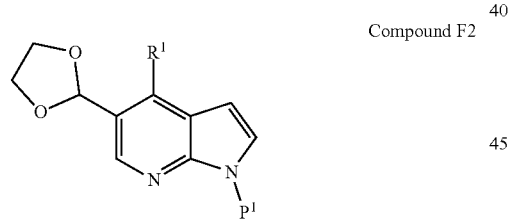

or a salt thereof, with N-formylmorpholine in the presence of base to form a mixture; and contacting the mixture with morpholine and an acid in the presence of a reducing agent.

In some embodiments, Compound F2 and Compound F3 are in their non-salt forms.

In some embodiments, the base in step f) is lithium diisopropylamide or lithium hexamethyldisilazide. In some embodiments, the reaction of Compound F2 with base is carried out in THF at a reduced temperature. In certain embodiments, the temperature is ≤−50° C., ≤−60° C., or ≤−70° C.

In some embodiments, the reducing agent in step f) is sodium triacetoxyborohydride, sodium borohydride, or sodium cyanoborohydride. In some embodiments, the acid in step f) is acetic acid. In some embodiments, the reacting in step f) is carried out at ambient temperature.

The present invention provides a process for preparing Compound 1 comprising:

a) contacting compound 2 having the formula:

Compound 2

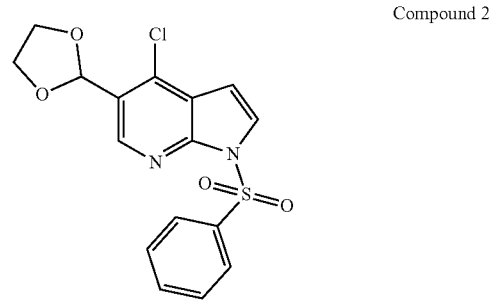 [SMILES: O=S(=O)(c1ccccc1)n1ccc2c(Cl)c(C3OCCO3)cnc21]

with N-formylmorpholine in the presence of a base to form compound 2a having the formula:

Compound 2a

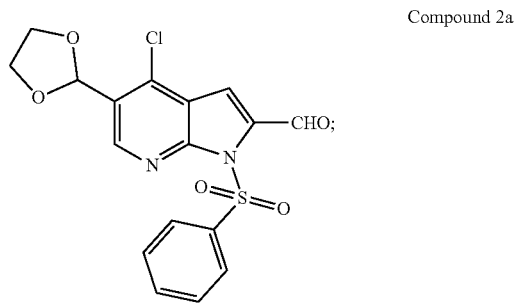 [SMILES: O=Cc1cc2c(Cl)c(C3OCCO3)cnc2n1S(=O)(=O)c1ccccc1]

b) reacting compound 2a with morpholine in the presence of an acid and a reducing agent to form compound 3 having the formula:

Compound 3

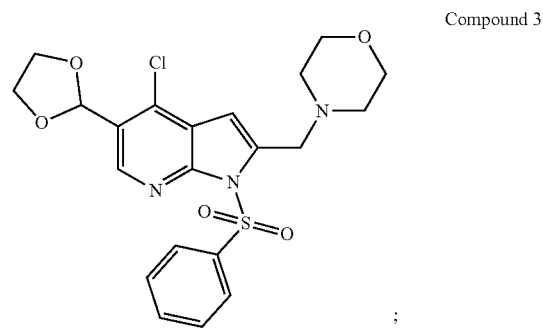 [SMILES: O=S(=O)(c1ccccc1)n1c(CN2CCOCC2)cc2c(Cl)c(C3OCCO3)cnc21]

c) converting compound 3 to compound 4 having the formula:

Compound 4

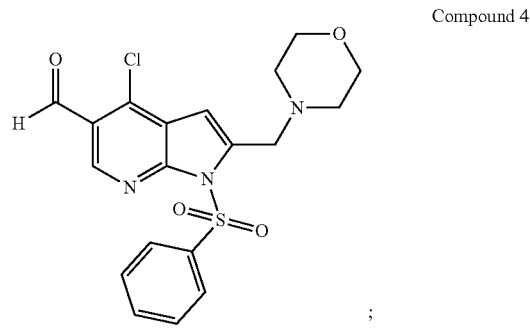 [SMILES: O=Cc1cnc2c(cc(CN3CCOCC3)n2S(=O)(=O)c2ccccc2)c1Cl]

d) reacting compound 4 with compound 5 having the formula:

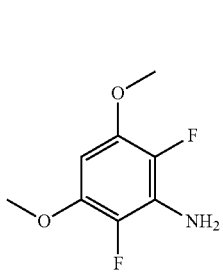

Compound 5 in the presence of a Lewis acid and a reducing agent to form compound 6 having the formula:

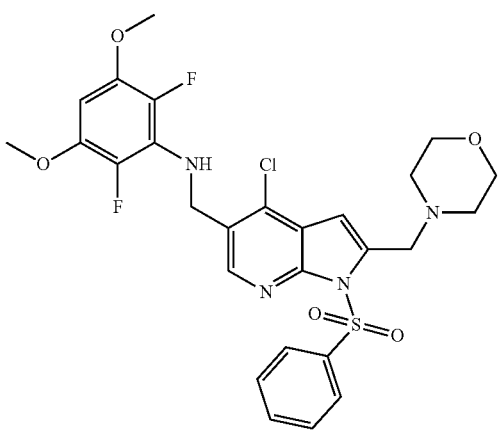

Compound 6

;

e) reacting compound 6 with ethyl isocyanate to form compound 7 having the formula:

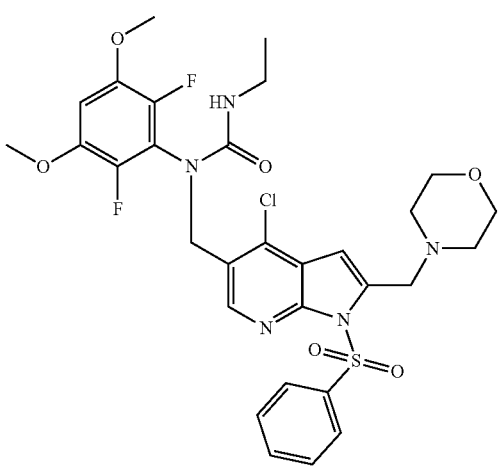

Compound 7

;

f) contacting compound 7 with a base to form compound 8 having the formula:

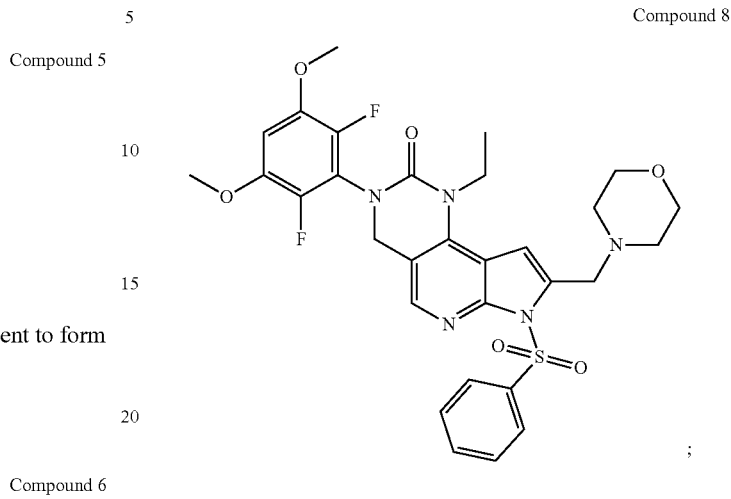

Compound 8

;

g) contacting compound 8 with a base to produce Form I of Compound 1.

In some embodiments, the process further comprises recrystallizing Compound 1 in a solvent to produce Form I of Compound 1. In some embodiments, the solvent is a mixture of dichloromethane and methyl t-butyl ether.

In some embodiments, the base in step a) is lithium diisopropyl amide.

In some embodiments, the acid in step b) is acetic acid. In some embodiments, the reducing agent in step b) is sodium triacetoxyborohydride. In some embodiments, the acid in step b) is acetic acid and the reducing agent in step b) is sodium triacetoxyborohydride.

In some embodiments, the converting in step c) is carried out in the presence of aqueous hydrochloric acid.

In some embodiments, the Lewis acid in step d) is chlorotrimethylsilane. In some embodiments, the reducing agent is $BH_3$-THF. In some embodiments, the Lewis acid in step d) is chlorotrimethylsilane and the reducing agent in step d) is $BH_3$-THF.

In some embodiments, the reacting in step e) further comprises purifying Compound 7.

In some embodiments, the base in step f) is lithium hexamethyldisilazide.

In some embodiments, the base in step g) is NaOH.

The present invention provides a process for preparing Compound 2 having the formula:

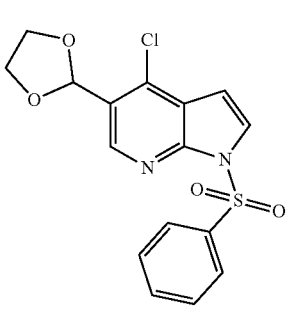

Compound 2 comprising:
- a) contacting 1H-pyrrolo[2,3-b]pyridine with an oxidizing agent to form 1H-pyrrolo[2,3-b]pyridine 7-oxide;
- b) reacting 1H-pyrrolo[2,3-b]pyridine 7-oxide with a chlorination agent to form 4-chloro-1H-pyrrolo[2,3-b]pyridine;
- c) reacting 4-chloro-1H-pyrrolo[2,3-b]pyridine with triisopropylsilyl chloride in the presence of a base to form 4-chloro-1-(triisopropylsilyl)-1H-pyrrolo[2,3-b]pyridine;
- d) reacting 4-chloro-1-(triisopropylsilyl)-1H-pyrrolo[2,3-b]pyridine with N,N-dimethylformamide in the presence of a base to form 4-chloro-1H-pyrrolo[2,3-b]pyridine-5-carbaldehyde;
- e) reacting 4-chloro-1H-pyrrolo[2,3-b] pyridine-5-carbaldehyde with benzenesulfonyl chloride in the presence of a base to form 4-chloro-1-(phenylsulfonyl)-1H-pyrrolo[2,3-b] pyridine-5-carbaldehyde; and
- f) reacting 4-chloro-1-(phenylsulfonyl)-1H-pyrrolo[2,3-b] pyridine-5-carbaldehyde with ethylene glycol in the presence of an acid to produce compound 2.

In some embodiments, the oxidizing agent in step a) is m-chloroperoxybenzoic acid or hydrogen peroxide. In some embodiments, the reaction is carried out in a suitable solvent. In some embodiments, the reaction is carried out in dichloromethane. In some embodiments, the reaction is carried out at a reduced temperature. In some embodiments, the reaction was carried out between −5-15° C. or between 0-10° C.

In some embodiments, the chlorination agent in step b) is methanesulfonyl chloride, thionyl chloride, or N-chlorosuccinimide. In some embodiments, the reaction is carried out in a suitable solvent. In some embodiments, the reaction is carried out in DMF. In some embodiments, the reaction is carried out at an elevated temperature. In some embodiments, the reaction is carried out at ≥70° C., ≥80° C., or ≥90° C.

In some embodiments, the base in step c) is sodium hydride. In some embodiments, the reaction in step c) is carried out in a suitable solvent. In some embodiments, the reaction in step c) is carried out in THF. In some embodiments, the reaction in step c) is carried out at ambient temperature. In some embodiments, the reaction in step c) is carried out at ≤30° C. or ≤25° C.

In some embodiments, the base in step d) is n-butyllithium, s-butyllithium, or t-butyllithium. In some embodiments, the reaction in step d) is carried out at a reduced temperature. In some embodiments, the reaction in step d) is carried out at ≤30° C., ≤20° C., ≤10° C., or ≤5° C.

In some embodiments, the base in step e) is cesium carbonate. In certain embodiments, the reaction in step e) is carried out in a suitable solvent. In certain embodiments, the reaction in step e) is carried out in dimethyl formamide. In some embodiments, the reaction in step e) is carried out at a temperature of ≤30° C., ≤20° C., ≤10° C., or ≤5° C. In some embodiments, the reaction in step e) is carried out in a suitable solvent at a range of temperatures, i.e. from 0° C. to ambient temperature.

In some embodiments, the acid in step f) is p-toluenesulfonic acid or HCl. In some embodiments, step f) is carried out at an elevated temperature. In some embodiments, step f) is carried out at reflux.

The present invention provides a process for preparing Compound 4 having the formula:

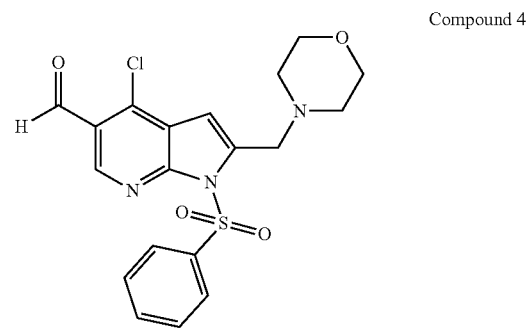 [SMILES: O=Cc1cnc2c(cc(CN3CCOCC3)n2S(=O)(=O)c2ccccc2)c1Cl]

Compound 4 comprising:
- a) contacting 2-amino-4-chloropyridine with a bromination agent to form 5-brom-4-chloropyridin-2-amine;
- b) contacting 5-brom-4-chloropyridin-2-amine with an iodination agent to form 5-bromo-4-chloro-3-iodopyridin-2-amine;
- c) reacting 5-bromo-4-chloro-3-iodopyridin-2-amine with 4-(prop-2-ynyl)morpholine in the presence of a catalyst to form Compound 9 having the formula:

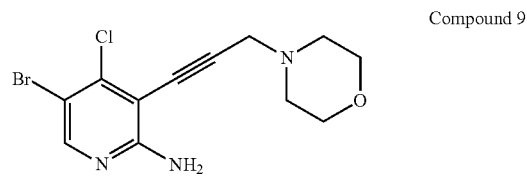 [SMILES: Nc1ncc(Br)c(Cl)c1C#CCN1CCOCC1]

Compound 9

- d) reacting Compound 9 with a base to form Compound 10 having the formula:

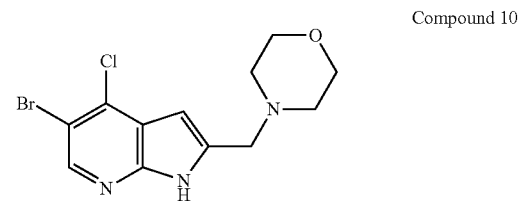 [SMILES: Clc1c(Br)cnc2[nH]c(CN3CCOCC3)cc12]

Compound 10

- e) reacting compound 10 with benzenesulfonyl chloride in the presence of a base to form compound 11 having the formula:

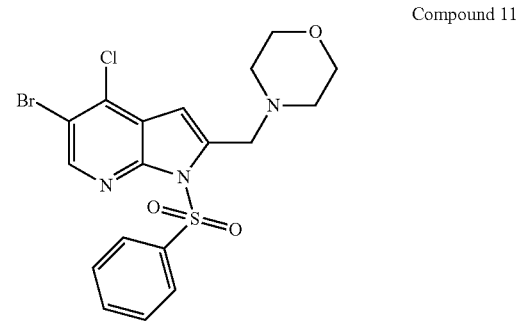 [SMILES: O=S(=O)(c1ccccc1)n1c(CN2CCOCC2)cc2c(Cl)c(Br)cnc21]

Compound 11 f) contacting compound 11 with an alkyl-magnesium halide agent to form a mixture and adding N,N-dimethylformamide to the mixture to produce Compound 4.

In some embodiments, the bromination agent in step a) is N-bromosuccinimide. In some embodiments, the contacting in step a) is carried out in a suitable solvent. In some embodiments, the contacting in step a) is carried out in acetonitrile. In some embodiments, the contacting in step a) is carried out at a reduced temperature. In some embodiments, the contacting in step a) is carried out at ≤20° C. or ≤15° C. In some embodiments, the contacting in step a) is carried out between 10-25° C. or between 15-20° C.

In some embodiments, the iodination agent in step b) is iodine. In some embodiments, the contacting in step b) is performed in the presence of one or more acids. In some embodiments, the contacting in step b) is performed in the presence of sulfuric acid and periodic acid. In some embodiments, the contacting in step b) is carried out at an elevated temperature. In some embodiments, the contacting in step b) is carried out between 75-85° C. or 77-83° C.

In some embodiments, the catalyst in step c) is a transition metal catalyst. In some embodiments, the catalyst in step c) comprises a combination of CuI and Pd(PPh$_3$)$_4$. In some embodiments, the reaction in step c) is carried out in a suitable solvent. In certain embodiments, the reaction in step c) is carried out in toluene. In certain embodiments, the reaction in step c) is carried out at an elevated temperature. In certain embodiments, the reaction in step c is carried out at ≥40° C., ≥50° C., or ≥60° C.

In some embodiments, the base in step d) is KOtBu. In some embodiments, the reaction in step d) is carried out in a suitable solvent. In some embodiments, the reaction in step d) is carried out in THF. In certain embodiments, the reaction in step d) carried out at an elevated temperature. In certain embodiments, reaction in step d) is carried out between 25-40° C. or between 30-35° C.

In some embodiments, the base in step e) is NaH. In some embodiments, the reaction in step e) is carried out in a suitable solvent. In some embodiments, the reaction in step e) is carried out in THF. In some embodiments, the reaction in step e) is carried out was carried out between −5-10° C. or 0-5° C.

In some embodiments, the alkyl-magnesium halide agent in step e) is isopropylmagnesium chloride. In some embodiments, the contacting in step f) is carried out in a suitable solvent. In some embodiments, the contacting in step f) is carried out in THF. In some embodiments, the contacting in step f) is carried out between −15-5° C. or −10-0° C.

The present invention provides a process for preparing Compound 5 having the formula:

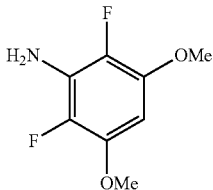

Compound 5 comprising:
a) contacting pentafluorobenzoic acid with an alkyl alcohol in the presence of thionyl chloride to form methyl pentafluorobenzoate;

b) reacting pentafluorobenzoate with benzylamine in the presence of base to form methyl-4-(benzylamino)-2,3,5,6-tetrafluorobenzoate;

c) contacting methyl-4-(benzylamino)-2,3,5,6-tetrafluorobenzoate with sodium methoxide to form a mixture and adding water to the mixture to generate 4-(benzylamino)-3,5-difluoro-2,6-dimethoxybenzoic acid;

d) heating 4-(benzylamino)-3,5-difluoro-2,6-dimethoxybenzoic acid to generate N-benzyl-2,6-difluoro-3,5-dimethoxyaniline; and e) reacting N-benzyl-2,6-difluoro-3,5-dimethoxyaniline with ammonium formate in the presence of palladium on carbon to form Compound 5.

In some embodiments, the alkyl alcohol in step a) is methanol. In certain embodiments, the contacting in step a) is performed at an elevated temperature. In some embodiments, the contacting in step a) is performed at reflux.

In some embodiments, the base in step b) is a tertiary amine. In some embodiments, the base in step b) is N,N-diisopropyl ethylamine. In some embodiments, the reaction in step b) is carried out in a suitable solvent. In some embodiments, the reaction in step b) is carried out in N-methylpyrrolidinone. In some embodiments, the reaction in step b) is carried out at an elevated temperature. In some embodiments, the reaction in step b) is carried out at ≥55° C., ≥60° C., ≥65° C., or ≥70° C.

In some embodiments, the contacting in step c) is performed in a suitable solvent. In some embodiments, the contacting in step c) is performed in methanol. In some embodiments, the contacting in step c) is performed at an elevated temperature. In some embodiments, the contacting in step c) is performed between 60-75° C. or 76-70° C.

In some embodiments, the heating in step d) is carried out between 65-95° C., between 70-90° C., or between 75-85° C. In some embodiments, the heating in step d) is performed neat. In some embodiments, the heating in step d) is performed without a solvent.

In some embodiments, the reaction in step e) is carried out in a suitable solvent. In some embodiments, reaction in step e) is carried out in a mixture of ethanol and acetic acid. In certain embodiments, the reaction in step e) is carried out in a 6:1 mixture of ethanol and acetic acid. In certain embodiments, the reaction in step e) is carried out at an elevated temperature. In certain embodiments, the reaction in step e) is carried out at ≥40° C., ≥50° C., or ≥60° C.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation, trituration, or recrystallization. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, Greene's Protective Groups in Organic Synthesis, 4th Ed., John Wiley & Sons: New York, 2006, which is incorporated herein by reference in its entirety. As used herein, "amino protecting group" refers to any protecting group for the protection of amines. Example amino protecting groups include, but are not limited to, phenylsulfonyl, benzyloxycarbonyl (Cbz), 2,2,2-trichloroethoxycarbonyl (Troc), 2-(trimethylsilyl)ethoxycarbonyl (Teoc), 2-(4-trifluoromethylphenylsulphonyl)ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP), tri($C_{1-4}$ alkyl)silyl (e.g., tri(isopropyl)silyl), 1,1-diethoxymethyl, or N-pivaloyloxymethyl (POM).

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

In some embodiments, concentrating a solution as described herein refers to a solution where its volume is reduced by letting the solvent evaporate, by heating the solution, by subjecting the solution to reduced pressure, or any combination thereof.

As used herein, the phrase "transition metal catalyst" refers to a metal catalyst, wherein the metal is a group VIII element in the periodic table (e.g., palladium or nickel catalyst) suitable to catalyze a carbon-carbon coupling reaction. Example transition metal catalysts include, but are not limited to, $PdCl_2(PPh_3)_2$, $Pd(PPh_3)_4$, dichloro(bis{di-tert-butyl[4-(dimethylamino)phenyl]-phosphoranyl})palladium (Pd-132), $NiCl_2$(dppf), and $NiCl_2$ (dppp), where (dppf) refers to 1,1'-bis(diphenylphosphino)ferrocene and (dppp) refers to 1,3-bis(diphenylphosphino)propane.

Example palladium catalysts include but are not limited to $PdCl_2(PPh_3)_2$, $Pd(PPh_3)_4$, dichloro(bis {di-tert-butyl[4-(dimethylamino)phenyl]-phosphoranyl})palladium (Pd-132), palladium on carbon, $PdCl_2$, $Pd(OAc)_2$, $PdCl_2(MeCN)_2$, tris(dibenzylideneacetone)dipalladium(0) ($Pd_2$(dba)$_3$), 4-(di-tert-butylphosphino)-N,N-dimethylaniline-dichloropalladium (2:1), Pd(dppf)$Cl_2$ (e.g., Pd(dppf)$Cl_2$—$CH_2Cl_2$), and tetrakis(tri(o-tolyl)phosphine)palladium(0).

In some embodiments, anti-solvent as described herein refers to a solvent where Compound 1 is less soluble relative to another solvent or solvent mixture in the solution. For example, anti-solvent can include but not limited to benzene, cyclohexane, pentane, hexane, heptane (e.g., n-heptane), toluene, cycloheptane, methylcyclohexane, heptane, ethylbenzene, m-, o-, or p-xylene, octane, indane, nonane, or naphthalene.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane (methylene chloride), tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, tetrahydrofuran (THF), diethyl ether, ethylene glycol dimethyl ether, ethylene glycol diethyl ether, diethylene glycol dimethyl ether (diglyme), diethylene glycol diethyl ether, triethylene glycol dimethyl ether, anisole, tert-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, iso-butyl alcohol, tert-butyl alcohol, 2-ethoxyethanol, diethylene glycol, 1-, 2-, or 3-pentanol, neo-pentyl alcohol, tert-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

The reactions of the processes described herein can be carried out in air or under an inert atmosphere. Typically, reactions containing reagents or products that are substantially reactive with air can be carried out using air-sensitive synthetic techniques that are well known to the skilled artisan.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C. The term "elevated temperature" as used herein, is understood in the art, and refer generally to a temperature, e.g., a reaction temperature, that is above room temperature, e.g., above 30° C.

Compounds

Provided herein is a compound of Formula F1:

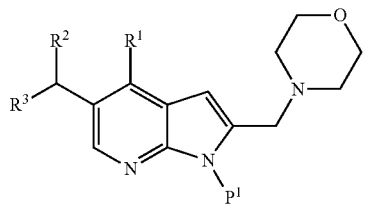

F1 wherein:
P¹ is an amino protecting group;
R¹ is Cl, Br or I;
R² and R³ are each independently $C_{1-6}$ alkoxy; or
R² and R³ taken together with the carbon atom to which they are attached form 1,3-dioxolan-2-yl or 1,3-dioxan-2-yl; or
R² and R³ taken together form oxo.

In some embodiments, the compound of Formula F1 has Formula F3:

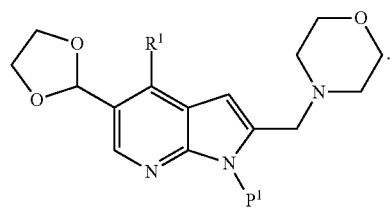

F3

In some embodiments, the compound of Formula F1 has Formula F4:

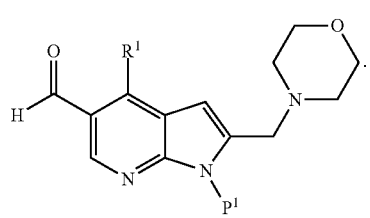

F4

In some embodiments, provided herein is a compound having Formula F6:

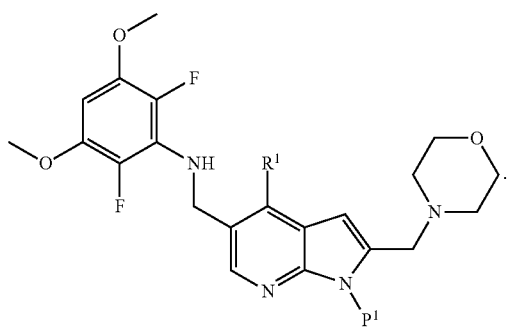

F6 wherein:
P¹ is an amino protecting group;
R¹ is Cl, Br or I.

In some embodiments, the compound having Formula F6 is Compound 6:

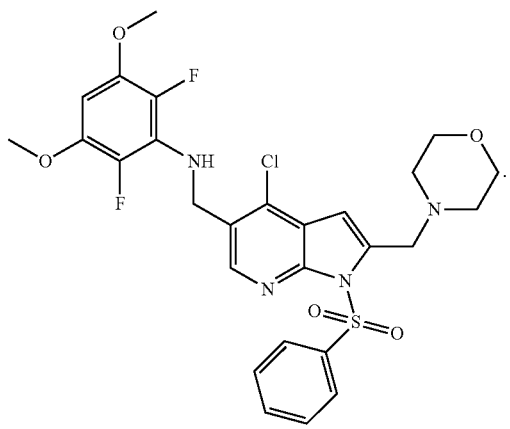

Compound 6

Provided herein is a compound having Formula F7:

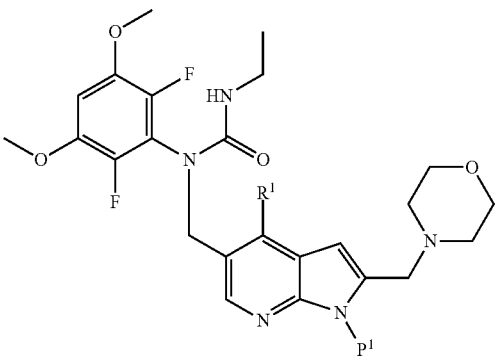

F7 wherein:
P¹ is an amino protecting group;
R¹ is Cl, Br or I.

In some embodiments, the compound having the F7 is Compound 7:

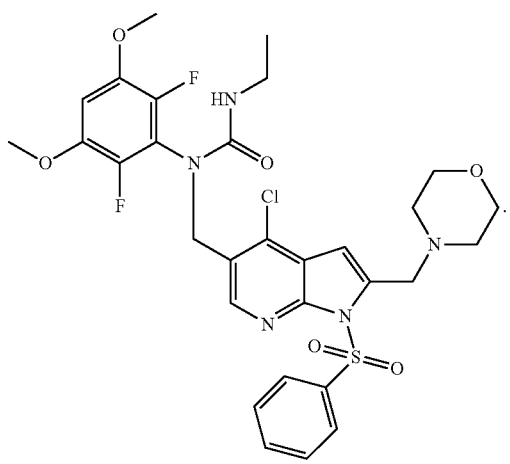

Compound 7

In some embodiments, provided herein is a compound of Formula F8:

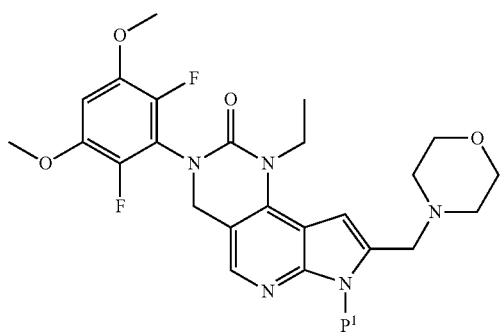

wherein P¹ is an amino protecting group.

In some embodiments, the compound of Formula F8 is Compound 8:

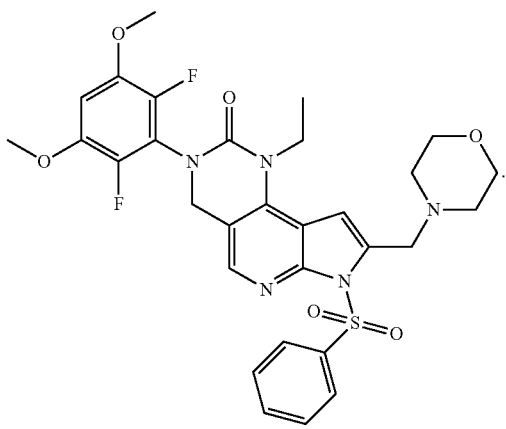

In some embodiments, provided herein is a compound of Formula F9:

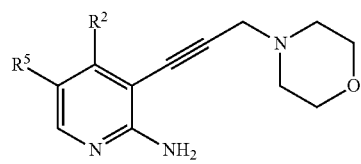

wherein R² and R⁵ are each independently Br, Cl or I.

In some embodiments, the compound of Formula F9 is compound 9:

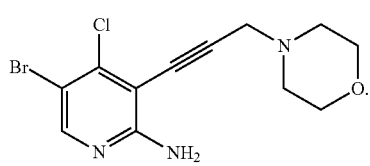

In some embodiments, provided herein is a compound of Formula F10:

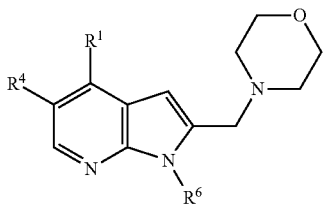

wherein $R^1$ and $R^4$ are each independently Br, Cl or I; and $R^6$ is H or benzenesulfonyl.

In some embodiments, the compound having the Formula F10 is Compound 10:

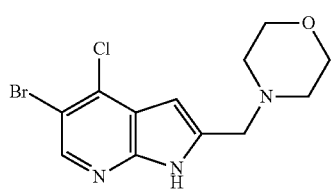

In some embodiments, the compound having the Formula F10 is Compound 11:

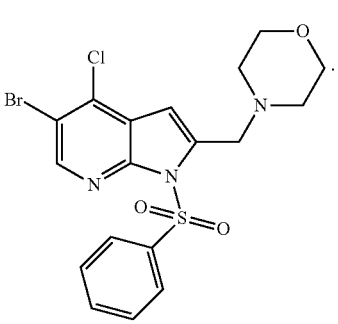

Methods of Use

Compound 1 or solid forms thereof as described herein can inhibit the activity of the FGFR enzyme. For example, Compound 1 can be used to inhibit activity of an FGFR enzyme in a cell or in an individual or patient in need of inhibition of the enzyme by administering an inhibiting amount of Compound 1 to the cell, individual, or patient.

As FGFR inhibitors, Compound 1 is useful in the treatment of various diseases associated with abnormal expression or activity of the FGFR enzyme or FGFR ligands. Compounds which inhibit FGFR will be useful in providing a means of preventing the growth or inducing apoptosis in tumors, particularly by inhibiting angiogenesis. It is therefore anticipated that Compound 1 will prove useful in treating or preventing proliferative disorders such as cancers. In particular tumors with activating mutants of receptor tyrosine kinases or upregulation of receptor tyrosine kinases may be particularly sensitive to the inhibitors.

In certain embodiments, the disclosure provides a method for treating a FGFR-mediated disorder in a patient in need thereof, comprising the step of administering to said patient Compound 1, or a pharmaceutically acceptable composition thereof.

For example, Compound 1 or solid forms thereof are useful in the treatment of cancer. Example cancers include bladder cancer, breast cancer (e.g., hormone R positive, triple negative), cervical cancer, colorectal cancer, cancer of the small intestine, colon cancer, rectal cancer, cancer of the anus, endometrial cancer, gastric cancer (e.g., gastrointestinal stromal tumors), head and neck cancer (e.g., cancers of the larynx, hypopharynx, nasopharynx, oropharynx, lips, and mouth, squamous head and neck cancers), kidney cancer (e.g., renal cell carcinoma, urothelial carcinoma, sarcoma, Wilms tumor), liver cancer (e.g., hepatocellular carcinoma, cholangiocellular carcinoma, liver angiosarcoma, hepatoblastoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, vulvar cancer, esophageal cancer, gall bladder cancer, pancreatic cancer (e.g. exocrine pancreatic carcinoma), stomach cancer, thyroid cancer, parathyroid cancer, neuroendocrine cancer (e.g., pheochromocytoma, Merkel cell cancer, neuroendocrine carcinoma), skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., 8p11 myeloproliferative syndrome, polycythemia vera, essential thrombocythemia, and primary myelofibrosis), myelodysplastic syndrome, chronic eosinophilic leukemia, Waldenstrom's Macroglubulinemia, hairy cell lymphoma, chronic myelogenic lymphoma, acute lymphoblastic lymphoma, AIDS-related lymphomas, and Burkitt's lymphoma.

In certain embodiments, provided herein is a method of treating myeloid/lymphoid neoplasms in a patient in need thereof. In certain embodiments, the myeloid/lymphoid neoplasms are 8p11 myeloproliferative syndrome. As used herein, the term "8p11 myeloproliferative syndrome" (EMS) is meant to refer to myeloid/lymphoid neoplasms associated with eosinophilia and abnormalities of FGFR1 or myeloid/lymphoid neoplasms (MLN) with FGFR1 rearrangement. Eight P eleven myeloproliferative syndrome is reviewed in Jackson, Courtney C., et. al. *Human Pathology*, 2010, 41, 461-476. The defining feature of EMS is the presence of a translocation involving FGFR1 gene located on the chromosome 8p11 locus, and at least 10 additional translocations and 1 insertion have been identified in EMS, each disrupting FGFR1 and creating novel fusion genes with various partners. See Jackson, Courtney C., et. al. *Human Pathology*, 2010, 41, 461-476.

In some embodiments, the myeloid/lymphoid neoplasm is characterized by FGF/FGFR genetic alteration. In certain embodiments, the myeloid/lymphoid neoplasm exhibits FGFR1 fusion. The FGFR1 fusion can be a translocation, interstitial deletion, or a chromosomal inversion. In some embodiments, the FGFR1 fusion is an FGFR1 translocation. In certain embodiments, the myeloid/lymphoid neoplasm exhibits an 8p11 translocation. In certain embodiments, the 8p11 translocation is associated with activation of FGFR1. In some embodiments, the myeloid/lymphoid neoplasm exhibits FGF/FGFR alterations other than FGFR1 translocations. In certain embodiments, the patient has failed at least one previous treatment for myeloid/lymphoid neoplasms (e.g., 8p11 myeloproliferative syndrome). In some embodiments, the previous treatment is surgery or radiation therapy. In some embodiments, the patient has a history of hepatitis. In some embodiments, the hepatitis is chronic hepatitis B or hepatitis C. In some embodiments, the patient does not have a history of hepatitis.

In certain embodiments, provided herein is a method of treating cancer comprising administering to a patient in need thereof a therapeutically effect amount of Compound 1 or a solid form thereof. In certain embodiments, the cancer is selected from bladder cancer, breast cancer, cervical cancer, cancer of the small intestine, colorectal cancer, endometrial cancer, gastric cancer, head and neck cancer, kidney cancer, liver cancer, lung cancer, ovarian cancer, prostate cancer, testicular cancer, uterine cancer, vulvar cancer, esophageal cancer, gall bladder cancer, pancreatic cancer, thyroid cancer, skin cancer, brain cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, myeloproliferative neoplasms, chronic myelogenic lymphoma, acute lymphoblastic lymphoma, T lymphoblastic lymphoma, hairy cell lymphoma, Burkett's lymphoma, glioblastoma, melanoma, rhabdosarcoma, lymphosarcoma, and osteosarcoma.

In certain embodiments, the cancer is bladder cancer (e.g., urothelial carcinoma, squamous cell carcinoma, adenocarcinoma).

In certain embodiments, the liver cancer is cholangiocellular carcinoma (e.g., intrahepatic, hilar or perihilar, distal extrahepatic). As used herein, cholangiocellular carcinoma is the same as cholangiocarcinoma or bile duct cancer. In certain embodiments, the cholangiocarcinoma is advanced or metastatic cholangiocarcinoma. In certain embodiments, the cholangiocarcinoma is surgically unresectable. In certain embodiments, the cholangiocarcinoma is intrahepatic. In certain embodiments, the cholangiocarcinoma is extrahepatic. In certain embodiments, the cholangiocarcinoma exhibits FGFR2 tyrosine kinase fusions which define a certain molecular subtype as described in Arai, Yasuhito, et. al. *Hepatology*, 2014, 59, 1427-1434. In some embodiments, the cholangiocarcinoma is characterized by FGF/FGFR genetically altered tumors. In some embodiments, the tumors exhibit FGFR2 fusions. The FGFR2 fusion can be a translocation, interstitial deletion, or a chromosomal inversion. In some embodiments, the FGFR2 fusion is an FGFR2 translocation. The FGFR2 translocations can be selected from a group including, but not limited to, FGFR2-BICC1, FGFR2-AHCYL1, FGFR2-MACF1, FGFR2 intron 17 rearrangement. In some embodiments, the tumor exhibits FGF/FGFR alterations other than FGFR2 translocations. In some embodiments, the cholangiocarcinoma does not exhibit FGF/FGFR genetically altered tumors.

Other cancers treatable with Compound 1 or solid forms thereof include tumors of the eye, glioblastoma, melanoma, rhabdosarcoma, lymphosarcoma, leiomyosarcoma, urothelial carcinoma (e.g., ureter, urethra, bladder, urachus), and osteosarcoma.

Compound 1 or solid forms thereof can also be useful in the inhibition of tumor metastases.

In some embodiments, compound 1 or solid forms as described herein can be used to treat Alzheimer's disease, HIV, or tuberculosis.

In addition to oncogenic neoplasms, the compounds of the invention can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds of provided herein may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

In some embodiments, the compounds provided herein can be used in the treatment of a hypophosphatemia disorder such as, for example, X-linked hypophosphatemic rickets, autosomal recessive hypophosphatemic rickets, and autosomal dominant hypophosphatemic rickets, or tumor-induced osteomalacia.

In some embodiments, provided herein is a method of increasing survival or progression-free survival in a patient, comprising administering a compound provided herein to the patient. In some embodiments, the patient has cancer. In some embodiments, the patient has a disease or disorder described herein. In some embodiments, the patient has cholangiocarcinoma. In some embodiments, provided herein is a method of increasing survival or progression-free survival in a patient that has cholangiocarcinoma, wherein the cholangiocarcinoma is characterized by an FGFR2 fusion, comprising administering a compound provided herein to the patient. As used herein, progression-free survival refers to the length of time during and after the treatment of a solid tumor that a patient lives with the disease but it does not get worse. Progression-free survival can refer to the length of time from first administering the compound until the earlier of death or progression of the disease. Progression of the disease can be defined by RECIST v. 1.1 (Response Evaluation Criteria in Solid Tumors), as assessed by an independent centralized radiological review committee. In some embodiments, administering of the compound results in a progression free survival that is greater than about 1 month, about 2 months, about 3 months, about 4 months, about 5 months, about 6 months, about 8 months, about 9 months, about 12 months, about 16 months, or about 24 months. In some embodiments, the administering of the compound results in a progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months. In some embodiments, the administering of the compound results in an increase of progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound described herein (e.g., Compound 1) includes the administration of a compound described herein to an individual or patient, such as a human, having FGFR, as well as, for example, introducing a compound described herein (e.g., Compound 1) into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with Compound 1 for treatment of FGFR-associated diseases, disorders or conditions, or diseases or conditions as described herein. The agents can be combined with the present compounds in a single dosage form, or the agents can be administered simultaneously or sequentially as separate dosage forms.

Compound 1 or solid forms thereof as described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the FGFR inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, Compound 1 or solid forms thereof as described herein can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, Compound 1 or solid forms thereof as described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, Compound 1 or solid forms thereof as described herein can be used in combination with targeted therapies, including JAK kinase inhibitors (Ruxolitinib, additional JAK1/2 and JAK1-selective, baricitinib or INCB39110), Pim kinase inhibitors (e.g., INCB53914), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors, TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as INCB54329 or INCB57643), LSD1 inhibitors (e.g., INCB59872 or INCB60003), arginase inhibitors (e.g., INCB1158), indoleamine 2,3-dioxygenase inhibitors (e.g., epacadostat, NLG919 or BMS-986205), and PARP inhibiors (e.g., olaparib or rucaparib).

For treating cancer and other proliferative diseases, Compound 1 or solid forms thereof as described herein can be used in combination with chemotherapeutic agents, agonists or antagonists of nuclear receptors, or other anti-proliferative agents. Compound 1 or solid forms thereof can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, baricitinib, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, niraparib, nofetumomab, olaparib, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, rucaparib, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, veliparib, talazoparib and zoledronate.

In some embodiments, Compound 1 or solid forms thereof as described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012, nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is nivolumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736. In some embodiments, the PD-L1 inhibitor is INCB086550.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383.

In some embodiments, the salts of Compound 1 as described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with Compound 1 can comprise nucleoside and nucleotide reverse transcriptase inhibitors (NRTIs), nonnucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with Compound 1 for the treatment of cancer include chemotherapeutic agents, targeted cancer therapies, immunotherapies or radiation therapy. Compound 1 may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable antihormone agents used for treatment of prostate and other cancers may also be combined with Compound 1. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compound 1 may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with Compound 1 include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with Compound 1. In some embodiments, the JAK inhibitor is selective for JAK1 over JAK2 and JAK3.

Other suitable agents for use in combination with Compound 1 include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with Compound 1 include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compound 1 may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "*Physicians' Desk Reference*" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, Compound 1 as described herein can be administered in the form of pharmaceutical compositions which refers to a combination of Compound 1 as described herein, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, Compound 1 in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of Compound 1. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the Compound 1, or compositions as described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of Compound 1 can vary according to, for example, the particular use for which the treatment is made, the manner of administration of the compound, the health and condition of the patient, and the judgment of the prescribing physician. The proportion or concentration of Compound 1 in a pharmaceutical composition can vary depending upon a number of factors including dosage, chemical characteristics (e.g., hydrophobicity), and the route of administration. For example, Compound 1 can be provided in an aqueous physiological buffer solution containing about 0.1 to about 10% w/v of the compound for parenteral administration. Some typical dose ranges are from about 1 µg/kg to about 1 g/kg of body weight per day.

In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Compound 1 can also be formulated in combination with one or more additional active ingredients which can include any pharmaceutical agent such as anti-viral agents, vaccines, antibodies, immune enhancers, immune suppressants, anti-inflammatory agents and the like.

In some embodiments, Compound 1 is administered orally. In some embodiments, Compound 1 is administered once daily. In some embodiments, Compound 1 is administered in a daily dose of about 5 mg to about 20 mg. In some embodiments, Compound 1 is administered in a daily dose of about 10 mg to about 15 mg. In some embodiments, Compound 1 is administered in a daily dose of about 9 mg. In some embodiments, Compound 1 is administered in a daily dose of about 13.5 mg. In some embodiments, Compound 1 is administered as a tablet. In some embodiments, the tablet comprises about 0.5 mg to about 10 mg of Compound 1. In some embodiments, the tablet comprises about 0.5 mg to about 5 mg Compound 1. In some embodiments, the tablet comprises about 2 mg, about 4.5 mg, about 9 mg, about 13.5 mg, or about 18 mg of Compound 1. In some embodiments, the tablet comprises about 0.5 mg of Compound 1. In some embodiments, the tablet comprises about 2 mg of Compound 1. In some embodiments, the tablet comprises about 4.5 mg of Compound 1. In some embodiments, the tablet comprises about 9 mg of Compound 1. In some embodiments, the tablet comprises about 13.5 mg of Compound 1. In some embodiments, the tablet comprises about 18 mg of Compound 1.

In some embodiments, Compound 1 is administered once daily in a continuous dosing regimen. In some embodiments, Compound 1 is administered in a 21-day dosing regimen, wherein the 21-day dosing regimen comprises:
(a) a first period wherein Compound 1 is administered once daily for 14 days; and
(b) a second period wherein Compound 1 is not administered for 7 days.

In some embodiments, Compound 1 is administered in consecutive 21-day dosing regimens, wherein the 21-day dosing regimen comprises:
(a) a first period wherein Compound 1 is administered once daily for 14 days; and (b) a second period wherein Compound 1 is not administered for 7 days.

EXAMPLES

In the below examples, X-Ray Powder Diffraction analysis was carried out on a Rigaku MiniFlex X-ray Powder Diffractometer (XRPD) instrument. The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

Differential Scanning Calorimetry (DSC) was carried out on a TA Instruments Differential Scanning Calorimetry, Model Q200 with autosampler. The DSC instrument conditions were as follows: 30-300° C. at 10° C./min; Tzero aluminum sample pan and lid; and nitrogen gas flow at 50 mL/min.

Thermogravimetric analysis (TGA) was carried out on a TA Instrument Thermogravimetric Analyzer, Model Q500. The general experimental conditions for TGA were: ramp from 20° C.-600° C. at 20° C./min; nitrogen purge, gas flow at 40 mL/min followed by balance of the purge flow; sample purge flow at 60 mL/min; platinum sample pan.

Example 1

Synthesis of 3-(2,6-difluoro-3,5-dimethoxyphenyl)-1-ethyl-8-(morpholin-4-ylmethyl)-1,3,4, 7-tetra-hydro-2H-pyrrolo[3',2':5,6]pyrido[4,3-d]pyrimidin-2-one (Compound 1)

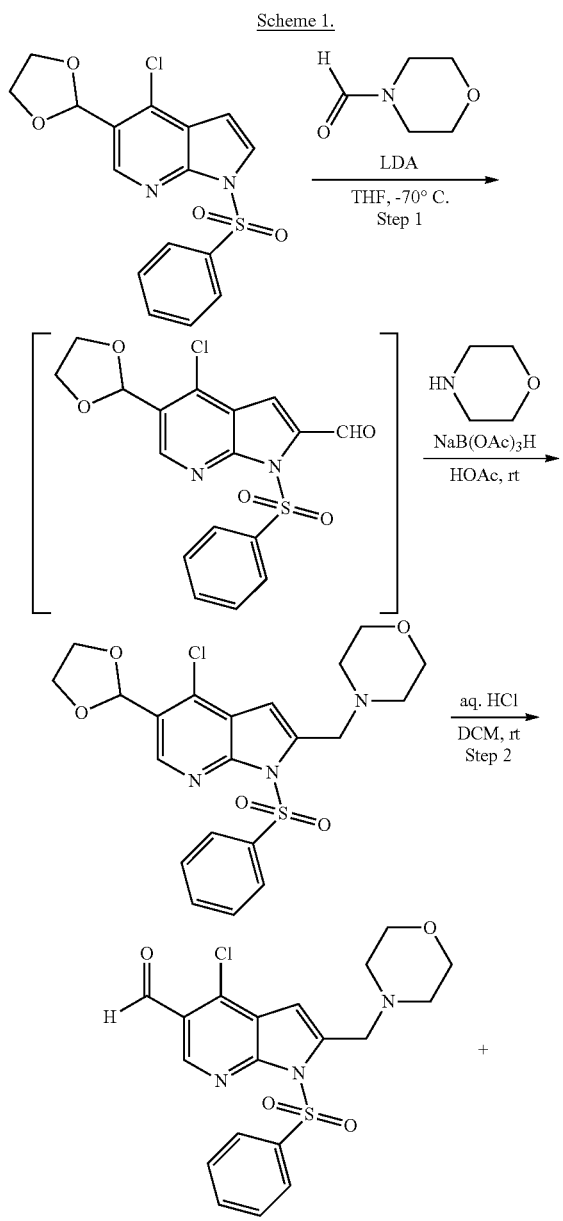

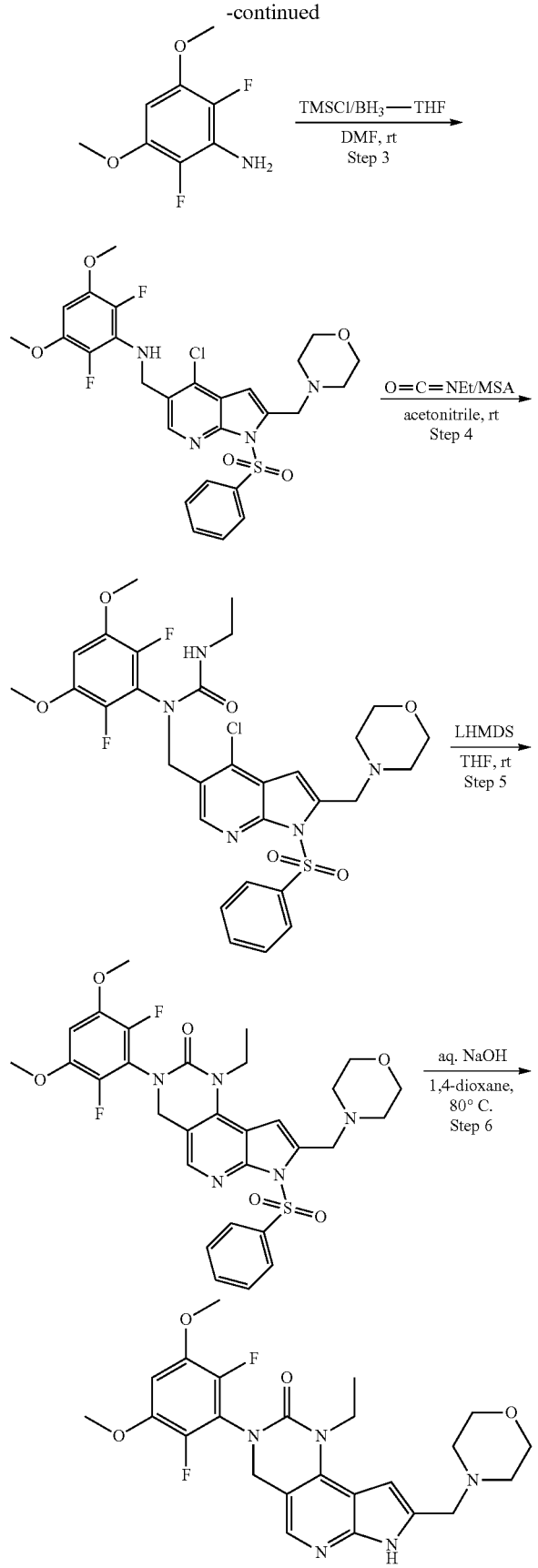

Step 1: Synthesis of 4-((4-chloro-5-(1,3-dioxolan-2-yl)-1-(phenylsulfonyl)-1H-pyrrolo[2, 3-b]pyridin-2-yl) methyl) morpholine To a 1-L flask was added 4-chloro-5-(1,3-dioxolan-2-yl)-1-(phenylsulfonyl)-1H-pyrrolo[2,3-b] pyridine (50.0 g, 137 mmol) (see, e.g., Example 2) and tetrahydrofuran (THF, 266 g, 300 mL) under $N_2$. To this mixture at −70° C. was added 2.0 M lithium diisopropylamide in THF/heptane/ethyl benzene (77.4 g, 95 mL, 190 mmol, 1.4 eq.). The mixture was stirred at −70° C. for 1 h. To the mixture was added N-formylmorpholine (29.7 g, 258 mmol, 1.9 eq.) in THF (22.2 g, 25 mL) dropwise. The reaction was done in 30 min after addition. LC/MS showed that the desired product, 4-chloro-5-(1, 3-dioxolan-2-yl)-1-(phenylsulfonyl)-1H-pyrrolo[2, 3-b]pyridine-2-carbaldehyde, was formed cleanly. The reaction was quenched with acetic acid (16.4 g, 15.6 mL, 274 mmol, 2.0 eq.) and the dry ice cooling was removed. To the mixture was added morpholine (33.7 g, 33.5 mL, 387 mmol, 2.83 eq.) followed by acetic acid (74.0 g, 70 mL, 1231 mmol, and 9.0 eq.) at 0° C. (internal temperature rose from 0° C. to 18° C.) and stirred overnight. Sodium triacetoxyborohydride (52.50 g, 247.7 mmol, 1.8 eq.) was added and the reaction mixture temperature rose from 20° C. to 32° C. The mixture was stirred at room temperature for 30 min. HPLC & LC/MS indicated the reaction was complete. Water (100 g, 100 mL) was added followed by 2.0 M sodium carbonate ($Na_2CO_3$) in water (236 g, 200 mL, 400 mmol, 2.9 eq.) slowly (off gas!). The mixture was stirred for about 30 min. The organic layer was separated and water (250 g, 250 mL) and heptane (308 g, 450 mL) were added. The resulting slurry was stirred for 1 h and the solid was collected by filtration. The wet cake was washed with heptane twice (75.00 mL×2, 51.3 g×2) before being dried in oven at 50° C. overnight to give the desired product, 4-((4-chloro-5-(1,3-dioxolan-2-yl)-1-(phenylsulfonyl)-1H-pyrrolo[2,3-b]pyridin-2-yl)methyl)morpholine as a light brown solid (52.00 g, 81.8% yield): LCMS calculated for $C_{21}H_{23}ClN_2O_5S$ $[M+H]^+$: 464.00; Found: 464.0; $^1H$ NMR (400 MHz, DMSO-$d_6$) δ 8.48 (s, 1H), 8.38 (m, 2H), 7.72 (m, 1H), 7.64 (m, 2H), 6.83 (s, 1H), 6.13 (s, 1H), 4.12 (m, 2H), 4.00 (m, 2H), 3.92 (s, 2H), 3.55 (m, 4H), 2.47 (m, 4H).

Step 2: Synthesis of 4-chloro-2-(morpholinomethyl)-1-(phenylsulfonyl)-1H-pyrrolo[2, 3-b]pyridine-5-carbaldehyde To a 2 L reactor with a thermocouple, an addition funnel, and a mechanical stirrer was charged 4-((4-chloro-5-(1,3-dioxolan-2-yl)-1-(phenylsulfonyl)-1H-pyrrolo[2,3-b]pyridin-2-yl)methyl)morpholine (20.00 g, 43.1 mmol) and dichloromethane (265 g, 200 mL) at room temperature. The resulting mixture was stirred at room temperature (internal temperature was 19.5° C.) to achieve a solution. To the resulting solution was added an aqueous hydrochloric acid solution (0.5 M, 240 g, 200.0 ml, 100 mmol, 2.32 eq.) at room temperature in 7 min. After over 23 h agitations at room temperature, the bilayer reaction mixture turned into a thick colorless suspension. When HPLC showed the reaction was complete, the slurry was cooled to 0-5° C. and aqueous sodium hydroxide solution (1 N, 104 g, 100 mL, 100 mmol, and 2.32 eq.) was added in about 10 min to adjust the pH of the reaction mixture to 10-11. n-Heptane (164 g, 240 mL) was added and the reaction mixture and the mixture were stirred at room temperature for 1 h. The solid was collected by filtration and the wet cake was washed with water (2×40 mL), heptane (2×40 ml) before being dried in oven at 50° C. under vacuum to afford the desired product, 4-chloro-2-(morpholinomethyl)-1-(phenylsulfonyl)-1H-pyrrolo[2,3-b]pyridine-5-carbaldehyde as a light brown solid (16.9 g, 93% yield): LCMS calculated for $C_{19}H_{19}ClN_3O_4S$ [M+H]$^+$: 420.00; Found: 420.0; $^1$H NMR (400 MHz, DMSO-d$_6$) δ 10.33 (s, 1H), 8.76 (s, 1H), 8.42 (m, 2H), 7.74 (m, 1H), 7.65 (m, 2H), 6.98 (s, 1H), 3.96 (m, 2H), 3.564 (m, 4H), 2.51 (m, 4H).

Step 3: Synthesis of N-((4-chloro-2-(morpholinomethyl)-1-(phenylsulfonyl)-1H-pyrrolo[2, 3-b]pyridin-5-yl) methyl)-2, 6-difluoro-3,5-dimethoxyaniline To a 2-L reactor equipped with a thermocouple, a nitrogen inlet and mechanical stirrer were charged N,N-dimethyl formamide (450 mL, 425 g), 4-chloro-2-(morpholinomethyl)-1-(phenylsulfonyl)-1H-pyrrolo[2,3-b]pyridine-5-carbaldehyde (30.0 g, 71.45 mmol) and 2,6-difluoro-3,5-dimethoxyaniline (14.2 g, 75.0 mmol). To this suspension (internal temperature 20° C.) was added chlorotrimethylsilane (19.4 g, 22.7 mL, 179 mmol) dropwise in 10 min at room temperature (internal temperature 20-23° C.). The suspension changed into a solution in 5 min after the chlorotrimethylsilane addition. The solution was stirred at room temperature for 1.5 h before cooled to 0-5° C. with ice-bath. Borane-THF complex in THF (1.0 M, 71.4 mL, 71.4 mmol, 64.2 g, 1.0 eq.) was added dropwise via additional funnel over 30 min while maintaining temperature at 0-5° C. After addition, the mixture was stirred for 4 h. Water (150 g, 150 mL) was added under ice-bath cooling in 20 min, followed by slow addition of ammonium hydroxide solution (28% NH$_3$, 15.3 g, 17 ml, 252 mmol, 3.53 eq.) to pH 9-10 while maintaining the temperature below 10° C. More water (250 mL, 250 g) was added through the additional funnel. The slurry was stirred for 30 min and the solids were collected by filtration. The wet cake was washed with water (90 g×2, 90 ml×2) and heptane (61.6 g×2, 90 ml×2). The product was suction dried overnight to give the desired product N-((4-chloro-2-(morpholinomethyl)-1-(phenylsulfonyl)-1H-pyrrolo[2,3-b]pyridin-5-yl)methyl)-2,6-difluoro-3,5-dimethoxyaniline (41.6 g, 96% yield): LCMS calculated for $C_{27}H_{28}ClF_2N_4O_5S$[M+H]$^+$: 593.10; Found: 593.1; $^1$H NMR (400 MHz, DMSO-d$_6$) δ 8.36 (m, 2H), 8.28 (s, 1H), 7.72 (m, 1H), 7.63 (m, 2H), 6.78 (s, 1H), 6.29 (m, 1H), 5.82 (m, 1H), 4.58 (m, 2H), 3.91 (s, 2H), 3.76 (s, 6H), 3.56 (m, 4H), 2.47 (m, 4H).

Step 4: Synthesis of 1-((4-chloro-2-(morpholinomethyl)-1-(phenylsulfonyl)-1H-pyrrolo[2, 3-b]pyridin-5-yl) methyl)-1-(2,6-difluoro-3,5-dimethoxyphenyl)-3-ethylurea To a 2-L, 3-neck round bottom flask fitted with a thermocouple, a nitrogen bubbler inlet, and a magnetic stir were charged N-((4-chloro-2-(morpholinomethyl)-1-(phenylsulfonyl)-1H-pyrrolo[2,3-b]pyridin-5-yl)methyl)-2,6-difluoro-3,5-dimethoxyaniline (67.0 g, 113 mmol) and acetonitrile (670 ml, 527 g). The suspension was cooled to 0-5° C. To the mixture was charged ethyl isocyanate (17.7 mL, 15.9 g, 224 mmol, 1.98 eq.) over 30 sec. The temperature stayed unchanged at 0.7° C. after the charge. Methanesulfonic acid (16.1 mL, 23.9 g, 248 mmol, 2.2 eq.) was charged dropwise over 35 min while maintaining the temperature below 2° C. The mixture was warmed to room temperature and stirred overnight. At 24 h after addition showed that the product was 93.7%, unreacted SM was 0.73% and the major impurity (bis-isocyanate adduct) was 1.3%. The mixture was cooled with an ice-bath and quenched with sodium hydroxide (NaOH) solution (1.0M, 235 mL, 244 g, 235 mmol, 2.08 eq.) over 20 min and then saturated aqueous sodium bicarbonate (NaHCO$_3$) solution (1.07 M, 85 mL, 91 g, 0.091 mol, 0.80 eq.) over 10 min. Water (550 mL, 550 g) was added and the liquid became one phase. The mixture was stirred for 2 h and the solids were collected by filtration, washed with water (165 mL, 165 g) to give 1-((4-chloro-2-(morpholinomethyl)-1-(phenylsulfonyl)-1H-pyrrolo[2,3-b]pyridin-5-yl)methyl)-1-(2,6-difluoro-3,5-dimethoxyphenyl)-3-ethylurea (70.3 g, 93.7% yield).

The crude 1-((4-chloro-2-(morpholinomethyl)-1-(phenylsulfonyl)-1H-pyrrolo[2, 3-b]pyridin-5-yl) methyl)-1-(2, 6-difluoro-3, 5-dimethoxyphenyl)-3-ethylurea (68.5 g, 103 mmol) was added in to acetonitrile (616 mL, 485 g). The mixture was heated 60-65° C. and an amber colored thin suspension was obtained. The solid was filtered off with celite and the celite was washed with acetonitrile (68.5 mL, 53.8 g). To the pale yellow filtrate was added water (685 g, 685 ml) to form a slurry. The slurry was stirred overnight at room temperature and filtered. The solid was added to water (685 mL, 685 g) and stirred at 60° C. for 2 h. The solid was filtered and re-slurried in heptane (685 mL, 469 g) overnight. The product was dried in an oven at 50° C. under vacuum for 48 h to afford 1-((4-chloro-2-(morpholinomethyl)-1-(phenylsulfonyl)-1H-pyrrolo[2,3-b]pyridin-5-yl)methyl)-1-(2,6-difluoro-3,5-dimethoxyphenyl)-3-ethylurea as a colorless solid (62.2 g, 90.8% yield, 99.9% purity by HPLC area %). KF was 0.028%. Acetonitrile (by $^1$H NMR) was about 1.56%, DCM (by $^1$H NMR) 2.0%: LCMS calculated for $C_{30}H_{33}ClF_2N_5O_6S$ [M+H]$^+$: EM: 664.17; Found: 664.2; $^1$H NMR (400 MHz, DMSO-d$_6$) δ 8.33 (m, 2H), 8.31 (s, 1H), 7.72 (m, 1H), 7.64 (m, 1H), 6.96 (m, 2H), 6.73 (s, 1H), 6.43 (m, 1H), 4.87 (s, 2H), 3.90 (s, 2H), 3.77 (s, 6H), 3.54 (m, 4H), 3.03 (m, 2H), 2.46 (m, 4H), 0.95 (m, 3H).

Step 5: Synthesis of 3-(2,6-difluoro-3,5-dimethoxyphenyl)-1-ethyl-8-(morpholin-4-ylmethyl)-7-(phenylsulfonyl)-1,3,4,7-tetrahydro-2H-pyrrolo[3',2':5,6]pyrido[4,3-d]pyrimidin-2-one To a 2000 mL flask equipped with a thermal couple, a nitrogen inlet, and a mechanical stirrer were charged dry 1-((4-chloro-2-(morpholinomethyl)-1-(phenylsulfonyl)-1H-pyrrolo[2,3-b]pyridin-5-yl)methyl)-1-(2,6-difluoro-3,5-dimethoxyphenyl)-3-ethylurea (30.0 g, 45.2 mmol, KF=0.11%) and tetrahydrofuran (1200 mL, 1063 g). To this suspension at room temperature was charged 1.0 M lithium hexamethyldisilazide in THF (62.3 mL, 55.5 g, 62.3 mmol, 1.38 eq). The mixture turned into a solution after the base addition. The reaction mixture was stirred for 2 h and HPLC shows the starting material was not detectable. To this mixture was added 1.0 M hydrochloric acid (18.1 mL, ~18.1 g. 18.1 mmol, 0.4 eq.). The solution was concentrated to 600 mL and water (1200 mL, 1200 g) was added. Slurry was formed after water addition. The slurry was stirred for 30 min at room temperature and the solid was collected by filtration. The wet cake was washed with water twice (60 mL×2, 60 g×2) and dried at 50° C. overnight to give 3-(2,6-difluoro-3,5-dimethoxyphenyl)-1-ethyl-8-(morpholin-4-ylmethyl)-7-(phenyl sulfonyl)-1,3,4, 7-tetrahydro-2H-pyrrolo[3',2':5,6]pyrido[4,3-d]pyrimidin-2-one as a light brown solid (26.58 g, as-is yield 93.7%): THF by $^1$H NMR 0.32%, KF 5.26%, adjusted yield was 88.5%: LCMS calculated for $C_{30}H_{32}F_2N_5O_6S$ [M+H]$^+$: EM: 628.20; Found:

628.2; ¹H NMR (400 MHz, DMSO-d₆) δ 8.41 (m, 2H), 8.07 (s, 1H), 7.70 (m, 1H), 7.63 (m, 2H), 7.05 (m, 1H), 6.89 (s, 1H), 4.76 (s, 2H), 4.09 (m, 2H), 3.93 (s, 2H), 3.89 (s, 6H), 3.60 (m, 4H), 2.50 (m, 4H), 1.28 (m, 3H).

Step 6: Synthesis of 3-(2,6-difluoro-3,5-dimethoxyphenyl)-1-ethyl-8-(morpholin-4-ylmethyl)-1,3, 4,7-tetrahydro-2H-pyrrolo[3',2':5,6]pyrido[4,3-d]pyrimidin-2-one To a stirring suspension of 3-(2,6-difluoro-3,5-dimethoxyphenyl)-1-ethyl-8-(morpholinomethyl)-7-(phenylsulfonyl)-1,3,4,7-tetrahydro-2H-pyrrolo[3',2':5,6]pyrido[4,3-d]pyrimidin-2-one (10.0 g, 15.93 mmol) in 1,4-dioxane (100 ml, 103 g) in a 500 mL flask equipped with a nitrogen inlet, a condenser, a thermocouple and a heating mantle was added 1 M aqueous sodium hydroxide (63.7 ml, 66.3 g, 63.7 mmol). The reaction mixture was heated at 75° C. for 18 h. LCMS showed the reaction was complete. Water (100 mL, 100 g) was added to give a thick suspension. This slurry was stirred at room temperature for 1 h and filtered. The cake was washed with water (3×10 mL, 3×10 g) and heptane (2×10 mL, 2×6.84 g). The cake was dried overnight by pulling a vacuum through the filter cake and then dried in an oven at 50° C. under vacuum overnight to give 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one (6.8 g, 87.6% yield): LCMS calculated for C₂₄H₂₈F₂N₅O₄ [M+H]⁺: 488.20; Found: 488.2.

Example 2. Synthesis of 4-chloro-5-(1,3-dioxolan-2-yl)-1-(phenylsulfonyl)-1H-pyrrolo[2,3-b]pyridine

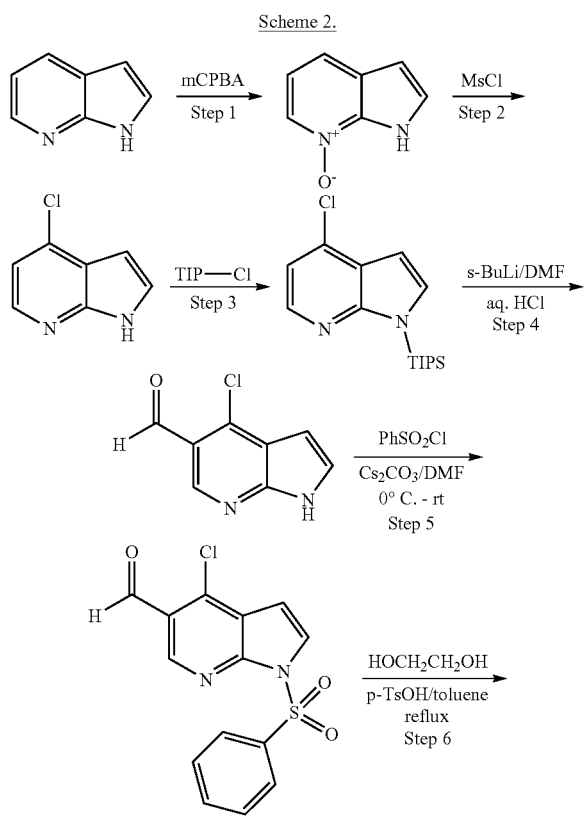

Scheme 2.

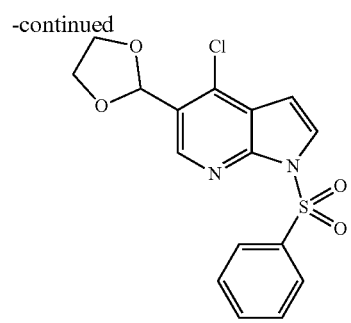

Step 1: Synthesis of 1H-pyrrolo[2,3-b]pyridine-7-oxide m-Chloroperoxybenzoic acid (105.5 Kg, 612 mol, 1.2 eq) was added to a solution of 1H-pyrrolo[2,3-b]pyridine (60 Kg, 507.6 mol) in dichloromethane (600 L) over 5 h with stirring at 0-10° C. After completion of the addition, the mixture was stirred at 0-10° C. for 3 h. The resulting solid was collected by filtration, washed with heptane, and dried to give 1H-pyrrolo[2,3-b]pyridine 7-oxide. The mother liquid was concentrated and the residue was treated with dichloromethane:heptane (2:3), and filtered to recover extra materials. The crude 1H-pyrrolo 2, 3-b]pyridine-7-oxide was obtained (72 Kg, 96% purity), which was used to next step without purification.

Step 2: Synthesis of 4-chloro-1H-pyrrolo[2, 3-b]pyridine

The crude 1H-pyrrolo[2, 3-b]pyridine-7-oxide (72 Kg, 253 mol) was dissolved in DMF (360 L) and heated at 50° C. A solution of methanesulfonyl chloride (85.2 Kg, 746 mol, 3.0 eq.) was added drop-wise to the solution while maintaining a temperature below 70° C. After being stirred at 90° C. for 2 h, the reaction solution was cooled to room temperature, and added to 720 Kg of ice/water. The mixture was neutralized with 6.0 M NaOH at 0° C. The resulting precipitate was collected by filtration, and washed with water. The solid was mixed with 72 L water, 48 L ethanol, and 29 L 30% NaOH, and stirred at room temperature for 1-2 h. Water (144 L) was added, and the mixture was treated with 37% HCl to adjust the pH to ~1. The product was collected by filtration and dried to give 4-chloro-1H-pyrrolo [2, 3-b]pyridine (crude 26 kg, 97% purity, which was used without purification): ¹HNMR (400 MHz, CDCl₃) δ 11.30 (s, 1H), 8.25 (m, 1H), 7.44 (m, 1H), 7.16 (m, 1H), 6.65 (m, 1H).

Step 3: Synthesis of 4-chloro-1-(triisopropylsilyl)-1H-pyrrolo[2, 3-b]pyridine

A solution of crude 4-chloro-1H-pyrrolo[2,3-b]pyridine (24 Kg, 155.2 mol) in THF (216 L) was stirred 0° C. as NaH (60%, 7.56 Kg, 188.6 mol, 1.3 eq.) was added portion-wise under N₂. After addition, the mixture was stirred at rt for 1 h. Triisopropylsilyl chloride (39.6 Kg, 188.6 mol, 1.3 eq) was added drop-wise while maintaining a temperature below 25° C. After stirring for 20 h, the mixture was quenched with 144 L water and extracted with 144 L heptane. The water layer was back extracted with 72 L methyl t-butyl ether. The combined organic layers were dried over anhydrous MgSO₄ and concentrated under vacuum to give crude 4-chloro-1-(triisopropylsilyl)-1H-pyrrolo[2, 3-b]pyridine as a liquid. The material was used without purification, but its water content was controlled to below 0.1%.

Step 4: Synthesis of 4-chloro-1H-pyrrolo[2, 3-b] pyridine-5-carbaldehyde

To a 1000 L cryogenic reactor was charged crude 4-chloro-1-(triisopropylsilyl)-1H-pyrrolo[2,3-b]pyridine (50 Kg, ~138 mol) and anhydrous THF (150 Kg). The mixture was cooled to −75° C., and stirred under $N_2$ as S-BuLi (1.3 M in cyclohexane, 230 L, 300 mol, 2.2 eq.) was added drop-wise over about 6.0 h while maintaining internal temperature below −60° C. The mixture was stirred at −75° C. for additional 2 h. N, N-Dimethylformamide (30.4 Kg, 416. Imol, 3.0 eq.) was added drop-wise over a period of ~3.0 h to control the internal temperature below −65° C. After being stirred at −65~-75° C. for 2 h, the mixture was quenched by drop-wise addition of a solution of 20% HCl in isopropyl alcohol (115 Kg, 635 mol, 4.5 eq.). The mixture was then stirred at room temperature (20-25° C.) overnight. The pH was adjusted to 7-8 by charging saturated $NaHCO_3$. The precipitate formed was collected by filtration. The filter cake was washed with 76 L water to give 4-chloro-1H-pyrrolo[2, 3-b] pyridine-5-carbaldehyde (14 Kg, 58% yield): $^1$HNMR (400 MHz, DMSO-$d_6$) δ 12.54 (s, 1H), 10.35 (s, 1H), 8.67 (s, 1H), 7.74 (m, 1H), 6.72 (m, 1H).

Step 5: Synthesis of 4-chloro-1-(phenylsulfonyl)-1H-pyrrolo[2, 3-b] pyridine-5-carbaldehyde To a 500 L reactor was charged N, N-dimethylformamide (108 L) and 4-chloro-1H-pyrrolo[2, 3-b]pyridine-5-carbaldehyde (10.8 Kg, 59.8 mol) and cooled to 0-5° C. To the resulting thick slurry was charged cesium carbonate (39 Kg, 120 mol) at 0-5° C. The slurry was stirred at 0° C. for about 20 min and the mixture changed to an amber colored thin slurry. To the thin slurry at below 10° C. was added benzenesulfonyl chloride (11.6 Kg, 65.8 mol, 1.1 eq.) drop-wise through an addition funnel. The resulting slurry was stirred for 1 h at below 10° C. and HPLC indicated the reaction was complete. Extended agitation at room temperature overnight had little impact on reaction mixture profile. To this mixture was added water (160 L) and the slurry was stirred for 1 h. The solid was collected by filtration (slow). The filter cake was washed with water and dried in oven under vacuum to give 4-chloro-1-(phenylsulfonyl)-1H-pyrrolo[2,3-b]pyridine-5-carbaldehyde as a light brown solid (17.8 Kg, 93% yield): LCMS calculated for $C_{14}H_{10}ClN_2O_3S$ [M+H]$^+$: 321.00; Found: 320.9; $^1$HNMR (400 MHz, DMSO-$d_6$) δ: 10.34 (s, 1H), 8.78 (s, 1H), 8.18 (m, 3H), 7.77 (m, 1H), 7.66 (m, 2H), 7.05 (m, 1H).

Step 6: Synthesis of 4-chloro-5-(1,3-dioxolan-2-yl)-1-(phenylsulfonyl)-1H-pyrrolo[2,3-b]pyridine)

To a 1000 L reactor were charged toluene (270 L), 4-chloro-1-(phenylsulfonyl)-1H-pyrrolo[2,3-b]pyridine-5-carbaldehyde (27 Kg, 84.2 mmol), p-toluenesulfonic acid monohydrate (217 g, 1.26 mol, 0.015 eq.), and 1,2-ethanediol (73.7 Kg, 1187 mol, 14.1 eq.). The mixture was stirred and heated to reflux to remove water (some ethylene glycol was also removed as the reaction progresses) for 9 h (LCMS showed reaction complete). After overnight stirring at room temperature, the mixture was diluted with ethyl acetate (135 L) and washed with saturated $NaHCO_3$ solution. The layers were separated and the organic layer was washed with 10% aq. NaCl solution and concentrated. Heptane (108 L) was added and slurry was formed. The solid was collected by filtration. The solid was dissolved in dichloromethane (108 L) and filtered in order to remove the mechanical impurities. The filtrate was concentrated, then dissolved in 67.5 L (2.5V) of hot ethyl acetate and stirred for 2 h. The mixture was allowed to cool as the solid formed. The solid was collected by filtration to give 4-chloro-5-(1,3-dioxolan-2-yl)-1-(phenylsulfonyl)-1H-pyrrolo[2,3-b]pyridine as an off-white solid (22 Kg, 70% yield): LCMS calculated for $C_{16}H_{14}ClN_2O_4S$ [M+H]$^+$: 365.03; Found: 365.1; $^1$H NMR (400 MHz, DMSO-$d_6$) δ 8.51 (s, 1H), 8.13 (m, 2H), 8.07 (m, 1H), 7.73 (m, 1H), 7.63 (m, 2H), 6.90 (m, 1H), 6.13 (s, 1H), 4.12 (m, 2H), 3.98 (m, 2H).

Example 3. An alternate synthesis of 4-chloro-2-(morpholin-4-ylmethyl)-1-(phenylsulfonyl)-1H-pyrrolo[2,3-b]pyridine-5-carbaldehyde

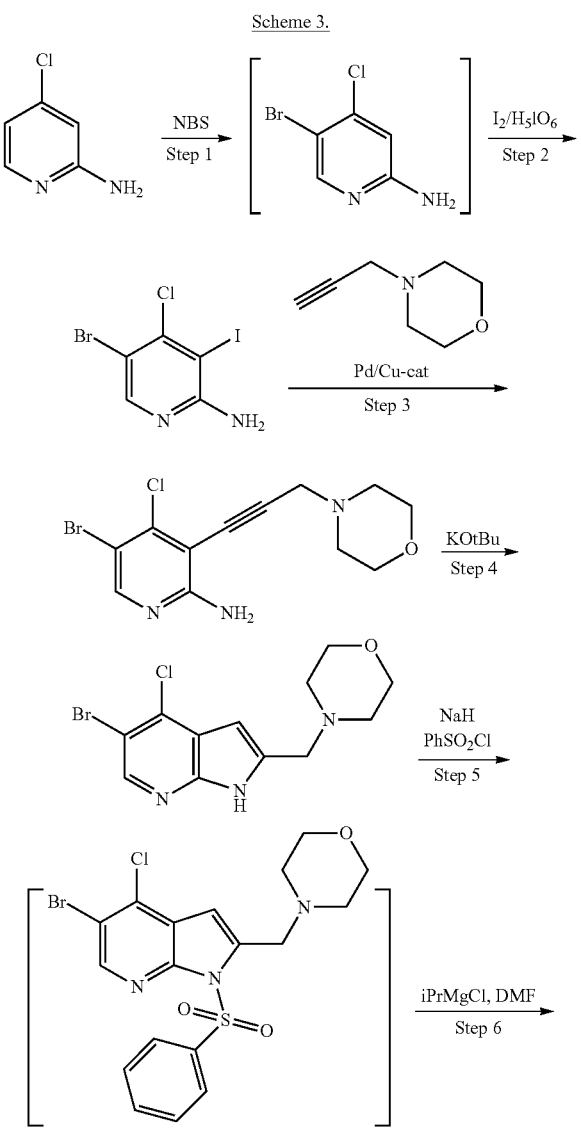

Scheme 3.

-continued

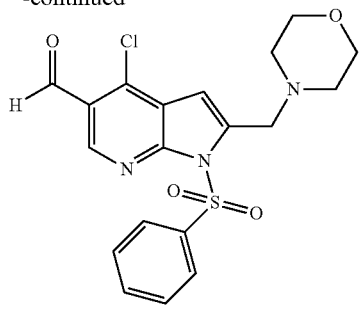

Step 1: Synthesis of 5-bromo-4-chloropyridin-2-amine

A slurry of 2-amino-4-chloropyridine (100 g, 777.8 mmol, 1.0 eq.) in acetonitrile (500 mL, 5 rel. vol.) at 15-20° C. was added N-bromosuccinimide (131.5 g, 738.9 mmol, 0.95 eq.) in portions over 2 h keeping the temperature at 15-20° C. The reaction was stirred for 30 min and the conversion was checked by HPLC. Depending on the conversion, 0-5 mol % of additional N-bromosuccinimide was added and the mixture was stirred for another 15 min. After HPLC indicated the conversion was complete, the reaction mixture was heated and acetonitrile (300 mL) was distilled off at normal pressure. Water (250 mL) was added and the temperature was adjusted to 50-55° C. and slurry was formed. The resulting slurry was stirred for 30 min and water (350 mL) was added over 1 h. The slurry was cooled to 20-25° C., stirred for 1 h and the solid was collected by filtration. The wet cake was washed with a mixture of water (75 mL) and acetonitrile (25 mL) to give the wet product 5-bromo-4-chloropyridin-2-amine (191 g, 92.1% by HPLC area % purity). The wet product was dissolved in acetic acid (500 mL, 5 rel. vol. on 2-amino-4-chloropyridine, 55-70° C.) and the solution was directly used in the next step.

Step 2: Synthesis of 5-bromo-4-chloro-3-iodopyridin-2-amine

The solution of 5-bromo-4-chloropyridin-2-amine in acetic acid (191 g, 5-bromo-4-chloropyridin-2-amine in 500 mL acetic acid) was distilled under reduced pressure at 40-60° C. to remove the solvents. Then, sulfuric acid (39.7 g, 96%-w/w, 388.9 mmol, 0.5 eq.) and iodine (76.2 g, 300.3 mmol, 0.386 eq.) were added and the temperature was adjusted to 77-83° C. At this temperature, a solution of periodic acid (50%-w/w, 54.89 g, 120.4 mmol, 0.155 eq.) was added over 2-3 h. The reaction was stirred for 2-3 h at 77-83° C. and the conversion was checked by HPLC (SM<1.0%-a/a). At 75-85° C., the reaction mixture was quenched by the addition of solid ammonium sulfite in portions of 4.53 g (0.05 eq.) until the KI/starch test was negative. Typically two portions (0.1 eq.) of ammonium sulfite were required. The end of the quench may also be seen by the absence of the purple color of iodine. Then, the reaction mixture was diluted with water (200 mL, 2.0 rel. vol., at room temperature), and the temperature was dropped to ~50° C. The product was precipitated out. At 45-60° C., the pH was adjusted to 3.0-3.5 with ammonia (25%-w/w in water, about 63.6 g, 0.93 mol, 1.2 eq. needed). The neutralization was strongly exothermic. The slurry was stirred for 30 min at 45-50° C. and then the solid was collected by filtration. The filter cake was washed with typically about 600 mL water and then washed with 2-propanol (200 mL). The wet product was dried in the vacuum cabinet at 60° C. to give 5-bromo-4-chloro-3-iodopyridin-2-amine as a yellow to beige solid (213.5 g, 82.3% yield): LCMS calculated for $C_5H_4BrClIN_2$ [M+H]$^+$: 332.82; Found: 332.8; $^1$H NMR (400 MHz, DMSO-d$_6$) δ 8.09 (s, 1H), 6.60 (s, 2H).

Step 3: Synthesis of 5-bromo-4-chloro-3-(3-morpholinoprop-1-yn-1-yl)pyridin-2-amine 5-Bromo-4-chloro-3-iodopyridin-2-amine (50 g, 150 mmol, 1.0 eq.), 4-(prop-2-ynyl)morpholine (22.5 g, 180 mmol, 1.20 eq.), diisopropylamine (18.2 g, 180 mmol, 1.2 eq.) and 150 mL of toluene were charged to a reactor. The solution was carefully degassed applying 3 vacuum argon cycles. Then, CuI (0.29 g, 1.5 mmol, 1 mol %) and Pd(PPh$_3$)$_4$ were added and the flask purged again with argon. The mixture was stirred at 50° C. overnight (17 h). Water (50 mL, 1 vol.) was added in one portion and the mixture was cooled to 20-25° C. The crude product was filtered off and washed consecutively with 10% ammonia (50 ml, 1.0 vol.), water (50 ml, 1 vol.), toluene (25 ml, 0.5 vol.), and with 2-isopropanol (50 ml, 1.0 vol.). After drying under vacuum at 50° C., 5-bromo-4-chloro-3-(3-morpholinoprop-1-yn-1-yl)pyridin-2-amine was obtained as light brown solid (41.6 g, 87% yield): LCMS calculated for $C_{12}H_{14}BrClN_5O$ [M+H]$^+$: 329.99; Found: 330.0; $^1$H NMR (400 MHz, DMSO-d$_6$) δ 8.13 (s, 1H), 6.69 (s, 2H), 3.64 (s, 2H), 3.61 (m, 4H), 2.54 (m, 4H).

Step 4: Synthesis of 4-((5-bromo-4-chloro-1H-pyrrolo[2,3-b]pyridin-2-yl)methyl)morpholine A solution of KOtBu (18.1 g, 1.4 eq., 112.21 mmol) in tetrahydrofuran (114 ml, 3 vol) was heated to 30-35° C. as 5-bromo-4-chloro-3-(3-morpholinoprop-1-yn-1-yl)pyridin-2-amine (38 g, 114.9 mmol, 1.0 eq.) was added in portions over 1.0 h at 30-35° C. After stirring for 2 h, the reaction was quenched with a solution of acetic acid (10.4 g, 172.4 mmol, 1.5 eq.) in water (76 mL, 2 vol.) and 76 mL of THF (76 mL) was removed by distillation. Then the solution was heated to reflux and MeOH (38 mL, 1 vol.) was added, and the resulting suspension was cooled to 23° C. over 1 h. After stirring for 0.5 h at 23° C., the solid was filtered off and washed with water (38 ml, 1 vol.), and MeOH (38 mL, 1 vol.). 4-((5-Bromo-4-chloro-1H-pyrrolo[2,3-b]pyridin-2-yl) methyl)morpholine as a light brown powder 4-((5-bromo-4-chloro-1H-pyrrolo[2,3-b]pyridin-2-yl)methyl)morpholine was obtained after drying under vacuum at 50° C. (32.8 g, 86% yield): LCMS calculated for $C_{12}H_{14}BrClN_5O$ [M+H]$^+$: 329.99; Found: 329.8; $^1$H NMR (400 MHz, DMSO-d$_6$) δ 12.22 (s, 1H), 8.34 (s, 1H), 6.40 (s, 1H), 3.65 (s, 2H), 3.58 (m, 4H), 2.42 (m, 4H).

Step 5: Synthesis of 4-((5-bromo-4-chloro-1-(phenylsulfonyl)-1H-pyrrolo[2,3-b]pyridin-2-yl) methyl) morpholine A slurry of 4-((5-Bromo-4-chloro-1H-pyrrolo[2,3-b]pyridin-2-yl)methyl)morpholine (10 g, 30.25 mmol, 1.0 eq., assay 94%-w/w) and NaH (1.69 g, 60%, 42.35 mmol, 1.4 eq.) in 38 mL of tetrahydrofuran was cooled to 0-5° C. as PhSO$_2$Cl (7.48 g, 42.35 mmol, 1.4 eq.) was added over 1 h. After 1.5 h, HPLC indicated the reaction was not complete. Additional NaH (0.34 g, 0.3 eq.) was added, whereupon gas evolution was observed. When HPLC showed the reaction was complete, the reaction mixture was quenched with acetic acid (0.5 g) and a mixture of water (15 mL) and methanol (15 mL). The pH was adjusted to 6.5 with caustic soda and the product was isolated by filtration. The wet cake was washed with 2-isopropanol (20 mL) and water (20 mL) and the wet product (14.8 g) was dried in the vacuum cabinet to give 4-((5-bromo-4-chloro-1-(phenylsulfonyl)-1H-pyrrolo[2,3-b]pyridin-2-yl)methyl)morpholine as a brown solid (12.57 g, 86% yield): LCMS calculated for $C_{18}H_{18}BrClN_3O_3S$ [M+H]$^+$: 469.99; Found: 470.0; $^1$H NMR (400 MHz, DMSO-d$_6$) δ 8.56 (s, 1H), 8.33 (m, 2H), 7.73 (m, 1H), 7.65 (m, 2H), 6.83 (s, 1H), 3.91 (s, 2H), 3.53 (m, 4H), 2.46 (m, 4H).

Step 6: Synthesis of 4-chloro-2-(morpholinomethyl)-1-(phenylsulfonyl)-1H-pyrrolo[2,3-b]pyridine-5-carbaldehyde To a suspension of 4-((5-bromo-4-chloro-1-(phenylsulfonyl)-1H-pyrrolo[2,3-b]pyridin-2-yl)methyl)morpholine (5.0 g, 10.6 mmol, 1.0 eq.) in 50 mL tetrahydrofuran at −10° C. to 0° C. was added iPrMgCl (6.9 mL, 2M in tetrahydrofuran, 13.80 mmol, 1.3 eq.). After stirring for 2 h N, N-dimethylformamide (1.55 g, 21.2 mmol, 2.0 eq.) was added to the reaction solution over 0.5 h at −5° C. to 0° C. The mixture was stirred for 0.5 h at −5° C. to 0° C., then warmed to 23° C. over 0.5 h and stirred for 1 h at 23° C. The pH was adjusted to 6-7 by adding 1.5 mL acetic acid and 10 mL water. To the biphasic mixture was added 25 mL MeOH and 15 mL water. After stirring for 1 h, the product was filtered off and washed with 20 mL MeOH/water (1/1) and 30 mL water. After drying under vacuum at 50° C., 4-chloro-2-(morpholinomethyl)-1-(phenylsulfonyl)-1H-pyrrolo[2,3-b]pyridine-5-carbaldehyde was obtained as an off-white powder (3.39 g, 76% yield): LCMS calculated for $C_{19}H_{19}ClN_3O_4S$ [M+H]$^+$: 420.07; Found: 420.0; $^1$H NMR (400 MHz, DMSO-d$_6$) δ 10.33 (s, 1H), 8.76 (s, 1H), 8.42 (m, 2H), 7.74 (m, 1H), 7.65 (m, 2H), 6.98 (s, 1H), 3.96 (m, 4H), 3.564 (m, 4H), 2.51 (m, 4H).

Example 4. Synthesis of 2,6-difluoro-3,5-dimethoxyaniline

Scheme 4.

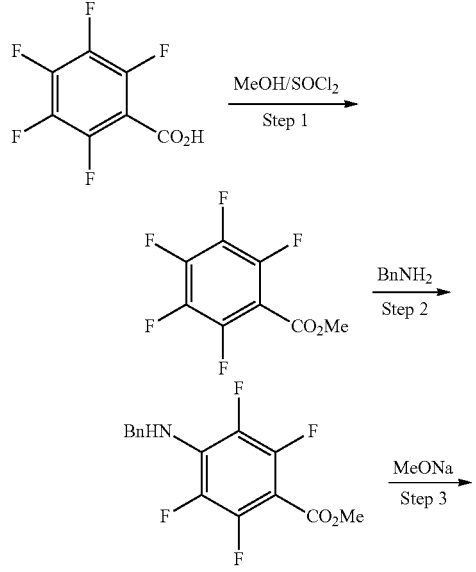

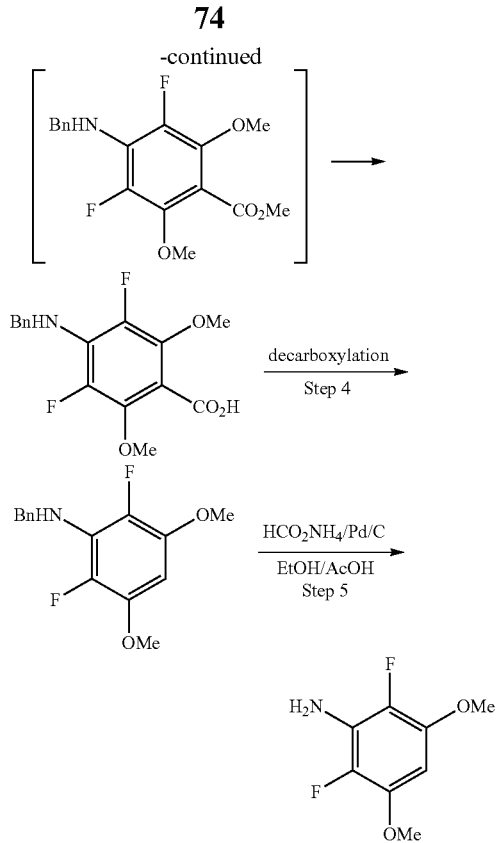

Step 1: Synthesis of Methyl Pentafluorobenzoate

To a solution of pentafluorobenzoic acid (40 Kg, 188.6 mol) in 68 L of methanol was added SOCl$_2$ (29.2 Kg, 245.2 mol, 1.3 eq.) drop-wise over 4.0 h at 20-50° C. The mixture was then heated to reflux for 17 h. Methanol was removed by vacuum distillation, and the residue was dissolved in methyl t-butyl ether (77 L). The solution was washed with saturated NaHCO$_3$ (37 L), dried over MgSO$_4$, and evaporated to give methyl pentafluorobenzoate as a colorless oil (39 kg, 91% yield): $^1$H NMR (400 MHz, CDCl$_3$) δ 3.90 (s, 3H).

Step 2: Synthesis of methyl-4-(benzylamino)-2,3,5,6-tetrafluorobenzoate

Methyl pentafluorobenzoate (39 Kg, 172.5 mol) and N,N-diisopropyl ethylamine (26.8 Kg, 207 mol, 1.2 eq.) were dissolved in N-methylpyrrolidinone (39 L). A solution of benzylamine (18.5 Kg, 172.5 mol, 1.0 eq.) in 19.5 L of N-methylpyrrolidinone was added drop-wise over 3.5 h while maintaining the internal temperature below 50° C. The resulting thick yellow slurry was heated to 65° C. and stirred another 1 h. The mixture was poured into a 195 L solution of aqueous acetic acid (10% acetic acid and 90% H$_2$O), and the slurry was stirred for 1 h and filtered. The filter cake was washed with water and heptane, and dried at 35° C. under vacuum to give Methyl-4-(benzylamino)-2, 3, 5, 6-tetrafluorobenzoate (38 Kg, 70% yield): $^1$H NMR (400 MHz, CDCl$_3$) δ 7.37 (m, 5H), 4.67 (m, 2H), 4.58 (m, 1H), 3.93 (s, 3H).

Step 3: Synthesis of 4-(benzylamino)-3,5-difluoro-2,6-dimethoxybenzoic acid

Methyl-4-(benzylamino)-2,3,5,6-tetrafluorobenzoate (38 Kg, 121.3 mol) in methanol (72 L), was stirred at room temperature under $N_2$ as a solution of NaOMe in methanol (25 wt %, 110.8 Kg, 545.85 mol, 4.5 eq.) was added drop-wise over 3.0 h while maintaining a temperature below 50° C. After heating to 65-70° C. for 18 h, 18 L of water was added to the reaction mixture and the resulting solution was stirred 1 h. The solvent was removed by vacuum distillation. Water (54 L) was added and the resulting solution was acidified to pH 2 with 37% HCl. The mixture was extracted three times with ethyl acetate (54 Kg each). The combined organic extracts were washed with water (43 L) and concentrated to dryness to form a solid. The solid was triturated with heptane (43 L) to remove the impurities. The solid was collected and dried at 40° C. under vacuum to give 4-(benzylamino)-3,5-difluoro-2,6-dimethoxybenzoic acid (35 Kg, 86% yield): $^1$H NMR (400 MHz, CDCl$_3$) δ 12.74 (s, 1H), 7.37 (m, 5H), 6.62 (s, 1H), 4.67 (m, 2H), 3.96 (s, 6H).

Step 4: Synthesis of n-benzyl-2, 6-difluoro-3,5-dimethoxyaniline 4-(Benzylamino)-3,5-difluoro-2,6-dimethoxybenzoic acid (17 Kg) was heated neat to 75-85° C. under nitrogen atmosphere for 3-4 h. After the reaction was completed, 40 L of methyl t-butyl ether and 20 L of 1M NaOH were added. The mixture was stirred at room temperature for 30 min. The organic layer was separated, and was washed with water (20 L) and brine (20 L). The organic phase was concentrated under reduced pressure to give the crude product. The crude was triturated with heptane and dried at 35° C. under vacuum to give N-benzyl-2,6-difluoro-3,5-dimethoxyaniline (12 Kg, 82% yield): $^1$H NMR (400 MHz, CDCl$_3$) δ 7.35 (m, 5H), 6.09 (m, 1H), 4.53 (m, 2H), 4.00 (s, 1H), 3.85 (s, 6H).

Step 5: Synthesis of 2,6-difluoro-3,5-dimethoxyaniline

N-Benzyl-2,6-difluoro-3,5-dimethoxyaniline (24 Kg, 85.9 mol) was dissolved in mixed solvents of ethanol (120 L) and acetic acid (20 L) as ammonium formate (13.2 Kg), and 1.68 Kg of Pd/C was added. The mixture was heated at 50° C. for 2-3 h. The reaction mixture was then filtered through a pad of Celite®, and washed with ethanol (1.2 L×2) and concentrated. The crude was added to 80 L of water, and the resulting slurry was filtered. The crude was added to 60 L methyl t-butyl ether and 2.5 Kg activated carbon, and the mixture was heated to reflux for 3 h. After filtration, and concentration, the resulting solid was added to 36 L heptane and stirred for 2 h at room temperature. The mixture was filtered and dried at 35° C. under vacuum to give 2,6-difluoro-3,5-dimethoxyaniline as a light brown solid (15.2 Kg, 93% yield): LCMS calculated for $C_5H_{10}F_2NO_2$ [M+H]$^+$: 190.16; Found: 190.1; $^1$H NMR (400 MHz, DMSO-d$_6$) δ 6.16 (m, 1H), 5.18 (s, 2H), 3.78 (s, 6H).

Example 5

Preparation and Characterization of Form I

A 100 L glass reactor and a 200 L glass reactor were assembled with overhead stirring, condenser, thermocouple, addition funnel, and a nitrogen inlet and each apparatus was purged with nitrogen. Methanol (1.39 L), methylene chloride (21.7 L) and crude 3-(2,6-difluoro-3,5-dimethoxyphenyl)-1-ethyl-8-(morpholin-4-ylmethyl)-1,3,4,7-tetrahydro-2H-pyrrolo[3',2':5, 6]pyrido[4,3-d]pyrimidin-2-one (3330 g) were charged sequentially to the 100 L reactor and the reaction mixture was heated to about 33° C. and stirred at about 33° C. for about 43 minutes until a clear solution was obtained. The reaction mixture was filtered through an in-line filter using methylene chloride (2.1 L) to rinse the reactor through the filter. The filtrate was partially concentrated (using 2 rotavapors for convenience) under vacuum at about 30° C. to a target total volume remaining of 15.5 L (~4.6 L per kg of product charged). The distillation residue (15.5 L) was charged to the 200 L reactor using filtered methylene chloride (1.3 L) to assist with the transfer. The reaction mixture was heated to about 39° C. and stirred for about 3 minutes until a clear solution was obtained. Polish filtered methyl t-butyl ether (23.1 L) was charged while maintaining the reaction temperature at about 39° C. The reaction mixture was stirred at about 36° C. for about 5.25 h, cooled to about 30° C., and stirred at about 23° C. for about 10.5 hours. The reaction mixture was filtered, and the filter cake was washed with polish filtered methyl t-butyl ether (3.3 L). The product was air dried on the filter for about 3.25 h and then dried under vacuum at 25-50° C. to afford 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one as a white to off-white solid (3002 g, 91.0% yield): LCMS calculated for $C_{24}H_{28}F_2N_5O_4$ [M+H]$^+$: 488.20; Found: 488.2; $^1$H NMR (400 MHz, DMSO-d$_6$) δ 11.74 (s, 1H), 7.92 (s, 1H), 7.05 (m, 1H), 6.48 (s, 1H), 4.75 (s, 2H), 4.15 (m, 2H), 3.90 (s, 6H), 3.60 (m, 6H), 2.44 (m, 4H), 1.33 (m, 3H).

The solid product was confirmed as a crystalline solid having Form I according to XRPD analysis. The XRPD pattern of Form I is shown in FIG. 1 and the peak data is given below in Table 1.

TABLE 1

| XRPD Peak Data for Form I | | |
|---|---|---|
| 2-Theta | Height | I % |
| 3.8 | 194 | 2.5 |
| 6.8 | 7767 | 100 |
| 7.9 | 105 | 1.4 |
| 9.6 | 563 | 7.2 |
| 10.1 | 70 | 0.9 |
| 11.4 | 96 | 1.2 |
| 12.2 | 56 | 0.7 |
| 12.9 | 1131 | 14.6 |
| 13.4 | 132 | 1.7 |
| 14.4 | 327 | 4.2 |
| 15.9 | 181 | 2.3 |
| 17.6 | 217 | 2.8 |
| 18.2 | 91 | 1.2 |
| 18.6 | 723 | 9.3 |
| 19.4 | 550 | 7.1 |
| 19.9 | 174 | 2.2 |
| 20.5 | 192 | 2.5 |
| 21.8 | 77 | 1 |
| 22.3 | 197 | 2.5 |
| 22.6 | 752 | 9.7 |
| 24.0 | 133 | 1.7 |
| 24.8 | 127 | 1.6 |
| 25.4 | 1761 | 22.7 |
| 25.8 | 3393 | 43.7 |
| 26.2 | 5024 | 64.7 |
| 27.5 | 1568 | 20.2 |
| 28.4 | 120 | 1.5 |
| 29.5 | 205 | 2.6 |
| 30.0 | 88 | 1.1 |
| 30.7 | 75 | 1 |

TABLE 1-continued

XRPD Peak Data for Form I

| 2-Theta | Height | I % |
|---|---|---|
| 31.0 | 81 | 1 |
| 31.8 | 112 | 1.4 |
| 32.7 | 64 | 0.8 |
| 33.7 | 69 | 0.9 |
| 34.5 | 62 | 0.8 |
| 36.6 | 72 | 0.9 |
| 37.9 | 76 | 1 |
| 39.1 | 119 | 1.5 |
| 43.8 | 51 | 0.7 |

Form I exhibits a DSC thermogram having endotherm peaks at temperatures of about 201° C. and about 276° C. FIG. 2 shows a DSC thermogram of Form I. FIG. 3 shows a TGA thermogram of Form I.

Example 6

Crystalline Form Screening Methods and Results

New crystalline forms of the compound of Formula I were obtained from the various screening methods described below. Form I, as described above in Example 5, was used as the starting material in the screens unless otherwise indicated.

Solubility Measurement

Form I was saturated in different solvent systems (Table 2) at 25° C. and 50° C., which were stirred for 24 h and its solubility was measured by HPLC. Form I was found to be completely soluble (≥50 mg/mL) in many solvents including DMF (50° C.), DCM, chloroform, DMSO, and DCM/MeOH (9/1) at 25° C. and 50° C. It was also found to be soluble in most of the other solvents but almost insoluble in water, heptane and hexane, sparingly soluble in MTBE, toluene, IPAc, methanol, and IPA at 25° C. Its solubility generally increased in all the solvents at 50° C.

TABLE 2

Solubility Screening

| Solvent | Solubility at 25° C. (mg/mL) | Solubility at 50° C. (mg/mL) |
|---|---|---|
| MeCN | 5.39 | 8.39 |
| Chloroform | >50 | >50 |
| Dichloromethane | >50[1] | >50 |
| DCM/MeOH (9/1) | >50 | >50 |
| DMF | 41.99 | >50 |
| 1,4-Dioxane | 2.23[2] | 5.69[2] |
| Methanol | 0.64[3] | 2.05 |
| 2-Methoxyethanol | 15.28 | 20.49 |
| MIBK | 0.43[4] | 1.12 |
| Toluene | 0.45 | 0.82 |
| Hexane | 0.00 | 0.00 |
| THF | 4.11 | 10.04[5] |
| Acetone | 2.68[6] | 6.67 |
| n-BuOH | 0.82 | 1.65 |
| MTBE | 0.05[7] | 0.19 |
| DMSO | >50[8] | >50 |
| EtOH | 0.97 | 2.73 |
| EtOAc | 0.70[9] | 2.26 |
| Ethyl formate | 4.16[10] | 15.29 |
| Heptane | 0.00 | 0.00 |
| Isobutyl acetate | 0.46 | 0.58 |
| IPAc | 0.88 | 1.33 |
| 1-Propanol | 1.16 | 2.50 |
| IPA | 0.56 | 1.37 |
| IPA/water (4/1) | 5.35 | 8.77 |
| MEK | 1.20 | 3.22 |

Note:
[1]Solubility of Form II in DCM;
[2]Solubility of Form III in 1,4-Dioxane;
[3]Solubility of Form VI in methanol;
[4]Solubility of Form VII in MIBK;
[5]Solubility of Form XIII in THF
[6]Solubility of Form VIII in acetone;
[7]Solubility of Form IX in MTBE;
[8]A slurry was obtained after stirring the clear solution of 60 mg Form I in 1 mL DMSO and the solubility of the saturated solution is 6.13 mg/mL.
[9]Solubility of Form X in ethyl acetate;
[10]Solubility of Form XI in ethyl formate Phase Equilibrium Screen at 25, 40, and 50° C.

Phase equilibration studies were designed to provide information on a predominant crystal form for phase identification. Based on its solubility in various solvent systems (Table 2), Form I was equilibrated in a representative group of solvents at 25±1° C. (Table 3), 40° C. (Table 4a) and 50±1° C. (Table 4). After equilibration, the supernatant was removed by centrifugation or the solid was filtered. XRPD was used to study the solid-state morphology of the crystalline forms.

Phase equilibration at 25° C. resulted in several polymorphic forms including Form II (DCM, 9:1 DCM-MeOH), Form III (1,4-dioxane, centrifuged), Form IV ((1,4-dioxane, filtered), Form V (1,4-dioxane, crystalline solid from saturated solution), Form VI (MeOH), Form VII (MIBK), Form VIII (acetone and MEK), Form IX (MTBE), Form X (ethyl acetate), Form XI (ethyl formate), and partially amorphous or amorphous forms (DMF, DMSO and water).

Phase equilibration at 40° C. resulted in Form II (DCM, DCM/MeOH).

Phase equilibration at 50° C. resulted in two new polymorphic forms including Form XII (1,4-dioxane) and Form XIII (THF). Form VII resulted from MIBK.

TABLE 3

Crystal form for phase equilibration at 25° C.

| Solvent | Solid State Form |
|---|---|
| N/A | I |
| MeCN | I |
| Chloroform | I |
| Dichloromethane | II |
| DCM/MeOH (9/1) | II |
| DMF | Some crystal + amorphous |
| 1,4-Dioxane | III |
| 1,4-Dioxane | IV |
| 1,4-Dioxane | V |
| Methanol | VI |
| 2-Methoxyethanol | I |
| MIBK | VII |
| Toluene | I |
| Hexane | I |
| THF | I |
| Acetone | VIII |
| n-BuOH | I |
| MTBE | IX |
| DMSO | Amorphous + crystalline form |
| EtOH | I |
| EtOAc | X |
| Ethyl formate | XI |
| Heptane | I |

TABLE 3-continued

Crystal form for phase equilibration at 25° C.

| Solvent | Solid State Form |
|---|---|
| Isobutyl acetate | I |
| IPAc | I |
| 1-Propanol | I |
| IPA | I |
| IPA/water (4/1) | I |
| Water | Amorphous |
| MEK | VIII |

TABLE 4

Crystal form for phase equilibration at 50° C.

| Solvent | Sold State Form |
|---|---|
| N/A | I |
| MeCN | I |
| 1,4-Dioxane | XII |
| MeOH | I |
| 2-Methoxyethanol | I |
| MIBK | VII |
| Toluene | I |
| Hexane | I |
| THF | XIII |
| Acetone | I |
| n-BuOH | I |
| MTBE | I |
| EtOH | I |
| EtOAc | I |
| Ethyl formate | I |
| Heptane | I |
| Isobutyl acetate | I |
| IPAc | I |
| 1-Propanol | I |
| IPA | I |
| IPA/water (4/1) | I |
| Water | I |
| MEK | VIII-a |

TABLE 4a

Crystal form for phase equilibration at 40° C.

| Form I (mg) | Solvent (mL) | Result (Solid State Form) |
|---|---|---|
| 100.2 | DCM (0.5 mL) | Slurry (Form II) |
| 100.3 | DCM/MeOH (9/1, 0.5 mL) | Slurry (Form II) |
| 100.4 | DCM/MeOH/MTBE (0.47/0.03/0.7; 1.2 mL) | Added 0.5 mL of DCM/MeOH to give clear solution at 25° C., added MTBE to give slurry (Form I) |
| 100.1 | DCM/MeOH (0.47/0.03, 0.5 mL) | Slurry (Form II) |
| 99.01 | DCM/MeOH (0.47/0.03; 0.6 mL) | Clear solution |

Evaporation Screen at 25 and 50° C.

Evaporation studies were carried out to identify the predominant crystal form during uncontrolled precipitation. Experiments that did not result in any particulate solids (i.e. clear thin films and oils) were not studied further. XRPD was used to study the solid-state morphology of the crystalline forms of the evaporation samples at 25° C. and 50° C. The results are presented in Table 5 (25° C.) and Table 6 (50° C.).

TABLE 5

Crystal form identification from evaporation at 25° C.

| Solvent | Solid state form |
|---|---|
| N/A | I |
| MeCN | I |
| Chloroform | I + IV |
| Dichloromethane | II-a |
| DCM/MeOH (9/1) | II-a |
| DMF | I |
| DMF | XIV |
| 1,4-Dioxane | Amorphous + crystalline form |
| Methanol | N/A |
| 2-Methoxy-ethanol | N/A |
| MIBK | N/A |
| Toluene | N/A |
| Hexane | N/A |
| THF | I |
| Acetone | I |
| n-BuOH | I |
| MTBE | II-a |
| DMSO | XV |
| EtOH | I |
| EtOAc | I |
| Ethyl formate | I |
| Heptane | N/A |
| Isobutyl acetate | I |
| IPAc | I |
| 1-Propanol | I |
| IPA | I |
| IPA/water (4/1) | I |
| Water | N/A |
| MEK | I |

N/A: Not available. Ether clear solution or the amount of the precipitate was too small to be analyzed by XRPD.

TABLE 6

Crystal form identification from evaporation at 50° C.

| Solvent | Solid state form |
|---|---|
| N/A | I |
| MeCN | I |
| Chloroform | I |
| DCM | II |
| DCM/MeOH (9/1) | I |
| DMF | I |
| 1,4-Dioxane | I |
| Methanol | I |
| 2-Methoxyethanol | I |
| MIBK | I |
| Toluene | N/A |
| Hexane | N/A |
| THF | XVI |
| Acetone | I |
| n-BuOH | I |
| MTBE | N/A |
| DMSO | XVII |
| EtOH | I |
| EtOAc | I |
| Ethyl formate | I |
| Heptane | N/A |
| Isobutyl acetate | I |
| IPAc | I |
| 1-Propanol | I |
| IPA | I |
| IPA/water (4/1) | I |
| Water | N/A |
| MEK | I |

N/A: Not available. Ether clear solution or the amount of the precipitate was too small to be analyzed by XRPD.

Antisolvent Addition Screen

Saturated or near saturated solutions of Compound 1 were prepared by adding Form I to a solvent. An anti-solvent was added to induce precipitation. Heptane, hexane, MTBE, water, MeOH, IPA, IPAc, ethyl acetate and toluene were selected as the anti-solvents. Experiments that did not produce any particulate solids on anti-solvent addition were not studied further.

Antisolvent addition resulted in several polymorphic forms including Form XVIII (chloroform/hexane, DCM/toluene and DCM-MeOH/toluene) and Form XIX (DCM/MeOH).

TABLE 7

Antisolvent addition

| Solvent/Antisolvent | Form |
|---|---|
| MeCN (0.5 mL)/MTBE (4 mL) | N/A |
| MeCN (0.5 mL)/water (4 mL) | N/A |
| Chloroform (1 mL)[1]/Heptane (3 mL) | I |
| Chloroform (1 mL)[1]/Hexane (3 mL) | XVIII |
| Chloroform (1 mL)[1]/MTBE (3 mL) | I |
| DCM (0.5 mL)[2]/Heptane (0.5 mL) | I |
| DCM (0.5 mL)[2]/Hexane (0.5 mL) | I |
| DCM (0.5 mL)[2]/MTBE (1 mL) | I |
| DCM (0.5mL)[2]/Toluene (4 mL) | XVIII |
| DCM (0.5 mL)[2]/IPA (4 mL) | I |
| DCM (0.5 mL)[2]/MeOH (5 mL) | XIX |
| DCM-MeOH (9/1, 0.5 mL)[3]/Heptane (0.5 mL) | I |
| DCM-MeOH (9/1, 0.5 mL)[3]/Hexane (0.5 mL) | I |
| DCM-MeOH (9/1, 0.5 mL)[3]/MTBE (1.0 mL) | I |
| DCM-MeOH (9/1, 0.5 mL)[3]/Toluene (4.0 mL) | XVIII |
| DCM-MeOH (9/1, 0.5 mL)[3]/IPA (4.0 mL) | I |
| DCM-MeOH (9/1, 0.5 mL)[3]/MeOH (3.0 mL) | I |
| DMF (saturated, 0.8 mL)/water (4 mL) | I (major) + amorphous |
| 2-methoxyethanol (saturated, 0.7 mL)/water (4 mL) | N/A |
| THF (saturated, 1.4 mL)/Heptane (3.6 mL) | I |
| THF (saturated, 1.5 mL)/Hexane (4 mL) | I |
| THF (saturated, 1.5 mL)/MTBE (4 mL) | N/A |
| THF (saturated, 1.5 mL)/water (4 mL) | N/A |

Notes:
N/A: not available, samples were too small to analyzed by XRPD
[1] The concentration of Compound 1 in chloroform is 83.7 mg/mL
[2] The concentration of Compound 1 in DCM is 92 mg/mL
[3] The concentration of Compound 1 in DCM/MeOH (9:1) is 80 mg/mL Reverse Addition Screen Saturated or near saturated solutions of Compound 1 were prepared in the solvents listed in Table 8, and added to a larger volume of a miscible anti-solvent (i.e. heptane, hexane, MTBE, water, toluene, MeOH, IPA and ethyl acetate). Experiments that did not produce any particulate solids upon addition to the anti-solvent were not studied further.

Reverse addition resulted in several polymorphic forms including Form XX (DCM/MTBE), Form XXI (DCM/toluene), and Form XXII (DCM-MeOH/MeOH), and Form IX (THF/MTBE).

TABLE 8

Reverse addition

| Solvent/Antisolvent | Form |
|---|---|
| MeCN/MTBE | N/A |
| MeCN/water | N/A |
| Chloroform (1 mL)[1]/Heptane (2 mL) | I |
| Chloroform (1 mL)[1]/Hexane (2.0 mL) | I |
| Chloroform (1 mL)[1]/MTBE (2.0 mL) | I |
| DCM (0.8 mL)[2]/Heptane (4.0 mL) | I |
| DCM (0.8 mL)[2]/Hexane (4.0 mL) | I |
| DCM (0.8 mL)[2]/MTBE (4.0 mL) | XX |
| DCM (0.8 mL)[2]/Toluene (4.0 mL) | XXI |
| DCM (0.8 mL)[2]/IPA (4.0 mL) | I |
| DCM (0.8 mL)[2]/MeOH (4 mL) | I |
| DCM (0.8 mL)[2]/IPAc (4 mL) | I |
| DCM (0.8 mL)[2]/EtOAc (4 mL) | I |

TABLE 8-continued

Reverse addition

| Solvent/Antisolvent | Form |
|---|---|
| DCM-MeOH (9/1, 0.8 mL)[3]/Heptane (4.0 mL) | I |
| DCM-MeOH (9/1, 0.8 mL)[3]/Hexane (4.0 mL) | I |
| DCM-MeOH (9/1, 0.8 mL)[3]/MTBE (4.0 mL) | I |
| DCM-MeOH (9/1, 0.8 mL)[3]/Toluene (4.0 mL) | I |
| DCM-MeOH (9/1, 0.8 mL)[3]/IPA (4.0 mL) | I |
| DCM-MeOH (9/1, 0.8 mL)[3]/MeOH (4.0 mL) | XXII |
| DMF (saturated, 0.8 mL)/water (4 mL) | I (major) + amorphous |
| Sample 1922-120-7-2-8 was air-dried for 18 h | I |
| THF (saturated, 1.5 mL)/Heptane (4.0 mL) | I |
| THF (saturated, 1.5 mL)/Hexane (4.0 mL) | I |
| THF (saturated, 1.5 mL)/MTBE (4 mL) | IX |
| THF (saturated, 1.5 mL)/water (4 mL) | N/A |

Notes:
N/A: not available, samples were too small to analyzed by XRPD
[1] The concentration of Compound 1 in chloroform is 83.7 mg/mL
[2] The concentration of Compound 1 in DCM is 55 mg/mL
[3] The concentration of Compound 1 in DCM/MeOH (9:1) is 80 mg/mL Quench Cool of Saturated Solution Saturated solutions were quench cooled to about −20° C. to induce precipitation of higher energy forms. Representative solvents were chosen based on solubility data measured at 25° C. and 50° C. The studied solvents and the crystal form of the sample in each of the solvent were shown in Table 4.

Quench cool of saturated solutions resulted in Form XXIII (dichloromethane).

TABLE 9

Crystal form identification from quench cooling

| Solvent | Form |
|---|---|
| MeCN (filtered after cooled for 5 h at −20° C.) | I |
| Chloroform | N/A |
| Dichloromethane (filtered after cooled for 3 h at −20° C.) | XXIII |
| DCM/MeOH (9/1) | N/A |
| DMF | N/A |
| 1,4-Dioxane | N/A |
| 2-Methoxyethanol | N/A |
| THF (filtered after cooled for 3 h at −20° C.) | XIII-a |
| Ethyl formate | N/A |
| IPA/water (4/1) | N/A |

N/A: Ether a clear solution or the amount of the precipitate was too small to be analyzed by XRPD.

Example 7

Stability of the Crystalline Forms

Crystallization of Saturated Solution with Heating and Cooling Recycles

Saturated solutions were prepared at 30° C. or 50° C., and cooled in a bath slowly by using a programmed circulating bath. The formed slurry was then heated to 50° C. over 2 hours and then cooled down to 5° C. over 2 hours. This process was repeated for 3 days and the solid was filtered for further analysis. The results are presented in Table 10.

In heating and cooling cycles (Table 10) two new forms were identified including Form XXIV (DMF) and Form XXV (DMSO).

TABLE 10

Crystallization of saturated solution with heating and cooling recycles

| Solvent | Solid State Form |
|---|---|
| MeCN | I |
| DMF | XXIV |
| 1,4-Dioxane | XIII |
| 2-Methoxyethanol | I |
| THF | I |
| Acetone | VIII |
| DMSO (almost saturated solution was stirred to give slurry) | XXV |
| Ethyl formate | I |
| IPA/WATER (4/1) | I |

Mixed Samples of Compound 1 Polymorphs in IPA, EtOH and Acetonitrile

To evaluate the transformation of solid forms of Compound 1, competitive slurry experiments were performed as follows. To the saturated solution of Form I in the solvent as listed in Table 11 was added Form I (5 mg), then 5 mg each of Form II through Form XXVI.

The slurry was stirred overnight, filtered and analyzed by XRPD. The results in Table 11 revealed that Form I appears to be most stable in IPA, ethanol and acetonitrile.

TABLE 11

Mixed samples in different solvents (competitive slurries)

| Solvent | Solid State Form |
|---|---|
| Iso-propanol (1.7 mL) | Form I |
| Ethanol (1.7 mL) | Form I |
| Acetonitrile (1.7 mL) | Form I |

Mixed Samples of Compound 1 Polymorphs in Dichloromethane/Methanol (9/1)

A competitive slurry experiment was conducted in dichloromethane/methanol (9/1) according to the procedure in Table 12. The mixture of forms (Form I through Form XXVI) was converted to Form II after 15 min as shown by XRPD at various time points including 15 mins, 1 h, 18 h and 3 days, which indicated the Form II was consistently obtained. Form II is the stable polymorphic form in the solvent system.

TABLE 12

Competitive Slurry Experiment

| OP# | Operation | Result |
|---|---|---|
| 1 | The cloudy solution of 97 mg of Form I in DCM/MeOH (9:1, 0.6 mL) was added to the mixture of 5 mg each of Compound 1 polymorphs (Form I through Form XXVI) | |
| 2 | Stirred for 15 min, XRPD (Form II) | Form II |
| 3 | Stirred for 60 min, XRPD (Form II) | Form II |
| 4 | Stirred for 18 h, XRPD (Form II) | Form II |
| 5 | Stirred for 3 days, XRPD (Form II) | Form II |

Conversion of Form II to Form I in Different Solvents

The Form II was converted to Form I in acetonitrile, ethanol and IPA respectively as described in Table 13.

TABLE 13

Conversion of Form II to Form I in different solvents

| OP# | Form II | Solvent (mL) | Result |
|---|---|---|---|
| 1 | 18 mg | MeCN (0.7) | Form I |
| 2 | 18 mg | IPA (0.7) | Form I |
| 3 | 18 mg | EtOH (0.7) | Form I |

Example 8

Preparation and Characterization of Form II

About 3 mL of saturated solution of Form I in DCM were evaporated under air without stirring at 50±1° C. to give solid, which was characterized by XRPD, DSC and TGA as Form II.

TABLE 14

XRPD Peak Data for Form II

| 2-Theta | Height | I % |
|---|---|---|
| 6.8 | 3218 | 100 |
| 8.0 | 46 | 1.4 |
| 9.5 | 412 | 12.8 |
| 12.8 | 134 | 4.2 |
| 13.3 | 118 | 3.7 |
| 16.3 | 102 | 3.2 |
| 17.5 | 53 | 1.6 |
| 19.0 | 134 | 4.2 |
| 19.4 | 63 | 2 |
| 20.5 | 115 | 3.6 |
| 22.6 | 382 | 11.9 |
| 25.8 | 505 | 15.7 |
| 26.2 | 679 | 21.1 |
| 27.4 | 247 | 7.7 |
| 29.4 | 63 | 2 |

Form II exhibits a DSC thermogram having an endotherm peak at a temperature of about 276° C. FIG. 5 shows a DSC thermogram of Form II. FIG. 6 shows a TGA thermogram of Form II.

Example 9

Preparation and Characterization of Form II-a

About 3 mL of saturated solution of Compound 1, Form I in DCM were evaporated under air without stirring at 25±1° C. to give solid, which was characterized by XRPD, DSC and TGA as Form II-a.

TABLE 15

XRPD Peak Data for Form II-a

| 2-Theta | Height | I % |
|---|---|---|
| 4.6 | 43 | 2.5 |
| 6.9 | 1742 | 100 |
| 9.4 | 751 | 43.1 |
| 10.1 | 53 | 3 |
| 12.9 | 197 | 11.3 |
| 13.3 | 246 | 14.1 |
| 14.5 | 115 | 6.6 |
| 15.1 | 131 | 7.5 |
| 16.3 | 391 | 22.4 |
| 17.5 | 265 | 15.2 |
| 19.0 | 221 | 12.7 |
| 19.9 | 449 | 25.8 |
| 22.0 | 196 | 11.3 |

TABLE 15-continued

XRPD Peak Data for Form II-a

| 2-Theta | Height | I % |
|---|---|---|
| 22.5 | 577 | 33.1 |
| 24.3 | 116 | 6.7 |
| 26.1 | 977 | 56.1 |
| 27.4 | 260 | 14.9 |
| 30.6 | 106 | 6.1 |
| 36.6 | 75 | 4.3 |

Form II-a exhibits a DSC thermogram having an endotherm peak at a temperature of about 275° C. FIG. 8 shows a DSC thermogram of Form IIa. FIG. 9 shows a TGA thermogram of Form IIa.

Example 10

Preparation and Characterization of Form III

To about 5 mL of cloudy solutions of Compound 1, Form I, prepared in 1,4-dioxane was added about 20 mg of Compound 1, Form I followed by stirring at 25±1° C. for 2 days, of which the supernatant was removed by centrifugation. The solid analyzed by XRPD as Form III.

TABLE 16

XRPD Peak Data for Form III

| 2-Theta | Height | I % |
|---|---|---|
| 3.5 | 532 | 50.1 |
| 6.7 | 151 | 14.2 |
| 7.4 | 37 | 3.5 |
| 8.5 | 203 | 19.1 |
| 9.3 | 56 | 5.3 |
| 9.9 | 113 | 10.7 |
| 10.7 | 109 | 10.3 |
| 11.3 | 38 | 3.6 |
| 13.9 | 627 | 59.1 |
| 15.0 | 388 | 36.6 |
| 15.3 | 493 | 46.5 |
| 16.0 | 170 | 16 |
| 16.8 | 366 | 34.5 |
| 18.6 | 1061 | 100 |
| 19.3 | 209 | 19.7 |
| 20.5 | 104 | 9.8 |
| 21.5 | 478 | 45.1 |
| 22.1 | 98 | 9.2 |
| 22.9 | 253 | 23.8 |
| 23.4 | 193 | 18.2 |
| 24.2 | 392 | 36.9 |
| 25.2 | 58 | 5.5 |
| 25.9 | 257 | 24.2 |
| 26.5 | 107 | 10.1 |
| 27.6 | 71 | 6.7 |
| 28.2 | 115 | 10.8 |
| 29.3 | 136 | 12.8 |
| 30.2 | 96 | 9 |
| 30.9 | 60 | 5.7 |
| 31.2 | 62 | 5.8 |
| 32.5 | 60 | 5.7 |
| 33.1 | 73 | 6.9 |
| 34.4 | 54 | 5.1 |
| 36.1 | 60 | 5.7 |
| 41.0 | 70 | 6.6 |
| 42.7 | 42 | 4 |
| 43.2 | 36 | 3.4 |

Form III exhibits a DSC thermogram having endotherm peaks at temperatures of about 101° C., about 204° C., and about 276° C. FIG. 11 shows a DSC thermogram of Form III. FIG. 12 shows a TGA thermogram of Form III.

Example 11

Preparation and Characterization of Form IV

To about 5 mL of saturated or cloudy solutions of Compound 1, Form I, prepared in 1,4-dioxane was added about 20 mg of Compound 1, Form I followed by stirring at 25±1° C. for 6 days, which was filtered and analyzed by XRPD as Form IV.

TABLE 17

XRPD Peak Data for Form IV

| 2-Theta | Height | I % |
|---|---|---|
| 5.8 | 83 | 2.2 |
| 10.1 | 1486 | 39.4 |
| 11.5 | 374 | 9.9 |
| 13.0 | 1078 | 28.6 |
| 14.0 | 2326 | 61.6 |
| 14.8 | 426 | 11.3 |
| 15.6 | 1027 | 27.2 |
| 17.3 | 928 | 24.6 |
| 18.4 | 2315 | 61.3 |
| 20.2 | 567 | 15 |
| 21.0 | 162 | 4.3 |
| 21.4 | 523 | 13.9 |
| 22.2 | 3642 | 96.5 |
| 22.7 | 1261 | 33.4 |
| 23.5 | 225 | 6 |
| 24.3 | 3775 | 100 |
| 26.4 | 2703 | 71.6 |
| 26.8 | 1150 | 30.5 |
| 28.0 | 515 | 13.6 |
| 29.3 | 140 | 3.7 |
| 30.0 | 322 | 8.5 |
| 30.5 | 471 | 12.5 |
| 32.1 | 233 | 6.2 |
| 32.7 | 326 | 8.6 |
| 34.0 | 726 | 19.2 |
| 34.6 | 218 | 5.8 |
| 36.1 | 305 | 8.1 |
| 37.9 | 506 | 13.4 |
| 39.6 | 323 | 8.6 |
| 40.6 | 106 | 2.8 |
| 41.4 | 81 | 2.1 |
| 43.6 | 183 | 4.8 |
| 44.1 | 126 | 3.3 |

Form IV exhibits a DSC thermogram having endotherm peaks at temperatures of about 109° C., about 203° C., and about 278° C. FIG. 14 shows a DSC thermogram of Form IV. FIG. 15 shows a TGA thermogram of Form IV.

Example 12

Preparation and Characterization of Form V

A saturated solution of Compound 1, Form I, was placed in hood for more than 30 days to give crystalline solid, which was filtered and analyzed by XRPD as Form V.

TABLE 18

XRPD Peak Data for Form V

| 2-Theta | Height | I % |
|---|---|---|
| 6.7 | 833 | 1.3 |
| 7.4 | 64827 | 100 |
| 9.5 | 70 | 0.1 |
| 10.9 | 518 | 0.8 |
| 11.5 | 823 | 1.3 |
| 12.4 | 104 | 0.2 |
| 13.8 | 761 | 1.2 |
| 14.8 | 17728 | 27.3 |
| 15.3 | 750 | 1.2 |

TABLE 18-continued

XRPD Peak Data for Form V

| 2-Theta | Height | I % |
|---|---|---|
| 16.1 | 243 | 0.4 |
| 17.0 | 268 | 0.4 |
| 17.4 | 850 | 1.3 |
| 18.2 | 140 | 0.2 |
| 19.2 | 226 | 0.3 |
| 20.2 | 219 | 0.3 |
| 20.5 | 840 | 1.3 |
| 21.3 | 2445 | 3.8 |
| 22.0 | 1989 | 3.1 |
| 22.3 | 11335 | 17.5 |
| 23.2 | 478 | 0.7 |
| 23.9 | 313 | 0.5 |
| 24.2 | 148 | 0.2 |
| 25.9 | 331 | 0.5 |
| 26.3 | 217 | 0.3 |
| 26.7 | 649 | 1 |
| 27.2 | 195 | 0.3 |
| 28.1 | 331 | 0.5 |
| 29.2 | 690 | 1.1 |
| 30.0 | 88 | 0.1 |
| 30.4 | 94 | 0.1 |
| 31.6 | 137 | 0.2 |
| 33.1 | 219 | 0.3 |
| 34.4 | 87 | 0.1 |
| 35.2 | 91 | 0.1 |
| 36.8 | 184 | 0.3 |
| 37.6 | 829 | 1.3 |
| 42.9 | 219 | 0.3 |

Form V exhibits a DSC thermogram having endotherm peaks at temperatures of about 91° C., about 203° C., and about 276° C. FIG. 17 shows a DSC thermogram of Form V.

Example 13

Preparation and Characterization of Form VI

To about 5 mL of saturated or cloudy solutions of Compound 1, Form I, prepared in methanol was added about 20 mg of Compound 1, Form I, followed by stirring at 25±1° C. for 3 days, which was filtered and analyzed by XRPD as Form VI.

TABLE 19

XRPD Peak Data for Form VI

| 2-Theta | Height | I % |
|---|---|---|
| 7.8 | 102 | 10.3 |
| 9.1 | 757 | 76.6 |
| 9.5 | 388 | 39.3 |
| 10.2 | 230 | 23.3 |
| 11.4 | 279 | 28.2 |
| 12.1 | 278 | 28.1 |
| 12.6 | 106 | 10.7 |
| 13.4 | 188 | 19 |
| 14.4 | 464 | 47 |
| 15.9 | 234 | 23.7 |
| 17.6 | 514 | 52 |
| 18.6 | 458 | 46.4 |
| 19.2 | 324 | 32.8 |
| 19.9 | 443 | 44.8 |
| 20.4 | 77 | 7.8 |
| 21.0 | 75 | 7.6 |
| 22.3 | 716 | 72.5 |
| 22.7 | 265 | 26.8 |
| 23.4 | 66 | 6.7 |
| 24.1 | 83 | 8.4 |
| 25.4 | 536 | 54.3 |
| 26.2 | 988 | 100 |
| 27.5 | 207 | 21 |

TABLE 19-continued

XRPD Peak Data for Form VI

| 2-Theta | Height | I % |
|---|---|---|
| 29.1 | 136 | 13.8 |
| 31.1 | 67 | 6.8 |
| 36.6 | 64 | 6.5 |

Form VI exhibits a DSC thermogram having an endotherm peak at a temperature of about 275° C. FIG. 19 shows a DSC thermogram of Compound 1, Form VI. FIG. 20 shows a TGA thermogram of Compound 1, Form VI.

Example 14

Preparation and Characterization of Form VII

To about 5 mL of saturated or cloudy solutions of Compound 1, Form I, prepared in methyl isobutyl ketone was added about 20 mg of Compound 1, Form I followed by stirring at 25±1° C. for 3 days, which was filtered and analyzed by XRPD as Form VII.

TABLE 20

XRPD Peak Data for Form VII

| 2-Theta | Height | I % |
|---|---|---|
| 8.2 | 116 | 15.1 |
| 9.8 | 768 | 100 |
| 12.3 | 96 | 12.5 |
| 15.4 | 519 | 67.6 |
| 16.0 | 84 | 10.9 |
| 16.2 | 132 | 17.2 |
| 17.4 | 93 | 12.1 |
| 17.9 | 223 | 29 |
| 18.8 | 375 | 48.8 |
| 19.6 | 554 | 72.1 |
| 20.1 | 357 | 46.5 |
| 21.1 | 266 | 34.6 |
| 22.3 | 191 | 24.9 |
| 22.8 | 127 | 16.5 |
| 23.1 | 130 | 16.9 |
| 23.7 | 112 | 14.6 |
| 24.3 | 236 | 30.7 |
| 25.5 | 139 | 18.1 |
| 26.7 | 74 | 9.6 |
| 27.6 | 48 | 6.3 |
| 29.3 | 62 | 8.1 |
| 29.7 | 67 | 8.7 |
| 30.5 | 40 | 5.2 |
| 32.1 | 37 | 4.8 |
| 35.9 | 32 | 4.2 |
| 38.6 | 58 | 7.6 |
| 42.1 | 56 | 7.3 |

Form VII exhibits a DSC thermogram having endotherm peaks at temperatures of about 88° C., about 201° C., and about 276° C. FIG. 22 shows a DSC thermogram of Form VII. FIG. 23 shows a TGA thermogram of Form VII.

Example 15

Preparation and Characterization of Form VII

To about 5 mL of cloudy solutions of Compound 1, Form I, prepared in acetone was added about 20 mg of Compound 1, Form I, followed by stirring at 25±1° C. for 3 days, which was filtered and analyzed by XRPD as Form VIII.

TABLE 21

XRPD Peak Data for Form VIII

| 2-Theta | Height | I % |
|---|---|---|
| 9.1 | 953 | 39.6 |
| 9.9 | 196 | 8.1 |
| 15.2 | 409 | 17 |
| 16.7 | 650 | 27 |
| 18.2 | 2409 | 100 |
| 18.6 | 589 | 24.4 |
| 20.2 | 2079 | 86.3 |
| 21.4 | 196 | 8.1 |
| 22.5 | 768 | 31.9 |
| 23.8 | 64 | 2.7 |
| 24.6 | 701 | 29.1 |
| 25.4 | 83 | 3.4 |
| 26.8 | 376 | 15.6 |
| 27.5 | 123 | 5.1 |
| 29.8 | 376 | 15.6 |
| 30.6 | 64 | 2.7 |
| 31.4 | 239 | 9.9 |
| 32.0 | 61 | 2.5 |
| 34.8 | 87 | 3.6 |
| 35.9 | 162 | 6.7 |
| 40.0 | 50 | 2.1 |

Form VIII exhibits a DSC thermogram having endotherm peaks at temperatures of about 201° C. and about 277° C. FIG. 25 shows a DSC thermogram of Compound 1, Form VIII. FIG. 26 shows a TGA thermogram of Compound 1, Form VIII.

Example 16

Preparation and Characterization of Form VII-a

To about 5 mL of cloudy solutions of Compound 1, Form I prepared in methyl ethyl ketone was added about 30 mg of Compound 1, Form I followed by stirring at 50±1° C. for 2 days, which was filtered and analyzed by XRPD as Form VIII-a.

TABLE 22

XRPD Peak Data for Form VIII-a

| 2-Theta | Height | I % |
|---|---|---|
| 7.7 | 104 | 1.7 |
| 8.9 | 1887 | 30.7 |
| 9.7 | 311 | 5.1 |
| 14.6 | 346 | 5.6 |
| 15.0 | 492 | 8 |
| 15.5 | 230 | 3.7 |
| 16.2 | 1484 | 24.1 |
| 18.0 | 6145 | 100 |
| 18.4 | 1644 | 26.8 |
| 19.3 | 291 | 4.7 |
| 19.9 | 6032 | 98.2 |
| 21.1 | 1654 | 26.9 |
| 22.0 | 2276 | 37 |
| 22.9 | 144 | 2.3 |
| 23.5 | 804 | 13.1 |
| 24.1 | 1923 | 31.3 |
| 24.3 | 1489 | 24.2 |
| 25.3 | 429 | 7 |
| 25.8 | 202 | 3.3 |
| 26.3 | 846 | 13.8 |
| 27.1 | 516 | 8.4 |
| 28.0 | 144 | 2.3 |
| 28.5 | 100 | 1.6 |
| 29.1 | 317 | 5.2 |
| 29.5 | 1196 | 19.5 |
| 30.2 | 84 | 1.4 |
| 30.9 | 570 | 9.3 |
| 31.3 | 541 | 8.8 |
| 31.6 | 271 | 4.4 |
| 32.1 | 90 | 1.5 |
| 32.6 | 439 | 7.1 |
| 34.1 | 187 | 3 |
| 35.5 | 643 | 10.5 |
| 36.1 | 172 | 2.8 |
| 36.9 | 143 | 2.3 |
| 38.0 | 187 | 3 |
| 39.4 | 276 | 4.5 |
| 40.4 | 82 | 1.3 |
| 41.0 | 116 | 1.9 |
| 42.1 | 181 | 2.9 |
| 42.7 | 92 | 1.5 |

Example 17

Preparation and Characterization of Form IX

To about 5 mL of cloudy solutions of Compound 1, Form I prepared in MTBE was added about 20 mg of Compound 1, Form I, followed by stirring at 25±1° C. for 3 days, which was filtered and analyzed by XRPD as Form IX.

TABLE 23

XRPD Peak Data for Form IX

| 2-Theta | Height | I % |
|---|---|---|
| 8.5 | 424 | 31 |
| 9.2 | 982 | 71.8 |
| 12.1 | 521 | 38.1 |
| 13.9 | 304 | 22.2 |
| 14.6 | 813 | 59.5 |
| 15.6 | 692 | 50.6 |
| 16.8 | 361 | 26.4 |
| 18.6 | 893 | 65.3 |
| 19.3 | 413 | 30.2 |
| 22.4 | 1188 | 86.9 |
| 22.9 | 1367 | 100 |
| 24.6 | 528 | 38.6 |
| 26.1 | 107 | 7.8 |
| 29.4 | 259 | 18.9 |
| 30.1 | 98 | 7.2 |
| 31.4 | 339 | 24.8 |
| 32.8 | 62 | 4.5 |
| 35.7 | 67 | 4.9 |

Form IX exhibits a DSC thermogram having endotherm peaks at temperatures of about 201° C., and about 276° C. FIG. 29 shows a DSC thermogram of Form IX. FIG. 30 shows a TGA thermogram of Form IX.

Example 18

Preparation and Characterization of Form X

To about 5 mL of cloudy solutions of Compound 1, Form I, prepared in ethyl acetate was added about 20 mg of Compound 1, Form I followed by stirring at 25±1° C. for 3 days, which was filtered and analyzed by XRPD as Form X.

TABLE 24

XRPD Peak Data for Form X

| 2-Theta | Height | I % |
|---|---|---|
| 4.9 | 113 | 9.6 |
| 10.1 | 971 | 82.7 |
| 11.3 | 167 | 14.2 |

TABLE 24-continued

XRPD Peak Data for Form X

| 2-Theta | Height | I % |
| --- | --- | --- |
| 12.3 | 95 | 8.1 |
| 13.7 | 63 | 5.4 |
| 14.6 | 696 | 59.3 |
| 15.4 | 603 | 51.4 |
| 15.7 | 1174 | 100 |
| 17.2 | 186 | 15.8 |
| 18.1 | 974 | 83 |
| 19.5 | 245 | 20.9 |
| 20.0 | 637 | 54.3 |
| 22.3 | 912 | 77.7 |
| 23.8 | 234 | 19.9 |
| 25.3 | 370 | 31.5 |
| 25.7 | 495 | 42.2 |
| 26.3 | 579 | 49.3 |
| 30.3 | 56 | 4.8 |
| 30.9 | 56 | 4.8 |
| 32.0 | 128 | 10.9 |
| 34.4 | 101 | 8.6 |
| 37.8 | 46 | 3.9 |

Form X exhibits a DSC thermogram having endotherm peaks at temperatures of about 202° C. and about 276° C. FIG. 32 shows a DSC thermogram of Form X. FIG. 33 shows a TGA thermogram of Form X.

Example 19

Preparation and Characterization of Form XI

To about 5 mL of cloudy solutions of Compound 1, Form I, prepared in ethyl formate was added about 20 mg of Compound 1, Form I, followed by stirring at 25±1° C. for 3 days, which was filtered and analyzed by XRPD as Form XI

TABLE 25

XRPD Peak Data for Form XI

| 2-Theta | Height | I % |
| --- | --- | --- |
| 3.9 | 381 | 42.9 |
| 4.3 | 231 | 26 |
| 7.5 | 548 | 61.6 |
| 8.6 | 70 | 7.9 |
| 11.8 | 70 | 7.9 |
| 13.0 | 889 | 100 |
| 13.7 | 167 | 18.8 |
| 15.0 | 156 | 17.5 |
| 16.5 | 104 | 11.7 |
| 17.3 | 377 | 42.4 |
| 19.1 | 207 | 23.3 |
| 19.9 | 340 | 38.2 |
| 21.4 | 557 | 62.7 |
| 22.2 | 117 | 13.2 |
| 22.8 | 442 | 49.7 |
| 23.7 | 86 | 9.7 |
| 24.6 | 68 | 7.6 |
| 25.2 | 646 | 72.7 |
| 26.2 | 418 | 47 |
| 26.9 | 255 | 28.7 |
| 27.7 | 178 | 20 |
| 29.4 | 131 | 14.7 |
| 30.3 | 115 | 12.9 |
| 31.0 | 83 | 9.3 |
| 31.5 | 66 | 7.4 |
| 33.3 | 125 | 14.1 |
| 33.9 | 67 | 7.5 |
| 35.7 | 78 | 8.8 |
| 37.4 | 54 | 6.1 |
| 40.3 | 59 | 6.6 |
| 42.6 | 56 | 6.3 |

Form XI exhibits a DSC thermogram having endotherm peaks at temperatures of about 141° C. and about 279° C. FIG. 35 shows a DSC thermogram of Form XI. FIG. 36 shows a TGA thermogram of Form XI.

Example 20

Preparation and Characterization of Form XII

To about 5 mL of cloudy solutions of Compound 1, Form I, prepared in 1,4-dioxane was added about 30 mg of Compound 1, Form I, followed by stirring at 50±1° C. for 2 days, which was filtered and analyzed by XRPD as Form XII.

TABLE 26

XRPD Peak Data for Form XII

| 2-Theta | Height | I % |
| --- | --- | --- |
| 3.9 | 151 | 12.4 |
| 7.5 | 161 | 13.3 |
| 9.8 | 199 | 16.4 |
| 11.5 | 112 | 9.2 |
| 12.9 | 233 | 19.2 |
| 14.1 | 721 | 59.4 |
| 14.9 | 87 | 7.2 |
| 17.3 | 391 | 32.2 |
| 18.3 | 797 | 65.7 |
| 20.5 | 128 | 10.6 |
| 22.1 | 1213 | 100 |
| 22.7 | 719 | 59.3 |
| 23.6 | 140 | 11.5 |
| 24.3 | 408 | 33.6 |
| 26.3 | 844 | 69.6 |
| 26.9 | 178 | 14.7 |
| 28.3 | 69 | 5.7 |
| 30.5 | 138 | 11.4 |
| 32.6 | 71 | 5.9 |
| 34.1 | 154 | 12.7 |
| 36.3 | 89 | 7.3 |
| 37.8 | 119 | 9.8 |
| 39.5 | 70 | 5.8 |

Form XII exhibits a DSC thermogram having endotherm peaks at temperatures of about 105° C. and about 276° C. FIG. 38 shows a DSC thermogram of Form XII. FIG. 39 shows a TGA thermogram of Form XII.

Example 21

Preparation and Characterization of Form XIII

To about 5 mL of cloudy solutions of Compound 1, Form I, prepared in THF was added about 30 mg of Compound 1, Form I, followed by stirring at 50±1° C. for 2 days, which was filtered and analyzed by XRPD as Form XIII.

TABLE 27

XRPD Peak Data for Form XIII

| 2-Theta | Height | I % |
| --- | --- | --- |
| 4.0 | 162 | 11.3 |
| 7.7 | 1438 | 100 |
| 10.9 | 166 | 11.5 |
| 11.6 | 175 | 12.2 |
| 14.2 | 302 | 21 |
| 15.2 | 629 | 43.7 |
| 15.7 | 1150 | 80 |
| 16.6 | 78 | 5.4 |
| 17.8 | 368 | 25.6 |
| 19.0 | 424 | 29.5 |
| 21.9 | 922 | 64.1 |

TABLE 27-continued

XRPD Peak Data for Form XIII

| 2-Theta | Height | I % |
|---|---|---|
| 22.2 | 436 | 30.3 |
| 23.1 | 1034 | 71.9 |
| 25.6 | 595 | 41.4 |
| 26.1 | 1333 | 92.7 |
| 31.6 | 89 | 6.2 |
| 34.8 | 80 | 5.6 |
| 37.0 | 143 | 9.9 |

Form XIII exhibits a DSC thermogram having an endotherm peak at a temperature of about 276° C. FIG. 41 shows a DSC thermogram of Form XIII. FIG. 42 shows a TGA thermogram of Form XIII.

Example 22

Preparation and Characterization of Form XIII-a

About 10 mL of saturated solution of Compound 1, Form I, in THF, prepared at 35° C., was quenched to about −20° C., and kept at the temperature for 3 h to give thin slurry, which was filtered and analyzed by XRPD as Form XIII-a.

TABLE 28

XRPD Peak Data for Form XIII-a

| 2-Theta | Height | I % |
|---|---|---|
| 3.6 | 132 | 4.8 |
| 6.9 | 1047 | 38.2 |
| 7.7 | 2739 | 100 |
| 8.3 | 289 | 10.6 |
| 9.5 | 156 | 5.7 |
| 10.4 | 760 | 27.7 |
| 10.9 | 208 | 7.6 |
| 11.4 | 169 | 6.2 |
| 12.1 | 259 | 9.5 |
| 14.4 | 241 | 8.8 |
| 15.2 | 864 | 31.5 |
| 17.3 | 223 | 8.1 |
| 18.6 | 425 | 15.5 |
| 19.7 | 565 | 20.6 |
| 20.1 | 177 | 6.5 |
| 20.6 | 113 | 4.1 |
| 21.5 | 687 | 25.1 |
| 22.3 | 297 | 10.8 |
| 22.6 | 562 | 20.5 |
| 23.0 | 459 | 16.8 |
| 25.5 | 541 | 19.8 |
| 26.2 | 942 | 34.4 |
| 27.5 | 233 | 8.5 |
| 28.3 | 160 | 5.8 |
| 31.2 | 88 | 3.2 |

Form XIII-a exhibits a DSC thermogram having endotherm peaks at temperatures of about 75° C. and about 276° C. FIG. 44 shows a DSC thermogram of Form XIIIa.

Example 23

Preparation and Characterization of Form XIV

Approximately 2.0 mL of saturated solution of Compound 1, Form I, in DMF were evaporated under air without stirring at 25±1° C. and the resulting solid was analyzed by XRPD as Form XV.

TABLE 29

XRPD Peak Data for Form XIV

| 2-Theta | Height | I % |
|---|---|---|
| 7.0 | 722 | 84.5 |
| 8.6 | 175 | 20.5 |
| 9.2 | 179 | 21 |
| 9.6 | 249 | 29.2 |
| 10.3 | 241 | 28.2 |
| 11.5 | 218 | 25.5 |
| 12.2 | 173 | 20.3 |
| 12.8 | 79 | 9.3 |
| 13.5 | 62 | 7.3 |
| 14.1 | 854 | 100 |
| 14.5 | 289 | 33.8 |
| 16.1 | 488 | 57.1 |
| 16.8 | 55 | 6.4 |
| 17.6 | 246 | 28.8 |
| 18.3 | 240 | 28.1 |
| 18.7 | 198 | 23.2 |
| 19.3 | 283 | 33.1 |
| 20.0 | 805 | 94.3 |
| 20.9 | 136 | 15.9 |
| 22.0 | 661 | 77.4 |
| 22.3 | 407 | 47.7 |
| 22.9 | 339 | 39.7 |
| 23.6 | 123 | 14.4 |
| 24.0 | 70 | 8.2 |
| 25.8 | 774 | 90.6 |
| 26.2 | 365 | 42.7 |
| 27.5 | 97 | 11.4 |
| 29.0 | 106 | 12.4 |
| 30.2 | 66 | 7.7 |
| 33.2 | 45 | 5.3 |
| 34.7 | 90 | 10.5 |
| 36.7 | 47 | 5.5 |

Form XIV exhibits a DSC thermogram having endotherm peaks at temperatures of about 78° C., about 118° C., and about 277° C. FIG. 46 shows a DSC thermogram of Form XIV. FIG. 47 shows a TGA thermogram of Form XIV.

Example 24

Preparation and Characterization of Form XV

Approximately 2.0 mL of saturated solution of Compound 1, Form I, in DMSO were evaporated under air without stirring at 25±1° C. and the resulting solid was analyzed by XRPD as Form XV.

TABLE 30

XRPD Peak Data for Form XV

| 2-Theta | Height | I % |
|---|---|---|
| 3.9 | 120 | 8.1 |
| 8.9 | 172 | 11.6 |
| 9.2 | 419 | 28.2 |
| 14.3 | 59 | 4 |
| 15.2 | 59 | 4 |
| 15.6 | 279 | 18.8 |
| 16.6 | 183 | 12.3 |
| 18.5 | 1485 | 100 |
| 19.8 | 74 | 5 |
| 20.3 | 294 | 19.8 |
| 21.1 | 122 | 8.2 |
| 21.4 | 470 | 31.6 |
| 21.8 | 289 | 19.5 |
| 22.4 | 1467 | 98.8 |
| 23.2 | 86 | 5.8 |
| 23.8 | 133 | 9 |
| 24.5 | 221 | 14.9 |
| 24.9 | 220 | 14.8 |
| 25.5 | 129 | 8.7 |
| 25.8 | 218 | 14.7 |

TABLE 30-continued

XRPD Peak Data for Form XV

| 2-Theta | Height | I % |
|---|---|---|
| 27.2 | 136 | 9.2 |
| 28.0 | 97 | 6.5 |
| 29.4 | 129 | 8.7 |
| 30.0 | 320 | 21.5 |
| 31.1 | 339 | 22.8 |
| 31.9 | 267 | 18 |
| 32.4 | 208 | 14 |
| 33.2 | 342 | 23 |
| 33.7 | 135 | 9.1 |
| 35.1 | 93 | 6.3 |
| 36.0 | 55 | 3.7 |
| 36.7 | 109 | 7.3 |
| 37.2 | 70 | 4.7 |
| 38.7 | 83 | 5.6 |
| 40.0 | 56 | 3.8 |
| 42.8 | 160 | 10.8 |
| 43.1 | 126 | 8.5 |

Form XV exhibits a DSC thermogram having endotherm peaks at temperatures of about 119° C. and about 276° C. FIG. 49 shows a DSC thermogram of Form XV. FIG. 50 shows a TGA thermogram of Form XV.

Example 25

Preparation and Characterization of Form XVI

Approximately 4.0 mL of saturated solution of Compound 1, Form I, in THF were evaporated under air without stirring at 50±1° C. and the resulting solid was analyzed by XRPD as Form XVI.

TABLE 31

XRPD Peak Data for Form XVI

| 2-Theta | Height | I % |
|---|---|---|
| 6.8 | 907 | 68.7 |
| 9.4 | 327 | 24.8 |
| 10.1 | 170 | 12.9 |
| 10.7 | 440 | 33.3 |
| 11.4 | 169 | 12.8 |
| 12.1 | 143 | 10.8 |
| 12.8 | 66 | 5 |
| 13.3 | 62 | 4.7 |
| 14.0 | 758 | 57.4 |
| 14.9 | 1320 | 100 |
| 16.0 | 364 | 27.6 |
| 17.5 | 277 | 21 |
| 18.2 | 150 | 11.4 |
| 18.5 | 209 | 15.8 |
| 19.2 | 222 | 16.8 |
| 19.9 | 951 | 72 |
| 20.9 | 218 | 16.5 |
| 22.2 | 691 | 52.3 |
| 22.7 | 168 | 12.7 |
| 23.5 | 335 | 25.4 |
| 24.5 | 276 | 20.9 |
| 25.4 | 338 | 25.6 |
| 25.7 | 573 | 43.4 |
| 26.1 | 529 | 40.1 |
| 27.3 | 241 | 18.3 |
| 29.0 | 72 | 5.5 |
| 30.2 | 603 | 45.7 |
| 32.5 | 49 | 3.7 |
| 36.6 | 168 | 12.7 |

Form XVI exhibits a DSC thermogram having an endotherm peak at a temperature of about 276° C. FIG. 52 shows a DSC thermogram of Form XVI. FIG. 53 shows a TGA thermogram of Form XVI.

Example 26

Preparation and Characterization of Form XVII

Approximately 2.0 mL of saturated solution of Compound 1, Form I, in DMSO were evaporated under air without stirring at 50±1° C. and the resulting solid was analyzed by XRPD as Form XVII.

TABLE 32

XRPD Peak Data for Form XVII

| 2-Theta | Height | I % |
|---|---|---|
| 3.8 | 135 | 0.6 |
| 7.9 | 96 | 0.4 |
| 8.8 | 52 | 0.2 |
| 10.1 | 57 | 0.3 |
| 14.1 | 86 | 0.4 |
| 15.7 | 3210 | 14.8 |
| 15.9 | 179 | 0.8 |
| 16.2 | 178 | 0.8 |
| 16.5 | 240 | 1.1 |
| 18.1 | 2253 | 10.4 |
| 18.4 | 21691 | 100 |
| 18.8 | 292 | 1.3 |
| 20.1 | 304 | 1.4 |
| 21.0 | 52 | 0.2 |
| 21.7 | 817 | 3.8 |
| 22.3 | 117 | 0.5 |
| 24.0 | 153 | 0.7 |
| 24.5 | 736 | 3.4 |
| 24.8 | 56 | 0.3 |
| 25.6 | 147 | 0.7 |
| 28.4 | 107 | 0.5 |
| 29.3 | 339 | 1.6 |
| 29.9 | 148 | 0.7 |
| 30.1 | 95 | 0.4 |
| 31.7 | 81 | 0.4 |
| 32.2 | 3360 | 15.5 |
| 32.5 | 259 | 1.2 |
| 33.0 | 61 | 0.3 |
| 33.5 | 75 | 0.3 |
| 34.9 | 270 | 1.2 |
| 35.8 | 88 | 0.4 |
| 36.4 | 59 | 0.3 |
| 37.0 | 174 | 0.8 |
| 38.7 | 286 | 1.3 |
| 39.7 | 276 | 1.3 |
| 40.7 | 185 | 0.9 |
| 41.9 | 242 | 1.1 |
| 43.2 | 46 | 0.2 |

Form XVII exhibits a DSC thermogram having endotherm peaks at temperatures of about 119° C. and about 276° C. FIG. 55 shows a DSC thermogram of Form XVII. FIG. 56 shows a TGA thermogram of Form XVII.

Example 27

Preparation and Characterization of Form XVII

To about 1 mL of saturated solution of Compound 1, Form I, prepared in chloroform was added 3.0 mL hexane to give a slurry, which was filtered and analyzed by XRPD as Form XVIII.

TABLE 33

XRPD Peak Data for Form XVIII

| 2-Theta | Height | I % |
|---|---|---|
| 6.8 | 958 | 17.2 |
| 9.4 | 5580 | 100 |
| 10.3 | 985 | 17.7 |
| 11.9 | 1397 | 25 |
| 12.6 | 792 | 14.2 |

TABLE 33-continued

XRPD Peak Data for Form XVIII

| 2-Theta | Height | I % |
|---|---|---|
| 13.4 | 798 | 14.3 |
| 13.9 | 389 | 7 |
| 14.6 | 3188 | 57.1 |
| 16.2 | 1820 | 32.6 |
| 17.5 | 1759 | 31.5 |
| 18.3 | 939 | 16.8 |
| 18.8 | 3352 | 60.1 |
| 19.7 | 288 | 5.2 |
| 20.8 | 744 | 13.3 |
| 21.4 | 545 | 9.8 |
| 22.3 | 2328 | 41.7 |
| 22.7 | 3594 | 64.4 |
| 23.6 | 360 | 6.5 |
| 24.0 | 557 | 10 |
| 24.6 | 73 | 1.3 |
| 25.4 | 1582 | 28.4 |
| 26.0 | 506 | 9.1 |
| 26.6 | 1676 | 30 |
| 27.0 | 101 | 1.8 |
| 27.9 | 219 | 3.9 |
| 28.5 | 303 | 5.4 |
| 29.4 | 671 | 12 |
| 29.9 | 447 | 8 |
| 30.8 | 626 | 11.2 |
| 31.5 | 136 | 2.4 |
| 33.4 | 157 | 2.8 |
| 33.7 | 232 | 4.2 |
| 34.4 | 116 | 2.1 |
| 34.8 | 77 | 1.4 |
| 36.1 | 594 | 10.6 |
| 36.8 | 108 | 1.9 |
| 38.0 | 154 | 2.8 |
| 38.2 | 269 | 4.8 |
| 40.4 | 141 | 2.5 |
| 40.9 | 81 | 1.5 |
| 41.4 | 91 | 1.6 |
| 42.0 | 77 | 1.4 |
| 42.6 | 91 | 1.6 |
| 43.0 | 98 | 1.8 |
| 44.0 | 126 | 2.3 |

Form XVIII exhibits a DSC thermogram having an endotherm peak at a temperature of about 276° C. FIG. 58 shows a DSC thermogram of Form XVIII. FIG. 59 shows a TGA thermogram of Form XVIII.

Example 28

Preparation and Characterization of Form XIX

To about 0.5 mL of saturated solution of Compound 1, Form I, prepared in DCM was added 5.0 mL methanol to give a slurry, which was filtered and analyzed by XRPD as Form XIX.

TABLE 34

XRPD Peak Data for Form XIX

| 2-Theta | Height | I % |
|---|---|---|
| 3.9 | 188 | 4.2 |
| 4.7 | 44 | 1 |
| 6.7 | 986 | 22.1 |
| 8.5 | 83 | 1.9 |
| 9.4 | 459 | 10.3 |
| 10.0 | 1260 | 28.3 |
| 11.3 | 189 | 4.2 |
| 12.0 | 151 | 3.4 |
| 12.6 | 106 | 2.4 |
| 13.6 | 593 | 13.3 |
| 14.3 | 257 | 5.8 |
| 14.9 | 232 | 5.2 |

TABLE 34-continued

XRPD Peak Data for Form XIX

| 2-Theta | Height | I % |
|---|---|---|
| 15.7 | 106 | 2.4 |
| 16.7 | 205 | 4.6 |
| 17.4 | 971 | 21.8 |
| 18.0 | 4459 | 100 |
| 19.4 | 186 | 4.2 |
| 20.2 | 1645 | 36.9 |
| 20.5 | 420 | 9.4 |
| 21.4 | 1036 | 23.2 |
| 22.1 | 980 | 22 |
| 22.8 | 252 | 5.7 |
| 23.4 | 161 | 3.6 |
| 24.0 | 186 | 4.2 |
| 24.8 | 397 | 8.9 |
| 25.0 | 682 | 15.3 |
| 26.0 | 263 | 5.9 |
| 26.9 | 357 | 8 |
| 27.3 | 105 | 2.4 |
| 28.1 | 77 | 1.7 |
| 28.6 | 216 | 4.8 |
| 30.2 | 207 | 4.6 |
| 31.3 | 188 | 4.2 |
| 31.7 | 362 | 8.1 |
| 33.8 | 108 | 2.4 |
| 34.6 | 53 | 1.2 |
| 35.7 | 56 | 1.3 |
| 37.3 | 91 | 2 |
| 39.0 | 112 | 2.5 |
| 40.1 | 67 | 1.5 |
| 41.8 | 63 | 1.4 |
| 42.2 | 57 | 1.3 |

Form XIX exhibits a DSC thermogram having an endotherm peak at a temperature of about 276° C. FIG. 61 shows a DSC thermogram of Form XIX. FIG. 62 shows a TGA thermogram of Form XIX.

Example 29

Preparation and Characterization of Form XX

To 4.0 mL of MTBE was added 0.8 mL of saturated solution of Compound 1, Form I, prepared in dichloromethane to give slurry, which was filtered and analyzed by XRPD as XX.

TABLE 35

XRPD Peak Data for Form XX

| 2-Theta | Height | I % |
|---|---|---|
| 3.6 | 121 | 1.4 |
| 9.2 | 8874 | 100 |
| 12.1 | 349 | 3.9 |
| 13.9 | 395 | 4.5 |
| 14.7 | 3145 | 35.4 |
| 15.6 | 1104 | 12.4 |
| 16.9 | 507 | 5.7 |
| 18.6 | 2044 | 23 |
| 19.4 | 187 | 2.1 |
| 21.1 | 84 | 0.9 |
| 22.3 | 1340 | 15.1 |
| 22.5 | 2189 | 24.7 |
| 23.0 | 5723 | 64.5 |
| 24.7 | 1414 | 15.9 |
| 25.5 | 232 | 2.6 |
| 26.1 | 140 | 1.6 |
| 28.3 | 66 | 0.7 |
| 29.5 | 1207 | 13.6 |
| 30.1 | 146 | 1.6 |
| 31.4 | 456 | 5.1 |
| 32.0 | 219 | 2.5 |
| 32.8 | 326 | 3.7 |

TABLE 35-continued

XRPD Peak Data for Form XX

| 2-Theta | Height | I % |
|---|---|---|
| 34.8 | 56 | 0.6 |
| 36.0 | 185 | 2.1 |
| 37.1 | 121 | 1.4 |
| 38.2 | 113 | 1.3 |
| 38.8 | 63 | 0.7 |
| 41.9 | 265 | 3 |

Form XX exhibits a DSC thermogram having endotherm peaks at temperatures of about 108° C., about 202° C., and about 277° C. FIG. 64 shows a DSC thermogram of Form XX. FIG. 65 shows a TGA thermogram of Form XX.

Example 30

Preparation and Characterization of Form XXI

To 4.0 mL of toluene was added 0.8 mL of saturated solution of Compound 1, Form I, prepared in dichloromethane to give slurry, which was filtered and analyzed by XRPD as XXI.

TABLE 36

XRPD Peak Data for Form XXI

| 2-Theta | Height | I % |
|---|---|---|
| 3.9 | 150 | 5.9 |
| 6.5 | 158 | 6.3 |
| 6.9 | 116 | 4.6 |
| 9.2 | 81 | 3.2 |
| 10.3 | 2523 | 100 |
| 11.3 | 130 | 5.2 |
| 12.2 | 187 | 7.4 |
| 13.2 | 319 | 12.6 |
| 14.2 | 1367 | 54.2 |
| 17.5 | 439 | 17.4 |
| 19.4 | 379 | 15 |
| 20.7 | 1031 | 40.9 |
| 21.5 | 112 | 4.4 |
| 22.6 | 1331 | 52.8 |
| 24.2 | 2072 | 82.1 |
| 26.5 | 149 | 5.9 |
| 27.1 | 458 | 18.2 |
| 28.5 | 147 | 5.8 |
| 33.3 | 57 | 2.3 |
| 35.8 | 77 | 3.1 |
| 36.8 | 125 | 5 |
| 42.9 | 102 | 4 |

Form XXI exhibits a DSC thermogram having endotherm peaks at temperatures of about 201° C., and about 277° C. FIG. 67 shows a DSC thermogram of Compound 1, Form XXI.

Example 31

Preparation and Characterization of Form XXII

To 4.0 mL of methanol was added 0.8 mL of saturated solution of Compound 1, Form I, prepared in the mixture of dichloromethane and methanol (9:1) to give a slurry, which was filtered and analyzed by XRPD as XXII.

TABLE 37

XRPD Peak Data for Form XXII

| 2-Theta | Height | I % |
|---|---|---|
| 3.5 | 118 | 6.1 |
| 4.7 | 70 | 3.6 |
| 6.8 | 1950 | 100 |
| 7.9 | 59 | 3 |
| 9.4 | 861 | 44.2 |
| 10.1 | 553 | 28.4 |
| 11.4 | 533 | 27.3 |
| 12.1 | 407 | 20.9 |
| 12.6 | 152 | 7.8 |
| 13.3 | 230 | 11.8 |
| 14.3 | 571 | 29.3 |
| 15.8 | 301 | 15.4 |
| 17.5 | 620 | 31.8 |
| 18.0 | 229 | 11.7 |
| 18.5 | 620 | 31.8 |
| 19.2 | 399 | 20.5 |
| 19.8 | 521 | 26.7 |
| 20.3 | 154 | 7.9 |
| 20.9 | 97 | 5 |
| 22.2 | 874 | 44.8 |
| 22.6 | 291 | 14.9 |
| 23.5 | 71 | 3.6 |
| 24.0 | 93 | 4.8 |
| 25.3 | 599 | 30.7 |
| 26.1 | 1022 | 52.4 |
| 27.4 | 214 | 11 |
| 29.0 | 159 | 8.2 |
| 30.9 | 79 | 4.1 |
| 31.6 | 51 | 2.6 |
| 34.5 | 47 | 2.4 |
| 36.4 | 64 | 3.3 |
| 39.5 | 46 | 2.4 |
| 40.0 | 50 | 2.6 |

Form XXII exhibits a DSC thermogram having an endotherm peak at a temperature of about 276° C. FIG. 69 shows a DSC thermogram of Compound 1, Form XXII.

Example 32

Preparation and Characterization of Form XXIII

About 2 mL of saturated solution of Compound 1, Form I, in DCM was quenched to about −20° C., and kept at the temperature for 3 h to give a slurry, which was filtered and analyzed by XRPD as Form XXIII

TABLE 38

XRPD Peak Data for Form XXIII

| 2-Theta | Height | I % |
|---|---|---|
| 6.7 | 251 | 2.9 |
| 8.7 | 59 | 0.7 |
| 12.0 | 6208 | 72.1 |
| 12.7 | 7944 | 92.2 |
| 13.2 | 817 | 9.5 |
| 14.3 | 714 | 8.3 |
| 16.4 | 360 | 4.2 |
| 17.3 | 214 | 2.5 |
| 18.9 | 1521 | 17.7 |
| 19.6 | 923 | 10.7 |
| 21.0 | 3317 | 38.5 |
| 22.7 | 520 | 6 |
| 24.9 | 2536 | 29.4 |
| 25.6 | 8613 | 100 |
| 26.5 | 311 | 3.6 |
| 28.7 | 293 | 3.4 |
| 29.6 | 78 | 0.9 |
| 30.7 | 193 | 2.2 |
| 31.1 | 187 | 2.2 |
| 34.5 | 72 | 0.8 |

TABLE 38-continued

XRPD Peak Data for Form XXIII

| 2-Theta | Height | I % |
| --- | --- | --- |
| 35.4 | 90 | 1 |
| 36.4 | 150 | 1.7 |
| 37.6 | 145 | 1.7 |
| 39.9 | 84 | 1 |
| 42.8 | 104 | 1.2 |
| 43.7 | 217 | 2.5 |

Form XXIII exhibits a DSC thermogram having an endotherm peak at a temperature of about 277° C. FIG. 71 shows a DSC thermogram of Form XXIII. FIG. 72 shows a TGA thermogram of Form XXIII.

Example 33

Preparation and Characterization of Form XXIV

Approximately 3 mL of saturated solutions of Compound 1, Form I, in DMF was prepared at 30° C. to 50° C. and cooled to 25° C. in a bath slowly by using a programmed circulating bath. The formed solution was heated to 50° C. over 2 hours and then cooled to 5° C. over 2 hours. This process was repeated for 76 hrs and the solid was isolated by filtration and analyzed by XRPD as Form XXIV.

TABLE 39

XRPD Peak Data for Form XXIV

| 2-Theta | Height | I % |
| --- | --- | --- |
| 8.6 | 1794 | 38.4 |
| 9.7 | 659 | 14.1 |
| 11.5 | 97 | 2.1 |
| 13.8 | 325 | 7 |
| 15.6 | 4674 | 100 |
| 16.1 | 102 | 2.2 |
| 16.5 | 95 | 2 |
| 17.4 | 566 | 12.1 |
| 18.1 | 1472 | 31.5 |
| 18.6 | 95 | 2 |
| 19.4 | 1000 | 21.4 |
| 20.4 | 2789 | 59.7 |
| 21.1 | 545 | 11.7 |
| 22.2 | 1511 | 32.3 |
| 22.9 | 3619 | 77.4 |
| 23.6 | 524 | 11.2 |
| 24.2 | 1442 | 30.9 |
| 24.9 | 488 | 10.4 |
| 25.5 | 1577 | 33.7 |
| 26.0 | 1382 | 29.6 |
| 27.5 | 916 | 19.6 |
| 27.9 | 1312 | 28.1 |
| 28.7 | 874 | 18.7 |
| 29.1 | 179 | 3.8 |
| 29.8 | 658 | 14.1 |
| 30.7 | 359 | 7.7 |
| 31.0 | 402 | 8.6 |
| 32.8 | 153 | 3.3 |
| 33.5 | 435 | 9.3 |
| 34.3 | 464 | 9.9 |
| 35.3 | 490 | 10.5 |
| 36.0 | 361 | 7.7 |
| 36.4 | 237 | 5.1 |
| 38.1 | 82 | 1.8 |
| 38.9 | 189 | 4 |
| 39.3 | 218 | 4.7 |
| 40.3 | 141 | 3 |
| 40.6 | 230 | 4.9 |
| 41.4 | 225 | 4.8 |
| 43.1 | 248 | 5.3 |

TABLE 39-continued

XRPD Peak Data for Form XXIV

| 2-Theta | Height | I % |
| --- | --- | --- |
| 43.9 | 210 | 4.5 |
| 44.2 | 131 | 2.8 |

Form XXIV exhibits a DSC thermogram having an endotherm peak at a temperature of about 277° C. FIG. 74 shows a DSC thermogram of Form XXIV. FIG. 75 shows a TGA thermogram of Form XXIV.

Example 34

Preparation and Characterization of Form XXV

Approximately 2 mL of saturated solutions of Compound 1, Form I, in DMSO was prepared at 30° C. to 50° C. and cooled to 25° C. in a bath slowly by using a programmed circulating bath. The formed solution was heated to 50° C. over 2 hours and then cooled to 5° C. over 2 hours. This process was repeated for 76 hrs and the solid was isolated by filtration and analyzed by XRPD as Form XXV.

TABLE 40

XRPD Peak Data for Form XXV

| 2-Theta | Height | I % |
| --- | --- | --- |
| 16.6 | 190 | 22.7 |
| 18.4 | 837 | 100 |
| 20.4 | 374 | 44.7 |
| 21.7 | 181 | 21.6 |
| 22.4 | 572 | 68.3 |
| 24.4 | 423 | 50.5 |
| 24.9 | 300 | 35.8 |
| 25.7 | 149 | 17.8 |
| 26.6 | 60 | 7.2 |
| 27.1 | 166 | 19.8 |
| 29.9 | 331 | 39.5 |
| 31.1 | 142 | 17 |
| 31.9 | 162 | 19.4 |
| 32.4 | 108 | 12.9 |
| 33.3 | 130 | 15.5 |
| 33.8 | 67 | 8 |
| 35.2 | 67 | 8 |
| 35.8 | 203 | 24.3 |
| 36.8 | 108 | 12.9 |
| 38.9 | 202 | 24.1 |
| 41.9 | 116 | 13.9 |
| 42.7 | 157 | 18.8 |
| 43.1 | 105 | 12.5 |

Form XXV exhibits a DSC thermogram having endotherm peaks at temperatures of about 113° C. and about 276° C. FIG. 77 shows a DSC thermogram of Form XXV.

Example 35

Preparation and Characterization of Form XXVI

Form V was dried under vacuum at 50° C. for 3 days to yield Form XXVI.

TABLE 41

XRPD Peak Data for Form XXVI

| 2-Theta | Height | I % |
| --- | --- | --- |
| 6.8 | 1089 | 98.6 |
| 9.4 | 198 | 17.9 |
| 9.9 | 1104 | 100 |
| 10.6 | 74 | 6.7 |

TABLE 41-continued

XRPD Peak Data for Form XXVI

| 2-Theta | Height | I % |
|---|---|---|
| 12.7 | 66 | 6 |
| 13.3 | 49 | 4.4 |
| 17.5 | 50 | 4.5 |
| 19.9 | 246 | 22.3 |
| 21.8 | 51 | 4.6 |
| 22.5 | 64 | 5.8 |
| 25.7 | 115 | 10.4 |
| 26.1 | 216 | 19.6 |
| 27.4 | 112 | 10.1 |
| 30.2 | 33 | 3 |
| 39.9 | 53 | 4.8 |

Example 36

Preparation and Characterization of Amorphous Compound 1

To about 5 mL of cloudy solutions of Compound 1, Form I, prepared in water was added about 30 mg of Compound 1, Form I followed by stirring at 25±1° C. for 2 days, which was filtered and determined as amorphous by XRPD.

Example A

FGFR Enzymatic Assay

The inhibitor potency of Compound 1 was measured in an enzyme assay that measures peptide phosphorylation using FRET measurements to detect product formation. Compound 1 was serially diluted in DMSO and a volume of 0.5 µL was transferred to the wells of a 384-well plate. For FGFR3, a 10 µL volume of FGFR3 enzyme (Millipore) diluted in assay buffer (50 mM HEPES, 10 mM $MgCl_2$, 1 mM EGTA, 0.01% Tween-20, 5 mM DTT, pH 7.5) was added to the plate and pre-incubated for 5-10 minutes. Appropriate controls (enzyme blank and enzyme with no inhibitor) were included on the plate. The assay was initiated by the addition of a 10 µL solution containing biotinylated EQEDEPEGDYFEWLE peptide substrate (SEQ ID NO: 1) and ATP (final concentrations of 500 nM and 140 µM respectively) in assay buffer to the wells. The plate was incubated at 25° C. for 1 hr. The reactions were ended with the addition of 10 µL/well of quench solution (50 mM Tris, 150 mM NaCl, 0.5 mg/mL BSA, pH 7.8; 30 mM EDTA with Perkin Elmer Lance Reagents at 3.75 nM Eu-antibody PY20 and 180 nM APC-Streptavidin). The plate was allowed to equilibrate for ~1 hr before scanning the wells on a PheraStar plate reader (BMG Labtech).

FGFR1 and FGFR2 were measured under equivalent conditions with the following changes in enzyme and ATP concentrations: FGFR1, 0.02 nM and 210 µM, respectively and FGFR2, 0.01 nM and 100 µM, respectively. The enzymes were purchased from Millipore or Invitrogen.

GraphPad prism3 was used to analyze the data. The $IC_{50}$ values were derived by fitting the data to the equation for a sigmoidal dose-response with a variable slope. Y=Bottom+(Top−Bottom)/(1+10^((Log $IC_{50}$−X)*HillSlope)) where X is the logarithm of concentration and Y is the response. Compounds having an $IC_{50}$ of 1 µM or less are considered active.

Compound 1 of the invention were found to be inhibitors of one or more of FGFR1, FGFR2, and FGFR3 according to the above-described assay. $IC_{50}$ data is provided below in Table 1. The symbol "+" indicates an $IC_{50}$ less than 100 nM and the symbol "++" indicates an $IC_{50}$ of 100 to 500 nM.

TABLE 42

|  | FGFR1 IC50 (nM) | FGFR2 IC50 (nM) | FGFR3 IC50 (nM) |
|---|---|---|---|
| Compound 1 | + | + | + |

Example B

FGFR Cell Proliferation/Survival Assays

The ability of the example compounds to inhibit the growth of cells dependent on FGFR signaling for survival was measured using viability assays. A recombinant cell line over-expressing human FGFR3 was developed by stable transfection of the mouse pro-B $Ba/F_3$ cells (obtained from the Deutsche Sammlung von Mikroorganismen und Zellkulturen) with a plasmid encoding the full length human FGFR3. Cells were sequentially selected for puromycin resistance and proliferation in the presence of heparin and FGF1. A single cell clone was isolated and characterized for functional expression of FGFR3. This $Ba/F_3$-FGFR3 clone is used in cell proliferation assays, and compounds are screened for their ability to inhibit cell proliferation/survival. The $Ba/F_3$-FGFR3 cells are seeded into 96 well, black cell culture plates at 3500 cells/well in RPMI1640 media containing 2% FBS, 20 µg/mL Heparin and 5 ng/mL FGF1. The cells were treated with 10 µL of 10× concentrations of serially diluted compounds (diluted with medium lacking serum from 5 mM DSMO dots) to a final volume of 100 µL/well. After 72 hour incubation, 100 µL of Cell Titer Glo® reagent (Promega Corporation) that measures cellular ATP levels is added to each well. After 20 minute incubation with shaking, the luminescence is read on a plate reader. The luminescent readings are converted to percent inhibition relative to DMSO treated control wells, and the $IC_{50}$ values are calculated using GraphPad Prism software by fitting the data to the equation for a sigmoidal dose-response with a variable slope. Compounds having an $IC_{50}$ of 10 µM or less are considered active. Cell lines representing a variety of tumor types including KMS-11 (multiple myeloma, FGFR3 translocation), RT112 (bladder cancer, FGFR3 overexpression), KatoIII (gastric cancer, FGFR2 gene amplification), and H-1581 (lung, FGFR1 gene amplification) are used in similar proliferation assays. In some experiments, MTS reagent, Cell Titer 96® AQueous One Solution Reagent (Promega Corporation) is added to a final concentration of 333 µg/mL in place Cell Titer Glo and read at 490/650 nm on a plate reader. Compounds having an $IC_{50}$ of 5 µM or less are considered active.

Example C

Cell-Based FGFR Phosphorylation Assays

The inhibitory effect of compounds on FGFR phosphorylation in relevant cell lines ($Ba/F_3$-FGFR3, KMS-11, RT112, KatoIII, H-1581 cancer cell lines and HUVEC cell line) can be assessed using immunoassays specific for FGFR phosphorylation. Cells are starved in media with reduced serum (0.5%) and no FGF1 for 4 to 18 h depending upon the cell line then treated with various concentrations of individual inhibitors for 1-4 hours. For some cell lines, such as $Ba/F_3$-FGFR3 and KMS-11, cells are stimulated with Heparin (20 µg/mL) and FGF1 (10 ng/mL) for 10 min. Whole cell protein extracts are prepared by incubation in lysis buffer with protease and phosphatase inhibitors [50 mM HEPES (pH 7.5), 150 mM NaCl, 1.5 mM $MgCl_2$, 10% Glycerol, 1% Triton X-100, 1 mM sodium orthovanadate, 1 mM sodium fluoride, aprotinin (2 µg/mL), leupeptin (2 µg/mL), pepstatin A (2 µg/mL), and phenylmethylsulfonyl fluoride (1 mM)] at 4° C. Protein extracts are cleared of cellular debris by centrifugation at 14,000×g for 10 minutes and quantified using the BCA (bicinchoninic acid) microplate assay reagent (Thermo Scientific).

Phosphorylation of FGFR receptor in protein extracts was determined using immunoassays including western blotting, enzyme-linked immunoassay (ELISA) or bead-based immunoassays (Luminex). For detection of phosphorylated FGFR2, a commercial ELISA kit DuoSet IC Human Phospho-FGF R2α ELISA assay (R&D Systems, Minneapolis, Minn.) can be used. For the assay KatoIII cells are plated in 0.2% FBS supplemented Iscove's medium (50,000 cells/well/per 100 µL) into 96-well flat-bottom tissue culture treated plates (Corning, Corning, N.Y.), in the presence or absence of a concentration range of test compounds and incubated for 4 hours at 37° C., 5% $CO_2$. The assay is stopped with addition of 200 µL of cold PBS and centrifugation. The washed cells are lysed in Cell Lysis Buffer (Cell Signaling, #9803) with Protease Inhibitor (Calbiochem, #535140) and PMSF (Sigma, #P7626) for 30 min on wet ice. Cell lysates were frozen at −80° C. before testing an aliquot with the DuoSet IC Human Phospho-FGF R2α ELISA assay kit. GraphPad prism3 was used to analyze the data. The $IC_{50}$ values were derived by fitting the data to the equation for a sigmoidal dose-response with a variable slope.

For detection of phosphorylated FGFR3, a bead based immunoassay was developed. An anti-human FGFR3 mouse mAb (R&D Systems, cat #MAB7661) was conjugated to Luminex MAGplex microspheres, bead region 20 and used as the capture antibody. RT-112 cells were seeded into multi-well tissue culture plates and cultured until 70% confluence. Cells were washed with PBS and starved in RPMI+0.5% FBS for 18 hr. The cells were treated with 10 µL of 10× concentrations of serially diluted compounds for 1 hr at 37° C., 5% $CO_2$ prior to stimulation with 10 ng/mL human FGF1 and 20 µg/mL Heparin for 10 min. Cells were washed with cold PBS and lysed with Cell Extraction Buffer (Invitrogen) and centrifuged. Clarified supernatants were frozen at −80° C. until analysis.

For the assay, cell lysates are diluted 1:10 in Assay Diluent and incubated with capture antibody-bound beads in a 96-well filter plate for 2 hours at room temperature on a plate shaker. Plates are washed three times using a vacuum manifold and incubated with anti-phospho-FGF R1-4 (Y653/Y654) rabbit polyclonal antibody (R&D Systems cat #AF3285) for 1 hour at RT with shaking. Plates are washed three times. The diluted reporter antibody, goat anti-rabbit-RPE conjugated antibody (Invitrogen Cat. #LHB0002) is added and incubated for 30 minutes with shaking. Plates are washed three times. The beads are suspended in wash buffer with shaking at room temperature for 5 minutes and then read on a Luminex 200 instrument set to count 50 events per sample, gate settings 7500-13500. Data is expressed as mean fluorescence intensity (MFI). MFI from compound treated samples are divided by MFI values from DMSO controls to determine the percent inhibition, and the $IC_{50}$ values are calculated using the GraphPad Prism software. Compounds having an $IC_{50}$ of 1 µM or less are considered active.

Example D

FGFR Cell-Based Signaling Assays
Activation of FGFR leads to phosphorylation of Erk proteins. Detection of pErk is monitored using the Cellu'Erk HTRF (Homogeneous Time Resolved Flurorescence) Assay (CisBio) according to the manufacturer's protocol. KMS-11 cells are seeded into 96-well plates at 40,000 cells/well in RPMI medium with 0.25% FBS and starved for 2 days. The medium is aspirated and cells are treated with 30 µL of 1× concentrations of serially diluted compounds (diluted with medium lacking serum from 5 mM DSMO dots) to a final volume of 30 L/well and incubated for 45 min at room temperature. Cells are stimulated by addition of 10 µL of Heparin (100 µg/mL) and FGF1 (50 ng/mL) to each well and incubated for 10 min at room temperature. After lysis, an aliquot of cell extract is transferred into 384-well low volume plates, and 4 µL of detection reagents are added followed by incubation for 3 hr at room temperature. The plates are read on a PheraStar instrument with settings for HTRF. The normalized fluorescence readings are converted to percent inhibition relative to DMSO treated control wells, and the $IC_{50}$ values are calculated using the GraphPad Prism software. Compounds having an $IC_{50}$ of 1 µM or less are considered active.

Example E

VEGFR2 Kinase Assay
40 µL Enzyme reactions are run in black 384 well polystyrene plates for 1 hour at 25° C. Wells are dotted with 0.8 µL of test compound in DMSO. The assay buffer contains 50 mM Tris, pH 7.5, 0.01% Tween-20, 10 mM $MgCl_2$, 1 mM EGTA, 5 mM DTT, 0.5 µM Biotin-labeled EQEDEPEGDYFEWLE peptide substrate (SEQ ID NO: 1), 1 mM ATP, and 0.1 nM enzyme (Millipore catalogue number 14-630). Reactions are stopped by addition of 20 µL Stop Buffer (50 mM Tris, pH=7.8, 150 mM NaCl, 0.5 mg/mL BSA, 45 mM EDTA) with 225 nM LANCE Streptavidin Surelight® APC (PerkinElmer catalogue number CR130-100) and 4.5 nM LANCE Eu-W1024 anti phosphotyrosine (PY20) antibody (PerkinElmer catalogue number AD0067). After 20 minutes of incubation at room temperature, the plates are read on a PheraStar FS plate reader (BMG Labtech). $IC_{50}$ values can be calculated using GraphPad Prism by fitting the data to the equation for a sigmoidal dose-response with a variable slope. Compounds having an $IC_{50}$ of 1 µM or less are considered active.

Example F

Clinical Study Evaluating Compound 1 in the Treatment of Patients with Advanced/Metastatic or Surgically Unresectable Cholangiocarcinoma This Example describes an ongoing Phase 2 clinical study to evaluate the efficacy of Compound 1 in subjects with advanced/metastatic or surgically unresectable cholangiocarcinoma with FGFR 2 translocation who have failed at least one previous treatment. The study further evaluates the efficacy of Compound 1 in subjects with advanced/metastatic or surgically unresectable cholangiocarcinoma with different molecular subgroups. The study also evaluates the safety of Compound 1 in subjects with advanced/metastatic or surgically unresectable cholangiocarcinoma. An additional objective is to identify and evaluate covariates that may influence the pharmacokinetics of Compound 1 in this subject population through population pharmacokinetic analysis. The study also considers exposure-response analyses for key efficacy and safety parameters. This study further explores the pharmacodynamics and potential biomarkers of Compound 1 in subjects with advanced/metastatic or surgically unresectable cholangiocarcinoma, as well as evaluate the impact of Compound 1 on the quality of life of these said subjects.

The study is an open-label, monotherapy study of Compound 1 in subjects with advanced/metastatic or surgically unresectable cholangiocarcinoma with FGFR2 translocations, with other FGF/FGFR alterations, or who are negative for FGF/FGFR alterations. The study enrolls approximately 100 subjects into Cohort A (FGFR2 translocations), 20 subjects into Cohort B (other FGF/FGFR alterations), and 20 subjects into Cohort C (US only, negative for FGF/FGFR alterations). Subjects receive a once daily (QD) dose of Compound 1 at 13.5 mg on a 2-week-on therapy and 1-week-off therapy schedule. Treatment will start on Day 1. Subjects undergo regular safety assessments during treatment as well as regular efficacy assessments. Subjects are allowed to continue administration in 21-day cycles until documented disease progression or unacceptable toxicity is reported.

Compound 1 is self-administered as a QD oral treatment on 2-weeks-on therapy and 1-week off therapy schedule. Each dose of Compound 1 is taken immediately upon rising or after a 2-hour fast; subjects fast for an additional 1 hour after taking Compound 1. Tablets are available in strengths of 2 mg and 4.5 mg. The starting dose is 13.5 mg. One cycle is defined as 21 days. In addition to Compound 1, each tablet contains microcrystalline cellulose, sodium starch glycolate, and magnesium stearate.

The study subjects are those with advanced/metastatic or surgically unresectable cholangiocarcinoma with FGFR2 translocations, with other FGF/FGFR alterations, or who are negative for any FGF/FGFR alterations, who failed at least 1 previous treatment.

The key inclusion criteria include men and women, aged 18 or older. The subjects have histologically or cytologically confirmed advanced/metastatic or surgically unresectable cholangiocarcinoma. Subjects in Cohort A have FGFR2 translocations with a documented fusion partner in central laboratory report. Subjects in Cohort B have other FGF/FGFR alterations. Subjects in Cohort C (US only) are negative for FGF/FGFR alterations. Additional key inclusion criteria include radiographically measureable disease per RECIST v. 1.1; documentation of FGF/FGFR gene alteration status; documented disease progression after at least 1 line of prior systemic therapy; ECOG performance status of 0 to 2; a life expectancy greater than or equal to 12 weeks; adequate hepatic function; adequate renal function; serum phosphate≤institutional ULN; and serum calcium within institutional normal range.

The key exclusion criteria include prior receipt of a selective FGFR inhibitor; history of and/or current evidence of ectopic mineralization/calcification, including but not limited to soft tissue, kidneys, intestine, myocardia, or lung, excepting calcified lymph nodes and asymptomatic arterial or cartilage/tendon calcifications; current evidence of clinically significant corneal or retinal disorder confirmed by ophthalmologic examination; and use of any potent CYP3A4 inhibitors or inducers within 14 days or 5 half-lives, whichever is shorter, before the first dose of study drug (topical ketoconazole is allowed).

The study schedule and procedures include regularly scheduled study visits at the clinical site as part of a 21-day cycle. Study visits begin with a prescreening to obtain FGF/FGFR status if unknown (results within approximately 2 years of screening are valid). Screening takes place on day −28 through day −1. Cycle 1 occurs on days 1, 8, and 15. Cycles 2+ begin on day 1. A safety follow up occurs 30 days (+5 days) from date of last dose. Disease status follow-up occurs every 9 weeks for subjects who discontinue for reasons other than disease progression. There is a survival follow-up every 12 weeks after discontinuation. Up to 28 days are allowed for screening, followed by continuous treatment in consecutive 21-day cycles as long as subjects are receiving benefit and do not meet any criteria for study withdrawal, and 30 days (+5 days) for safety follow-up following the last dose of the study drug. Study visits include sample collection for hematology, chemistry, coagulation, endocrine monitoring, lipids, and urinalysis testing. Additionally, HIV screening (required for subjects outside the US) and hepatitis screening (serology) is done at screening. Pregnancy testing is also be done at screening, Day 1 of every cycle before dose administration, and at end-of-treatment. FGF/FGFR status may be determined locally.

Tumor tissue is evaluated through the central laboratory for confirmation of FGF/FGFR alteration status. Blood samples for population pharmacokinetic analysis and whole blood pharmacodynamics and correlative studies are collected at various time points throughout the study and analyzed at the central laboratory or designee.

Adverse event assessments, vital signs, electrocardiograms, physical examination, ECOG performance status comprehensive eye examination, and tumor and disease response assessments are performed by the investigative site. An objective assessment of disease status is performed at screening. Subsequently, disease status including RECIST radiological response assessment is assessed every 2 cycles for the first 4 cycles and every 3 cycles thereafter. A central radiology group provides centralized reading on all assessments.

The primary endpoint of the study is to determine the objective response rate (ORR) in subjects with FGFR2 translocations based on the central genomics laboratory results. Objective response rate is defined as the proportion of subjects who achieved a complete response (CR; disappearance of all target lesions) or a partial response (PR; greater than or equal to 30% decrease in the sum of the longest diameters of target lesions) based on RECIST version 1.1 Clinical response is determined by an independent radiological review committee.

Secondary endpoints include ORR in subjects with FGF/FGFR alterations other than FGFR2 translocations (Cohort B); ORR in all subjects with FGF/FGFR alterations (Cohorts A and B); ORR in subjects negative for FGF/FGFR alterations (Cohort C [US only]); progression free survival (first dose to progressive disease or death; all cohorts); duration of response (time from the date of CR or PR until progressive disease; all cohorts); disease control rate (CR+PR+stable disease; all cohorts); overall survival (first dose to death of any cause; all cohorts); and population pharmacokinetics (all cohorts). Further, safety and tolerability is assessed by evaluating the frequency, duration, and severity of adverse events; through review findings of physical examinations, changes in vital signs, and electrocardiograms, and through clinical laboratory blood and urine sample evaluations (all cohorts).

Exploratory endpoints include profiling tumor and blood samples for baseline and on-treatment characteristics associated with response, resistance, and safety, including examinations of plasma markers and tumor and blood cell characteristics. Additional, exploratory endpoints include comparison of local genomic testing results versus central genomic testing results. Finally, exploratory endpoints include quality-of-life evaluation (European Organization for Research and Treatment of Cancer Quality-of-Life Questionnaire [EORTC QLQ]-C30 and EORTC QLQ-BIL21).

Primary analysis is performed on FGFR2 translocated subjects. Approximately 100 subjects with documentation of FGFR2 translocation from the central genomics laboratory are planned for the final analysis of the primary endpoint of ORR. With the assumed rates of 33% for the intervention, a sample size of approximately 100 subjects will provide >95% probability to have a 95% confidence interval with lower limit of >15% assuming 10% lost to follow-up. Up to 20 subjects will be enrolled in Cohorts B and C (US only), respectively, which will provide >80% chance of observing at least 4 responders in each cohort if the underlying ORR is 30%.

Safety analyses are performed on all patients enrolled in the study who received at least 1 dose of study drug; efficacy analyses are performed on all patients enrolled in the study who received at least 1 dose of study drug and who have a known FGF/FGFR alteration or who have a negative FGF/FGFR alteration from the central genomics laboratory.

The proportion of subjects with ORR and DCR will be estimated with 95% CI. The PFS, DOR, and OS will be analyzed by the Kaplan-Meier method.

For Cohort A (FGFR2 translocations), futility analysis will be performed when approximately 25 subjects are enrolled into the cohort and have at least 1 tumor assessment or have permanently discontinued study treatment. Cohort A can be stopped for futility if 2 or less responders are observed, for which there is less than 10% probability of claiming ORR >15% based on a 60 subject cohort.

Cohorts B (other FGF/FGFR alterations) and C (US only; negative for FGF/FGFR alterations) can be stopped if 1 or less responders are observed within the first 10 subjects who have at least 2 cycles of data.

Preliminary Data

The following preliminary data is drawn from a total of 91 patients in Cohort A, 22 patients in Cohort B, and 18 patients in Cohort C. The analysis of the Cohort A data focuses on the first 47 patients enrolled in Cohort A who were followed for greater than or equal to 8 months.

The median number of treatment cycles in Cohort A was 11 (range: 1-23); median duration of treatment was 217 days (range: 14-489 days). The median number of cycles in Cohort B was 2.5 (1-14); and the median duration of treatment was 47.5 days (range: 7-287 days). The median number of cycles in Cohort C was 2.0 (1-7); and the median duration of treatment was 39 days (range: 7-142 days).

The patient disposition by cohort is summarized in Table 43 below.

Baseline and disease characteristics presented for all cohorts are shown in Table 44. In cohort A, the median age of patients was 55 years (range: 26-76), 53.2% were female, and 98% had iCCA. In addition:
- 98% of patients had ECOG PS≤1
- 49% of patients received ≥2 prior therapies
- 94% of patients were from regions other than Asia
- 66% of patients had Stage 4 disease at enrollment
- 1 patient each had a history of chronic hepatitis B or hepatitis C.

TABLE 44

| Baseline and disease characteristics | | | |
|---|---|---|---|
| | Cohort A (n = 47) | Cohort B (n = 22) | Cohort C (n = 18) |
| Age, median (range), years | 55 (26-76) | 63 (28-78) | 65 (31-78) |
| Sex, n (%) | | | |
| Male | 22 (46.8) | 11 (50.0) | 10 (55.6) |
| Female | 25 (53.2) | 11 (50.0) | 8 (44.4) |
| Region, n (%) | | | |
| Asia | 3 (6.4) | 11 (50.0) | 0 (0.0) |
| Outside of Asia | 44 (93.6) | 11 (50.0) | 18 (100.0) |
| ECOG PS, n (%) | | | |
| 0 | 15 (31.9) | 7 (31.8) | 7 (38.9) |
| 1 | 31 (66.0) | 12 (54.5) | 8 (44.4) |
| 2 | 1 (2.1) | 3 (13.6) | 3 (16.7) |
| Number of prior systemic therapies, n (%) | | | |
| 1 | 24 (51.1) | 13 (59.1) | 11 (61.1) |
| 2 | 15 (31-9) | 5 (22.7) | 3 (16.7) |
| ≥3 | 8 (17.0) | 4 (18.2) | 4 (22.2) |
| Prior surgery, n (%) | 16 (34.0) | 7 (31.8) | 6 (33.3) |
| Prior radiation, n (%) | 9 (19.1) | 4 (18.2) | 5 (27.8) |
| Stage at initial diagnosis, n (%) | | | |
| 1 | 5 (10.6) | 1 (4.5) | 1 (5.6) |
| 2 | 6 (12.8) | 1 (4.5) | 1 (5.6) |
| 3 | 3 (6.4) | 3 (13.6) | 1 (5.6) |
| 4 | 31 (66.0) | 17 (77.3) | 12 (66.7) |
| Missing | 2 (4.3) | 0 (0.0) | 3 (16.7) |
| Tumor location, n (%) | | | |
| Intrahepatic | 46 (97.9) | 15 (68.2) | 11 (61.1) |
| Extrahepatic | 0 (0.0) | 3 (13.6) | 7 (38.9) |
| Other | 0 (0.0) | 4 (18.2) | 0 (0.0) |
| Unknown | 1 (2.1) | 0 (0.0) | 0 (0.0) |
| History of hepatitis, n (%) | | | |
| Chronic hepatitis B | 1 (2.1) | 1 (4.5) | 0 (0.0) |
| Hepatitis C | 1 (2.1) | 1 (4.5) | 0 (0.0) |

TABLE 43

| Cohort A (FGFR2 translocations; N = 47) | Cohort B (other FGF/FGFR genetic alterations; N = 22) | Cohort C (no FGF/FGFR genetic alterations; N = 18) |
|---|---|---|
| Discontinued treatment: n = 28 | Discontinued treatment: n = 20 | Discontinued treatment: n = 18 |
| PD: n = 20 | PD: n= 14 | PD: n= 11 |
| AE: n = 2 | AE: n = 2 | AE: n = 2 |
| Death: n = 1 | Death: n = 1 | Lost to follow up: n = 1 |
| Physician decision: n = 2 | Physician decision: n = 1 | Withdrawal by subject: n = 2 |
| Withdrawal by subject: n = 2 | Withdrawal by subject: n = 2 | Other: n = 2 |
| Other: n = 1 | | |
| Treatment ongoing: n = 19 | Treatment ongoing: n = 2 | Treatment ongoing: n = 0 |

FGFR translocations of the patients are shown in Table 45. The most common FGFR2 translocation was FGFR2-BICC1 (29.8%), followed by FGFR2-AHCYL1 (4.3%), FGFR2-MACF1 (4.3%), and FGFR2 intron 17 rearrangement (4.3%).

TABLE 45

FGFR2 Translocations in Cohort A.

| FGFR2 Translocation, n (%) | Cohort A (n = 47) |
|---|---|
| FGFR2-BICC1 | 14 (29.8) |
| FGFR2-AHCYL1 | 2 (4.3) |
| FGFR2-MACF1 | 2 (4.3) |
| FGFR2 intron 17 rearrangement | 2 (4.3) |
| FGFR-NEDD4L | 1 (2.1) |
| FGFR2-SOGA1 | 1 (2.1) |
| FGFR2-POC1B | 1 (2.1) |
| FGFR2-NOL4 | 1 (2.1) |
| FGFR2-ACLY | 1 (2.1) |
| FGFR2-SLMAP | 1 (2.1) |
| FGFR2-FILIP1 | 1 (2.1) |
| FGFR2-SPICE1 | 1 (2.1) |
| FGFR2-KIAA1217/FGFR2 exon 1-17 | 1 (2.1) |

TABLE 45-continued

FGFR2 Translocations in Cohort A.

| FGFR2 Translocation, n (%) | Cohort A (n = 47) |
|---|---|
| FGFR2-KIAA1217 | 1 (2.1) |
| FGFR2-TTC28 | 1 (2.1) |
| FGFR2-CCDC158 | 1 (2.1) |
| FGFR2-AFR | 1 (2.1) |
| FGFR2-SHROOM | 1 (2.1) |
| FGFR2-NRAP | 1 (2.1) |
| FGFR2-COL16A1 | 1 (2.1) |
| FGFR2-GOPC | 1 (2.1) |
| FGFR2-NOL4 | 1 (2.1) |
| FGFR2 amp/FGFR2-RABPGAP1L and FGFR2-LAMC1 | 1 (2.1) |
| FGFR2-ARH GAP24 | 1 (2.1) |
| FGFR2-PAWR | 1 (2.1) |
| FGFR2-GAB2 | 1 (2.1) |
| FGFR2-RASSF4 | 1 (2.1) |
| FGFR2-ARHGAP24 | 1 (2.1) |
| FGFR2-TACC1 | 1 (2.1) |
| FGFR2-STRN4 | 1 (2.1) |
| FGFR2-ATF2 | 1 (2.1) |

Preliminary efficacy data is shown in Table 46 below.

TABLE 46

Primary and Secondary Endpoints by Patient Cohort (assessed by independent reviewer).

| Variable | Cohort A (n = 47) | Cohort B (n = 22) | Cohort C (n = 18) |
|---|---|---|---|
| ORR, % (95% CI) | 40.4 (26.4-55.7) | 0 (0.0-15.4) | 0 (0.0-18.5) |
| Best OR, n (%) | | | |
| CR | 0 (0.0) | 0 (0.0) | 0 (0.0) |
| PR | 19 (40.4) | 0 (0.0) | 0 (0.0) |
| SD | 21 (44.7) | 10 (45.5) | 4 (22.2) |
| PD | 5 (10.6) | 7 (31.8) | 10 (55.6) |
| NE | 2 (4.3) | 5 (22.7) | 4 (22.2) |
| Median DOR, months (95% CI) | NE (6.93-NE) | NE (NE-NE) | NE (NE-NE) |
| DCR, % (95% CI) | 85.1 (71.7-93.8) | 45.5 (24.4-67.8) | 22.2 (6.4-47.6) |

NE = not evaluable, upper limit was not reached.

Table 46 shows the preliminary results for the primary endpoints. ORR in cohort A was 40.4%. 19 patients (40.4%) had a confirmed PR. 21 patients (44.7%) had a best response of stable disease.

For secondary endpoints, median duration of response (DOR) in Cohort A has not been reached; the probability of maintaining response for greater than or equal to six months was 86.2%. Disease control rate (DCR) was 85.1% in Cohort A. DCR in Cohorts B and C was 45.5% and 22.2%, respectively.

Figure 79:
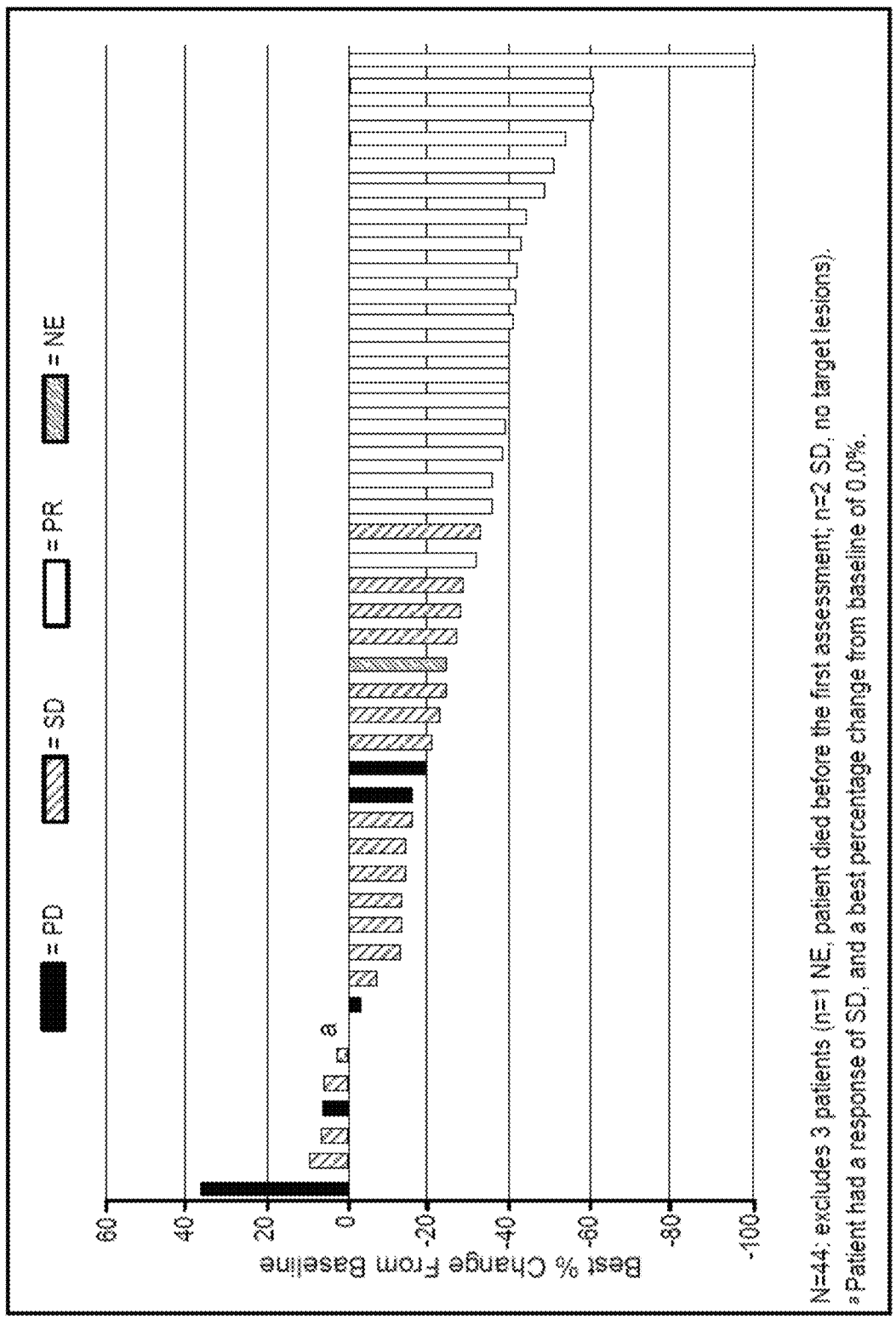
FIG. 79 shows the best percentage change from baseline in target lesion size in patients with CCA and FGFR2 translocations (Cohort A) as per independent reviewer.
Figure 80:
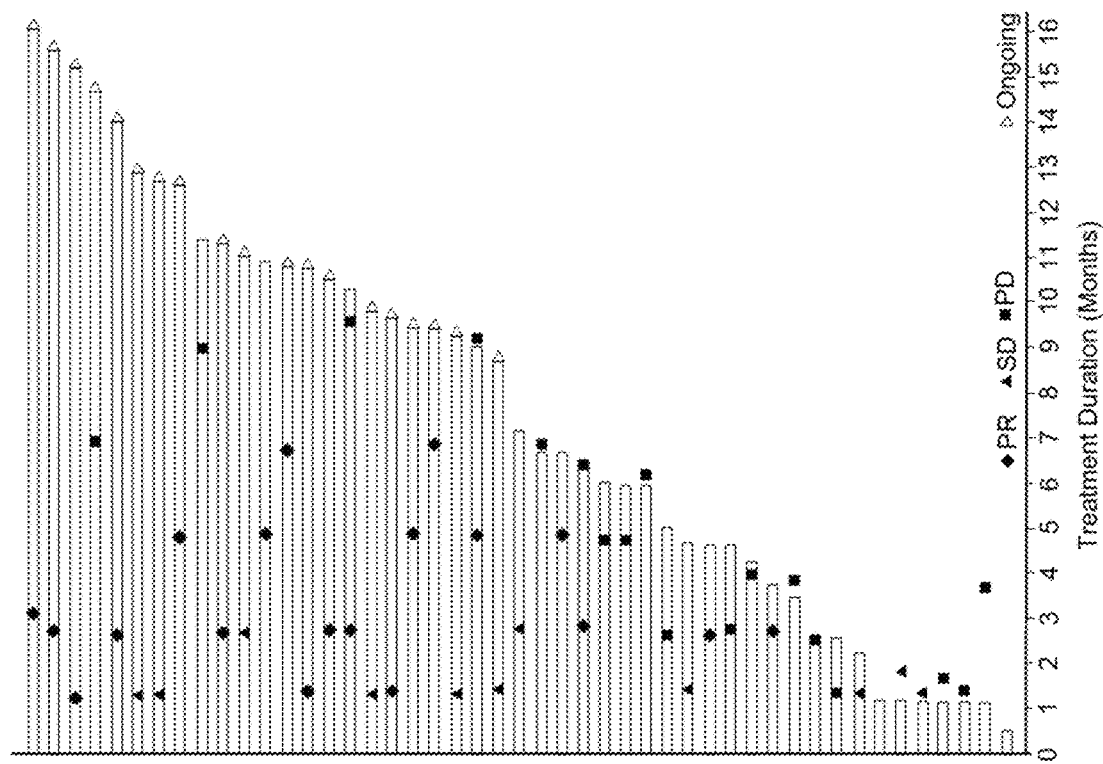
FIG. 80 shows the duration of treatment and confirmed response in patients with CCA and FGFR2 translocations (Cohort A) as per independent reviewer.

FIG. 79 shows the best percentage change from baseline in target lesion size in patients with CCA and FGFR2 translocations (Cohort A) as per independent reviewer. FIG. 80 shows the duration of treatment and confirmed response in patients with CCA and FGFR2 translocations (Cohort A) as per independent reviewer.

Figure 81:
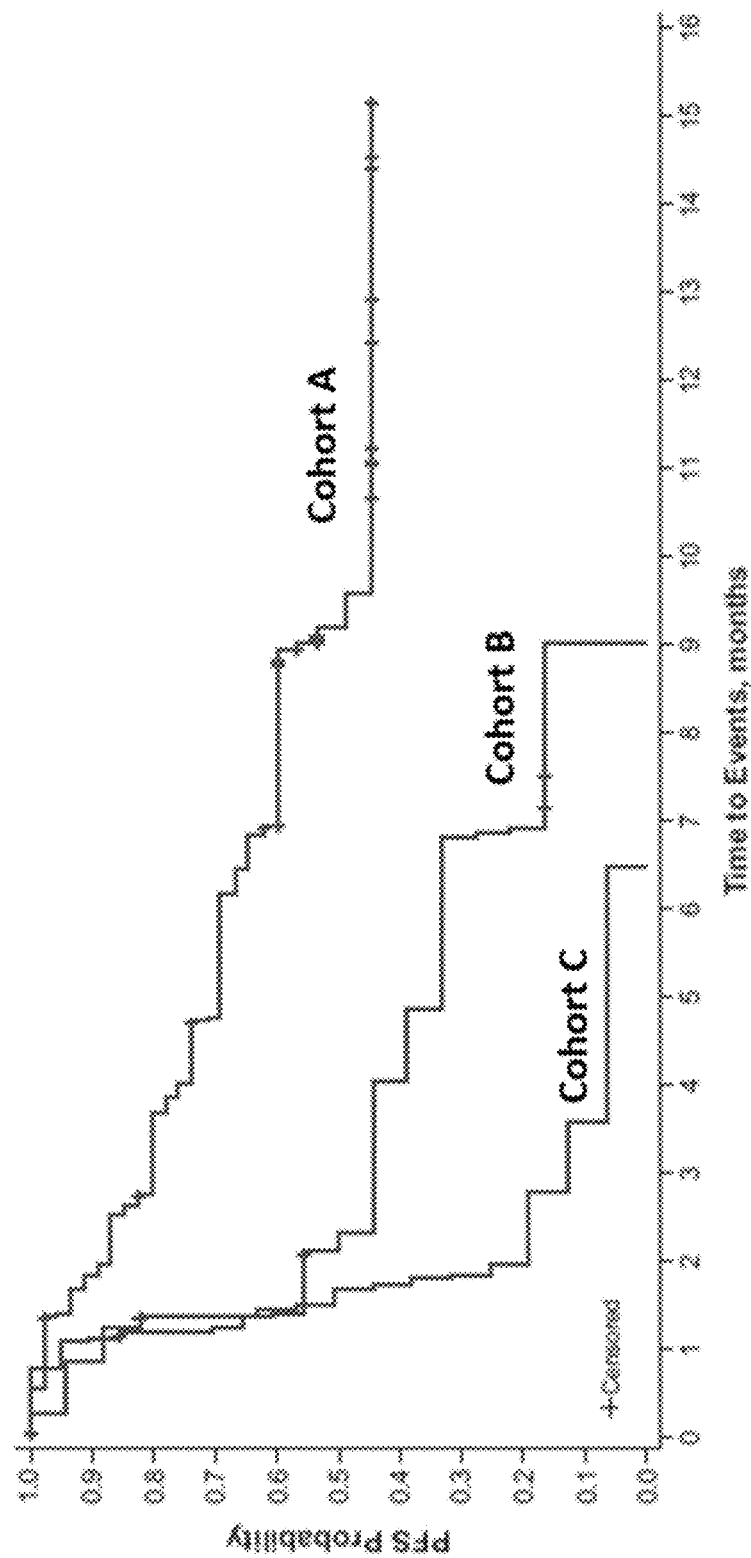
FIG. 81 shows the Kaplan-Meier estimates of progression free survival (PFS; estimated by independent reviewer) in Cohort A, B, and C.

FIG. 81 shows the Kaplan-Meier estimates of progression free survival (PFS; estimated by independent reviewer) in Cohort A, B, and C. PFS is defined as the length of time from the start of the study drug (Day 1) until the earlier of death or progression disease by RECIST as assessed by the independent centralized radiological review committee. Censoring for PFS follows in, e.g., the following situations: no baseline tumor assessment, no adequate postbaseline response assessment, no progression, study discontinued for undocumented progression, new anticancer treatment started, and death or progression after more than one missed assessment. As shown in Table 47 below, median PFS was 9.2 months in Cohort A. Median PFS in Cohorts B and C were 2.1 and 1.7 months, respectively. Median OS was 15.8 months in Cohort A. Median OS in Cohorts B and C were 6.8 and 4.0 months, respectively.

TABLE 47

|  | Cohort A | Cohort B | Cohort C |
|---|---|---|---|
| Evaluable patients, n | 47 | 22 | 18 |
| Events, n (%) | 22 (46.8%) | 17 (77.3%) | 16 (88.9%) |
| Censored, n (%) | 25 (53.2%) | 5 (22.7%) | 3 (11.1%) |
| Median time to events (95% CI), months | 9.20 (6.44-NE) | 2.10 (1.18-6.80) | 1.68 (1.38-1.84) |

TABLE 48

Number of patients at risk

| Time to Event | Number of Patients at Risk | | |
|---|---|---|---|
| (Months) | Cohort A | Cohort B | Cohort C |
| 0 | 47 | 22 | 18 |
| 1 | 46 | 20 | 15 |
| 2 | 40 | 11 | 3 |
| 3 | 36 | 8 | 2 |
| 4 | 34 | 8 | 1 |
| 5 | 30 | 6 | 1 |
| 6 | 30 | 6 | 1 |
| 7 | 23 | 3 | 0 |
| 8 | 23 | 1 | 0 |
| 9 | 17 | 1 | 0 |
| 10 | 10 | 0 | 0 |
| 11 | 9 | 0 | 0 |
| 12 | 5 | 0 | 0 |
| 13 | 3 | 0 | 0 |
| 14 | 3 | 0 | 0 |
| 15 | 1 | 0 | 0 |
| 16 | 0 | 0 | 0 |

Safety and Tolerability

The most common treatment-emergent adverse events (TEAEs) in all patients were hyperphosphatemia (60.7%), alopecia (41.6%), diarrhea (39.3%), decreased appetite (37.1%), fatigue (36.0%), and dysgeusia (36.0%). Hyperphosphatemia was managed with diet, phosphate binders, or dose modification. Grade 3 or greater TEAEs in greater than 5% of all patients include hypophosphatemia (13.5%), hyponatremia (7.9%), abdominal pain (6.7%), and arthralgia (6.7%). Five patients had TEAEs with a fatal outcome, none of which were related to study treatment: in Cohort A, 1 patient died due to failure to thrive; in Cohort B, 3 patients died due to abdominal distension, sepsis, malignant neoplasm progression, dyspnea, and pleural effusions; in Cohort C, 1 patient died due to cholangitis. The most common TEAEs and TRAEs are shown below in Table 49.

TABLE 49

Most Common TEAEs and TRAEs Occurring in ≥20%[a] of Patients With CCA.

| Adverse event, n | TEAEs - All Cohorts (N = 89)[b] | | TRAEs - All Cohorts (N = 89)[b] | |
|---|---|---|---|---|
| (%) | All Grades | Grade 3/4 | All Grades | Grade 3/4 |
| Hyperphosphatemia | 54 (60.7) | 0 (0.0) | 49 (55.1) | 0 (0.0) |
| Alopecia | 37 (41.6) | 0 (0.0) | 33 (37.1) | 0 (0.0) |
| Diarrhea | 35 (39.3) | 2 (2.2) | 26 (29.2) | 2 (2.2) |
| Decreased appetite | 33 (37.1) | 2 (2.2) | 22 (24.7) | 1 (1.1) |
| Fatigue | 32 (36.0) | 4 (4.5) | 21 (23.6) | 1 (1.1) |
| Dysgeusia | 21 (36.0) | 0 (0.0) | 31 (34.8) | 0 (0.0) |
| Constipation | 27 (30.3) | 0 (0.0) | 10 (11.2) | 0 (0.0) |
| Stomatitis | 27 (30.3) | 3 (3.4) | 24 (27.0) | 3 (3.4) |
| Dry mouth | 26 (29.2) | 0 (0.0) | 21 (23.6) | 0 (0.0) |
| Nausea | 26 (29.2) | 0 (0.0) | 14 (15.7) | 0 (0.0) |
| Hypophosphatemia | 23 (25.8) | 12 (13.5) | 9 (10.1) | 5 (5.6) |
| Arthralgia | 21 (23.6) | 6 (6.7) | 10 (11.2) | 4 (4.5) |
| Edema peripheral | 20 (22.5) | 1 (11) | 3 (3.4) | 0 (0.0) |
| Dry eye | 18 (20.2) | 1 (11) | 12 (13.5) | 1 (1.1) |

TEAE, treatment-emergent adverse event;
TRAE, treatment-related adverse event.
[a]Patients were counted once under each Medical Dictionary for Regulatory Activities (MedDRA) preferred term.
[b]Two patients were classified as "other" due to having no FGF/FGFR alteration confirmed by central lab, therefore, no cohort assignment was done.

Conclusion

In this interim analysis of patients from Cohort who had at least 8 months follow up, Compound 1 was generally well tolerated and demonstrated preliminary efficacy in previously treated patients with CCA harboring FGFR2 translocations. The ORR was 40.4%. The most common TEAEs include hyperphosphatemia, alopecia, and diarrhea. These results support continued development of Compound 1 as a treatment for patients with CCA harboring FGFR2 translocations.

Example G. Clinical Study Evaluating Compound 1 in the Treatment of Patients with Myeloid/Lymphoid Neoplasms with FGFR1 Rearrangement This Example describes an ongoing Phase 2 clinical study to evaluate the efficacy of Compound 1 in subjects with myeloid/lymphoid neoplasms with FGFR1 rearrangement. The study further evaluates the safety of Compound 1 in subjects with myeloid/lymphoid neoplasms with FGFR1 rearrangement. Additional exploratory objectives are to evaluate pharmacokinetics, biomarkers, and quality of life of subjects with myeloid/lymphoid neoplasms with FGFR1 rearrangement treated with Compound 1.

This study is an open-label, monotherapy study of Compound 1 in subjects with myeloid/lymphoid neoplasm with FGFR1 rearrangement. Subjects receive a once daily (QD) dose of Compound 1 at 13.5 mg on a 2-week-on-therapy and 1-week-off-therapy schedule. In addition, the administration was adjusted such that newly enrolled subjects receive Compound 1 at 13.5 mg continuous administration (no planned dose hold). Subjects receiving treatment under previous versions may be switched to continuous administration after completing at least 3 cycles if there are no ongoing Grade 2 or higher related TEAEs.

All potential subjects must have documentation of an 8p11 translocation known to activate FGFR1 through the site's own cytogenetics laboratory. Once documentation has been provided, the subject undergoes screening to meet the rest of the inclusion/exclusion criteria. Once a subject has completed screening and has enrolled into the study, treatment starts on Cycle 1 Day 1. Subjects undergo regular safety assessments during treatment as well as regular efficacy assessments.

Subjects are allowed to continue administration in 21-day cycles until loss of benefit from therapy or unacceptable toxicity is reported.

Compound 1 is self-administered as a QD oral treatment on a 2-weeks-on-therapy and 1-week-off-therapy schedule or continuous administration (no planned dose hold). Each dose of Compound 1 is taken immediately upon rising or after a 2-hour fast; subjects fast for an additional 1 hour after taking study drug. Tablets are available in strengths of 2 mg and 4.5 mg. The starting dose is 13.5 mg. One cycle is defined as 21 days of treatment. In addition to Compound 1, each tablet contains microcrystalline cellulose, sodium starch glycolate, and magnesium stearate.

The study population is subjects with myeloid/lymphoid neoplasms with FGFR1 rearrangement. Key inclusion criteria include: men and women aged 18 or older; documents lymphoid or myeloid neoplasm with 8p11 rearrangement known to lead to FGFR1 activation, based on standard diagnostic cytogenetic evaluation performed locally, before signing informed consent for this study; life expectancy of at least 12 weeks; ECOG performance status of 0 to 2. In addition, only subjects who are not candidates for stem cell transplantation, or have relapsed after stem cell transplantation and delayed lymphocyte infusion and who have progressed and are not candidates for other disease-modifying therapies are eligible for the study. All relapsed/refractory subjects must have evidence of either cytogenetic or hematological disease and have no evidence of residual toxicity (e.g., graft-versus-host disease requiring treatment).

Key exclusion criteria include prior receipt of a selective FGFR inhibitor; history of calcium and phosphate hemostasis disorder or systemic mineral imbalance with ectopic calcification of soft tissues (exception: commonly observed calcifications in soft tissues, such as the skin, kidney, tendons, or vessels due to injury, disease, and aging, in the absence of systemic mineral imbalance); active CNS disease; and use of any potent cytochrome P450 3A4 inhibitors or inducers within 14 days or 5 half-lives (whichever is shorter) before the first dose of study drug. Additional key exclusion criteria include current evidence of clinically significant corneal disorder/keratopathy (including but not limited to bullous/band keratopathy, corneal abrasion, inflammation/ulceration, and keratoconjunctivitis, etc) or retinal disorder (including but not limited to macular/retinal degeneration, diabetic retinopathy, retinal detachment, etc) as confirmed by ophthalmologic examination.

The study schedule and procedures include regularly scheduled study visits at the clinical site as part of a 21-day cycle. Study visits include a screening (day −28 through day −1); cycle 1 (days 1, 8, and 15 [±3 days]); cycles 2+(day 1 [±3 days]); end of treatment (upon permanently discontinuing study drug); safety follow-up (30 days [+5 days] from date of last dose); disease status (follow subject per standard of care until documents progression); and survival follow-up (every 12 weeks). Study visits may include sample collection for chemistry, hematology, coagulation, lipid panel, endocrine monitoring, and urinalysis testing. Additionally, hepatitis screening (serology) is done at screening, and pregnancy testing are done at screening, Day 1 of every cycle before dose administration, and end of treatment. A sample of bone marrow aspirate or peripheral blood is sent to the central laboratory for confirmation of FGFR1 rearrangement as well as a central pathology laboratory for analysis. In addition, sites provide slides and/or digitized images of bone marrow aspirate at baseline and at the time of achieving response and send them to a central pathology group for review. Adverse event assessments, physical examinations, vital signs, ECGs, comprehensive eye examinations, ECOG performance status, and disease response assessments are performed by the investigative site.

Once the subject's eligibility is confirmed through the site's laboratory, screening may begin. Up to 28 days are allowed for screening, followed by continuous treatment in consecutive 21-day cycles as long as the subject is receiving benefit (as judged by treating physician) and has not met any criteria for study withdrawal. Safety follow-up is 30 days (+5 days) after the last dose of the study drug. In addition, subjects are followed for overall survival after stopping treatment with study drug. Study participation is expected to average approximately 6 months per individual subject.

The primary endpoint of the study is to determine the overall clinical benefit rate by achieving one of the following: complete response (CR; normalization of BM (bone marrow) and peripheral blood and complete resolution of EMD (extramedullary disease)), partial response (PR; normalization of peripheral blood, complete resolution of EMD, and 50% reduction of BM blasts), complete hematologic response (CHR; normalization of peripheral blood), cytogenic response, marrow response, or clinical benefit (erythroid response, platelet response, neutrophil response, eosinophil response, and/or EMD response). A complete marrow response is defined as marrow criteria necessary for complete response without normalization of peripheral blood. A partial marrow response is defined as 50% reduction in BM blasts but remaining >5%, or reduction in grading of reticulin fibrosis from baseline on ≥2 BM evaluations spaced ≥2 months apart if there is no excess of blasts at baseline. A complete cytogenetic response (CCyR) is defined as 0% 8p11 translocated metaphases or FISH. A partial cytogenetic response (PCyR) is defined as ≥50% decrease from baseline in 8p11 translocated metaphases or FISH.

Secondary endpoints include duration of response/benefit; progression-free survival; overall survival; and safety and tolerability, as assessed by evaluating the frequency, duration, and severity of adverse events (through review of findings of physical examinations, changes in vital signs, and electrocardiograms, and through clinical laboratory blood and urine sample evaluations). Exploratory endpoints include population PK parameters, tumor molecular and gene expression profiling; peripheral blood molecular and gene expression profiling, cytokine and plasma biomarker levels at baseline and changes with treatment; and quality of life evaluation (European Organisation for Research and Treatment of Cancer Quality of Life Questionnaire Core 30 and Myeloproliferative Neoplasm Symptom Assessment Form).

Approximately 46 subjects are planned for the final analysis of the primary endpoint of overall clinical benefit rate. With the assumed rates of 35% for the intervention, a sample size of 46 subjects would provide >80% probability to have a 95% confidence interval with lower limit of >15% assuming 10% loss to follow-up.

The overall clinical benefit rate, defined as the proportion of subjects who achieve CR, PR, cytogenetic response, CHR, marrow response, or clinical benefit, will be estimated with 95% CI. The progression-free survival, duration of response/benefit, and overall survival will be analyzed by the Kaplan-Meier method.

Preliminary Data

The following preliminary data is drawn from a total of 14 patients. One patient did not have FGFR 8p11 rearrangement known to lead to FGFR1 activation and was excluded from the efficacy analysis. Patients received a median of 6 cycles of Compound 1 (range: 2-25 cycles).

The patient disposition by cohort is summarized in Table 50 below.

TABLE 50

| Patient disposition | |
|---|---|
| Patients Enrolled | 14 |
| Patients Treated | 14 |
| Treatment Ongoing | 6 |
| Treatment Discontinued | 8 |
| Reason for discontinuation | |
| Bridge to HSCT | 3 |
| Adverse Event | 2 |
| Progressive Disease | 3 |

A summary of the demographics and disease characteristics of the patients treated is shown in Table 51 below.

TABLE 51

| Baseline demographics and disease characteristics (N = 14) | |
|---|---|
| Age, median (range), years | 61.5 (39-78) |
| Sex, n (%) | |
| Male | 7 (50) |
| Female | 7 (50) |
| MLN characteristics, n (%) [a] | |
| MLN | 3 (21) |
| MLN + lymphoma | 2 (14) |
| MLN + myeloid sarcoma | 3 (21) |
| MLN blast phase | 5 (36) |
| Prior therapies, median (range), n[b] | 2 (0-4) |
| ECOG PS | |
| 0 | 5 (36) |
| 1 | 8 (57) |
| 2 | 1 (7) |

[a] One patient in the MLN group did not have FGFR1 8p11 rearrangement known to lead to FGFR1 activity and was excluded from the efficacy analysis but was included in safety analysis
[b] One patient was identified as not having received prior therapy Clinical and cytogenetic responses for the patients treated are shown below in Table 52.

TABLE 52

| | | | | | | |
|---|---|---|---|---|---|---|
| Age/Sex | Disease | Fusion Partner[a] | Prior Therapy | Clinical Response[b] | Response in EMD | Cytogenetic Response[c] |
| 48 F | MLN | BCR | HU | CR | — | CCyR |
| 39 F | MLN (aCML) | BCR | HU, ponatinib | CR | — | PCyR |
| 66 F | MLN + splenomegaly | TPR and ZMYM2 | HU | CR | — | PCyR |
| 71 M | MLN + EMD (lymphoma[d]) | ZMYM2 | Hyper CVAD, steroids | CR | — | CCyR |
| 50 M | MLN + EMD (lymphoma) | ZMYM2 | CHOEP | CR | CR | CCyR |
| 78 F | MLN + EMD (myeloid sarcoma) | ZMYM2 | MITO-FLAG, dauno | PR | SD | PCyR |
| 63 M | MLN + EMD (myeloid sarcoma) | ZMYM2 | None | PR | PD | CCyR |
| 60 M | MLN + EMD (myeloid sarcoma) | ZMYM2 | FLAI | PR | PD | CCyR |
| 68 F | MLN blast phase (lymphoid) | BCR | NILG-ALL, Blina, HU, MTX-Ara-C | PD (myeloid blast crisis) | — | None |
| 67 M | MLN blast phase (lymphoid) | BCR | HU, HSCT | CR | — | PCyR |
| 46 F | MLN blast phase (lymphoid) | ZMYM2 | R-IEV, FLA, ponatinib | CR | — | CCyR |
| 51 M | MLN blast phase (myeloid) | BCR | CLAG-M | PR | — | None |
| 41 F | MLN blast phase (myeloid) | TRIM24 | 3 + 7, MEC, FLAI, AraC | SD | — | None |

CBC = complete blood count;
NGS = next-generation sequencing;
PD = progressive disease;
SD = stable disease
[a] Fusion partners listed were determined by NGS retrospectively and were not used to assess patient eligibility
[b] CR: bone marrow (BM) with <5% blasts and normal cellularity, normal CBC, complete resolution of EMD; PR, same as CR except 50% reduction of BM blasts (and blast equivalents), but with <5% remaining fibrosis and dysplasia.
[c] CCyR: 0% abnormal metaphases; PCyR: decrease of ≥50% abnormal metaphases
[d] Not present at baseline.

Figure 82:
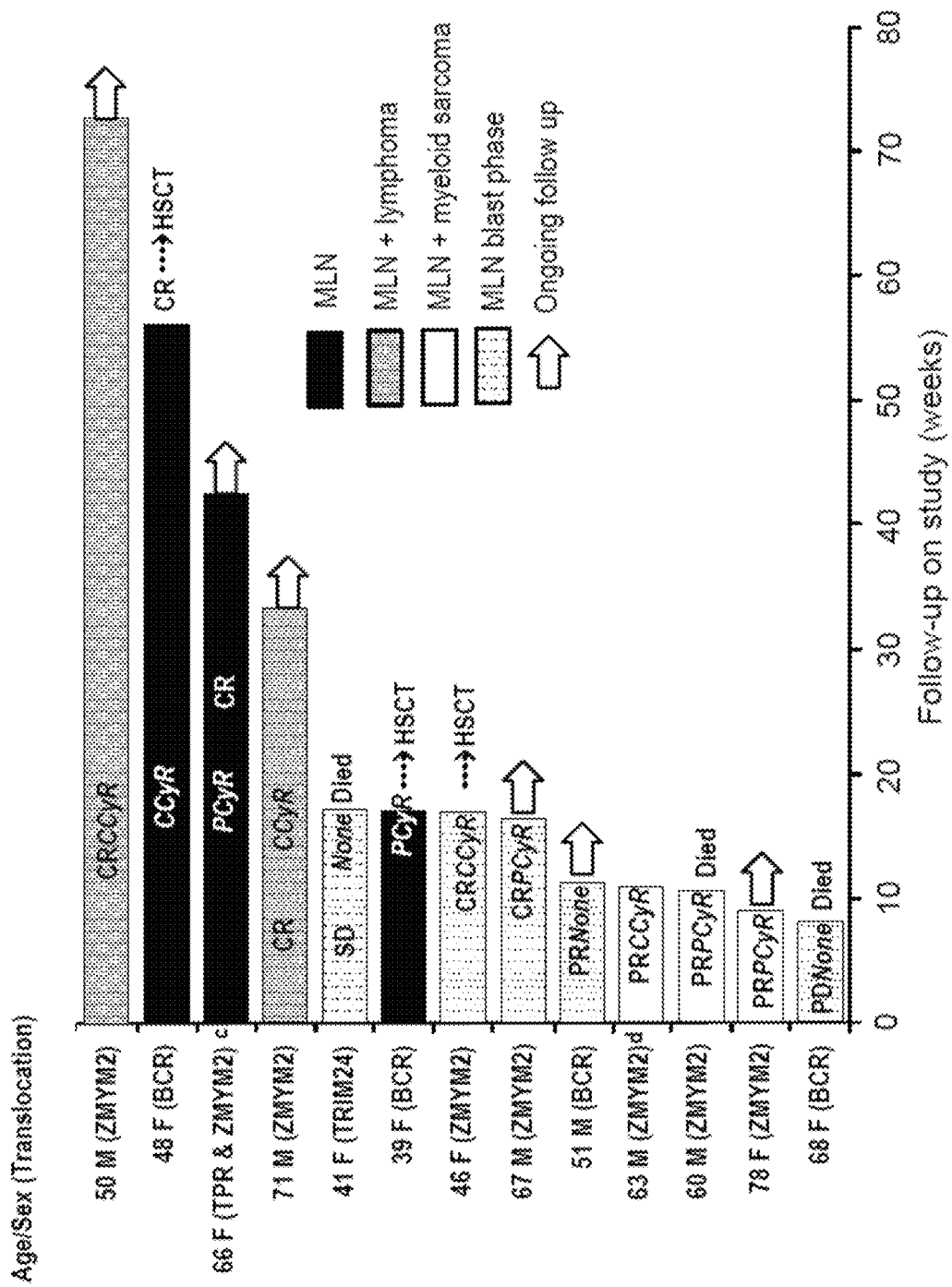
FIG. 82 shows a summary of the clinical and cytogenetic responses in patients with myeloid/lymphoid neoplasms with rearrangements of FGFR1.

A summary of the clinical and cytogenetic responses is also shown in FIG. 82. 11 of 13 (85%) evaluable patients achieved clinical response, including clinical and cytogenetic responses, as shown below in Table 53.

TABLE 53

| Best Responses | | | |
|---|---|---|---|
| Best Responses | ORR | CR (n) | PR (n) |
| Clinical responses[a] | 85% | 7 | 4 |
| Cytogenetic Responses[b] | 77% | 6 | 4 |

[a]CR, bone marrow with <5% blasts and normal cellularity, normal CBC, complete resolution of EMD;
PR, same as CR except 50% reduction of bone marrow blasts (and blast equivalents), but with <5% remaining fibrosis and dysplasia.
[b]CCyR, 0% abnormal metaphases;
PCyR, decrease of ≥50% of abnormal metaphases.

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
1               5                   10                  15
```

Figure 83:
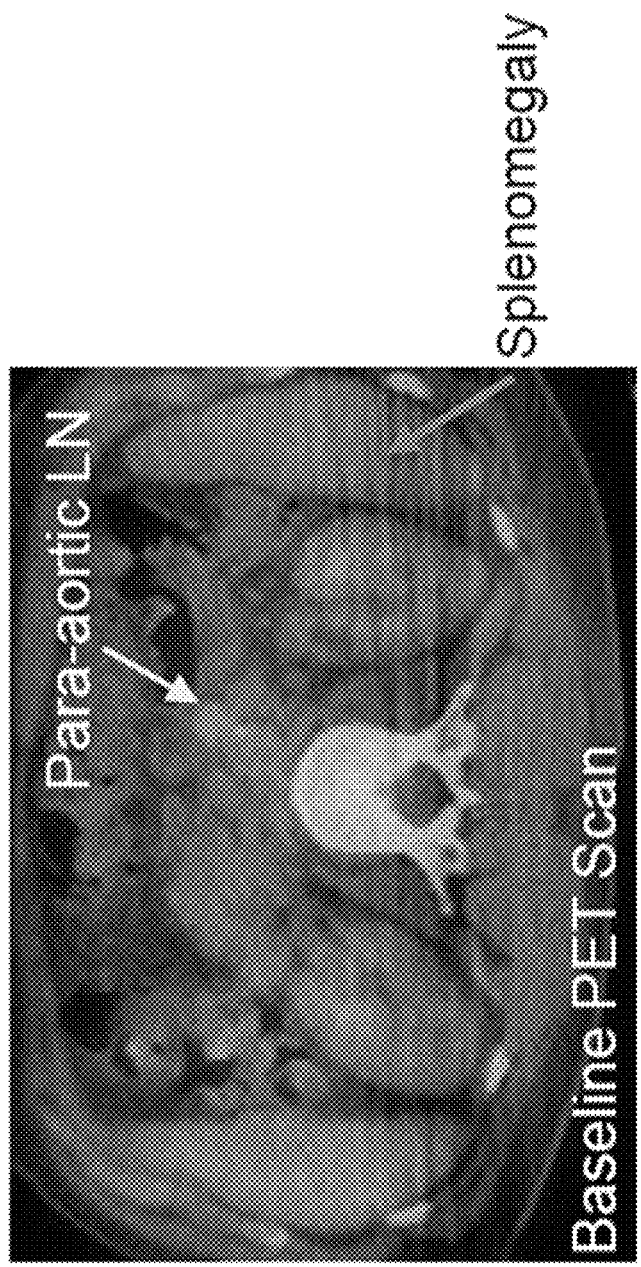
FIG. 83 shows a baseline PET scan of a patient with myeloproliferation and T-lymphoblastic lymphoma (TLL) before treatment with Compound 1.
Figure 84:
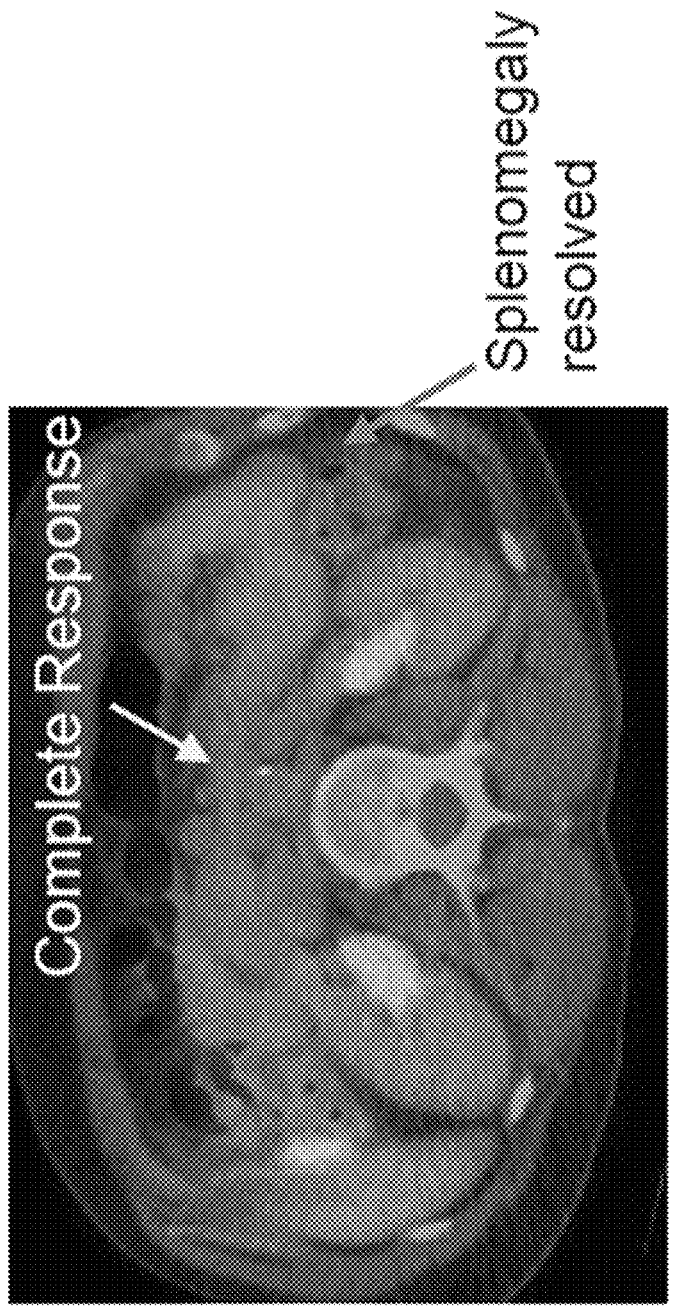
FIG. 84 shows a baseline PET scan of a patient with myeloproliferation and T-lymphoblastic lymphoma (TLL) after treatment with Compound 1.

FIGS. 83 and 84 show a baseline PET scan of a patient with myeloproliferation and T-lymphoblastic lymphoma (TLL) before (FIG. 83) and after (FIG. 84) treatment with Compound 1. The patient was a 50-year-old male, presented with myeloproliferation and TLL, who had received CHOEP chemotherapy (chemotherapy with cyclophosphamide, doxorubicin, etoposide, vincristine and prednisone) with no response. The patient exhibited para-aortic lymphadenopathy and a large spleen. His cytogenetics show ZMYM2-FGFR1 fusion. Following 13.5 mg daily dosing of Compound 1 (2 weeks on, 1 week off), the patient achieved complete cytogenetic remission and complete lymph node remission by PET scan at 4 months (beginning of cycle 6). In addition, the splenomegaly resolved. The patient remained on treatment after more than 1.5 years with minimal side effects.

Safety and Tolerability

Compound 1 was generally well tolerated. The most common treatment related adverse event (TRAE) were hyperphosphatemia (n=9; 64%; managed with diet and phosphate binders), diarrhea (n=5; 36%), alopecia (n=4; 29%), increased blood alkaline phosphatase (n=3, 21%), dyspepsia, and fatigue, and stomatitis (n=2; 14% each). Three patients had grade 3 TRAEs: diarrhea (n=1; led to dose reduction); leukopenia (n=1); and alkaline phosphatase increase (n=1; led to discontinuation of Compound 1). Two patients had fatal TEAEs unrelated to treatment. One patient died due to multiorgan failure and disease progression. One patient died due to chloroma, myeloid sarcoma, and septic shock.

CONCLUSION

Compound 1 showed clinical and cytogenetic activity. The clinical response rate was 65% (CR in 7 patients and PR in 4 patients). The major cytogenetic response rate was 77% (CCyR in 6 patients, and PCyR in 4 patients). Compound 1 was generally well tolerated by patients in the study.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating cholangiocarcinoma in a patient in need thereof comprising administering to the patient a therapeutically effective amount of Compound 1 having the formula:

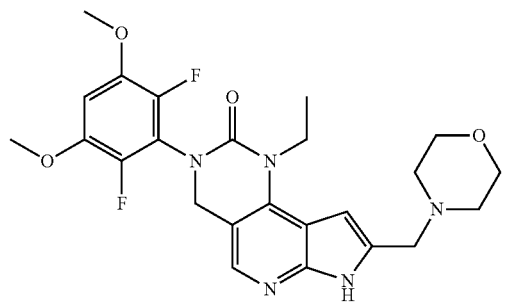

Compound 1 wherein Compound 1 is administered in a daily dose of about 5 mg to about 20 mg.

2. The method of claim 1, wherein the cholangiocarcinoma is advanced or metastatic cholangiocarcinoma.

3. The method of claim 1, wherein the cholangiocarcinoma is surgically unresectable.

4. The method of claim 1, wherein the cholangiocarcinoma is intrahepatic.

5. The method of claim 1, wherein the cholangiocarcinoma is extrahepatic.

6. The method of claim 1, wherein the cholangiocarcinoma is hilar or perihilar.

7. The method of claim 1, wherein the cholangiocarcinoma is distal extrahepatic.

8. The method of claim 1, wherein the cholangiocarcinoma is characterized by FGF/FGFR genetically altered tumors.

9. The method of claim 8, wherein the tumor exhibits FGFR2 translocations.

10. The method of claim 9, wherein the FGFR2 translocation is selected from the group consisting of FGFR2-BICC1, FGFR2-AHCYL1, FGFR2-MACF1, and FGFR2 intron 17 rearrangement.

11. The method of claim 8, wherein the tumor exhibits FGF/FGFR alterations other than FGFR2 translocations.

12. The method of claim 1, wherein the cholangiocarcinoma does not exhibit FGF/FGFR genetically altered tumors.

13. The method of claim 1, wherein the patient has failed at least one previous treatment.

14. The method of claim 13, wherein the previous treatment is surgery or radiation therapy.

15. The method of claim 1, wherein the patient has a history of hepatitis.

16. The method of claim 15, wherein the hepatitis is chronic hepatitis B or hepatitis C.

17. The method of claim 1, wherein Compound 1 is administered in a daily dose of about 10 mg to about 15 mg.

18. The method of claim 1, wherein Compound 1 is administered in a daily dose of about 13.5 mg.

19. The method of claim 1, wherein Compound 1 is administered as a tablet.

20. The method of claim 1, wherein Compound 1 is administered in a daily dose of about 9 mg.

21. A method of treating cholangiocarcinoma in a patient in need thereof comprising administering to the patient a therapeutically effective amount of Compound 1 having the formula:

Compound 1

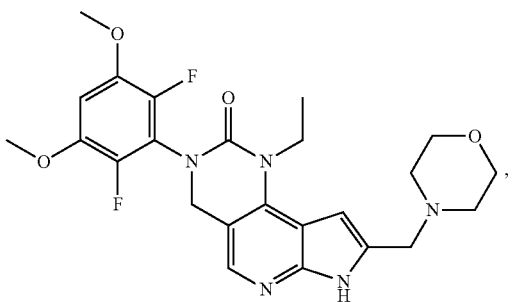

wherein Compound 1 is administered once daily as a tablet, and wherein the tablet comprises about 0.5 to about 10 mg of Compound 1.

22. The method of claim 21, wherein the tablet comprises about 0.5 mg to about 5 mg of Compound 1.

23. The method of claim 21, wherein the tablet comprises about 9 mg of Compound 1.

24. The method of claim 21, wherein the tablet comprises about 4.5 mg of Compound 1.

25. The method of claim 21, wherein the cholangiocarcinoma is advanced or metastatic cholangiocarcinoma.

26. The method of claim 21, wherein the cholangiocarcinoma is surgically unresectable.

27. The method of claim 21, wherein the cholangiocarcinoma is intrahepatic.

28. The method of claim 21, wherein the cholangiocarcinoma is extrahepatic.

29. The method of claim 21, wherein the cholangiocarcinoma is hilar or perihilar.

30. The method of claim 21, wherein the cholangiocarcinoma is distal extrahepatic.

31. The method of claim 21, wherein the cholangiocarcinoma is characterized by FGF/FGFR genetically altered tumors.

32. The method of claim 31, wherein the tumor exhibits FGFR2 translocations.

33. The method of claim 32, wherein the FGFR2 translocation is selected from the group consisting of FGFR2-BICC1, FGFR2-AHCYL1, FGFR2-MACF1, and FGFR2 intron 17 rearrangement.

34. The method of claim 31, wherein the tumor exhibits FGF/FGFR alterations other than FGFR2 translocations.

35. The method of claim 21, wherein the cholangiocarcinoma does not exhibit FGF/FGFR genetically altered tumors.

36. The method of claim 21, wherein the patient has failed at least one previous treatment.

37. The method of claim 36, wherein the previous treatment is surgery or radiation therapy.

38. A method of treating cholangiocarcinoma in a patient in need thereof comprising administering to the patient a therapeutically effective amount of Compound 1 having the formula:

Compound 1

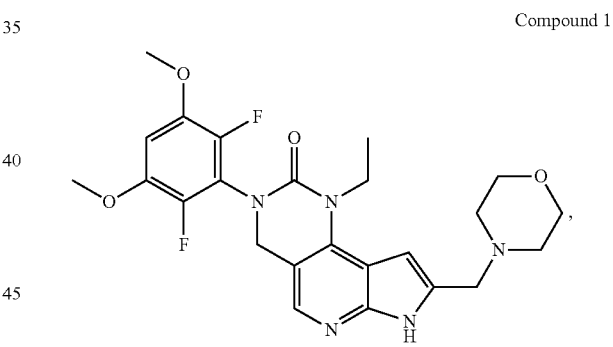

wherein Compound 1 is administered in a 21-day dosing regimen, wherein the 21-day dosing regimen comprises:
  (a) a first period wherein Compound 1 is administered once daily for 14 days; and
  (b) a second period wherein Compound 1 is not administered for 7 days.

39. The method of claim 38, wherein Compound 1 is administered in a daily dose of about 5 mg to about 20 mg during the first period.

40. The method of claim 38, wherein Compound 1 is administered in a daily dose of about 10 mg to about 15 mg during the first period.

41. The method of claim 38, wherein Compound 1 is administered in a daily dose of about 13.5 mg during the first period.

42. The method of claim 38, wherein Compound 1 is administered in a daily dose of about 9 mg during the first period.

43. The method of claim 38, wherein Compound 1 is administered as a tablet during the first period.

44. The method of claim 43, wherein the tablet comprises about 0.5 mg to about 10 mg of Compound 1.

45. The method of claim 43, wherein the tablet comprises about 0.5 mg to about 5 mg of Compound 1.

46. The method of claim 43, wherein the tablet comprises about 9 mg of Compound 1.

47. The method of claim 43, wherein the tablet comprises about 4.5 mg of Compound 1.

48. The method of claim 38, wherein the cholangiocarcinoma is advanced or metastatic cholangiocarcinoma.

49. The method of claim 38, wherein the cholangiocarcinoma is surgically unresectable.

50. The method of claim 38, wherein the cholangiocarcinoma is intrahepatic.

51. The method of claim 38, wherein the cholangiocarcinoma is extrahepatic.

52. The method of claim 38, wherein the cholangiocarcinoma is hilar or perihilar.

53. The method of claim 38, wherein the cholangiocarcinoma is distal extrahepatic.

54. The method of claim 38, wherein the cholangiocarcinoma is characterized by FGF/FGFR genetically altered tumors.

55. The method of claim 54, wherein the tumor exhibits FGFR2 translocations.

56. The method of claim 55, wherein the FGFR2 translocation is selected from the group consisting of FGFR2-BICC1, FGFR2-AHCYL1, FGFR2-MACF1, and FGFR2 intron 17 rearrangement.

57. The method of claim 54, wherein the tumor exhibits FGF/FGFR alterations other than FGFR2 translocations.

58. The method of claim 38, wherein the cholangiocarcinoma does not exhibit FGF/FGFR genetically altered tumors.

59. The method of claim 38, wherein the patient has failed at least one previous treatment.

60. The method of claim 59, wherein the previous treatment is surgery or radiation therapy.

* * * * *